US008034909B2

(12) United States Patent
Wengel et al.

(10) Patent No.: US 8,034,909 B2
(45) **Date of Patent: *Oct. 11, 2011**

(54) OLIGONUCLEOTIDE ANALOGUES

(75) Inventors: Jesper Wengel, Odense (DK); Poul Nielsen, Odense (DK)

(73) Assignee: Exiqon A/S, Vedbaek (DK)

( * ) Notice: Subject to any disclaimer, the term of this patent is extended or adjusted under 35 U.S.C. 154(b) by 255 days.

This patent is subject to a terminal disclaimer.

(21) Appl. No.: 12/192,581

(22) Filed: Aug. 15, 2008

(65) Prior Publication Data

US 2010/0279895 A1 Nov. 4, 2010

Related U.S. Application Data

(63) Continuation of application No. 11/132,650, filed on May 18, 2005, now Pat. No. 7,572,582, which is a continuation of application No. 10/208,650, filed on Jul. 29, 2002, now Pat. No. 7,034,133, which is a continuation of application No. 09/152,059, filed on Sep. 11, 1998, now Pat. No. 6,794,499.

(60) Provisional application No. 60/058,541, filed on Sep. 12, 1997, provisional application No. 60/068,293, filed on Dec. 19, 1997, provisional application No. 60/071,682, filed on Jan. 16, 1998, provisional application No. 60/076,591, filed on Mar. 3, 1998, provisional application No. 60/083,507, filed on Apr. 29, 1998, provisional application No. 60/088,309, filed on Jun. 5, 1998, provisional application No. 60/094,355, filed on Jul. 28, 1998.

(51) Int. Cl.

| | |
|---|---|
| ***C07H 21/00*** | (2006.01) |
| ***C07H 21/02*** | (2006.01) |
| *C12Q 1/68* | (2006.01) |

(52) U.S. Cl. .................. 536/23.1; 536/24.3; 536/24.33; 536/25.3; 435/6; 422/61

(58) Field of Classification Search ................ 536/23.1, 536/24, 3, 24.33, 25.3; 435/6; 422/61
See application file for complete search history.

(56) References Cited

U.S. PATENT DOCUMENTS 5,502,177 A 3/1996 Matteucci et al.

(Continued)

FOREIGN PATENT DOCUMENTS

EP 0 538 194 4/1993

(Continued)

OTHER PUBLICATIONS

Abe et al., "Normonoterpenoids and Their Allopyranosides from the Leaves of Cerbera Species (Studies on Cerbera. VIII)," Chem. Pharm. Bull. (1989) 37(10):2639-2642.

(Continued)

*Primary Examiner* — Jezia Riley

(74) *Attorney, Agent, or Firm* — Edwards Angell Palmer & Dodge LLP; Peter F. Corless; Mark D. Russett

(57) ABSTRACT

The present invention relates to novel bicyclic and tricyclic nucleoside and nucleotide analogues as well as to oligonucleotides comprising such elements. The nucleotide analogues, LNAs (Locked Nucleoside Analogues), are able to provide valuable improvements to oligonucleotides with respect to affinity and specificity towards complementary RNA and DNA oligomers. The novel type of LNA modified oligonucleotides, as well as the LNAs as such, are useful in a wide range of diagnostic applications as well as therapeutic applications. Among these can be mentioned antisense applications, PCR applications, strand displacement oligomers, as substrates for nucleic acid polymerases, as nucleotide based drugs, etc. The present invention also relates to such applications.

29 Claims, 36 Drawing Sheets

U.S. PATENT DOCUMENTS

| | | | | |
|---|---|---|---|---|
| 5,582,981 | A | 12/1996 | Toole et al. | |
| 6,268,490 | B1 | 7/2001 | Imanishi et al. | |
| 6,670,461 | B1 | 12/2003 | Wengel et al. | |
| 6,794,499 | B2 | 9/2004 | Wengel et al. | |
| 7,034,133 | B2 | 4/2006 | Wengel et al. | |
| 7,084,125 | B2 * | 8/2006 | Wengel | 514/44 A |
| 2003/0082807 | A1 | 5/2003 | Wengel et al. | |
| 2003/0087230 | A1 | 5/2003 | Wengel et al. | |
| 2003/0144231 | A1 | 7/2003 | Wengel et al. | |

FOREIGN PATENT DOCUMENTS

| | | | |
|---|---|---|---|
| EP | 0593901 | A2 | 4/1994 |
| WO | 91/06556 | | 5/1991 |
| WO | 92/03568 | | 3/1992 |
| WO | WO-9214841 | A1 | 9/1992 |
| WO | WO-9221692 | A1 | 12/1992 |
| WO | 93/07883 | | 4/1993 |
| WO | 93/10820 | | 6/1993 |
| WO | WO-9312130 | A1 | 6/1993 |
| WO | WO-9400467 | A1 | 1/1994 |
| WO | WO-9506474 | A1 | 3/1995 |
| WO | 95/14706 | | 6/1995 |
| WO | WO-9611938 | A1 | 4/1996 |
| WO | WO-9628460 | A1 | 9/1996 |
| WO | 9 822 489 | | 5/1998 |
| WO | WO-9829124 | A1 | 7/1998 |
| WO | 9 839 352 | | 9/1998 |

OTHER PUBLICATIONS

Abe et al., “10-Carboxyloganin, Normonoterpenoid Gluosides and Dinormonoterpenoid Glucosides from the Leaves of Cerbera manghas (Studies on Cerbera. 10),” Chem. Pharma. Bull. (1996) 44(10)1797-1800.

Albaek et al., “Two Carbocyclic Locked Nucleic Acid Analogues Give Structural Information About the Role of Hydration in A-Type Duplexes,” Nucleosides, Nucleotides and Nucleic Acids (2007) 26:1529-1532.

Chattopadhyaya, Conformationally-2', 4'-Locked Aza-ENA and Carbocyclic ribo-Thymidine (2007) Nucleic Acids Symposium Series 51: 69-70.

Duncan et al., “Stereoselective Thermal Rearrangement of syn-7-(1,2-Butadienyl)-1-methylbicyclo[2.2.1]hept-2-3n3 [syn-7-(3-Methylallenyl)-1-methylnorbornene],” J. Am. Chem. Soc. (1990) 112:8433-8442.

Ferles et al., “Mixed Electrolytic Reduction of 1,4-Dimethylpyridinium Methyl Sulfate with Acetone and of 1-Methylpyridiniummethyl Sulfate with Cyclopentanone,” Collection Czechoslov. Chem. Commun. (1975) 40:2183-2190.

Freier, Susan M., presentation in “Topological Recognition, Base/ Backbone Modification, and DNA Stability” session of Purines, Pyrimidines and Related Substances section, 1997 Gordon Conference, Jun. 29, 1997-Jul. 4, 1997, Newport RI.

Galan et al., “Diels-Alder Reactions with an a,b-Unsaturated Aldehydo-sugar. A Route to 6-Oxabicyclo[3.2.1]octanes,” Tetrahedron Letters (1993) 34(11):1811-1814.

Gavrilyuk et al., Zhurnal Organicheskol Khimil (1992) 28(8):1602-1614.

Griffey et al., “New Twists on Nucleic Acids: Structural Properties of Modified Nucleosides Incorporated into Oligonnucleotides,” Carbohydrate Modifications in Anti sense Research, Chapter 14, Sanghvi, Y.S., Cook, P.D. Eds.; Oxford University Press (1994) pp. 212-224.

Haaima et al., “Increased DNA binding and sequence discrimination of PNA oligomers containing 2,6-diaminopurine,” Nucleic Acids Research (1997) 25(22):4639-4643.

Hari et al., Synthesis and properties of oligonucleotides containing novel 2',4'-BNA analogues (2',4'-BNAcoc), Nucleic Acids Research, (2002), supp. 2: 147-148.

Jung et al., “An Intramolecular Prins Double Cyclization Catalyzed by Silyl Triflates,” J. Org. Chem. (1997) 62:9182-9187.

Kawasaki et al., “Synthesis and Biophysical Studies of 2'-dRIBO-2'-F Modified Oligonucleotides,” Conference on Nucleic Acid Therapeutics, Jan. 13, 1991.

Lee et al., “Synthesis and Reactions of 3-C-Branched-Chain Analogues of 3,6-Anhydrodeoxynojirimycin,” J. Carbohydrate Chem. (1997) 16(1):49-62.

Miyazawa et al., “Resolution of racemic 2,6,6-trimethyl-7-oxa-bicyclo[3.1.1]octan-2-ol and 1,6,6-trimethyl-7-oxa-bicyclo[3.1.1]octan-2-ol by microbial esterification,” Tetrahedron: Asymmetry (1997) 8(13):2131-2132.

Morita et al., “Synthesis and Properties of 2'-O,4'-C-Ethylene-Bridged Nucleic Acids (ENA) as Effective Antisense Oligonucleotides,” Bioorganic and Medicinal Chemistry (2003) 11:2211-2226.

Nielsen et al., “A novel class of conformationally restricted oligonucleotide analogues: synthesis of 2',3'-bridged monomers and RNA-selective hybridisation,” Chem. Commun. (1997) 9:825-826.

Polovinka et al., Zhurnal Organicheskoi Khimil (1992) 28(1):2253-2267.

Rajwanshi et al., “LNA stereoisomers: xylo-LNA (b-D-xylo configured locked nucleic acid) and a-L-LNA (a-L-ribo configured locked nucleic acid),” Chem. Commun. (1999) 1395-1396.

Ruiz-Perez et al., “Structured of 5-Hydroxymethyl-7,7-dimethyl-6-oxabicyclo[3.2.1]octane-1-carboxylic Acid,” Acta Crystallographica (1990), C46:1507-1509.

Shibahara et al., “Site-directed cleavage of RNA,” Nucleic Acids Res. (1987) 15:4403-4415.

Uhlmann et al., “Antisense Oligonucleotides: A New Therapeutic Principle,” Chemical Reviews (1990) 90(4):544-584.

Zigeuner et al., Chemical Abstracts (1969) 70(1), abstract No. 3737b.

Zigeuner et al., “Heterocycles. XVI. 1,4-Dimethyl-3-acetoxy-7-acetamido-2-oxabicyclo[2.2.1]heptane,” Heterocyclic Compounds (1969) 70:343, col. 1.

Zigeuner et al., Monatsch. Chem. (1968) 99:2111-2120.

National Seminar on Perspectives in Interfacial Areas of Chemistry and Biology, University of Delhi, Jan. 20-22, 1998.

Declaration of Susan Freier regarding Gordon Conference presentations in 1997.

Imanishi, T., et al. “Synthesis And Property of Novel Conformationally Constrained Nucleoside And Oligonucleotide Analogs”, The Sixteenth International Congress Of Heterocyclic Chemistry, Aug. 10-15, 1997, 4 pages.

Tarkoy et al., “31. Nucleic-Acid Analogues with Constraint Conformational Flexibility in the Sugar-Phosphate Backbone (Bicyclo-DNA)”, *Chim. Acta*, 76:481-510, (1993).

Tarkoy et al., “Synthesis and pairing Properties of Decanucleotides from (3'S,5'R)-2,Deoxy-3',5',-ethano-D-ribofuranosyladenine and -thymine**”, *Angew. Chem. Int. Ed. Engl.*, 32 (10) 1432-1434, (1993).

Egil et al., “Crystal Structure of a Parallel-Stranded Duplex of a Deoxycytidylyl-(3'-5')-deoxycytidine Analogue Containing Intranucleosidyl C(3')-C(5') Ethylene Bridges”, *American Chemical Society*, 115:5855-5856, 1993.

Tarkoy et al., “71. Nucleic-Acid Analogues with Restricted Conformational Flexibility in the Sugar-Phosphate Backbone (‘Bicyclo-DNA’)”, *Helvetica Chmica Acta*, 77:716-745, (1994).

Bolli et al., “Triple-Helix Formation of Oligodeoxynucleotides Containing [(3'S,5'R)-2'-Deoxy-3',5'-ethano-D-ribofuranosyl]nucleosides (“Bicyclo-deoxynucleosides”)**”, *Angew. Chem. Int. Ed. Engl.*, 34 (6) 694-696 (1995).

Bolli et al., 157. Nucleic-Acid Analogs with. Restricted Conforamtional Flexibility in the Sugar-Phosphate Backbone (‘Bicyclo-DNA’), *Helvetica Chmicia Acta*, 78:2077-2095, (1995).

Litten et al., “Bicyclo-Oligonucleotides with Inverted Configuration at C(5'): Synthesis and Properties” *Biooganic & Medicinal Chemisrty Letters*, 5 (12) 1231-1234, (1995).

Litten et al., 99. Nucleic-Acid Analogs with Restricted Conformational Flexibility in Sugar-Phosphate Backson (‘Bicyclo-DNA’), *Helvetica Chimica Acta*, 79:1129-1147, (1996).

Bolli et al., “Bicyclo-DNA: a Hoogsteen-selective pairing system”, *Chemistry & Biology*, 3 (3) 197-207, (1996).

Bolli et al., “Watson-Crick base-pairing properties of bicyclo-DNA”, *Nucleic Acids Research* 24 (23) 4660-4667, (1996).

Altmann et al., “4',6-Methano Carbocyclic Thymidine: A Conformationally Constrained Building Block for Oligonucleotides”, *Tetrahedron Letters*, 35 (15) 2331-2334, (1994).

Altmann et al., "1',6'-Methano Carbocyclic Thymidine: Synthesis, X-ray Crystal Structure, and Effect on Nucleic Acid Duplex Stability", *Tetrahedron Letters*, 35 (41) 7625-7628, (1994).
Marquez et al., "Nucleosides with a Twist. Can Fixed Forms of Sugar Ring Pucker Influence Biological Activity in Nucleosides and Oligonucleotides?", *J. Med. Chem.*, 39:3739-3747, (1996).
Ezzitouni et al., "Conformationally locked carbocyclic nucleosides built on a bicyclo[3.1.0]hexane template with a fixed Southern conformation. Synthesis and antiviral activity", *J. Chem. Soc., Perkin Trans.* 1:1073-1078, (1997).
Jones et al., "Oligonucleotides Containing a Covalent Conformationally Restricted Phosphodiester Analog for High-Affinity Triple Helix Formation: The Riboacetral Internucleotide Linkage", *J. Am. Chem. Soc.*, 115:9816-9817, (1993).
Wang et al., "The Synthesis and Binding Properties of Oligonucleotide Analogs Containing Diastereomerically Pure Conformationally Restricted Acetal Linkages", *Bioorganic & Medicinal Chemistry Letters*, 7 (2) 229-232 (1997).
Yannopoulus et al., "2',3'-Cyclopropanated Nucleoside Dimers", *Synlett*, 378-380, (1997).
CHIMA, 36th IUPAC Congress, organized by Swiss Chemical Society. Poster No. SB-B$: Steffens, R. and Leumann Ch. Tricyclo-DNA: synthesis, enzymatic stability, and pairing properties, 1997.
K.D. Neilsen, "Syntese og indbygning of 4'-C(hydroxymethyl) uridin i oligonucleotider", Master Thesis (Odense University, Denmark), 67-71, (1995).
Youssefyeh at al., "4'-Substituted Nucleosided Nucleosides. 4. Synthesis of Some 4'-Hydroxymethyl Nucleodsides", *J. Org. Chem.*, 44 (8) 1301-1308, (1979).
Jones et al., "4'-Substituted Nucleoosides. 5. Hydroxymethylation of Nucleoside 5'-Aldehydes" 44 (8) 1309-1317, (1979).
Yang et al., "Synthesis of 4'-Cyanothymidine and Analogs as Potent Inhibitors of HIV.", *Tetrahedron Letters* 33 (1) 37-40, (1992).
Thrane et al., "Novel Linear and Branched Oligodeoxynucleotide Analogues Containing 4'-C-(Hydroxymethyl) thymidine", *Tetrahedron Letters*, 51 (37) 10389-10402, (1995).
Nielsen et al.,"Oligonucleotide Analogues Containing 4'-C-(Hydroxymethyl)uridine: Synthesis, Evaluation and Mass Spectrometric Analysis", *Bioorganic & Medicinal Chemistry*, 3 (11) 1493-1502, (1995).
Freier et al., "The ups and downs of nucleic acid duplex stability: structure-stability studies on chemically-modified DNA:RNA duplexes", *Nucleic Acids Research*, 25 (22) 4429-4443 (1997).
Haly et al., "Conformationally Constrained DNA Mimics: Synthesis of a Novel Cyclopropyl-Amide Linked Dimer" *Synlett*, 687-689, (1996).
Zou et al., Synthesis and Hybridization Properties of an Oligonucleotide Analog Containing a Glucose-derived Conformation-restricted Ribose Moiety and 2',5'Formacetal Linkages, Tetrahedron Letters, vol. 37, No. 7, pp. 941-944, 1996.
Piet Herdewijn, "Targeting RNA with Conformationally Restricted Oligonucleotides", *Liebigs Ann.*, 1337-1348 (1996).
Obika et al., "Stability and structural features of the duplexes containing nucleoside analogues with a fixed N-type conformation, 2'-O,4'-C-methyleneribonucleosides", *Tetrahedron Letter*, 39:5401-5404, (1998).
Obika et al., "Synthesis of 2'-O,4'-C-Methyleneuridine and -cytidine. Novel Bicyclic Nucleosides Having a fixed c-endo Sugar Puckering", *Tetrahedron Letters*, 38:8735-8738, (1997).
7th Antisense Symposium, Nov. 21-22, 1997. Poster No. 32 and 33: Obika, D.N.; Morio, K. andImanishi, T. Synthesis and properties of oligonucleotides containing novel bicyclic nucleosides with a fixed N-form sugar puckering.
Chima, 36th IUPAC Congress, organized by the Swiss Chemical Society. Poster No. SB-B12: Egger, A. and Leumann Ch. Designe, synthesis and properties of bicyclo [3.2.1]-amino nucleic acids, 1997.
Chima, 36th IUPAC Congress, organized by the Swiss Chemical Society. Poster No. SB-B5: Epple, C. Ch., Pompizi I. and Leumann Ch. Bicyclo [3.2.1]-DNA: an oligonucleotide analogue with a conformationally preorganized phosphodiester backbone and flexible sugar-base linkage, 1997.
Sep. 6-10, 1998: 13th International Round Table-Nucleoside, Nucleotides and their Biological Applications, Montpeilleir: Oral Communication 1: Wang, G. and Gunic, E. "Conformationally Locked Nucleoside Analogs. Synthesis of 2'-Deoxy-2'C,4'-C-Bridged Bicyclic Nucleoside".
Sep. 6-10, 1998: 13th International Round Table—Nucleoside, Nucleotides and their Biological Applications, Montpeilleir: Poster No. 288: Meldgaard, M. et al. "LNA (Locked Nucleic Acids): Synthesis and Thermal Denaturation Studies".
Sep. 6-10, 1998: 13th International Round Table—Nucleotides and their Biological Applications Montpeilleir: Potter No. 287 and Proceeding: Koshkin, A.A. et al. "Locked Nucleic Acids as synthetic RNA Mimics for Effective Complementary Recognition."
Sep. 6-10, 1998: 13th International Round Table—Nucleoside, Nucleotides and their Biological Applications, Montpeilleir: Poster No. 67: Nielsen, P. and Wengel, J. A New Convergent Synthetic Approach Towards a-and-B-LNA (Locked Nucleic Acids).
Oct. 8, 1998: Antisense 98, Targeting the Molecular Basis of Disease: Poster No. 24: Havsteen, M. et al.: LNA (Locked Nucleic Acids): A New Class of High Affinity Nucleic Acids With Prime Potential as Antisense and Antigene Agents.
Jan. 21, 1998: National Seminar on Perspectives in Interfacial Areas of Chemistry and Biology, Delhi, university: Wengel, J. "LNA (Locked Nucleic Acids): Synthesis and High Affinity Nucleic Acid Recognition—Stop the Twisting."
27 Marts 1998: Workshop of Young European Bioorganic Chemists, Munchen: Wengel, J. "LNA (Locked Nucleic Acids): Synthesis and High Affinity Nucleic Acids Recognition—Stop the Twisting."
Aug. 20, 1998: Arsmodet for Center for Medicinsk Biotecknologi, KVL: Wengel, J. "LNA (Locked Nucleic Acids)".
Sep. 8, 1998: Meeting in Lund, Sweden: Jakobsen, M. H. "LNA (Locked Nucleic Acidsd): A New Class of High Affinity Nucleic Acids With Prime Potential as Antisense and Antigene Agents".
Nielsen et al., "Synthesis of 2'-O,3'-C-linked bicyclic nucleosides and bicyclic oligonucleotides", *J.Chem Soc., Perkin Trans.*, 1:3423-3433, (1997).
Nielsen et al., "A novel class of conformationally restricted oligonucleotide analogues: synthesis of 2',3'-bridges monomers and RNA-selective hybridisation", *Chem Commun.*, 9:825-826, (1997).
Singh et al., "LNA (locked nucleic acids): synthesis and high-affinity nucleic acid recognition" *Chem Commun.*, 455-456, (1998).
Koshkin et al., "LNA (Locked Nucleic Acids): Synthesis of the Adenine, Cytosine, Guanine, 5-Methylcytosine Thymine and Uracil Bicycloinucleoside Monomers, Oligomerisation, and Unprecedented Nucleic Acids Recognition" *Tetrahedron*, 54:3607-3630, (1998).
Koshkin et al., "Novel Convenient Syntheses of LNA [2.2.1]Bicyclo (1998) Nucleosides", *Tetrahedron*, 39:4381-4384 (1998).
Singh et al., "Universality of LNA-mediated high-affinity nucleic acid recognition", *Chem. Commun.*, 1247-1248 (1998).
Singh et al., "Synthesis of Novel Bicyclo[2.2.1] Ribonucleosides: 2'-Amino- and 2'-Thio-LNA Monomeric Nucleosides", *J. Org. Chem.*, 63:6078-6079, (1998).
Christensen et al., "A Novel Class of Oligonucleotide Analogues Containing 2'-O,3'-C-Linked [3.2-0] Bicycloarabinonucleoside Monomers: Synthesis, Thermal Affinity Studies, and Molecular Modeling", *J. Am. Chem.* vol. 120, No. 22, 5458-5463, (1998).
Koshkin et al., "Synthesis of Novel 2',3'-Linked Bicyclic Thymine Ribonucleosides", *J. Org. Chem.* 63:2778-2781, (1998).
Kumar et al., "The First Analogues of LNA (Locked Nucleic Acids): Phosphorothioate-LNA and 2'-Thio-LNA" *Bioorganic & Medicinal Chemistry Letters*, 8:2219-2222, (1998).
Rajwanshi et al, "High-affinity nucleic acid recognition using 'LNA' (locked nucleic acid, β-D-ribo configured LNA), 'xylo -LNA' (β-D-xylo configured LNA) or 'a-l-LNA' (a-L-ribo configured LNA)", Chem. Commun., 1999, 2073-2074.
Gura, "Antisense Has Growing Pains", Science, vol. 270, 575-577, 1995.
Moore, " 'Antisense' Touted as Medical Hope, But Critics Ask If Promise is Reasonable", The Wall Street Journal, May 10, 1996.
Summerton et al., "Morpholino Antisense Oligomer: Design, Preparation, and Properties", Antisense & Nucleic Acid Drig Development vol. 7, 187-195 (1997).

Rahman et al., "Synthesis and properties of 2', 4'-BNA$^{NC}$, a second generation BNA" Nucleic Acids Symposium Series, No. 49, 5-6 (2005).
The Gordon Research Conferences: "What is GRC?", retrived from www.grc.org/about.aspx on May 2, 2008.
Chemical Abstracts (CA) Registry Substructure Search Results #1 "Str1complete," Dec. 2, 2005.
Chemical Abstracts (CA) Registry Substructure Search Results #2 "Str2_noQ_complete," Dec. 1, 2005.
Chemical Abstracts (CA) Registry Substructure Search Results #3 "Str3_noQ_complete," Dec. 1, 2005.

* cited by examiner

A

B

C

D

E

F

G

H

I

J

L M

K

N

O

P Q

V X Y zT: B = thymin-1-yl
zU: B = uracil-1-yl
zG: B = guanin-9-yl
zC: B = cytosin-1-yl
zA: B = adenin-9-yl
zMeC: B = 5-methylcytosin-1-yl 1 $R_1$=H, $R_2$=OAc

2 $R_1$=H, $R_2$=OH

3 $R_1$=H, $R_2$=OMs

4 $R_1$=OH, $R_2$=H

5

6 $R_1 = R_2 = H$

7 $R_1$ = DMT, $R_2$ = H

8 $R_1$ = DMT, $R_2$ = -P(O(CH$_2$)$_2$CN)(N(iPr)$_2$)

9

10 11 12

17 18

14: $R_1 = R_2 = CH_3$
15: $R_1 = CH_3$; $R_2 = H$
16: $R_1 = H$; $R_2 = CH_3$

19

12 13

20 21 22 23 24 25 26 27 28 29 30

32 33 34

35 35A 36

37 38 39

33 40

41 42 43

44 45 46

33 47

48 49 50

51 52 53

33

54

55

56

57

57A

57B

57C

57D

33

58

60

59

61

61A 61B 61C

61D 62 63 44

37

64 65

66

67 68 69

70 71 61B

35

72

73

74

74A

Monomer $Z^{TNH}$

74

74B

74C

74D

74E

74F

Monomer $Z^{TNMe}$

41

75

76

76A

76B

76C

76D

76E

76F

Monomer $Z^{US}$ 77 78 79 80 36

31 R=H
200 R=Ms
201 202 203
202
204 205

202/203

206

207 208

201

209

210

211

210

212

36 + 213 R=Bn

37 + 214 R=H

SEQUENCE LISTING

<160> NUMBER OF SEQ ID NOS: 146

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)..(15)
<223> OTHER INFORMATION: LNA monomer

<400> SEQUENCE: 1
tgtgtgaaat tgttat 16

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)..(12)
<223> OTHER INFORMATION: LNA monomer

<400> SEQUENCE: 2
ataaagtgta aag 13

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggtggtttgt ttg 13

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (6)..(9)
<223> OTHER INFORMATION: LNA monomer

<400> SEQUENCE: 4
ggtggtttgt ttg 13

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(12)
<223> OTHER INFORMATION: LNA monomer

<400> SEQUENCE: 5
ggtggtttgt ttg 13

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggtggtttgt ttg 13

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (7)
<223> OTHER INFORMATION: LNA monomer

<400> SEQUENCE: 7
ggtggtttgt ttg 13

<210> SEQ ID NO 8
<211> LENGTH: 13
<212> TYPE: DNA

<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (6)..(9)
<223> OTHER INFORMATION: LNA monomer

<400> SEQUENCE: 8
ggtggtttgt ttg 13

<210> SEQ ID NO 9
<211> LENGTH: 13
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)..(12)
<223> OTHER INFORMATION: LNA monomer

<400> SEQUENCE: 9
ggtggtttgt ttg 13

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
tgcatgtgct ggaga 15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
gcatgtgctg gagat 15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)
<223> OTHER INFORMATION: LNA monomer
<220> FEATURE:
<221> NAME/KEY: modified_base
<222> LOCATION: (5)
<223> OTHER INFORMATION: LNA monomer
<220> FEATURE:
<221> NAME/KEY: modified_base
<222> LOCATION: (7)
<223> OTHER INFORMATION: LNA monomer
<220> FEATURE:
<221> NAME/KEY: modified_base
<222> LOCATION: (10)
<223> OTHER INFORMATION: LNA monomer

<400> SEQUENCE: 12
tgcatgtgct ggaga 15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (15)
<223> OTHER INFORMATION: LNA monomer

<400> SEQUENCE: 13
gcatgtgctg gagat 15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 14
tgcatgtgct ggaga 15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 15
tgcatgtgct ggaga 15

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (10)..(24)
<223> OTHER INFORMATION: LNA monomer

<400> SEQUENCE: 16
atcgttccat ctccagcaca tgca 24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (10)..(24)
<223> OTHER INFORMATION: LNA monomer

<400> SEQUENCE: 17
gactagttct ctccagcaca tgca 24

```
<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (10)..(24)
<223> OTHER INFORMATION: LNA monomer

<400> SEQUENCE: 18

ctgatcggtt ctccagcaca tgca                                          24


<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (10)..(24)
<223> OTHER INFORMATION: LNA monomer

<400> SEQUENCE: 19

ctgatcaagt ctccagcaca tgca                                          24


<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

gcatgtgctg gagat                                                    15


<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (15)
<223> OTHER INFORMATION: LNA monomer

<400> SEQUENCE: 21

gcatgtgctg gagat                                                    15


<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

atcgttccat ctccagcaca tgca                                          24


<210> SEQ ID NO 23
<211> LENGTH: 16
```

<212> TYPE: DNA
<213> ORGANISM: Artificial Sequence
<220> FEATURE:
<223> OTHER INFORMATION: Description of Artificial Sequence: Primer

<400> SEQUENCE: 23
aacagctatg accatg 16

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 24
gtaaaacgac ggccagt 17

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 25
gataggtgcc tcactgat 18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 26
gtcgttcgct ccaagctg 18

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 27
atgcctgcag gtcgac 16

<210> SEQ ID NO 28
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 28
ggtggtttgt ttg 13

<210> SEQ ID NO 29
<211> LENGTH: 13
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: modified_base
<222> LOCATION: (1)..(12)
<223> OTHER INFORMATION: LNA monomer

<400> SEQUENCE: 29
ggtggtttgt ttg 13

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: modified_base
<222> LOCATION: (1)..(12)
<223> OTHER INFORMATION: LNA monomer

<400> SEQUENCE: 30
ggtggtttgt ttg 13

<210> SEQ ID NO 31
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 31
ggtggtttgt ttg 13

<210> SEQ ID NO 32
<211> LENGTH: 13
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: modified_base
<222> LOCATION: (1)..(12)
<223> OTHER INFORMATION: LNA monomer

<400> SEQUENCE: 32
ggtggtttgt ttg 13

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 33
ccagctctca gtagtttagt aca 23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 34
gtagagcttt ctggtatgac aca 23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 35
taagtcacag acgtatctca gac 23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 36
ctctgtttca gacatgaact gct 23

<210> SEQ ID NO 37
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
ttccacagca caa 13

<210> SEQ ID NO 38
<211> LENGTH: 13
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (6)..(9)
<223> OTHER INFORMATION: LNA monomer

<400> SEQUENCE: 38
ttccacagca caa 13

<210> SEQ ID NO 39
<211> LENGTH: 13
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)..(12)
<223> OTHER INFORMATION: LNA monomer

<400> SEQUENCE: 39
ttccacagca caa 13

<210> SEQ ID NO 40
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
agagccgata aca 13

<210> SEQ ID NO 41
<211> LENGTH: 13

<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (6)..(9)
<223> OTHER INFORMATION: LNA monomer

<400> SEQUENCE: 41
agagccgata aca 13

<210> SEQ ID NO 42
<211> LENGTH: 13
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)..(12)
<223> OTHER INFORMATION: LNA monomer

<400> SEQUENCE: 42
agagccgata aca 13

<210> SEQ ID NO 43
<211> LENGTH: 13
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (6)..(9)
<223> OTHER INFORMATION: LNA monomer

<400> SEQUENCE: 43
ggtggtttgt ttg 13

<210> SEQ ID NO 44
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 44
ggtggtttgt ttg 13

<210> SEQ ID NO 45
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
aaaaatcgac gctcaagtca gaaaagcatc tcacaaacaa acaaaccacc 50

<210> SEQ ID NO 46
<211> LENGTH: 13
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)..(9)
<223> OTHER INFORMATION: LNA monomer

<400> SEQUENCE: 46
ggtggtttgt ttg 13

<210> SEQ ID NO 47
<211> LENGTH: 13
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)
<223> OTHER INFORMATION: LNA monomer

<400> SEQUENCE: 47
ggtggtttgt ttg 13

<210> SEQ ID NO 48
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 48
ggtggtttgt ttg 13

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 49
gtggttcgct ccaagctg 18

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
cagcagtcga cagag 15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (7)
<223> OTHER INFORMATION: LNA monomer

<400> SEQUENCE: 51
cagcagtcga cagag 15

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 52
ctctgtcgaa tgctg 15

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 53
tgcatgtgct ggaga 15

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 54
atcgttccat ctccagcaca tgca 24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (6)
<223> OTHER INFORMATION: LNA monomer

<400> SEQUENCE: 55
atcgttccat ctccagcaca tgca 24

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 56
ttaacgtagg tgctggactt gtcgctgttg tactt 35

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (1)..(15)
<223> OTHER INFORMATION: LNA monomer

<400> SEQUENCE: 57
tgtgtgaaat tgttat 16

<210> SEQ ID NO 58
<211> LENGTH: 13
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)..(12)
<223> OTHER INFORMATION: LNA monomer

<400> SEQUENCE: 58
ataaagtgta aag 13

<210> SEQ ID NO 59
<211> LENGTH: 16
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)..(15)
<223> OTHER INFORMATION: LNA monomer

<400> SEQUENCE: 59
tgtgtgaaat tgttat 16

<210> SEQ ID NO 60
<211> LENGTH: 13
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)..(12)
<223> OTHER INFORMATION: LNA monomer

<400> SEQUENCE: 60
ataaagtgta aag 13

<210> SEQ ID NO 61
<211> LENGTH: 16
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)..(15)
<223> OTHER INFORMATION: LNA monomer

<400> SEQUENCE: 61
tgcctgcagg tcgact 16

<210> SEQ ID NO 62
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
tgcctgcagg tcgact 16

<210> SEQ ID NO 63
<211> LENGTH: 16
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)..(15)
<223> OTHER INFORMATION: LNA monomer

<400> SEQUENCE: 63
tgtgtgaaat tgttat 16

<210> SEQ ID NO 64
<211> LENGTH: 13
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)..(12)
<223> OTHER INFORMATION: LNA monomer

<400> SEQUENCE: 64
ataaagtgta aag 13

<210> SEQ ID NO 65
<211> LENGTH: 14
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (7)
<223> OTHER INFORMATION: LNA monomer

<400> SEQUENCE: 65
tttttttttt tttt 14

<210> SEQ ID NO 66
<211> LENGTH: 14
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (7)..(8)
<223> OTHER INFORMATION: LNA monomer

<400> SEQUENCE: 66
tttttttttt tttt 14

<210> SEQ ID NO 67
<211> LENGTH: 14
<212> TYPE: DNA
<213> ORGANISM: Artificial Sequence
<220> FEATURE:
<223> OTHER INFORMATION: Description of Artificial Sequence: LNA

```
      modified oligonucleotide
<220> FEATURE:
<221> NAME/KEY: modified_base
<222> LOCATION: (6)..(9)
<223> OTHER INFORMATION: LNA monomer

<400> SEQUENCE: 67

tttttttttt tttt                                                14


<210> SEQ ID NO 68
<211> LENGTH: 14
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (5)
<223> OTHER INFORMATION: LNA monomer
<220> FEATURE:
<221> NAME/KEY: modified_base
<222> LOCATION: (7)
<223> OTHER INFORMATION: LNA monomer
<220> FEATURE:
<221> NAME/KEY: modified_base
<222> LOCATION: (9)
<223> OTHER INFORMATION: LNA monomer
<220> FEATURE:
<221> NAME/KEY: modified_base
<222> LOCATION: (11)
<223> OTHER INFORMATION: LNA monomer

<400> SEQUENCE: 68

tttttttttt tttt                                                14


<210> SEQ ID NO 69
<211> LENGTH: 10
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(9)
<223> OTHER INFORMATION: LNA monomer

<400> SEQUENCE: 69

tttttttttt                                                     10


<210> SEQ ID NO 70
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70

tttttttttt tttttt                                              16


<210> SEQ ID NO 71
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
```

ggtggtttgt ttg 13

<210> SEQ ID NO 72
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
caaacaaacc aca 13

<210> SEQ ID NO 73
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
caaacaaacc aca 13

<210> SEQ ID NO 74
<211> LENGTH: 13
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (6)..(9)
<223> OTHER INFORMATION: LNA monomer

<400> SEQUENCE: 74
ggtggtttgt ttg 13

<210> SEQ ID NO 75
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
caaacaaacc aca 13

<210> SEQ ID NO 76
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
caaacaaacc aca 13

<210> SEQ ID NO 77
<211> LENGTH: 13
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:

<221> NAME/KEY: modified_base
<222> LOCATION: (1)..(12)
<223> OTHER INFORMATION: LNA monomer

<400> SEQUENCE: 77
ggtggtttgt ttg 13

<210> SEQ ID NO 78
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
caaacaaacc aca 13

<210> SEQ ID NO 79
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
caaacaaacc aca 13

<210> SEQ ID NO 80
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
tttttttttt tttt 14

<210> SEQ ID NO 81
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
aaaaaaaaaa aaaa 14

<210> SEQ ID NO 82
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
aaaaaaaaaa aaaa 14

<210> SEQ ID NO 83
<211> LENGTH: 14
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (7)
<223> OTHER INFORMATION: LNA monomer

<400> SEQUENCE: 83
tttttttttt tttt 14

<210> SEQ ID NO 84
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84
aaaaaaaaaa aaaa 14

<210> SEQ ID NO 85
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
aaaaaaaaaa aaaa 14

<210> SEQ ID NO 86
<211> LENGTH: 14
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (7)..(8)
<223> OTHER INFORMATION: LNA monomer

<400> SEQUENCE: 86
tttttttttt tttt 14

<210> SEQ ID NO 87
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
aaaaaaaaaa aaaa 14

<210> SEQ ID NO 88
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
aaaaaaaaaa aaaa 14

<210> SEQ ID NO 89
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (6)..(9)
<223> OTHER INFORMATION: LNA monomer

<400> SEQUENCE: 89
tttttttttt tttt 14

<210> SEQ ID NO 90
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
aaaaaaaaaa aaaa 14

<210> SEQ ID NO 91
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
aaaaaaaaaa aaaa 14

<210> SEQ ID NO 92
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (5)
<223> OTHER INFORMATION: LNA monomer
<220> FEATURE:
<221> NAME/KEY: modified_base
<222> LOCATION: (7)
<223> OTHER INFORMATION: LNA monomer
<220> FEATURE:
<221> NAME/KEY: modified_base
<222> LOCATION: (9)
<223> OTHER INFORMATION: LNA monomer
<220> FEATURE:
<221> NAME/KEY: modified_base
<222> LOCATION: (11)
<223> OTHER INFORMATION: LNA monomer

<400> SEQUENCE: 92
tttttttttt tttt 14

<210> SEQ ID NO 93
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
aaaaaaaaaa aaaa 14

<210> SEQ ID NO 94
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 94
aaaaaaaaaa aaaa 14

<210> SEQ ID NO 95
<211> LENGTH: 10
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (1)..(9)
<223> OTHER INFORMATION: LNA monomer

<400> SEQUENCE: 95
tttttttttt 10

<210> SEQ ID NO 96
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96
aaaaaaaaaa aaaa 14

<210> SEQ ID NO 97
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 97
aaaaaaaaaa aaaa 14

<210> SEQ ID NO 98
<211> LENGTH: 14
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (8)
<223> OTHER INFORMATION: LNA monomer

<400> SEQUENCE: 98
tttttttttt tttt 14

<210> SEQ ID NO 99
<211> LENGTH: 14

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 99
aaaaaaaaaa aaaa 14

<210> SEQ ID NO 100
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 100
aaaaaaaaaa aaaa 14

<210> SEQ ID NO 101
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (7)..(8)
<223> OTHER INFORMATION: LNA monomer

<400> SEQUENCE: 101
tttttttttt tttt 14

<210> SEQ ID NO 102
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 102
aaaaaaaaaa aaaa 14

<210> SEQ ID NO 103
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 103
aaaaaaaaaa aaaa 14

<210> SEQ ID NO 104
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (7)
<223> OTHER INFORMATION: LNA monomer
<220> FEATURE:
<221> NAME/KEY: modified_base
<222> LOCATION: (9)
<223> OTHER INFORMATION: LNA monomer

<400> SEQUENCE: 104
tttttttttt tttt 14

<210> SEQ ID NO 105
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 105
aaaaaaaaaa aaaa 14

<210> SEQ ID NO 106
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 106
aaaaaaaaaa aaaa 14

<210> SEQ ID NO 107
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (6)..(9)
<223> OTHER INFORMATION: LNA monomer

<400> SEQUENCE: 107
tttttttttt tttt 14

<210> SEQ ID NO 108
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 108
aaaaaaaaaa aaaa 14

<210> SEQ ID NO 109
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
aaaaaaaaaa aaaa 14

<210> SEQ ID NO 110
<211> LENGTH: 14
<212> TYPE: DNA

<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (5)
<223> OTHER INFORMATION: LNA monomer
<220> FEATURE:
<221> NAME/KEY: modified_base
<222> LOCATION: (7)
<223> OTHER INFORMATION: LNA monomer
<220> FEATURE:
<221> NAME/KEY: modified_base
<222> LOCATION: (9)
<223> OTHER INFORMATION: LNA monomer
<220> FEATURE:
<221> NAME/KEY: modified_base
<222> LOCATION: (11)
<223> OTHER INFORMATION: LNA monomer

<400> SEQUENCE: 110
tttttttttt tttt 14

<210> SEQ ID NO 111
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
aaaaaaaaaa aaaa 14

<210> SEQ ID NO 112
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
aaaaaaaaaa aaaa 14

<210> SEQ ID NO 113
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (1)..(13)
<223> OTHER INFORMATION: LNA monomer

<400> SEQUENCE: 113
tttttttttt tttt 14

<210> SEQ ID NO 114
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
aaaaaaaaaa aaaa 14

<210> SEQ ID NO 115
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
aaaaaaaaaa aaaa 14

<210> SEQ ID NO 116
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
aaaaaagaaa aaaa 14

<210> SEQ ID NO 117
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (8)
<223> OTHER INFORMATION: LNA monomer

<400> SEQUENCE: 117
tttttttttt tttt 14

<210> SEQ ID NO 118
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 118
aaaaaaaaaa aaaa 14

<210> SEQ ID NO 119
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 119
aaaaaaaaaa aaaa 14

<210> SEQ ID NO 120
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (7)..(8)
<223> OTHER INFORMATION: LNA monomer

<400> SEQUENCE: 120
tttttttttt tttt 14

<210> SEQ ID NO 121
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 121
aaaaaaaaaa aaaa 14

<210> SEQ ID NO 122
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
aaaaaaaaaa aaaa 14

<210> SEQ ID NO 123
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (7)
<223> OTHER INFORMATION: LNA monomer
<220> FEATURE:
<221> NAME/KEY: modified_base
<222> LOCATION: (9)
<223> OTHER INFORMATION: LNA monomer

<400> SEQUENCE: 123
tttttttttt tttt 14

<210> SEQ ID NO 124
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
aaaaaaaaaa aaaa 14

<210> SEQ ID NO 125
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
aaaaaaaaaa aaaa 14

<210> SEQ ID NO 126
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (6)..(9)
<223> OTHER INFORMATION: LNA monomer

<400> SEQUENCE: 126
tttttttttt tttt 14

<210> SEQ ID NO 127
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 127
aaaaaaaaaa aaaa 14

<210> SEQ ID NO 128
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
aaaaaaaaaa aaaa 14

<210> SEQ ID NO 129
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (8)
<223> OTHER INFORMATION: LNA monomer

<400> SEQUENCE: 129
tttttttttt tttt 14

<210> SEQ ID NO 130
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 130
aaaaaaaaaa aaaa 14

<210> SEQ ID NO 131
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 131
aaaaaaaaaa aaaa 14

<210> SEQ ID NO 132
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (7)..(8)
<223> OTHER INFORMATION: LNA monomer

<400> SEQUENCE: 132
tttttttttt tttt 14

<210> SEQ ID NO 133
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 133
aaaaaaaaaa aaaa 14

<210> SEQ ID NO 134
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 134
aaaaaaaaaa aaaa 14

<210> SEQ ID NO 135
<211> LENGTH: 14
<212> TYPE: DNA
<213> ORGANISM: Artificial Sequence
<220> FEATURE:
<223> OTHER INFORMATION: Description of Artificial Sequence: LNA
modified oligonucleotide
<220> FEATURE:
<221> NAME/KEY: modified_base
<222> LOCATION: (7)
<223> OTHER INFORMATION: LNA monomer
<220> FEATURE:
<221> NAME/KEY: modified_base
<222> LOCATION: (9)
<223> OTHER INFORMATION: LNA monomer

<400> SEQUENCE: 135
tttttttttt tttt 14

<210> SEQ ID NO 136
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 136

-continued aaaaaaaaaa aaaa 14

<210> SEQ ID NO 137
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
aaaaaaaaaa aaaa 14

<210> SEQ ID NO 138
<211> LENGTH: 14
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (6)..(9)
<223> OTHER INFORMATION: LNA monomer

<400> SEQUENCE: 138
tttttttttt tttt 14

<210> SEQ ID NO 139
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
aaaaaaaaaa aaaa 14

<210> SEQ ID NO 140
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 140
aaaaaaaaaa aaaa 14

<210> SEQ ID NO 141
<211> LENGTH: 14
<212> TYPE: DNA
<213> ORGANISM: Artificial Sequence
<220> FEATURE:
<223> OTHER INFORMATION: Description of Artificial Sequence: LNA modified oligonucleotide
<220> FEATURE:
<221> NAME/KEY: modified_base
<222> LOCATION: (5)
<223> OTHER INFORMATION: LNA monomer
<220> FEATURE:
<221> NAME/KEY: modified_base
<222> LOCATION: (7)
<223> OTHER INFORMATION: LNA monomer
<220> FEATURE:
<221> NAME/KEY: modified_base
<222> LOCATION: (9)
<223> OTHER INFORMATION: LNA monomer
<220> FEATURE:

```
<221> NAME/KEY: modified_base
<222> LOCATION: (11)
<223> OTHER INFORMATION: LNA monomer

<400> SEQUENCE: 141

tttttttttt tttt                                                    14


<210> SEQ ID NO 142
<211> LENGTH: 14
<212> TYPE: DNA
<213> ORGANISM: Artificial Sequence
<220> FEATURE:
<223> OTHER INFORMATION: Description of Artificial Sequence: LNA
      modified oligonucleotide

<400> SEQUENCE: 142

aaaaaaaaaa aaaa                                                    14


<210> SEQ ID NO 143
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143

aaaaaaaaaa aaaa                                                    14


<210> SEQ ID NO 144
<211> LENGTH: 14
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(13)
<223> OTHER INFORMATION: LNA monomer

<400> SEQUENCE: 144

tttttttttt tttt                                                    14


<210> SEQ ID NO 145
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145

aaaaaaaaaa aaaa                                                    14


<210> SEQ ID NO 146
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146

aaaaaaaaaa aaaa                                                    14
```

OLIGONUCLEOTIDE ANALOGUES

This application is a continuation application of U.S. patent application Ser. No. 11/132,650 filed May 18, 2005, which is a continuation application of U.S. patent application Ser. No. 10/208,650 filed Jul. 29, 2002, which is now issued as U.S. Pat. No. 7,034,133, which is a continuation application of U.S. patent application Ser. No. 09/152,059 filed Sep. 11, 1998, which is now issued as U.S. Pat. No. 6,794,499, which claims priority to U.S. Provisional Patent Applications 60/094,355, filed Jul. 28, 1998; 60/088,309 filed Jun. 5, 1998; 60/083,507, filed Apr. 29, 1998; 60/076,591, filed Mar. 3, 1998; 60/071,682 filed Jan. 16, 1998; 60/068,293, filed Dec. 19, 1997; and 60/058,541, filed Sep. 12, 1997, the entirety of each of which is incorporated herein by reference.

FIELD OF THE INVENTION

The present invention relates to the field of bi- and tricyclic nucleoside analogues and to the synthesis of such nucleoside analogues which are useful in the formation of synthetic oligonucleotides capable of forming nucleobase specific duplexes and triplexes with single stranded and double stranded nucleic acids. These complexes exhibit higher thermostability than the corresponding complexes formed with normal nucleic acids. The invention also relates to the field of bi- and tricyclic nucleoside analogues and the synthesis of such nucleosides which may be used as therapeutic drugs and which may be incorporated in oligonucleotides by template dependent nucleic acid polymerases.

BACKGROUND OF THE INVENTION

Synthetic oligonucleotides are widely used compounds in disparate fields such as molecular biology and DNA-based diagnostics and therapeutics.

Therapeutics

In therapeutics, e.g., oligonucleotides have been used successfully to block translation in vivo of specific mRNAs thereby preventing the synthesis of proteins which are undesired or harmful to the cell/organism. This concept of oligonucleotide mediated blocking of translation is known as the “antisense” approach. Mechanistically, the hybridising oligonucleotide is thought to elicit its effect by either creating a physical block to the translation process or by recruiting cellular enzymes that specifically degrades the mRNA part of the duplex (RNAseH).

More recently, oligoribonucleotides and oligodeoxyribonucleotides and analogues thereof which combine RNAse catalytic activity with the ability to sequence specifically interact with a complementary RNA target (ribozymes) have attracted much interest as antisense probes. Thus far ribozymes have been reported to be effective in cell cultures against both viral targets and oncogenes.

To completely prevent the synthesis of a given protein by the antisense approach it is necessary to block/destroy all mRNAs that encode that particular protein and in many cases the number of these mRNA are fairly large. Typically, the mRNAs that encode a particular protein are transcribed from a single or a few genes. Hence, by targeting the gene (“antigene” approach) rather than its mRNA products it should be possible to either block production of its cognate protein more efficiently or to achieve a significant reduction in the amount of oligonucleotides necessary to elicit the desired effect. To block transcription, the oligonucleotide must be able to hybridise sequence specifically to double stranded DNA. In 1953 Watson and Crick showed that deoxyribo nucleic acid (DNA) is composed of two strands (Nature, 1953, 171, 737) which are held together in a helical configuration by hydrogen bonds formed between opposing complementary nucleobases in the two strands. The four nucleobases, commonly found in DNA are guanine (G), adenine (A), thymine (T) and cytosine (C) of which the G nucleobase pairs with C, and the A nucleobase pairs with T. In RNA the nucleobase thymine is replaced by the nucleobase uracil (U) which similarly to the T nucleobase pairs with A. The chemical groups in the nucleobases that participate in standard duplex formation constitute the Watson-Crick face. In 1959, Hoogsteen showed that the purine nucleobases (G and A) in addition to their Watson-Crick face have a Hoogsteen face that can be recognised from the outside of a duplex, and used to bind pyrimidine oligonucleotides via hydrogen bonding, thereby forming a triple helix structure. Although making the “antigene” approach conceptually feasible the practical usefulness of triple helix forming oligomers is currently limited by several factors including the requirement for homopurine sequence motifs in the target gene and a need for unphysiologically high ionic strength and low pH to stabilise the complex.

The use of oligonucleotides known as aptamers are also being actively investigated. This promising new class of therapeutic oligonucleotides are selected in vitro to specifically bind to a given target with high affinity, such as for example ligand receptors. Their binding characteristics are likely a reflection of the ability of oligonucleotides to form three dimensional structures held together by intramolecular nucleobase pairing.

Likewise, nucleosides and nucleoside analogues have proven effective in chemotherapy of numerous viral infections and cancers.

Also, various types of double-stranded RNAs have been shown to effectively inhibit the growth of several types of cancers.

Diagnostics

In molecular biology, oligonucleotides are routinely used for a variety of purposes such as for example (i) as hybridisation probes in the capture, identification and quantification of target nucleic acids (ii) as affinity probes in the purification of target nucleic acids (iii) as primers in sequencing reactions and target amplification processes such as the polymerase chain reaction (PCR) (iv) to clone and mutate nucleic acids and (vi) as building blocks in the assembly of macromolecular structures.

Diagnostics utilises many of the oligonucleotide based techniques mentioned above in particular those that lend themselves to easy automation and facilitate reproducible results with high sensitivity. The objective in this field is to use oligonucleotide based techniques as a means to, for example (i) tests humans, animals and food for the presence of pathogenic micro-organisms (ii) to test for genetic predisposition to a disease (iii) to identify inherited and acquired genetic disorders, (iv) to link biological deposits to suspects in crime trials and (v) to validate the presence of micro-organisms involved in the production of foods and beverages.

General Considerations

To be useful in the extensive range of different applications outlined above, oligonucleotides have to satisfy a large number of different requirements. In antisense therapeutics, for instance, a useful oligonucleotide must be able to penetrate the cell membrane, have good resistance to extra- and intracellular nucleases and preferably have the ability to recruit endogenous enzymes like RNAseH. In DNA-based diagnostics and molecular biology other properties are important such as, e.g., the ability of oligonucleotides to act as efficient substrates for a wide range of different enzymes evolved to act on natural nucleic acids, such as e.g. polymerases, kinases, ligases and phosphatases. The fundamental property of oligonucleotides, however, which underlies all uses is their ability to recognise and hybridise sequence specifically to complementary single stranded nucleic acids employing either Watson-Crick hydrogen bonding (A-T and G-C) or other hydrogen bonding schemes such as the Hoogsteen mode. The are two important terms affinity and specificity are commonly used to characterise the hybridisation properties of a given oligonucleotide. Affinity is a measure of the binding strength of the oligonucleotide to its complementary target sequence (expressed as the thermostability ($T_m$) of the duplex). Each nucleobase pair in the duplex adds to the thermostability and thus affinity increases with increasing size (No. of nucleobases) of the oligonucleotide. Specificity is a measure of the ability of the oligonucleotide to discriminate between a fully complementary and a mismatched target sequence. In other words, specificity is a measure of the loss of affinity associated with mismatched nucleobase pairs in the target. At constant oligonucleotide size the specificity increases with increasing number of mismatches between the oligonucleotide and its targets (i.e. the percentage of mismatches increases). Conversely, specificity decreases when the size of the oligonucleotide is increased at a constant number of mismatches (i.e. the percentage of mismatches decreases). Stated another way, an increase in the affinity of an oligonucleotide occurs at the expense of specificity and vice-versa.

This property of oligonucleotides creates a number of problems for their practical use. In lengthy diagnostic procedures, for instance, the oligonucleotide needs to have both high affinity to secure adequate sensitivity of the test and high specificity to avoid false positive results. Likewise, an oligonucleotide used as antisense probes needs to have both high affinity for its target mRNA to efficiently impair its translation and high specificity to avoid the unintentional blocking of the expression of other proteins. With enzymatic reactions, like, e.g., PCR amplification, the affinity of the oligonucleotide primer must be high enough for the primer/target duplex to be stable in the temperature range where the enzymes exhibits activity, and specificity needs to be high enough to ensure that only the correct target sequence is amplified.

Given the shortcomings of natural oligonucleotides, new approaches for enhancing specificity and affinity would be highly useful for DNA-based therapeutics, diagnostics and for molecular biology techniques in general.

Conformationally Restricted Nucleosides

It is known that oligonucleotides undergo a conformational transition in the course of hybridising to a target sequence, from the relatively random coil structure of the single stranded state to the ordered structure of the duplex state.

A number of conformationally restricted oligonucleotides including bicyclic and tricyclic nucleoside analogues (FIGS. 1A and 1B in which B=nucleobase) have been synthesised, incorporated into oligonucleotide and oligonucleotide analogues and tested for their hybridisation and other properties.

Bicyclo[3.3.0] nucleosides (bcDNA) with an additional C-3',C-5'-ethano-bridge (A and B) have been synthesised with all five nucleobases (G, A, T, C and U) whereas (C) has been synthesised only with T and A nucleobases (M. Tarköy, M. Bolli, B. Schweizer and C. Leumann, *Helv. Chim. Acta,* 1993, 76, 481; Tarköy and C. Leumann, *Angew. Chem., Int. Ed. Engl.,* 1993, 32, 1432; M. Egli, P. Lubini, M. Dobler and C. Leumann, *J. Am. Chem. Soc.,* 1993, 115, 5855; M. Tarköy, M. Bolli and C. Leumann, *Helv. Chim. Acta,* 1994, 77, 716; M. Bolli and C. Leumann, *Angew. Chem., Int. Ed. Engl.,* 1995, 34, 694; M. Bolli, P. Lubini and C. Leumann, *Helv. Chim. Acta,* 1995, 78, 2077; J. C. Litten, C. Epple and C. Leumann, *Bioorg. Med. Chem. Lett.,* 1995, 5, 1231; J. C. Litten and C. Leumann, *Helv. Chim. Acta,* 1996, 79, 1129; M. Bolli, J. C. Litten, R. Schultz and C. Leumann, *Chem. Biol.,* 1996, 3, 197; M. Bolli, H. U. Trafelet and C. Leumann, *Nucleic Acids Res.,* 1996, 24, 4660). DNA oligonucleotides containing a few, or being entirely composed, of these analogues are in most cases able to form Watson-Crick bonded duplexes with complementary DNA and RNA oligonucleotides. The thermostability of the resulting duplexes, however, is either distinctly lower (C), moderately lower (A) or comparable to (B) the stability of the natural DNA and RNA counterparts. All bcDNA oligomers exhibited a pronounced increase in sensitivity to the ionic strength of the hybridisation media compared to the natural counterparts. The α-bicyclo-DNA (B) is more stable towards the 3'-exonuclease snake venom phosphordiesterase than the β-bicyclo-DNA (A) which is only moderately more stable than unmodified oligonucleotides.

Bicarbocyclo[3.1.0]nucleosides with an additional C-1',C-6'- or C-6',C-4'-methano-bridge on a cyclopentane ring (D and E, respectively) have been synthesised with all five nucleobases (T, A, G, C and U). Only the T-analogues, however, have been incorporated into oligomers. Incorporation of one or ten monomers D in a mixed poly-pyrimidine DNA oligonucleotide resulted in a substantial decrease in the affinity towards both DNA and RNA oligonucleotides compared to the unmodified reference oligonucleotide. The decrease was more pronounced with ssDNA than with ssRNA. Incorporation of one monomer E in two different poly-pyrimidine DNA oligonucleotides induced modest increases in $T_m$'s of 0.8° C. and 2.1° C. for duplexes towards ssRNA compared with unmodified reference duplexes. When ten T-analogues were incorporated into a 15mer oligonucleotide containing exclusively phosphorothioate internucleoside linkages, the $T_m$ against the complementary RNA oligonucleotide was increased approximately 1.3° C. per modification compared to the same unmodified phosphorothioate sequence. Contrary to the control sequence the oligonucleotide containing the bicyclic nucleoside E failed to mediate RNAseH cleavage. The hybridisation properties of oligonucleotides containing the G, A, C and U-analogues of E have not been reported. Also, the chemistry of this analogue does not lend itself to further intensive investigations on completely modified oligonucleotides (K.-H. Altmann, R. Kesselring, E. Francotte and G. Rihs, *Tetrahedron Lett.,* 1994, 35, 2331; K.-H. Altmann, R. Imwinkelried, R. Kesselring and G. Rihs, *Tetrahedron Lett.,* 1994, 35, 7625; V. E. Marquez, M. A. Siddiqui, A. Ezzitouni, P. Russ, J. Wang, R. W. Wagner and M. D. Matteucci, *J. Med. Chem.,* 1996, 39, 3739; A. Ezzitouni and V. E. Marquez, *J. Chem. Soc., Perkin Trans.* 1, 1997, 1073).

A bicyclo[3.3.0]nucleoside containing an additional C-2',C-3'-dioxalane ring has been synthesised as a dimer with an unmodified nucleoside where the additional ring is part of the internucleoside linkage replacing a natural phosphordiester linkage (F). This analogue was only synthesised as either thymine-thymine or thymine-5-methylcytosine blocks. A 15-mer polypyrimidine sequence containing seven of these dimeric blocks and having alternating phosphordiester- and riboacetal-linkages, exhibited a substantially decreased $T_m$ against complementary ssRNA compared to a control sequence with exclusively natural phosphordiester internucleoside linkages (R. J. Jones, S. Swaminathan, J. F. Millagan, S. Wadwani, B. S. Froehler and M. Matteucci, *J. Am. Chem. Soc.,* 1993, 115, 9816).

The two dimers (G and H) with additional C-2',C-3'-dioxane rings forming bicyclic[4.3.0]-systems in acetal-type internucleoside linkages have been synthesised as T-T dimers and incorporated once in the middle of 12mer polypyrimidine oligonucleotides. Oligonucleotides containing either G or H both formed significantly less stable duplexes with complementary ssRNA and ssDNA compared with the unmodified control oligonucleotide (J. Wang and M. D. Matteucci, *Bioorg. Med. Chem. Lett.,* 1997, 7, 229).

Dimers containing a bicyclo[3.1.0]nucleoside with a C-2', C-3'-methano bridge as part of amide- and sulfonamide-type (I and J) internucleoside linkages have been synthesised and incorporated into oligonucleotides. Oligonucleotides containing one or more of these analogues showed a significant reduction in $T_m$ compared to unmodified natural oligonucleotide references (C. G. Yannopoulus, W. Q. Zhou, P. Nower, D. Peoch, Y. S. Sanghvi and G. Just, *Synlett,* 1997, 378).

A trimer with formacetal internucleoside linkages and a bicyclo[3.3.0]glucose-derived nucleoside analogue in the middle (K) has been synthesised and connected to the 3'-end of an oligonucleotide. The $T_m$ against complementary ssRNA was decreased by 4° C., compared to a control sequence, and by 1.5° C. compared to a sequence containing two 2',5'-formacetal linkages in the 3'-end (C. G. Yannopoulus, W. Q. Zhou, P. Nower, D. Peoch, Y. S. Sanghvi and G. Just, *Synlett,* 1997, 378).

Very recently oligomers composed of tricyclic nucleoside-analogues (L) have been reported to show increased duplex stability compared to natural DNA (R. Steffens and C. Leumann (Poster SB-B4), *Chimia,* 1997, 51, 436).

An attempt to make the bicyclic uridine nucleoside analogue Q planned to contain an additional O-2',C-4'-five-membered ring, starting from 4'-C-hydroxymethyl nucleoside P, failed (K. D. Nielsen, *Specialerapport* (Odense University, Denmark), 1995).

Until now the pursuit of conformationally restricted nucleosides useful in the formation of synthetic oligonucleotides with significantly improved hybridisation characteristics has met with little success. In the majority of cases, oligonucleotides containing these analogues form less stable duplexes with complementary nucleic acids compared to the unmodified oligonucleotides. In other cases, where moderate improvement in duplex stability is observed, this relates only to either a DNA or an RNA target, or it relates to fully but not partly modified oligonucleotides or vice versa. An appraisal of most of the reported analogues are further complicated by the lack of data on analogues with G, A and C nucleobases and lack of data indicating the specificity and mode of hybridisation. In many cases, synthesis of the reported monomer analogues is very complex while in other cases the synthesis of fully modified oligonucleotides is incompatible with the widely used phosphoramidite chemistry standard.

SUMMARY OF THE INVENTION

In view of the shortcomings of the previously known nucleoside analogues, the present inventors have now provided novel nucleoside analogues (LNAs) and oligonucleotides have included LNA nucleoside analogues therein. The novel LNA nucleoside analogues have been provided with all commonly used nucleobases thereby providing a full set of nucleoside analogues for incorporation in oligonucleotides. As will be apparent from the following, the LNA nucleoside analogues and the LNA modified oligonucleotide provides a wide range of improvements for oligonucleotides used in the fields of diagnostics and therapy. Furthermore, the LNA nucleoside analogues and the LNA modified oligonucleotide also provides completely new perspectives in nucleoside and oligonucleotide based diagnostics and therapy.

Thus, the present invention relates to oligomers comprising at least one nucleoside analogue (hereinafter termed "LNA") of the general formula I

I

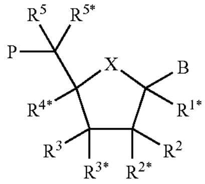

wherein X is selected from —O—, —S—, —$N(R^{N*})$—, —$C(R^6R^{6*})$—, —O—$C(R^7R^{7*})$—, —$C(R^6R^{6*})$—O—, —S—$C(R^7R^{7*})$—, —$C(R^6R^{6*})$—S—, —$N(R^{N*})$—$C(R^7R^{7*})$—, —$C(R^6R^{6*})$—$N(R^{N*})$—, and —$C(R^6R^{6*})$—$C(R^7R^{7*})$—;

B is selected from hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$;

one of the substituents $R^2$, $R^{2*}$, $R^3$, and $R^{3*}$ is a group P* which designates an internucleoside linkage to a preceding monomer, or a 3'-terminal group;

one or two pairs of non-geminal substituents selected from the present substituents of $R^{1*}$, $R^{4*}$, $R^5$, $R^{5*}$, $R^6$, $R^{6*}$, $R^7$, $R^{7*}$, $R^{N*}$, and the ones of $R^2$, $R^{2*}$, $R^3$, and $R^{3*}$ not designating P* each designates a biradical consisting of 1-8 groups/atoms selected from —$C(R^aR^b)$—, —$C(R^a)$=$C(R^a)$—, —$C(R^a)$=N—, —O—, —$Si(R^a)_2$—, —S—, —$SO_2$—, —$N(R^a)$—, and >C=Z, wherein Z is selected from —O—, —S—, and —$N(R^a)$—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents $R^a$ and $R^b$ together may designate optionally substituted methylene (=$CH_2$), and wherein two non-geminal or geminal substituents selected from $R^a$, $R^b$, and any of the substituents $R^{1*}$, $R^2$, $R^{2*}$, $R^3$, $R^{3*}$, $R^{4*}$, $R^5$, $R^{5*}$, $R^6$ and $R^{6*}$, $R^7$, and $R^{7*}$ which are present and not involved in P, P* or the biradical(s) together may form an associated biradical selected from biradicals of the same kind as defined before;

said pair(s) of non-geminal substituents thereby forming a mono- or bicyclic entity together with (i) the atoms to which said non-geminal substituents are bound and (ii) any intervening atoms; and each of the substituents $R^{1*}$, $R^2$, $R^{2*}$, $R^3$, $R^{4*}$, $R^5$, $R^{5*}$, $R^6$ and $R^{6*}$, $R^7$, and $R^{7*}$ which are present and not involved in P, P* or the biradical(s), is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/groups selected from —O—, —S—, and —($NR^N$)— where $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl;

and basic salts and acid addition salts thereof;

with the proviso that, (i) $R^3$ and $R^5$ do not together designate a biradical selected from —$CH_2$—$CH_2$—, —O—$CH_2$—, when LNA is a bicyclic nucleoside analogue;

(ii) $R^3$, $R^5$, and $R^{5*}$ do not together designate a triradical —$CH_2$—CH(−)—$CH_2$— when LNA is a tricyclic nucleoside analogue;

(iii) $R^{1*}$ and $R^{6*}$ do not together designate a biradical —$CH_2$— when LNA is a bicyclic nucleoside analogue; and (iv) $R^{4*}$ and $R^{6*}$ do not together designate a biradical —$CH_2$— when LNA is a bicyclic nucleoside analogue.

The present invention furthermore relates to nucleoside analogues (hereinafter LNAs) of the general formula II

II

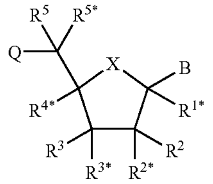

wherein the substituent B is selected from nucleobases, DNA intercalators, photochemically active groups, thermochemically active groups, chelating groups, reporter groups, and ligands;

X is selected from —O—, —S—, —N($R^{N*}$)—, and —C($R^6R^{6*}$)—;

one of the substituents $R^2$, $R^{2*}$, $R^3$, and $R^{3*}$ is a group Q*;

each of Q and Q* is independently selected from hydrogen, azido, halogen, cyano, nitro, hydroxy, Prot-O—, Act-O—, mercapto, Prot-S—, Act-S—, $C_{1-6}$-alkylthio, amino, Prot-N($R^H$)—, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, Act-O—$CH_2$—, aminomethyl, Prot-N($R^H$)—$CH_2$—, Act-N($R^H$)—$CH_2$—, carboxymethyl, sulphonomethyl, where Prot is a protection group for —OH, —SH, and —NH($R^H$), respectively, Act is an activation group for —OH, —SH, and —NH($R^H$), respectively, and $R^H$ is selected from hydrogen and $C_{1-6}$-alkyl;

(i) $R^{2*}$ and $R^{4*}$ together designate a biradical selected from —O—, —$(CR^*R^*)_{r+s+1}$—, —$(CR^*R^*)_r$—O—$(CR^*R^*)_s$—, —$(CR^*R^*)_r$—S—$(CR^*R^*)_s$—, —$(CR^*R^*)_r$—N($R^*$)—$(CR^*R^*)_s$—, —O—$(CR^*R^*)_{r+s}$—O—, —S—$(CR^*R^*)_{r+s}$—O—, —O—$(CR^*R^*)_{r+s}$—S—, —N($R^*$)—$(CR^*R^*)_{r+s}$—O—, —O—$(CR^*R^*)_{r+s}$—N($R^*$)—, —S—$(CR^*R^*)_{r+s}$—S—, —N($R^*$)—$(CR^*R^*)_{r+s}$—N($R^*$)—, —N($R^*$)—$(CR^*R^*)_{r+s}$—S—, and —S—$(CR^*R^*)_{r+s}$—N($R^*$)—;

(ii) $R^2$ and $R^3$ together designate a biradical selected from —O—, —$(CR^*R^*)_{r+s}$—, —$(CR^*R^*)_r$—O—$(CR^*R^*)_s$—, —$(CR^*R^*)_r$—S—$(CR^*R^*)_s$—, and —$(CR^*R^*)_r$—N($R^*$)—$(CR^*R^*)_s$—;

(iii) $R^{2*}$ and $R^3$ together designate a biradical selected from —O—, —$(CR^*R^*)_{r+s}$—, —$(CR^*R^*)_r$—O—$(CR^*R^*)_s$—, —$(CR^*R^*)_r$—S—$(CR^*R^*)_s$—, and —$(CR^*R^*)_r$—N($R^*$)—$(CR^*R^*)_s$—;

(iv) $R^3$ and $R^{4*}$ together designate a biradical selected from —$(CR^*R^*)_r$—O—$(CR^*R^*)_s$—, —$(CR^*R^*)_r$—S—$(CR^*R^*)_s$—, and —$(CR^*R^*)_r$—N($R^*$)—$(CR^*R^*)_s$—;

(v) $R^3$ and $R^5$ together designate a biradical selected from —$(CR^*R^*)_r$—O—$(CR^*R^*)_s$—, —$(CR^*R^*)_r$—S—$(CR^*R^*)_s$—, and —$(CR^*R^*)_r$—N($R^*$)—$(CR^*R^*)_s$—; or (vi) $R^{1*}$ and $R^{4*}$ together designate a biradical selected from —$(CR^*R^*)_r$—O—$(CR^*R^*)_s$—, —$(CR^*R^*)_r$—S—$(CR^*R^*)_s$—, and —$(CR^*R^*)_r$—N($R^*$)—$(CR^*R^*)_s$—;

(vii) $R^{1*}$ and $R^{2*}$ together designate a biradical selected from —$(CR^*R^*)_r$—O—$(CR^*R^*)_s$—, —$(CR^*R^*)_r$—S—$(CR^*R^*)_s$—, and —$(CR^*R^*)_r$—N($R^*$)—$(CR^*R^*)_s$—;

wherein each R* is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond, and each of r and s is 0-3 with the proviso that the sum r+s is 1-4;

each of the substituents $R^{1*}$, $R^2$, $R^{2*}$, $R^3$, $R^{4*}$, $R^5$, and $R^{5*}$, which are not involved in Q, $Q^*$ or the biradical, is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/groups selected from —O—, —S—, and —$(NR^N)$— where $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl;

and basic salts and acid addition salts thereof;

with the first proviso that, (i) $R^3$ and $R^5$ do not together designate a biradical selected from —$CH_2$—$CH_2$—, —O—$CH_2$—, and —O—Si$(^iPr)_2$—O—Si$(^iPr)_2$—O—;

and with the second proviso that any chemical group (including any nucleobase), which is reactive under the conditions prevailing in oligonucleotide synthesis, is optionally functional group protected.

The present invention also relates to the use of the nucleoside analogues (LNAs) for the preparation of oligomers, and the use of the oligomers as well as the nucleoside analogues (LNAs) in diagnostics, molecular biology research, and in therapy.

DETAILED DESCRIPTION OF THE INVENTION

Figure 1A:
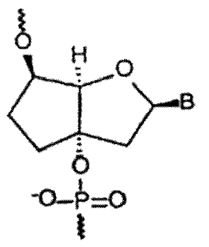
FIGS. 1A and 1B illustrate known conformationally restricted nucleotides.
Figure 1A:
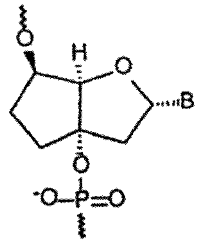
Figure 1A:
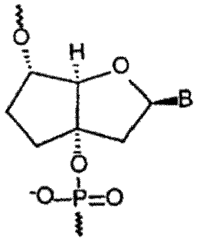
Figure 1A:
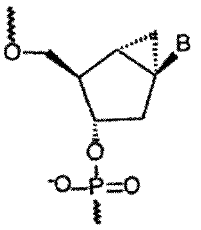
Figure 1A:
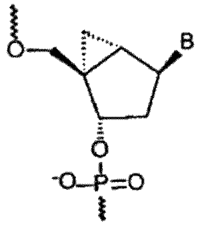
Figure 1A:
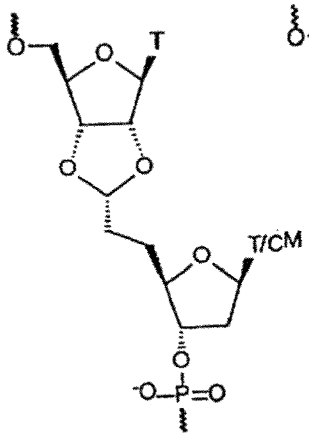
Figure 1A:
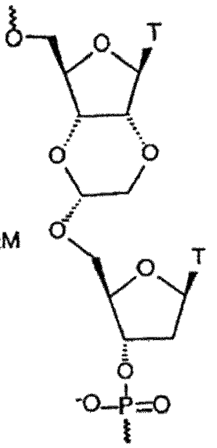
Figure 1A:
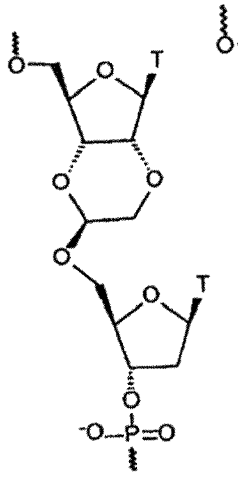
Figure 1A:
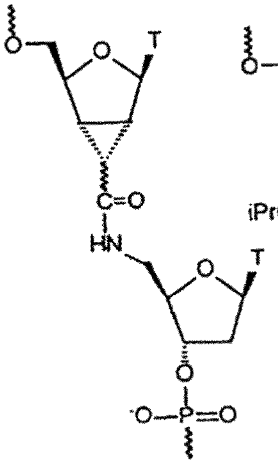
Figure 1A:
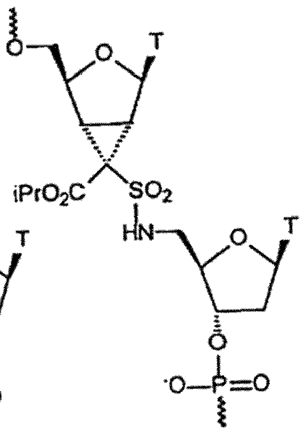
Figure 1B:
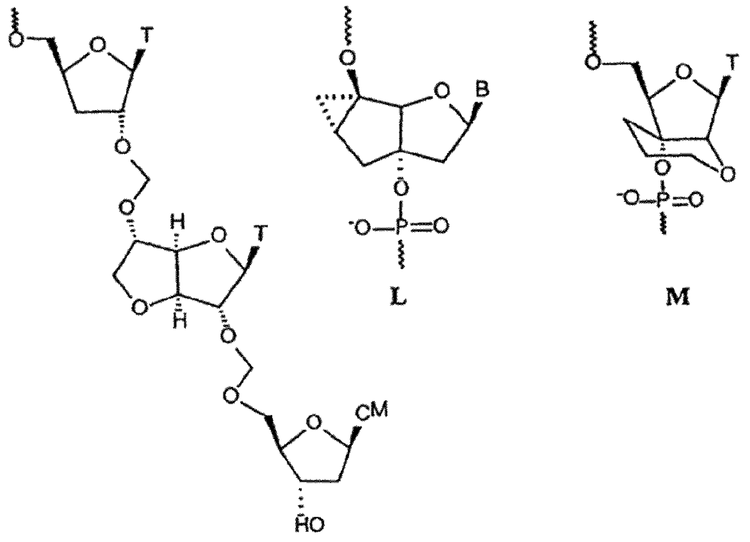
Figure 1B:
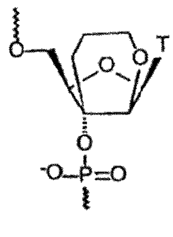
Figure 1B:
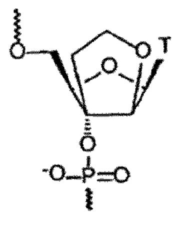
Figure 1B:
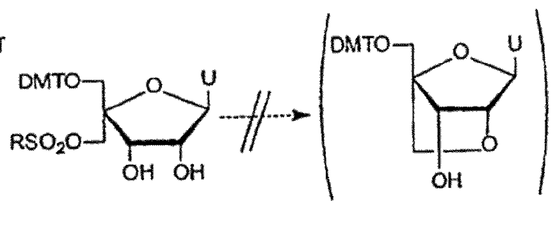

When used herein, the term "LNA" (Locked Nucleoside Analogues) refers to the bi- and tri-cyclic nucleoside analogues of the invention, either incorporated in the oligomer of the invention (general formula I) or as discrete chemical species (general formula II). The term "monomeric LNA" specifically refers to the latter case.

Oligomers and Nucleoside Analogues

As mentioned above, the present invention i.a. relates to novel oligomers (oligonucleotides) comprising one or more bi-, tri-, or polycyclic nucleoside analogues (hereinafter termed "LNA"). It has been found that the incorporation of such LNAs in place of, or as a supplement to, e.g., known nucleosides confer interesting and highly useful properties to an oligonucleotide. Bi- and tricyclic, especially bicyclic, LNAs seem especially interesting within the scope of the present invention.

Each of the possible LNAs incorporated in an oligomer (oligonucleotide) has the general formula I

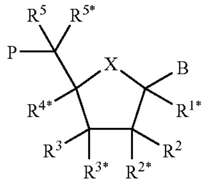

I wherein X is selected from —O— (the furanose motif), —S—, —$N(R^{N*})$—, —$C(R^6R^{6*})$—, —O—$C(R^7R^{7*})$—, —$C(R^6R^{6*})$—O—, —S—$C(R^7R^{7*})$—, —$C(R^6R^{6*})$—S—, —$N(R^{N*})$—$C(R^7R^{7*})$—, —$C(R^6R^{6*})$—$N(R^{N*})$—, and —$C(R^6R^{6*})$—$C(R^7R^{7*})$—, where $R^6$, $R^{6*}$, $R^7$, $R^{7*}$, and $R^{N*}$ are as defined further below. Thus, the LNAs incorporated in the oligomer may comprise an either 5- or 6-membered ring as an essential part of the bi-, tri-, or polycyclic structure. It is believed that 5-membered rings (X=—O—, —S—, —$N(R^{N*})$—, —$C(R^6R^{6*})$—) are especially interesting in that they are able to occupy essentially the same conformations (however locked by the introduction of one or more biradicals (see below)) as the native furanose ring of a naturally occurring nucleoside. Among the possible 5-membered rings, the situations where X designates —O—, —S—, and —N($R^{N*}$)— seem especially interesting, and the situation where X is —O— appears to be particularly interesting.

The substituent B may designate a group which, when the oligomer is complexing with DNA or RNA, is able to interact (e.g. by hydrogen bonding or covalent bonding or electronic interaction) with DNA or RNA, especially nucleobases of DNA or RNA. Alternatively, the substituent B may designate a group which acts as a label or a reporter, or the substituent B may designate a group (e.g. hydrogen) which is expected to have little or no interactions with DNA or RNA. Thus, the substituent B is preferably selected from hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4$,$N^4$-ethanocytosin, $N^6$,$N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

When used herein, the term "DNA intercalator" means a group which can intercalate into a DNA or RNA helix, duplex or triplex. Examples of functional parts of DNA intercalators are acridines, anthracene, quinones such as anthraquinone, indole, quinoline, isoquinoline, dihydroquinones, anthracyclines, tetracyclines, methylene blue, anthracyclinone, psoralens, coumarins, ethidium-halides, dynemicin, metal complexes such as 1,10-phenanthroline-copper, tris(4,7-diphenyl-1,10-phenanthroline)ruthenium-cobalt-enediynes such as calcheamicin, porphyrins, distamycin, netropcin, viologen, daunomycin. Especially interesting examples are acridines, quinones such as anthraquinone, methylene blue, psoralens, coumarins, and ethidium-halides.

In the present context, the term "photochemically active groups" covers compounds which are able to undergo chemical reactions upon irradiation with light. Illustrative examples of functional groups hereof are quinones, especially 6-methyl-1,4-naphtoquinone, anthraquinone, naphtoquinone, and 1,4-dimethyl-anthraquinone, diazirines, aromatic azides, benzophenones, psoralens, diazo compounds, and diazirino compounds.

In the present context "thermochemically reactive group" is defined as a functional group which is able to undergo thermochemically-induced covalent bond formation with other groups. Illustrative examples of functional parts thermochemically reactive groups are carboxylic acids, carboxylic acid esters such as activated esters, carboxylic acid halides such as acid fluorides, acid chlorides, acid bromide, and acid iodides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, and boronic acid derivatives.

In the present context, the term "chelating group" means a molecule that contains more than one binding site and frequently binds to another molecule, atom or ion through more than one binding site at the same time. Examples of functional parts of chelating groups are iminodiacetic acid, nitrilotriacetic acid, ethylenediamine tetraacetic acid (EDTA), aminophosphonic acid, etc.

In the present context, the term "reporter group" means a group which is detectable either by itself or as a part of an detection series. Examples of functional parts of reporter groups are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are dansyl (5-dimethylamino)-1-naphthalenesulfonyl), DOXYL (N-oxyl-4,4-dimethyloxazolidine), PROXYL (N-oxyl-2,2,5,5-tetramethylpyrrolidine), TEMPO(N-oxyl-2,2,6,6-tetramethylpiperidine), dinitrophenyl, acridines, coumarins, Cy3 and Cy5 (trademarks for Biological Detection Systems, Inc.), erytrosine, coumaric acid, umbelliferone, texas red, rhodamine, tetramethyl rhodamine, Rox, 7-nitrobenzo-2-oxa-1-diazole (NBD), pyrene, fluorescein, Europium, Ruthenium, Samarium, and other rare earth metals), radioisotopic labels, chemiluminescence labels (labels that are detectable via the emission of light during a chemical reaction), spin labels (a free radical (e.g. substituted organic nitroxides) or other paramagnetic probes (e.g. $Cu^{2+}$, $Mg^{2+}$) bound to a biological molecule being detectable by the use of electron spin resonance spectroscopy), enzymes (such as peroxidases, alkaline phosphatases, β-galactosidases, and glycose oxidases), antigens, antibodies, haptens (groups which are able to combine with an antibody, but which cannot initiate an immune response by itself, such as peptides and steroid hormones), carrier systems for cell membrane penetration such as: fatty acid residues, steroid moieties (cholesteryl), vitamin A, vitamin D, vitamin E, folic acid peptides for specific receptors, groups for mediating endocytose, epidermal growth factor (EGF), bradykinin, and platelet derived growth factor (PDGF). Especially interesting examples are biotin, fluorescein, Texas Red, rhodamine, dinitrophenyl, digoxigenin, Ruthenium, Europium, Cy5, Cy3, etc.

In the present context "ligand" means something which binds. Ligands can comprise functional groups such as: aromatic groups (such as benzene, pyridine, naphtalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, $C_1$-$C_{20}$ alkyl groups optionally interrupted or terminated with one or more heteroatoms such as oxygen atoms, nitrogen atoms, and/or sulphur atoms, optionally containing aromatic or mono/polyunsaturated hydrocarbons, polyoxyethylene such as polyethylene glycol, oligo/polyamides such as poly-β-alanine, polyglycine, polylysine, peptides, oligo/polysaccharides, oligo/polyphosphates, toxins, antibiotics, cell poisons, and steroids, and also "affinity ligands", i.e. functional groups or biomolecules that have a specific affinity for sites on particular proteins, antibodies, poly- and oligosaccharides, and other biomolecules.

It will be clear for the person skilled in the art that the above-mentioned specific examples under DNA intercalators, photochemically active groups, thermochemically active groups, chelating groups, reporter groups, and ligands correspond to the "active/functional" part of the groups in question. For the person skilled in the art it is furthermore clear that DNA intercalators, photochemically active groups, thermochemically active groups, chelating groups, reporter groups, and ligands are typically represented in the form M-K- where M is the "active/functional" part of the group in question and where K is a spacer through which the "active/functional" part is attached to the 5- or 6-membered ring. Thus, it should be understood that the group B, in the case where B is selected from DNA intercalators, photochemically active groups, thermochemically active groups, chelating groups, reporter groups, and ligands, has the form M-K-, where M is the "active/functional" part of the DNA intercalator, photochemically active group, thermochemically active group, chelating group, reporter group, and ligand, respectively, and where K is an optional spacer comprising 1-50 atoms, preferably 1-30 atoms, in particular 1-15 atoms, between the 5- or 6-membered ring and the "active/functional" part.

In the present context, the term "spacer" means a thermochemically and photochemically non-active distance-making group and is used to join two or more different moieties of the types defined above. Spacers are selected on the basis of a variety of characteristics including their hydrophobicity, hydrophilicity, molecular flexibility and length (e.g. see Hermanson et. al., "Immobilized Affinity Ligand Techniques", Academic Press, San Diego, Calif. (1992), p. 137-ff). Generally, the length of the spacers are less than or about 400 Å, in some applications preferably less than 100 Å. The spacer, thus, comprises a chain of carbon atoms optionally interrupted or terminated with one or more heteroatoms, such as oxygen atoms, nitrogen atoms, and/or sulphur atoms. Thus, the spacer K may comprise one or more amide, ester, amino, ether, and/or thioether functionalities, and optionally aromatic or mono/polyunsaturated hydrocarbons, polyoxyethylene such as polyethylene glycol, oligo/polyamides such as poly-β-alanine, polyglycine, polylysine, and peptides in general, oligosaccharides, oligo/polyphosphates. Moreover the spacer may consist of combined units thereof. The length of the spacer may vary, taking into consideration the desired or necessary positioning and spatial orientation of the "active/functional" part of the group in question in relation to the 5- or 6-membered ring. In particularly interesting embodiments, the spacer includes a chemically cleavable group. Examples of such chemically cleavable groups include disulphide groups cleavable under reductive conditions, peptide fragments cleavable by peptidases, etc.

In one embodiment of the present invention, K designates a single bond so that the "active/functional" part of the group in question is attached directly to the 5- or 6-membered ring.

In a preferred embodiment, the substituent B in the general formulae I and II is preferably selected from nucleobases, in particular from adenine, guanine, thymine, cytosine and uracil.

In the oligomers of the present invention (formula I), P designates the radical position for an internucleoside linkage to a succeeding monomer, or a 5'-terminal group. The first possibility applies when the LNA in question is not the 5'-terminal "monomer", whereas the latter possibility applies when the LNA in question is the 5'-terminal "monomer". It should be understood (which also will be clear from the definition of internucleoside linkage and 5'-terminal group further below) that such an internucleoside linkage or 5'-terminal group may include the substituent $R^5$ (or equally applicable: the substituent $R^{5*}$) thereby forming a double bond to the group P. (5'-Terminal refers to the position corresponding to the 5' carbon atom of a ribose moiety in a nucleoside.)

On the other hand, an internucleoside linkage to a preceding monomer or a 3'-terminal group (P*) may originate from the positions defined by one of the substituents $R^2$, $R^{2*}$, $R^3$, and $R^{3*}$, preferably from the positions defined by one of the substituents $R^3$ and $R^{3*}$. Analogously, the first possibility applies where the LNA in question is not the 3'-terminal "monomer", whereas the latter possibility applies when the LNA in question is the 3'-terminal "monomer". (3'-Terminal refers to the position corresponding to the 3' carbon atom of a ribose moiety in a nucleoside.)

In the present context, the term "monomer" relates to naturally occurring nucleosides, non-naturally occurring nucleosides, PNAs, etc. as well as LNAs. Thus, the term "succeeding monomer" relates to the neighbouring monomer in the 5'-terminal direction and the "preceding monomer" relates to the neighbouring monomer in the 3'-terminal direction. Such succeeding and preceding monomers, seen from the position of an LNA monomer, may be naturally occurring nucleosides or non-naturally occurring nucleosides, or even further LNA monomers.

Consequently, in the present context (as can be derived from the definitions above), the term "oligomer" means an oligonucleotide modified by the incorporation of one or more LNA(s).

The crucial part of the present invention is the presence of one or more rings fused to the 5- or 6-membered ring illustrated with the general formula I. Thus, one or two pairs of non-geminal substituents selected from the present substituents of $R^{1*}$, $R^{4*}$, $R^5$, $R^{5*}$, $R^6$, $R^{6*}$, $R^7$, $R^{7*}$, $R^{N*}$, and the ones of $R^2$, $R^{2*}$, $R^3$, and $R^{3*}$ not designating P* each designates a biradical consisting of 1-8 groups/atoms, preferably 1-4 groups/atoms, independently selected from $—C(R^aR^b)—$, $—C(R^a)═C(R^a)—$, $—C(R^a)═N—$, —O—, $—Si(R^a)_2—$, —S—, $—SO_2—$, $—N(R^a)—$, and >C═Z. (The term "present" indicates that the existence of some of the substituents, L e $R^6$, $R^{6*}$, $R^7$, $R^{7*}$, $R^{N*}$, is dependent on whether X includes such substituents.)

In the groups constituting the biradical(s), Z is selected from —O—, —S—, and $—N(R^a)—$, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands (where the latter groups may include a spacer as defined for the substituent B), where aryl and heteroaryl may be optionally substituted. Moreover, two geminal substituents $R^a$ and $R^b$ together may designate optionally substituted methylene ($═CH_2$ optionally substituted one or two times with substituents as defined as optional substituents for aryl), and two non-geminal or geminal substituents selected from $R^a$, $R^b$, and any of the substituents $R^{1*}$, $R^2$, $R^{2*}$, $R^3$, $R^{3*}$, $R^{4*}$, $R^5$, $R^{5*}$, $R^6$ and $R^{6*}$, $R^7$, and $R^{7*}$ which are present and not involved in P, P* or the biradical(s) may together form an associated biradical selected from biradicals of the same kind as defined before. It will be clear that each of the pair(s) of non-geminal substituents thereby forms a mono- or bicyclic entity together with (i) the atoms to which the non-geminal substituents are bound and (ii) any intervening atoms.

It is believed that biradicals which are bound to the ring atoms of the 5- or 6-membered rings are preferred in that inclusion of the substituents $R^5$ and $R^{5*}$ may cause an undesired sterical interaction with internucleoside linkage. Thus, it is preferred that the one or two pairs of non-geminal substituents, which are constituting one or two biradical(s), respectively, are selected from the present substituents of $R^{1*}$, $R^{4*}$, $R^6$, $R^{6*}$, $R^7$, $R^{7*}$, $R^{N*}$, and the ones of $R^2$, $R^{2*}$, $R^3$, and $R^{3*}$ not designating P*.

Preferably, the LNAs incorporated in the oligomers comprise only one biradical constituted by a pair of (two) non-geminal substituents. In particular, it is preferred that $R^{3*}$ designates P* and that the biradical is formed between $R^{2*}$ and $R^{4*}$ or $R^2$ and $R^3$.

This being said, it should be understood (especially with due consideration of the known bi- and tricyclic nucleoside analogues—see "Background of the Invention") that the present invention does not relate to oligomers comprising the following bi- or tricyclic nucleosides analogues:

(i) $R^2$ and $R^3$ together designate a biradical selected from $—O—CH_2—CH_2—$ and $—O—CH_2—CH_2—CH_2—$ when LNA is a bicyclic nucleoside analogue;

(ii) $R^3$ and $R^5$ together designate a biradical selected from $—CH_2—CH_2—$, $—O—CH_2—$, when LNA is a bicyclic nucleoside analogue;

(iii) $R^3$, $R^5$, and $R^{5*}$ together designate a triradical $—CH_2—CH(-)—CH_2—$ when LNA is a tricyclic nucleoside analogue;

(iv) $R^{1*}$ and $R^{6*}$ together designate a biradical $—CH_2—$ when LNA is a bicyclic nucleoside analogue; or (v) $R^{4*}$ and $R^{6*}$ together designate a biradical $—CH_2—$ when LNA is a bicyclic nucleoside analogue;

except where such bi- or tricyclic nucleoside analogues are combined with one or more of the novel LNAs defined herein.

In the present context, i.e. in the present description and claims, the orientation of the biradicals are so that the left-hand side represents the substituent with the lowest number and the right-hand side represents the substituent with the highest number, thus, when $R^3$ and $R^5$ together designate a biradical "$—O—CH_2—$", it is understood that the oxygen atom represents $R^3$, thus the oxygen atom is e.g. attached to the position of $R^3$, and the methylene group represents $R^5$.

Considering the numerous interesting possibilities for the structure of the biradical(s) in LNA(s) incorporated in oligomers according to the invention, it is believed that the biradical(s) constituted by pair(s) of non-geminal substituents preferably is/are selected from $—(CR^*R^*)_r—Y—(CR^*R^*)_s—$, $—Y—(CR^*R^*)_r—Y—(CR^*R^*)_s—Y—$, $—Y—(CR^*R^*)_{r+s}—Y—$, $—Y—(CR^*R^*)_r—Y—(CR^*R^*)_s—$, $—(CR^*R^*)_{r+s}—$, $—Y—$, $—Y—Y—$, wherein each Y is independently selected from $—O—$, $—S—$, $—Si(R^*)_2—$, $—N(R^*)—$, $>C{=}O$, $—C({=}O)—N(R^*)—$, and $—N(R^*)—C({=}O)—$, each R* is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond; and each of r and s is 0-4 with the proviso that the sum r+s is 1-5. Particularly interesting situations are those wherein each biradical is independently selected from $—Y—$, $—(CR^*R^*)_{r+s}—$, $—(CR^*R^*)_r—Y—(CR^*R^*)_s—$, and $—Y—(CR^*R^*)_{r+s}—Y—$, wherein and each of r and s is 0-3 with the proviso that the sum r+s is 1-4.

Considering the positioning of the biradical in the LNA(s), it is believed (based on the preliminary findings (see the examples)) that the following situations are especially interesting, namely where: $R^{2*}$ and $R^{4*}$ together designate a biradical selected from $—Y—$, $—(CR^*R^*)_{r+s+1}—$, $—(CR^*R^*)_r—Y—(CR^*R^*)_s—$, and $—Y—(CR^*R^*)_{r+s}—Y—$; $R^2$ and $R^3$ together designate a biradical selected from $—Y—$, $—(CR^*R^*)_{r+s}—$, $—(CR^*R^*)_r—Y—(CR^*R^*)_s—$, and $—Y—(CR^*R^*)_{r+s}—Y—$; $R^{2*}$ and $R^3$ together designate a biradical selected from $—Y—$, $—(CR^*R^*)_{r+s}—$, $—(CR^*R^*)_r—Y—(CR^*R^*)_s—$, and $—Y—(CR^*R^*)_{r+s}—Y—$; $R^3$ and $R^{4*}$ together designate a biradical selected from $—Y—$, $—(CR^*R^*)_{r+s}—$, $—(CR^*R^*)_r—Y—(CR^*R^*)_s—$, and $—Y—(CR^*R^*)_{r+s}—Y—$; $R^3$ and $R^5$ together designate a biradical selected from $—Y'—$, $—(CR^*R^*)_{r+s+1}—$, $—(CR^*R^*)_r—Y—(CR^*R^*)_s—$, and $—Y—(CR^*R^*)_{r+s}—Y—$; $R^{1*}$ and $R^{4*}$ together designate a biradical selected from $—Y'—$, $—(CR^*R^*)_{r+s+1}—$, $—(CR^*R^*)_r—Y—(CR^*R^*)_s—$, and $—Y—(CR^*R^*)_{r+s}—NR^*—$; or where $R^{1*}$ and $R^{2*}$ together designate a biradical selected from $—Y—$, $—(CR^*R^*)_{r+s}—$, $—(CR^*R^*)_r—Y—(CR^*R^*)_s—$, and $—Y—(CR^*R^*)_{r+s}—Y—$; wherein each of r and s is 0-3 with the proviso that the sum r+s is 1-4, Y is as defined above, and where Y' is selected from $—NR^*—C({=}O)—$ and $—C({=}O)—NR^*—$.

Particularly interesting oligomers are those wherein one of the following criteria applies for at least one LNA in an oligomer: $R^{2*}$ and $R^{4*}$ together designate a biradical selected from $—O—$, $—S—$, $—(CR^*R^*)_{r+s+1}—$, $—(CR^*R^*)_r—O—(CR^*R^*)_s—$, $—(CR^*R^*)_r—S—(CR^*R^*)_s—$, $—(CR^*R^*)_r—N(R^*)—(CR^*R^*)_s—$, $—O—(CR^*R^*)_{r+s}—O—$, $—S—(CR^*R^*)_{r+s}—O—$, $—O—(CR^*R^*)_{r+s}—S—$, $—N(R^*)—(CR^*R^*)_{r+s}—O—$, $—O—(CR^*R^*)_{r+s}—N(R^*)—$, $—S—(CR^*R^*)_{r+s}—S—$, $—N(R^*)—(CR^*R^*)_{r+s}—N(R)—$, $—N(R)—(CR^*R^*)_{r+s}—S—$, and $—S—(CR^*R^*)_{r+s}—N(R^*)—$; $R^2$ and $R^3$ together designate a biradical selected from $—O—$, $—(CR^*R^*)_{r+s}—$, $—(CR^*R^*)_r—O—(CR^*R^*)_s—$, $—(CR^*R^*)_r—S—(CR^*R^*)_s—$, and $—(CR^*R^*)_r—N(R^*)—(CR^*R^*)_s—$; $R^{2*}$ and $R^3$ together designate a biradical selected from $—O—$, $—(CR^*R^*)_{r+s}—$, $—(CR^*R^*)_r—O—(CR^*R^*)_s—$, $—(CR^*R^*)_r—S—(CR^*R^*)_s—$, and $—(CR^*R^*)_r—N(R^*)—(CR^*R^*)_s—$; $R^3$ and $R^{4*}$ together designate a biradical selected from $—(CR^*R^*)_r—O—(CR^*R^*)_s—$, $—(CR^*R^*)_r—S—(CR^*R^*)_s—$, and $—(CR^*R^*)_r—N(R^*)—(CR^*R^*)_s—$; $R^3$ and $R^5$ together designate a biradical selected from $—(CR^*R^*)_r—O—(CR^*R^*)_s—$, $—(CR^*R^*)_r—S—(CR^*R^*)_s—$, and $—(CR^*R^*)_r—N(R^*)—(CR^*R^*)_s—$; $R^{1*}$ and $R^{4*}$ together designate a biradical selected from $—(CR^*R^*)_r—O—(CR^*R^*)_s—$, $—(CR^*R^*)_r—S—(CR^*R^*)_s—$, and $—(CR^*R^*)_r—N(R^*)—(CR^*R^*)_s—$; or $R^{1*}$ and $R^{2*}$ together designate a biradical selected from $—(CR^*R^*)_r—O—(CR^*R^*)_s—$, $—(CR^*R^*)_r—S—(CR^*R^*)_s—$, and $—(CR^*R^*)_r—N(R^*)—(CR^*R^*)_s—$; wherein each of r and s is 0-3 with the proviso that the sum r+s is 1-4, and where $R^H$ designates hydrogen or $C_{1-4}$-alkyl.

It is furthermore preferred that one R* is selected from hydrogen, hydroxy, optionally substituted $C_{1-6}$-alkoxy, optionally substituted $C_{1-6}$-alkyl, DNA intercalators, photochemically active groups, thermochemically active groups, chelating groups, reporter groups, and ligands, and any remaining substituents R* are hydrogen.

In one preferred embodiment, one group R* in the biradical of at least one LNA is selected from DNA intercalators, photochemically active groups, thermochemically active groups, chelating groups, reporter groups, and ligands (where the latter groups may include a spacer as defined for the substituent B).

With respect to the substituents $R^{1*}$, $R^2$, $R^{2*}$, $R^3$, $R^{4*}$, $R^5$, $R^{5*}$, $R^6$ and $R^{6*}$, $R^7$, and $R^{7*}$, which are present and not involved in P, P* or the biradical(s), these are independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands (where the latter groups may include a spacer as defined for the substituent B), where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/groups selected from —O—, —S—, and —($NR^N$)— where $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl.

Preferably, each of the substituents $R^{1*}$, $R^2$, $R^{2*}$, $R^3$, $R^{3*}$, $R^{4*}$, $R^5$, $R^{5*}$, $R^6$, $R^{6*}$, $R^7$, and $R^{7*}$ of the LNA(s), which are present and not involved in P, P* or the biradical(s), is independently selected from hydrogen, optionally substituted $C_{1-6}$-alkyl, optionally substituted $C_{2-6}$-alkenyl, hydroxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)-aminocarbonyl, $C_{1-6}$-alkyl-carbonylamino, carbamido, azido, $C_{1-6}$-alkanoyloxy, sulphono, sulphanyl, $C_{1-6}$-alkylthio, DNA intercalators, photochemically active groups, thermochemically active groups, chelating groups, reporter groups, and ligands, and halogen, where two geminal substituents together may designate oxo, and where $R^{N*}$, when present and not involved in a biradical, is selected from hydrogen and $C_{1-4}$-alkyl.

In a preferred embodiment of the present invention, X is selected from —O—, —S—, and —$NR^{N*}$—, in particular —O—, and each of the substituents $R^{1*}$, $R^2$, $R^{2*}$, $R^3$, $R^{3*}$, $R^{4*}$, $R^5$, $R^{5*}$, $R^6$, $R^{6*}$, $R^7$, and $R^{7*}$ of the LNA(s), which are present and not involved in P, P* or the biradical(s), designate hydrogen.

In an even more preferred embodiment of the present invention, $R^{2*}$ and $R^{4*}$ of an LNA incorporated into an oligomer together designate a biradical. Preferably, X is O, $R^2$ selected from hydrogen, hydroxy, and optionally substituted $C_{1-6}$-alkoxy, and $R^{1*}$, $R^3$, $R^5$, and $R^{5*}$designate hydrogen, and, more specifically, the biradical is selected from —O—, —$(CH_2)_{0-1}$—O—$(CH_2)_{1-3}$—, —$(CH_2)_{0-1}$—S—$(CH_2)_{1-3}$—, —$(CH_2)_{0-1}$—N($R^N$)—$(CH_2)_{1-3}$—, and —$(CH_2)_{2-4}$—, in particular from —O—$CH_2$—, —S—$CH_2$—, and —$NR^H$—$CH_2$—. Generally, with due regard to the results obtained so far, it is preferred that the biradical constituting $R^{2*}$ and $R^{4*}$ forms a two carbon atom bridge, i.e. the biradical forms a five membered ring with the furanose ring (X═O).

In another embodiment of the present invention, $R^2$ and $R^3$ of an LNA incorporated into an oligomer together designate a biradical. Preferably, X is O, $R^{2*}$ is selected from hydrogen, hydroxy, and optionally substituted $C_{1-6}$-alkoxy, and $R^{1*}$, $R^{4*}$, $R^5$, and $R^{5*}$ designate hydrogen, and, more specifically, the biradical is selected from —$(CH_2)_{0-1}$—O—$(CH_2)_{1-3}$—, —$(CH_2)_{0-1}$—S—$(CH_2)_{1-3}$—, —$(CH_2)_{0-1}$—N($R^H$)—$(CH_2)_{1-3}$— and —$(CH_2)_{1-4}$—, in particular from —O—$CH_2$—, —S—$CH_2$—, —N($R^H$)—$CH_2$—. In the latter case, the amino and thio variants appears to be particularly interesting.

In a further embodiment of the present invention, $R^{2*}$ and $R^3$ of an LNA incorporated into an oligomer together designate a biradical. Preferably, X is O, $R^2$ is selected from hydrogen, hydroxy, and optionally substituted $C_{1-6}$-alkoxy, and $R^{1*}$, $R^{4*}$, $R^5$, and $R^{5*}$ designate hydrogen, and, more specifically, the biradical is selected from —$(CH_2)_{0-1}$—O—$(CH_2)_{1-3}$— and —$(CH_2)_{2-4}$—.

In a further embodiment of the present invention, $R^3$ and $R^{4*}$ of an LNA incorporated into an oligomer together designate a biradical. Preferably, X is O, $R^{2*}$ selected from hydrogen, hydroxy, and optionally substituted $C_{1-6}$-alkoxy, and $R^{1*}$, $R^2$, $R^5$, and $R^{5*}$ designate hydrogen, and, more specifically, the biradical is —$(CH_2)_{0-2}$—O—$(CH_2)_{0-2}$—.

In a further embodiment of the present invention, $R^3$ and $R^{5*}$ of an LNA incorporated into an oligomer together designate a biradical. Preferably, X is O, $R^{2*}$ selected from hydrogen, hydroxy, and optionally substituted $C_{1-6}$-alkoxy, and $R^{1*}$, $R^2$, $R^4$, and $R^5$ designate hydrogen, and, more specifically, the biradical is selected from —O—$(CHR^*)_{2-3}$— and —$(CHR^*)_{1-3}$—O—$(CHR^*)_{0-3}$—.

In a further embodiment of the present invention, $R^{1*}$ and $R^{4*}$ of an LNA incorporated into an oligomer together designate a biradical. Preferably, X is O, $R^{2*}$ selected from hydrogen, hydroxy, and optionally substituted $C_{1-6}$-alkoxy, and $R^2$, $R^3$, $R^5$, and $R^{5*}$ designate hydrogen, and, more specifically, the biradical is —$(CH_2)_{0-2}$—O—$(CH_2)_{0-2}$—.

In these embodiments, it is furthermore preferred that at least one LNA incorporated in an oligomer includes a nucleobase (substituent B) selected from adenine and guanine. In particular, it is preferred that an oligomer have LNA incorporated therein both include at least one nucleobase selected from thymine, uracil and cytosine and at least one nucleobase selected from adenine and guanine. For LNA monomers, it is especially preferred that the nucleobase is selected from adenine and guanine.

For these interesting embodiments, it is also preferred that the LNA(s) has/have the general formula Ia (see below).

Within a variant of these interesting embodiments, all monomers of a oligonucleotide are LNA monomers.

As it will be evident from the general formula I (LNA(s) in an oligomer) (and the general formula II (monomeric LNA)—see below) and the definitions associated therewith, there may be one or several asymmetric carbon atoms present in the oligomers (and monomeric LNAs) depending on the nature of the substituents and possible biradicals, cf. below. The oligomers prepared according to the method of the invention, as well as the oligomers per se, are intended to include all stereoisomers arising from the presence of any and all isomers of the individual monomer fragments as well as mixtures thereof, including racemic mixtures. When considering the 5- or 6-membered ring, it is, however, believed that certain stereochemical configurations will be especially interesting, e.g. the following

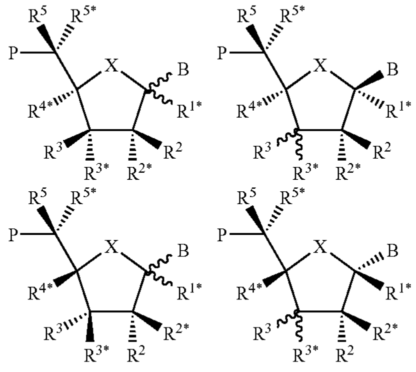

where the wavy lines represent the possibility of both diastereomers arising from the interchange of the two substituents in question.

An especially interesting stereoisomeric representation is the case where the LNA(s) has/have the following formula Ia

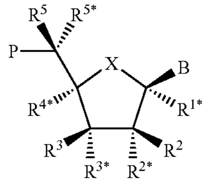

Ia

Also interesting as a separate aspect of the present invention is the variant of formula Ia where B is in the "α-configuration".

In these cases, as well as generally, $R^{3*}$ preferably designates P.

The oligomers according to the invention typically comprise 1-10000 LNA(s) of the general formula I (or of the more detailed general formula Ia) and 0-10000 nucleosides selected from naturally occurring nucleosides and nucleoside analogues. The sum of the number of nucleosides and the number of LNA(s) is at least 2, preferably at least 3, in particular at least 5, especially at least 7, such as in the range of 2-15000, preferably in the range of 2-100, such as 3-100, in particular in the range of 2-50, such as 3-50 or 5-50 or 7-50.

Preferably at least one LNA comprises a nucleobase as the substituent B.

In the present context, the term "nucleoside" means a glycoside of a heterocyclic base. The term "nucleoside" is used broadly as to include non-naturally occurring nucleosides, naturally occurring nucleosides as well as other nucleoside analogues. Illustrative examples of nucleosides are ribonucleosides comprising a ribose moiety as well as deoxyribonucleosides comprising a deoxyribose moiety. With respect to the bases of such nucleosides, it should be understood that this may be any of the naturally occurring bases, e.g. adenine, guanine, cytosine, thymine, and uracil, as well as any modified variants thereof or any possible unnatural bases.

When considering the definitions and the known nucleosides (naturally occurring and non-naturally occurring) and nucleoside analogues (including known bi- and tricyclic analogues), it is clear that an oligomer may comprise one or more LNA(s) (which may be identical or different both with respect to the selection of substituent and with respect to selection of biradical) and one or more nucleosides and/or nucleoside analogues. In the present context "oligonucleotide" means a successive chain of nucleosides connected via internucleoside linkages, however, it should be understood that a nucleobase in one or more nucleotide units (monomers) in an oligomer (oligonucleotide) may have been modified with a substituent B as defined above.

The oligomers may be linear, branched or cyclic. In the case of a branched oligomer, the branching points may be located in a nucleoside, in an internucleoside linkage or, in an intriguing embodiment, in an LNA. It is believed that in the latter case, the substituents $R^2$, $R^{2*}$, $R^3$, and $R^{3*}$ may designate two groups P* each designating an internucleoside linkage to a preceding monomer, in particular, one of $R^2$ and $R^{2*}$ designate P* and one or $R^3$ and $R^{3*}$ designate a further P*.

As mentioned above, the LNA(s) of an oligomer are connected with other monomers via an internucleoside linkage. In the present context, the term "internucleoside linkage" means a linkage consisting of 2 to 4, preferably 3, groups/atoms selected from $—CH_2—$, —O—, —S—, $—NR^H—$, >C═O, $>C═NR^H$, >C═S, $—Si(R'')_2—$, —SO—, $—S(O)_2—$, $—P(O)_2—$, $—PO(BH_3)—$, —P(O,S)—, $—P(S)_2—$, —PO(R'')—, $—PO(OCH_3)—$, and $—PO(NHR^H)—$, where $R^H$ is selected form hydrogen and $C_{1-4}$-alkyl, and R'' is selected from $C_{1-6}$-alkyl and phenyl. Illustrative examples of such internucleoside linkages are $—CH_2—CH_2—CH_2—$, $—CH_2—CO—CH_2—$, $—CH_2—CHOH—CH_2—$, $—O—CH_2—O—$, $—O—CH_2—CH_2—$, $—O—CH_2—CH═$ (including $R^5$ when used as a linkage to a succeeding monomer), $—CH_2—CH_2—O—$, $—NR^H—CH_2—CH_2—$, $—CH_2—CH_2—NR^H—$, $—CH_2—NR^H—CH_2—$, $—O—CH_2—CH_2—NR^H—$, $—NR^H—CO—O—$, $—NR^H—CO—NR^H—$, $—NR^H—CS—NR^H—$, $—NR^H—C(═NR^H)—NR^H—$, $—NR^H—CO—CH_2—NR^H—$, —O—CO—O—, $—O—CO—CH_2—O—$, $—O—CH_2—CO—O—$, $—CH_2—CO—NR^H—$, $—O—CO—NR^H—$, $—NR^H—CO—CH_2—$, $—O—CH_2—CO—NR^H—$, $—O—CH_2—CH_2—NR^H—$, —CH═N—O—, $—CH_2—NR^H—O—$, $—CH_2—O—N═$ (including $R^5$ when used as a linkage to a succeeding monomer), $—CH_2—O—NR^H—$, $—CO—NR^H—CH_2—$, $—CH_2—NR^H—O—$, $—CH_2—NR^H—CO—$, $—O—NR^H—CH_2—$, $—O—NR^H—$, $—O—CH_2—S—$, $—S—CH_2—O—$, $—CH_2—S—CH_2—$, $—CH_2—SO—CH_2—$, $—CH_2—S—$, $—O—CH_2—CH_2—S—$, $—S—CH_2—CH═$ (including $R^5$ when used as a linkage to a succeeding monomer), $—S—CH_2—CH_2—$, $—S—CH_2—CH_2—O—$, $—S—CH_2—CH_2—S—$, $—CH_2—S—CH_2—$, $—CH_2—SO—CH_2—$, $—CH_2—SO_2—CH_2—$, —O—SO—O—, $—O—S(O)_2—O—$, $—O—S(O)_2—CH_2—$, $—O—S(O)_2—NR^H—$, $—NR^H—S(O)_2—CH_2—$, $—O—S(O)_2—CH_2—$, $—O—P(O)_2—O—$, —O—P(O,S)—O—, $—O—P(S)_2—O—$, $—S—P(O)_2—O—$, —S—P(O,S)—O—, $—S—P(S)_2—O—$, $—O—P(O)_2—S—$, —O—P(O,S)—S—, $—O—P(S)_2—S—$, $—S—P(O)_2—S—$, —S—P(O,S)—S—, $—S—P(S)_2—S—$, —O—PO(R'')—O—, $—O—PO(OCH_3)—O—$, $—O—PO(OCH_2CH_3)—O—$, $—O—PO(OCH_2CH_2S—R)—O—$, $—O—PO(BH_3)—O—$, $—O—PO(NHR^N)—O—$, $—O—P(O)_2—NR^H—$, $—NR^H—P(O)_2—O—$, $—O—P(O,NR^H)—O—$, $—CH_2—P(O)_2—O—$, $—O—P(O)_2—CH_2—$, and $—O—Si(R'')_2—O—$; among which $—CH_2—CO—NR^H—$, $—CH_2—NR^H—O—$, $—S—CH_2—O—$, $—O—P(O)_2—O—$, —O—P(O,S)—O—, $—O—P(S)_2—O—$, $—NR^H—P$ $(O)_2$—O—, —O—P(O,$NR^H$)—O—, —O—PO(R")—O—, —O—PO($CH_3$)—O—, and —O—PO($NHR^N$)—O—, where $R^H$ is selected form hydrogen and $C_{1-4}$-alkyl, and R" is selected from $C_{1-6}$-alkyl and phenyl, are especially preferred. Further illustrative examples are given in Mesmaeker et. al., Current Opinion in Structural Biology 1995, 5, 343-355. The left-hand side of the internucleoside linkage is bound to the 5- or 6-membered ring as substituent P*, whereas the right-hand side is bound to the 5'-position of a preceding monomer.

It is also clear from the above that the group P may also designate a 5'-terminal group in the case where the LNA in question is the 5'-terminal monomer. Examples of such 5'-terminal groups are hydrogen, hydroxy, optionally substituted $C_{1-6}$-alkyl, optionally substituted $C_{1-6}$-alkoxy, optionally substituted $C_{1-6}$-alkylcarbonyloxy, optionally substituted aryloxy, monophosphate, diphosphate, triphosphate, and —W-A', wherein W is selected from —O—, —S—, and —N($R^H$)— where $R^H$ is selected from hydrogen and $C_{1-6}$-alkyl, and where A' is selected from DNA intercalators, photochemically active groups, thermochemically active groups, chelating groups, reporter groups, and ligands (where the latter groups may include a spacer as defined for the substituent B).

In the present description and claims, the terms "monophosphate", "diphosphate", and "triphosphate" mean groups of the formula: —O—$P(O)_2$—$O^-$, —O—$P(O)_2$—O—$P(O)_2$—$O^-$, and —O—$P(O)_2$—O—$P(O)_2$—O—$P(O)_2$—$O^-$, respectively.

In a particularly interesting embodiment, the group P designates a 5'-terminal groups selected from monophosphate, diphosphate and triphosphate. Especially the triphosphate variant is interesting as a substrate Analogously, the group P* may designate a 3'-terminal group in the case where the LNA in question is the 3'-terminal monomer. Examples of such 3'-terminal groups are hydrogen, hydroxy, optionally substituted $C_{1-6}$-alkoxy, optionally substituted $C_{1-6}$-alkylcarbonyloxy, optionally substituted aryloxy, and —W-A', wherein W is selected from —O—, —S—, and —N($R^H$)— where $R^H$ is selected from hydrogen and $C_{1-6}$-alkyl, and where A' is selected from DNA intercalators, photochemically active groups, thermochemically active groups, chelating groups, reporter groups, and ligands (where the latter groups may include a spacer as defined for the substituent B).

In a preferred embodiment of the present invention, the oligomer has the following formula V:

$$G\text{-}[Nu\text{-}L]_{n(0)}\text{-}\{[LNA\text{-}L]_{m(q)}\text{-}[Nu\text{-}L]_{n(q)}\}_q\text{-}G^* \qquad V$$

wherein q is 1-50;

each of n(0), . . . , n(q) is independently 0-10000;

each of m(1), . . . , m(q) is independently 1-10000;

with the proviso that the sum of n(0), . . . , n(q) and m(1), . . . , m(q) is 2-15000;

G designates a 5'-terminal group;

each Nu independently designates a nucleoside selected from naturally occurring nucleosides and nucleoside analogues;

each LNA independently designates a nucleoside analogue;

each L independently designates an internucleoside linkage between two groups selected from Nu and LNA, or L together with G* designates a 3'-terminal group; and each LNA-L independently designates a nucleoside analogue of the general formula I as defined above, or preferably of the general formula Ia as defined above.

Within this embodiment, as well as generally, the present invention provides the intriguing possibility of including LNAs with different nucleobases, in particular both nucleobases selected from thymine, cytosine and uracil and nucleobases selected from adenine and guanine.

In another embodiment of the present invention, the oligomer further comprises a PNA mono- or oligomer segment of the formula

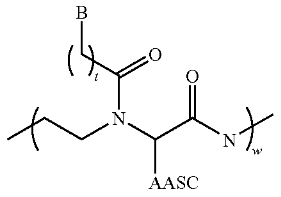

wherein B is a defined above for the formula I, AASC designates hydrogen or an amino acid side chain, t is 1-5, and w is 1-50.

In the present context, the term "amino acid side chain" means a group bound to the α-atom of α-amino acids, i.e. corresponding to the α-amino acid in question without the glycine moiety, preferably an either naturally occurring or a readily available α-amino acid. Illustrative examples are hydrogen (glycine itself), deuterium (deuterated glycine), methyl (alanine), cyanomethyl (β-cyano-alanine), ethyl, 1-propyl (norvaline), 2-propyl (valine), 2-methyl-1-propyl (leucine), 2-hydroxy-2-methyl-1-propyl (β-hydroxy-leucine), 1-butyl (norleucine), 2-butyl (isoleucine), methylthioethyl (methionine), benzyl (phenylalanine), p-amino-benzyl (p-amino-phenylalanine), p-iodo-benzyl (p-iodo-phenylalanine), p-fluoro-benzyl (p-fluoro-phenylalanine), p-bromo-benzyl (p-bromo-phenylalanine), p-chloro-benzyl (p-chloro-phenylalanine), p-nitro-benzyl (p-nitro-phenylalanine), 3-pyridylmethyl (β-(3-pyridyl)-alanine), 3,5-diiodo-4-hydroxy-benzyl (3,5-diiodo-tyrosine), 3,5-dibromo-4-hydroxy-benzyl (3,5-dibromo-tyrosine), 3,5-dichloro-4-hydroxy-benzyl (3,5-dichloro-tyrosine), 3,5-difluoro-4-hydroxy-benzyl (3,5-difluoro-tyrosine), 4-methoxy-benzyl (O-methyl-tyrosine), 2-naphtylmethyl (β-(2-naphtyl)-alanine), 1-naphtylmethyl (β-(1-naphtyl)-alanine), 3-indolylmethyl (tryptophan), hydroxymethyl (serine), 1-hydroxyethyl (threonine), mercaptomethyl (cysteine), 2-mercapto-2-propyl (penicillamine), 4-hydroxybenzyl (tyrosine), aminocarbonylmethyl (asparagine), 2-aminocarbonylethyl (glutamine), carboxymethyl (aspartic acid), 2-carboxyethyl (glutamic acid), aminomethyl (α, β-diamino-propionic acid), 2-aminoethyl (α,γ-diaminobutyric acid), 3-amino-propyl (ornithine), 4-amino-1-butyl (lysine), 3-guanidino-1-propyl (arginine), and 4-imidazolylmethyl (histidine).

PNA mono- or oligomer segment may be incorporated in a oligomer as described in EP 0672677 A2.

The oligomers of the present invention are also intended to cover chimeric oligomers. "Chimeric oligomers" means two or more oligomers with monomers of different origin joined either directly or via a spacer. Illustrative examples of such oligomers which can be combined are peptides, PNA-oligomers, oligomers containing LNA's, and oligonucleotide oligomers.

Apart from the oligomers defined above, the present invention also provides monomeric LNAs useful, e.g., in the preparation of oligomers, as substrates for, e.g., nucleic acid polymerases, polynucleotide kinases, terminal transferases, and as therapeutical agents, see further below. The monomeric LNAs correspond in the overall structure (especially with respect to the possible biradicals) to the LNAs defined as constituents in oligomers, however with respect to the groups P and P*, the monomeric LNAs differ slightly as will be explained below. Furthermore, the monomeric LNAs may comprise functional group protecting groups, especially in the cases where the monomeric LNAs are to be incorporated into oligomers by chemical synthesis.

An interesting subgroup of the possible monomeric LNAs comprises bicyclic nucleoside analogues (LNAs) of the general formula II

II

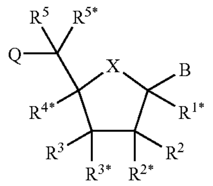

wherein the substituent B is selected from nucleobases, DNA intercalators, photochemically active groups, thermochemically active groups, chelating groups, reporter groups, and ligands; X is selected from —O—, —S—, —N($R^{N*}$)—, and —C($R^6R^{6*}$)—, preferably from —O—, —S—, and —N($R^{N*}$)—; one of the substituents $R^2$, $R^{2*}$, $R^3$, and $R^{3*}$ is a group Q*;

each of Q and Q* is independently selected from hydrogen, azido, halogen, cyano, nitro, hydroxy, Prot-O—, Act-O—, mercapto, Prot-S—, Act-S—, $C_{1-6}$-alkylthio, amino, Prot-N($R^H$)—, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, Act-O—$CH_{2-5}$-aminomethyl, Prot-N($R^H$)—$CH_2$—, Act-N($R^H$)—$CH_2$—, carboxymethyl, sulphonomethyl, where Prot is a protection group for —OH, —SH, and —NH($R^H$), respectively, Act is an activation group for —OH, —SH, and —NH($R^H$), respectively, and $R^H$ is selected from hydrogen and $C_{1-6}$-alkyl;

$R^{2*}$ and $R^{4*}$ together designate a biradical selected from —O—, —S—, —N(R*)—, —$(CR^*R^*)_{r+s+1}$—, —$(CR^*R^*)_r$—O—$(CR^*R^*)_s$—, —$(CR^*R^*)_r$—S—$(CR^*R^*)_s$—, —$(CR^*R^*)_r$—N(R*)—$(CR^*R^*)_s$—, —O—$(CR^*R^*)_{r+s}$—O—, —S—$(CR^*R^*)_{r+s}$—O—, —O—$(CR^*R^*)_{r+s}$—S—, —N(R*)—$(CR^*R^*)_{r+s}$—O—, —O—$(CR^*R^*)_{r+s}$—N(R*)—, —S—$(CR^*R^*)_{r+s}$—S—, —N(R*)—$(CR^*R^*)_{r+s}$—N(R*)—, —N(R*)—$(CR^*R)_{r+s}$—S—, and —S—$(CR^*R^*)_{r+s}$—N(R*)—; $R^2$ and $R^3$ together designate a biradical selected from —O—, —$(CR^*R^*)_{r+s}$—, —$(CR^*R^*)_r$—O—$(CR^*R^*)_s$—, —$(CR^*R^*)_r$—S—$(CR^*R^*)_s$—, and —$(CR^*R^*)_r$—N(R*)—$(CR^*R^*)_s$—; $R^{2*}$ and $R^3$ together designate a biradical selected from —O—, —$(CR^*R^*)_{r+s}$—, —$(CR^*R^*)_r$—O—$(CR^*R^*)_s$—, —$(C^*R^*)_r$—S—$(CR^*R^*)_s$—, and —$(CR^*R^*)_r$—N(R*)—$(CR^*R^*)_s$—; $R^3$ and $R^{4*}$ together designate a biradical selected from —$(CR^*R^*)_r$—O—$(CR^*R^*)_s$—, —$(CR^*R^*)_r$—S—$(CR^*R^*)_s$—, and —$(CR^*R^*)_r$—N(R*)—$(CR^*R^*)_s$—; $R^3$ and $R^5$ together designate a biradical selected from —$(CR^*R^*)_r$—O—$(CR^*R^*)_s$—, —$(CR^*R^*)_r$—S—$(CR^*R^*)_s$—, and —$(CR^*R^*)_r$—N(R*)—$(CR^*R^*)_s$—; $R^{1*}$ and $R^{4*}$ together designate a biradical selected from —$(CR^*R^*)_r$—O—$(CR^*R^*)_s$—, —$(CR^*R^*)_r$—S—$(CR^*R^*)_s$—, and —$(CR^*R^*)_r$—N(R)—$(CR^*R^*)_s$—; or $R^{1*}$ and $R^{2*}$ together designate a biradical selected from —$(C^*R^*)_r$—O—$(CR^*R^*)_s$—, —$(CR^*R^*)_r$—S—$(CR^*R^*)_s$—, and —$(CR^*R^*)_r$—N(R*)—$(CR^*R^*)_s$—; wherein R* is as defined above for the oligomers; and each of the substituents $R^{1*}$, $R^2$, $R^{2*}$, $R^3$, $R^{4*}$, $R^5$, and $R^{5*}$, which are not involved in Q, Q* or the biradical, are as defined above for the oligomers.

It should furthermore be understood, with due consideration of the known bicyclic nucleoside analogues, that $R^3$ and $R^5$ do not together designate a biradical selected from —$CH_2$—$CH_2$—, —O—$CH_2$—, and —O—Si($^i$Pr)$_2$—O—Si($^i$Pr)$_2$—O—.

The monomeric LNAs also comprise basic salts and acid addition salts thereof. Furthermore, it should be understood that any chemical group (including any nucleobase), which is reactive under the conditions prevailing in chemical oligonucleotide synthesis, is optionally functional group protected as known in the art. This means that groups such as hydroxy, amino, carboxy, sulphono, and mercapto groups, as well as nucleobases, of a monomeric LNA are optionally functional group protected. Protection (and deprotection) is performed by methods known to the person skilled in the art (see, e.g., Greene, T. W. and Wuts, P. G. M., "Protective Groups in Organic Synthesis", 2$^{nd}$ ed., John Wiley, N.Y. (1991), and M. J. Gait, Oligonucleotide Synthesis, IRL Press, 1984).

Illustrative examples of hydroxy protection groups are optionally substituted trityl, such as 4,4'-dimethoxytrityl (DMT), 4-monomethoxytrityl (MMT), and trityl, optionally substituted 9-(9-phenyl)xanthenyl (pixyl), optionally substituted ethoxycarbonyloxy, p-phenylazophenyl-oxycarbonyloxy, tetraahydropyranyl (thp), 9-fluorenylmethoxycarbonyl (Fmoc), methoxytetrahydropyranyl (mthp), silyloxy such as trimethylsilyl (TMS), triisopropylsilyl (TIPS), tert-butyldimethylsilyl (TBDMS), triethylsilyl, and phenyldimethylsilyl, benzyloxycarbonyl or substituted benzyloxycarbonyl ethers such as 2-bromo benzyloxycarbonyl, tert-butylethers, alkyl ethers such as methyl ether, acetals (including two hydroxy groups), acyloxy such as acetyl or halogen substituted acetyls, e.g. chloroacetyl or fluoroacetyl, isobutyryl, pivaloyl, benzoyl and substituted benzoyls, methoxymethyl (MOM), benzyl ethers or substituted benzyl ethers such as 2,6-dichlorobenzyl (2,6-$Cl_2$Bzl). Alternatively, the hydroxy group may be protected by attachment to a solid support optionally through a linker.

Illustrative examples of amino protection groups are Fmoc (fluorenylmethoxycarbonyl), BOC (tert-butyloxycarbonyl), trifluoroacetyl, allyloxycarbonyl (alloc, AOC), benzyloxycarbonyl (Z, Cbz), substituted benzyloxycarbonyls such as 2-chloro benzyloxycarbonyl ((2-ClZ), monomethoxytrityl (MMT), dimethoxytrityl (DMT), phthaloyl, and 9-(9-phenyl) xanthenyl (pixyl).

Illustrative examples of carboxy protection groups are allyl esters, methyl esters, ethyl esters, 2-cyanoethylesters, trimethylsilylethylesters, benzyl esters (Obzl), 2-adamantyl esters (O-2-Ada), cyclohexyl esters (OcHex), 1,3-oxazolines, oxazoler, 1,3-oxazolidines, amides or hydrazides.

Illustrative examples of mercapto protecting groups are trityl (Trt), acetamidomethyl (acm), trimethylacetamidomethyl (Tacm), 2,4,6-trimethoxybenzyl (Tmob), tert-butylsulfenyl (StBu), 9-fluorenylmethyl (Fm), 3-nitro-2-pyridinesulfenyl (Npys), and 4-methylbenzyl (Meb).

Furthermore, it may be necessary or desirable to protect any nucleobase included in an monomeric LNA, especially when the monomeric LNA is to be incorporated in an oligomer according to the invention. In the present context, the term "protected nucleobases" means that the nucleobase in question is carrying a protection group selected among the groups which are well-known for a man skilled in the art (see e.g. Protocols for Oligonucleotides and Analogs, vol 20, (Sudhir Agrawal, ed.), Humana Press, 1993, Totowa, N.J.; S. L. Beaucage and R. P. Iyer, *Tetrahedron,* 1993, 49, 6123; S. L. Beaucage and R. P. Iyer, *Tetrahedron,* 1992, 48, 2223; and E. Uhlmann and A. Peyman, *Chem. Rev.,* 90, 543.). Illustrative examples are benzoyl, isobutyryl, tert-butyl, tert-butyloxycarbonyl, 4-chlorobenzyloxycarbonyl, 9-fluorenylmethyl, 9-fluorenylmethyloxycarbonyl, 4-methoxybenzoyl, 4-methoxytriphenylmethyl, optionally substituted triazolo, p-toluenesulphonyl, optionally substituted sulphonyl, isopropyl, optionally substituted amidines, optionally substituted trityl, phenoxyacetyl, optionally substituted acyl, pixyl, tetrahydropyranyl, optionally substituted silyl ethers, and 4-methoxybenzyloxycarbonyl. Chapter 1 in "Protocols for oligonucleotide conjugates", Methods in Molecular Biology, vol 26, (Sudhir Agrawal, ed.), Humana Press, 1993, Totowa, N.J. and S. L. Beaucage and R. P. Iyer, *Tetrahedron,* 1992, 48, 2223 disclose further suitable examples.

In a preferred embodiment, the group B in a monomeric LNA is preferably selected from nucleobases and protected nucleobases.

In an embodiment of the monomeric LNAs according to the present invention, one of Q and Q*, preferably Q*, designates a group selected from Act-O—, Act-S—, Act-N($R^H$)—, Act-O—$CH_2$—, Act-S—$CH_2$—, Act-N($R^H$)—$CH_2$—, and the other of Q and Q*, preferably Q, designates a group selected from hydrogen, azido, halogen, cyano, nitro, hydroxy, Prot-O—, mercapto, Prot-S—, $C_{1-6}$-alkylthio, amino, Prot-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, aminomethyl, Prot-N($R^H$)—$CH_2$—, carboxymethyl, sulphonomethyl, and $R^H$ is selected from hydrogen and $C_{1-6}$-alkyl.

In the case described above, the group Prot designates a protecting group for —OH, —SH, and —NH($R^H$), respectively. Such protection groups are selected from the same as defined above for hydroxy protection groups, mercapto protection group, and amino protection groups, respectively, however taking into consideration the need for a stable and reversible protection group. However, it is preferred that any protection group for —OH is selected from optionally substituted trityl, such as dimethoxytrityl (DMT), monomethoxytrityl (MMT), and trityl, and 9-(9-phenyl)xanthenyl (pixyl), optionally substituted, tetrahydropyranyl (thp) (further suitable hydroxy protection groups for phosphoramidite oligonucleotide synthesis are described in Agrawal, ed. "Protocols for Oligonucleotide Conjugates"; Methods in Molecular Biology, vol. 26, Humana Press, Totowa, N.J. (1994) and Protocols for Oligonucleotides and Analogs, vol 20, (Sudhir Agrawal, ed.), Humana Press, 1993, Totowa, N.J.), or protected as acetal; that any protection group for —SH is selected from trityl, such as dimethoxytrityl (DMT), monomethoxytrityl (MMT), and trityl, and 9-(9-phenyl)xanthenyl (pixyl), optionally substituted, tetrahydropyranyl (thp) (further suitable mercapto protection groups for phosphoramidite oligonucleotide synthesis are also described in Agrawal (see above); and that any protecting group for —NH($R^H$) is selected from trityl, such as dimethoxytrityl (DMT), monomethoxytrityl (MMT), and trityl, and 9-(9-phenyl)xanthenyl (pixyl), optionally substituted, tetrahydropyranyl (thp) (further suitable amino protection groups for phosphoramidite oligonucleotide synthesis are also described in Agrawal (see above).

In the embodiment above, as well as for any monomeric LNAs defined herein, Act designates an activation group for —OH, —SH, and —NH($R^H$), respectively. Such activation groups are, e.g., selected from optionally substituted O-phosphoramidite, optionally substituted O-phosphortriester, optionally substituted O-phosphordiester, optionally substituted H-phosphonate, and optionally substituted O-phosphonate.

In the present context, the term "phosphoramidite" means a group of the formula —P($OR^x$)—N($R^y$)$_2$, wherein $R^x$ designates an optionally substituted alkyl group, e.g. methyl, 2-cyanoethyl, or benzyl, and each of $R^y$ designate optionally substituted alkyl groups, e.g. ethyl or isopropyl, or the group —N($R^y$)$_2$ forms a morpholino group (—N($CH_2CH_2$)$_2$O). $R^x$ preferably designates 2-cyanoethyl and the two $R^y$ are preferably identical and designate isopropyl. Thus, an especially relevant phosphoramidite is N,N-diisopropyl-O-(2-cyanoethyl)phosphoramidite.

It should be understood that the protecting groups used herein for a single monomeric LNA or several monomeric LNAs may be selected so that when this/these LNA(s) are incorporated in an oligomer according to the invention, it will be possible to perform either a simultaneous deprotection or a sequential deprotection of the functional groups. The latter situation opens for the possibility of regioselectively introducing one or several "active/functional" groups such as DNA intercalators, photochemically active groups, thermochemically active groups, chelating groups, reporter groups, and ligands, where such groups may be attached via a spacer as described above.

In a preferred embodiment, Q is selected from hydrogen, azido, halogen, cyano, nitro, hydroxy, Prot-O—, mercapto, Prot-S—, $C_{1-6}$-alkylthio, amino, Prot-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, aminomethyl, Prot-N($R^H$)—$CH_2$—, carboxymethyl, sulphonomethyl, where Prot is a protection group for —OH, —SH, and —NH($R^H$), respectively, and $R^H$ is selected from hydrogen and $C_{1-6}$-alkyl; and Q* is selected from hydrogen, azido, halogen, cyano, nitro, hydroxy, Act-O—, mercapto, Act-S—, $C_{1-6}$-alkylthio, amino, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, DNA intercalators, photochemically active groups, thermochemically active groups, chelating groups, reporter groups, ligands, carboxy, sulphono, where Act is an activation group for —OH, —SH, and —NH($R^H$), respectively, and $R^H$ is selected from hydrogen and $C_{1-6}$-alkyl.

The monomeric LNAs of the general formula II may, as the LNAs incorporated into oligomers, represent various stereoisomers. Thus, the stereochemical variants described above for the LNAs incorporated into oligomers are believed to be equally applicable in the case of monomeric LNAs (however, it should be noted that P should then be replaced with Q).

In a preferred embodiment of the present invention, the monomeric LNA has the general formula IIa IIa

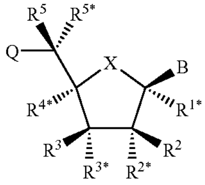

wherein the substituents are defined as above.

Furthermore, with respect to the definitions of substituents, biradicals, R*, etc. the same preferred embodiments as defined above for the oligomer according to the invention also apply in the case of monomeric LNAs.

In a particularly interesting embodiment of the monomeric LNAs of the present invention, B designates a nucleobase, preferably a nucleobase selected from thymine, cytosine, uracil, adenine and guanine (in particular adenine and guanine), X is —O—, $R^{2*}$ and $R^{4*}$ together designate a biradical selected from —$(CH_2)_{0-1}$—O—$(CH_2)_{1-3}$—, —$(CH_2)_{0-1}$—S—$(CH_2)_{1-3}$—, and —$(CH_2)_{0-1}$—N($R^N$)—$(CH_2)_{1-3}$—, in particular —O—$CH_2$—, —S—$CH_2$— and —$R^N$—$CH_2$—, where $R^N$ is selected from hydrogen and $C_{1-4}$-alkyl, Q designates Prot-O—, $R^{3*}$ is Q* which designates Act-OH, and $R^{1*}$, $R^2$, $R^3$, $R^5$, and $R^{5*}$ each designate hydrogen. In this embodiment, $R^N$ may also be selected from DNA intercalators, photochemically active groups, thermochemically active groups, chelating groups, reporter groups and ligands.

In a further particularly interesting embodiment of the monomeric LNAs of the present invention, B designates a nucleobase, preferably a nucleobase selected from thymine, cytosine, uracil, adenine and guanine (in particular adenine and guanine), X is —O—, $R^{2*}$ and $R^{4*}$ together designate a biradical selected from —$(CH_2)_{0-1}$—O—$(CH_2)_{1-3}$—, —$(CH_2)_{0-1}$—S—$(CH_2)_{1-3}$—, and —$(CH_2)_{0-1}$—N($R^N$)—$(CH_2)_{1-3}$—, in particular —O—$CH_2$—, —S—$CH_2$— and —$R^N$—$CH_2$—, where $R^N$ is selected from hydrogen and $C_{1-4}$-alkyl, Q is selected from hydroxy, mercapto, $C_{1-6}$-alkylthio, amino, mono- or di($C_{1-6}$-alkyl)amino, optionally substituted $C_{1-6}$-alkoxy, optionally substituted $C_{2-6}$-alkenyloxy, optionally substituted $C_{2-6}$-alkynyloxy, monophosphate, diphosphate, and triphosphate, $R^{3*}$ is Q* which is selected from hydrogen, azido, halogen, cyano, nitro, hydroxy, mercapto, $C_{1-6}$-alkylthio, amino, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, and optionally substituted $C_{2-6}$-alkynyloxy, $R^3$ is selected from hydrogen, optionally substituted $C_{1-6}$-alkyl, optionally substituted $C_{2-6}$-alkenyl, and optionally substituted $C_{2-6}$-alkynyl, and $R^{1*}$, $R^2$, $R^5$, and $R^{5*}$ each designate hydrogen. Also here, $R^N$ may also be selected from DNA intercalators, photochemically active groups, thermochemically active groups, chelating groups, reporter groups and ligands.

In a further particularly interesting embodiment of the monomeric LNAs of the present invention, B designates a nucleobase, X is —O—, $R^2$ and $R^3$ together designate a biradical selected from —$(CH_2)_{0-1}$—O—CH═CH—, —$(CH_2)_{0-1}$—S—CH═CH—, and —$(CH_2)_{0-1}$—N($R^N$)—CH═CH— where $R^N$ is selected from hydrogen and $C_{1-4}$-alkyl, Q is selected from hydroxy, mercapto, $C_{1-6}$-alkylthio, amino, mono- or di($C_{1-6}$-alkyl)amino, optionally substituted $C_{1-6}$-alkoxy, optionally substituted $C_{2-6}$-alkenyloxy, optionally substituted $C_{2-6}$-alkynyloxy, monophosphate, diphosphate, and triphosphate, $R^{3*}$ is Q* which is selected from hydrogen, azido, halogen, cyano, nitro, hydroxy, mercapto, $C_{1-6}$-alkylthio, amino, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, and optionally substituted $C_{2-6}$-alkynyloxy, and $R^{1*}$, $R^{2*}$, $R^{4*}$, $R^5$, and $R^{5*}$ each designate hydrogen.

One aspect of the invention is to provide various derivatives of LNAs for solid-phase and/or solution phase incorporation into an oligomer. As an illustrative example, monomers suitable for incorporation of (1S,3R,4R,7S)-7-hydroxy-1-hydroxymethyl-3-(thymin-1-yl)-2,5-dioxabicyclo[2.2.1]heptane, (1S,3R,4R,7S)-7-hydroxy-1-hydroxymethyl-3-(cytosin-1-yl)-2,5-dioxabicyclo[2.2.1]heptane, (1S,3R,4R,7S)-7-hydroxy-1-hydroxymethyl-3-(uracil-1-yl)-2,5-dioxabicyclo[2.2.1]heptane, (1S,3R,4R,7S)-7-hydroxy-1-hydroxymethyl-3-(guanin-1-yl)-2,5-dioxabicyclo[2.2.1]heptane, and (1S,3R,4R,7S)-7-hydroxy-1-hydroxymethyl-3-(adenin-1-yl)-2,5-dioxabicyclo[2.2.1]heptane using the phosphoramidite approach, the phosphortriester approach, and the H-phosphonate approach, respectively, are (1R,3R,4R,7S)-7-(2-Cyanoethoxy(diisopropylamino)phosphinoxy)-1-(4,4'-dimethoxytrityloxymethyl)-3-(thymin-1-yl)-2,5-dioxabicyclo[2.2.1]heptane, (1R,3R,4R,7S)-7-hydroxy-1-(4,4'-dimethoxytrityloxymethyl)-3-(thymin-1-yl)-2,5-dioxabicyclo[2.2.1]heptane-7-0-(2-chlorophenylphosphate), and (1R,3R,4R,7S)-7-hydroxy-1-(4,4'-dimethoxytrityloxymethyl)-3-(thymin-1-yl)-2,5-dioxabicyclo[2.2.1]heptane-7-O—(H-phosphonate) and the 3-(cytosin-1-yl), 3-(uracil-1-yl), 3-(adenin-1-yl) and 3-(guanin-1-yl) analogues thereof, respectively. Furthermore, the analogues where the methyleneoxy biradical of the monomers is substituted with a methylenethio, a methyleneamino, or a 1,2-ethylene biradical are also expected to constitute particularly interesting variants within the present invention. The methylenethio and methyleneamino analogues are believed to equally applicable as the methyleneoxy analogue and therefore the specific reagents corresponding to those mentioned for incorporation of (1S,3R,4R,7S)-7-hydroxy-1-hydroxymethyl-3-(thymin-1-yl)-2,5-dioxabicyclo[2.2.1]heptane, (1S,3R,4R,7S)-7-hydroxy-1-hydroxymethyl-3-(cytosin-1-yl)-2,5-dioxabicyclo[2.2.1]heptane, (1S,3R,4R,7S)-7-hydroxy-1-hydroxymethyl-3-(uracil-1-yl)-2,5-dioxabicyclo[2.2.1]heptane, (1S,3R,4R,7S)-7-hydroxy-1-hydroxymethyl-3-(guanin-1-yl)-2,5-dioxabicyclo[2.2.1]heptane, and (1S,3R,4R,7S)-7-hydroxy-1-hydroxymethyl-3-(adenin-1-yl)-2,5-dioxabicyclo[2.2.1]heptane should also be considered as particularly interesting reactive monomers within the present invention. For the methyleneamine analogue, it should be noted that the secondary amine may carry a substituent selected from optionally substituted $C_{1-6}$-alkyl such as methyl and benzyl, optionally substituted $C_{1-6}$-alkylcarbonyl such as trifluoroacetyl, optionally substituted arylcarbonyl and optionally substituted heteroarylcarbonyl.

In a particularly interesting embodiment, the present invention relates to an oligomer comprising at least one LNA of the general formula Ia Ia

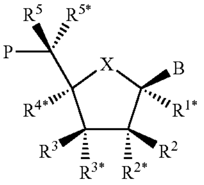

wherein X is —O—; B is selected from nucleobases, DNA intercalators, photochemically active groups, thermochemically active groups, chelating groups, reporter groups, and ligands; P designates the radical position for an internucleoside linkage to a succeeding monomer, or a 5'-terminal group, such internucleoside linkage or 5'-terminal group optionally including the substituent $R^5$; $R^{3*}$ is a group P* which designates an internucleoside linkage to a preceding monomer, or a 3'-terminal group; $R^{2*}$ and $R^{4*}$ together designate a biradical selected from —O—, —S, —$(CR^*R^*)_{r+s+1}$—, —$(CR^*R^*)_r$—O—$(CR^*R^*)_s$—, —$(CR^*R^*)_r$—S—$(CR^*R^*)_s$—, —$(CR^*R^*)_r$—N(R*)—$(CR'R')_s$—, —O—$(CR^*R^*)_{r+s}$—O—, —S—$(CR^*R^*)_{r+s}$—O—, —O—$(CR^*R^*)_{r+s}$—S—, —N(R*)—$(CR^*R^*)_{r+s}$—O—, —O—$(CR^*R^*)_{r+s}$—N(R*)—, —S—$(CR^*R^*)_{r+s}$—S—, —N(R*)—$(CR^*R^*)_{r+s}$—N(R)—, —N(R)—$(CR^*R^*)_{r+s}$—S—, and —S—$(CR^*R^*)_{r+s}$—N(R*)—; wherein each R* is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond, and each of r and s is 0-3 with the proviso that the sum r+s is 1-4; each of the substituents $R^{1*}$, $R^2$, $R^3$, $R^5$, and $R^{5*}$ is independently selected from hydrogen, optionally substituted $C_{1-6}$-alkyl, optionally substituted $C_{2-6}$-alkenyl, hydroxy, $C_{1-6}$-alkoxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)-amino-carbonyl, $C_{1-6}$-alkyl-carbonylamino, carbamido, azido, $C_{1-6}$-alkanoyloxy, sulphono, sulphanyl, $C_{1-6}$-alkylthio, DNA intercalators, photochemically active groups, thermochemically active groups, chelating groups, reporter groups, and ligands, and halogen, where two geminal substituents together may designate oxo; and basic salts and acid addition salts thereof. In particular, one R* is selected from hydrogen, hydroxy, optionally substituted $C_{1-6}$-alkoxy, optionally substituted $C_{1-6}$-alkyl, DNA intercalators, photochemically active groups, thermochemically active groups, chelating groups, reporter groups, and ligands, and any remaining substituents R* are hydrogen. Especially, the biradical is selected from —O—, —$(CH_2)_{0-1}$—O—$(CH_2)_{1-3}$—, —$(CH_2)_{0-1}$—S—$(CH_2)_{1-3}$—, —$(CH_2)$—$_{0-1}$—N($R^N$)—$(CH_2)_{1-3}$—, and —$(CH_2)_{2-4}$—.

In a further particularly interesting embodiment, the present invention relates to an LNA of the general formula IIa

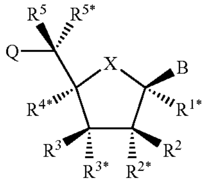

IIa wherein X is —O—; B is selected from nucleobases, DNA intercalators, photochemically active groups, thermochemically active groups, chelating groups, reporter groups, and ligands; $R^{3*}$ is a group Q*; each of Q and Q* is independently selected from hydrogen, azido, halogen, cyano, nitro, hydroxy, Prot-O—, Act-O—, mercapto, Prot-S—, Act-S—, $C_{1-6}$-alkylthio, amino, Prot-N($R^H$)—, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, Act-O—$CH_2$—, aminomethyl, Prot-N($R^H$)—$CH_2$—, Act-N($R^H$)—$CH_2$—, carboxymethyl, sulphonomethyl, where Prot is a protection group for —OH, —SH, and —NH($R^H$), respectively, Act is an activation group for —OH, —SH, and —NH($R^H$), respectively, and $R^H$ is selected from hydrogen and $C_{1-6}$-alkyl; $R^{2*}$ and $R^{4*}$ together designate a biradical selected from —O—, —S, —N(R*)—, —$(CR^*R^*)_{r+s+1}$—, —$(CR^*R^*)_r$—O—$(CR^*R^*)_s$—, —$(CR^*R^*)_r$—S—$(CR^*R^*)_s$—, —$(CR^*R^*)_r$—N(R)—$(CR^*R^*)_s$—, —O—$(CR^*R^*)_{r+s}$—O—, —S—$(CR^*R^*)_{r+s}$—O—, —N(R*)—$(CR^*R^*)_{r+s}$—O—, —O—$(CR^*R^*)_{r+s}$—N(R*)—, —S—$(CR^*R^*)_{r+s}$—S—, —N(R)—$(CR^*R^*)_{r+s}$—N(R*)—, —N(R)—$(CR^*R^*)_{r+s}$—S—, and —S—$(CR^*R^*)_{r+s}$—N(R*)—; wherein each R* is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond, and each of r and s is 0-3 with the proviso that the sum r+s is 1-4; each of the substituents $R^{1*}$, $R^2$, $R^3$, $R^5$, and $R^{5*}$ is independently selected from hydrogen, optionally substituted $C_{1-6}$-alkyl, optionally substituted $C_{2-6}$-alkenyl, hydroxy, $C_{1-6}$-alkoxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)-amino-carbonyl, $C_{1-6}$-alkyl-carbonylamino, carbamido, azido, $C_{1-6}$-alkanoyloxy, sulphono, sulphanyl, $C_{1-6}$-alkylthio, DNA intercalators, photochemically active groups, thermochemically active groups, chelating groups, reporter groups, and ligands, and halogen, where two geminal substituents together may designate oxo; and basic salts and acid addition salts thereof; and with the proviso that any chemical group (including any nucleobase), which is reactive under the conditions prevailing in oligonucleotide synthesis, is optionally functional group protected. Preferably, one R* is selected from hydrogen, hydroxy, optionally substituted $C_{1-6}$-alkoxy, optionally substituted $C_{1-6}$-alkyl, DNA intercalators, photochemically active groups, thermochemically active groups, chelating groups, reporter groups, and ligands, and any remaining substituents R* are hydrogen. Especially, the biradical is selected from —O—, —$(CH_2)_{0-1}$—O—$(CH_2)_{1-3}$—, —$(CH_2)_{0-1}$—S—$(CH_2)_{1-3}$—, —$(CH_2)_{0-1}$—N($R^N$)—$(CH_2)_{1-3}$—, and —$(CH_2)$—$_{2-4}$—.

Generally, the present invention provides oligomers having surprisingly good hybridisation properties with respect to affinity and specificity. Thus, the present invention provides an oligomer comprising at least one nucleoside analogue which imparts to the oligomer a $T_m$ with a complementary DNA oligonucleotide which is at least 2.5° C. higher, preferably at least 3.5° C. higher, in particular at least 4.0° C. higher, especially at least 5.0° C. higher, than that of the corresponding unmodified reference oligonucleotide which does not comprise any nucleoside analogue. In particular, the $T_m$ of the oligomer is at least 2.5×N ° C. higher, preferably at least 3.5×N ° C. higher, in particular at least 4.0×N ° C. higher, especially at least 5.0×N° C. higher, where N is the number of nucleoside analogues.

In the case of hybridisation with a complementary RNA oligonucleotide, the at least one nucleoside analogue imparts to the oligomer a $T_m$ with the complementary DNA oligonucleotide which is at least 4.0° C. higher, preferably at least 5.0° C. higher, in particular at least 6.0° C. higher, especially at least 7.0° C. higher, than that of the corresponding unmodified reference oligonucleotide which does not comprise any nucleoside analogue. In particular, the $T_m$ of the oligomer is at least 4.0×N ° C. higher, preferably at least 5.0×N ° C. higher, in particular at least 6.0×N ° C. higher, especially at least 7.0×N° C. higher, where N is the number of nucleoside analogues.

The term "corresponding unmodified reference oligonucleotide" is intended to mean an oligonucleotide solely consisting of naturally occurring nucleotides which represents the same nucleobases in the same absolute order (and the same orientation).

The $T_m$ is measured under one of the following conditions (i.e. essentially as illustrated in Example 129):

a) 10 mM $Na_2HPO_4$, pH 7.0, 100 mM NaCl, 0.1 mM EDTA;

b) 10 mM $Na_2HPO_4$ pH 7.0, 0.1 mM EDTA; or c) 3M tetramethylammoniumchlorid (TMAC), 10 mM $Na_2HPO_4$, pH 7.0, 0.1 mM EDTA;

preferably under conditions a), at equimolar amounts (typically 1.0 μM) of the oligomer and the complementary DNA oligonucleotide.

The oligomer is preferably as defined above, where the at least one nucleoside analogue has the formula I where B is a nucleobase. In particular interesting is the cases where at least one nucleoside analogue includes a nucleobase selected from adenine and guanine.

Furthermore, with respect to specificity and affinity, the oligomer, when hybridised with a partially complementary DNA oligonucleotide, or a partially complementary RNA oligonucleotide, having one or more mismatches with said oligomer, should exhibit a reduction in $T_m$, as a result of said mismatches, which is equal to or greater than the reduction which would be observed with the corresponding unmodified reference oligonucleotide which does not comprise any nucleoside analogues. Also, the oligomer should have substantially the same sensitivity of $T_m$ to the ionic strength of the hybridisation buffer as that of the corresponding unmodified reference oligonucleotide.

Oligomers defined herein are typically at least 30% modified, preferably at least 50% modified, in particular 70% modified, and in some interesting applications 100% modified.

The oligomers of the invention has substantially higher 3'-exonucleolytic stability than the corresponding unmodified reference oligonucleotide. This important property can be examined as described in Example 136.

DEFINITIONS

In the present context, the term "$C_{1-12}$-alkyl" means a linear, cyclic or branched hydrocarbon group having 1 to 12 carbon atoms, such as methyl, ethyl, propyl, iso-propyl, cyclopropyl, butyl, tert-butyl, iso-butyl, cyclobutyl, pentyl, cyclopentyl, hexyl, cyclohexyl, and dodecyl. Analogously, the term "$C_{1-6}$-alkyl" means a linear, cyclic or branched hydrocarbon group having 1 to 6 carbon atoms, such as methyl, ethyl, propyl, iso-propyl, pentyl, cyclopentyl, hexyl, cyclohexyl, and the term "$C_{1-4}$-alkyl" is intended to cover linear, cyclic or branched hydrocarbon groups having 1 to 4 carbon atoms, e.g. methyl, ethyl, propyl, isopropyl, cyclopropyl, butyl, iso-butyl, tert-butyl, cyclobutyl.

Preferred examples of "$C_{1-6}$-alkyl" are methyl, ethyl, propyl, iso-propyl, butyl, tert-butyl, isobutyl, pentyl, cyclopentyl, hexyl, cyclohexyl, in particular methyl, ethyl, propyl, iso-propyl, tert-butyl, iso-butyl and cyclohexyl. Preferred examples of "$C_{1-4}$-alkyl" are methyl, ethyl, propyl, iso-propyl, butyl, tert-butyl, and iso-butyl.

Similarly, the term "$C_{2-12}$-alkenyl" covers linear, cyclic or branched hydrocarbon groups having 2 to 12 carbon atoms and comprising one unsaturated bond. Examples of alkenyl groups are vinyl, allyl, butenyl, pentenyl, hexenyl, heptenyl, octenyl, dodecaenyl. Analogously, the term "$C_{2-6}$-alkenyl" is intended to cover linear, cyclic or branched hydrocarbon groups having 2 to 6 carbon atoms and comprising one unsaturated bond. Preferred examples of alkenyl are vinyl, allyl, butenyl, especially allyl.

Similarly, the term "$C_{2-12}$-alkynyl" means a linear or branched hydrocarbon group having 2 to 12 carbon atoms and comprising a triple bond. Examples hereof are ethynyl, propynyl, butynyl, octynyl, and dodecanyl.

In the present context, i.e. in connection with the terms "alkyl", "alkenyl", and "alkynyl", the term "optionally substituted" means that the group in question may be substituted one or several times, preferably 1-3 times, with group(s) selected from hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkoxycarbonyl, $C_{1-6}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkanoyloxy, sulphono, $C_{1-6}$-alkylsulphonyloxy, nitro, sulphanyl, $C_{1-6}$-alkylthio, halogen, where any aryl and heteroaryl may be substituted as specifically describe below for "optionally substituted aryl and heteroaryl".

Preferably, the substituents are selected from hydroxy, $C_{1-6}$-alkoxy, carboxy, $C_{1-6}$-alkoxycarbonyl, $C_{1-6}$-alkylcarbonyl, formyl, aryl, aryloxycarbonyl, arylcarbonyl, heteroaryl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, carbamido, halogen, where aryl and heteroaryl may be substituted 1-5 times, preferably 1-3 times, with $C_{1-4}$-alkyl, $C_{1-4}$-alkoxy, nitro, cyano, amino or halogen. Especially preferred examples are hydroxy, $C_{1-6}$-alkoxy, carboxy, aryl, heteroaryl, amino, mono- and di($C_{1-6}$-alkyl)amino, and halogen, where aryl and heteroaryl may be substituted 1-3 times with $C_{1-4}$-alkyl, $C_{1-4}$-alkoxy, nitro, cyano, amino or halogen.

In the present context the term "aryl" means a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl, among which phenyl is a preferred example.

The term "heteroaryl" means a fully or partially aromatic carbocyclic ring or ring system where one or more of the carbon atoms have been replaced with heteroatoms, e.g. nitrogen (=N— or —NH), sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrazinyl, pyridazinyl, piperidinyl, coumaryl, furyl, quinolyl, benzothiazolyl, benzotriazolyl, benzodiazolyl, benzooxozolyl, phthalazinyl, phthalanyl, triazolyl, tetrazolyl, isoquinolyl, acridinyl, carbazolyl, dibenzazepinyl, indolyl, benzopyrazolyl, phenoxazonyl.

In the present context, i.e. in connection with the terms "aryl" and "heteroaryl", the term "optionally substituted"

means that the group in question may be substituted one or several times, preferably 1-5 times, in particular 1-3 times) with group(s) selected from hydroxy (which when present in an enol system may be represented in the tautomeric keto form), $C_{1-6}$-alkyl, $C_{1-6}$-alkoxy, oxo (which may be represented in the tautomeric enol form), carboxy, $C_{1-6}$-alkoxycarbonyl, $C_{1-6}$-alkylcarbonyl, formyl, aryl, aryloxy, aryloxycarbonyl, arylcarbonyl, heteroaryl, amino, mono- and di($C_{1-6}$-alkyl)amino; carbamoyl, mono- and di($C_{1-6}$-alkyl) aminocarbonyl, amino-$C_{1-6}$-alkyl-aminocarbonyl, mono- and di($C_{1-6}$-alkyl)-amino-$C_{1-6}$-alkyl-aminocarbonyl, $C_{1-6}$-alkylcarbonylamino, cyano, guanidino, carbamido, $C_{1-6}$-alkanoyloxy, sulphono, $C_{1-6}$-alkylsulphonyloxy, nitro, sulphanyl, dihalogen-$C_{1-4}$-alkyl, trihalogen-$C_{1-4}$-alkyl, halogen, where aryl and heteroaryl representing substituents may be substituted 1-3 times with $C_{1-4}$-alkyl, $C_{1-4}$-alkoxy, nitro, cyano, amino or halogen. Preferred examples are hydroxy, $C_{1-6}$-alkyl, $C_{1-6}$-alkoxy, carboxy, $C_{1-6}$-alkoxycarbonyl, $C_{1-6}$-alkylcarbonyl, aryl, amino, mono- and di($C_{1-6}$-alkyl)amino, and halogen, wherein aryl may be substituted 1-3 times with $C_{1-4}$-alkyl, $C_{1-4}$-alkoxy, nitro, cyano, amino or halogen.

"Halogen" includes fluoro, chloro, bromo, and iodo.

It should be understood that oligomers (wherein LNAs are incorporated) and LNAs as such include possible salts thereof, of which pharmaceutically acceptable salts are especially relevant. Salts include acid addition salts and basic salts. Examples of acid addition salts are hydrochloride salts, sodium salts, calcium salts, potassium salts, etc. Examples of basic salts are salts where the (remaining) counter ion is selected from alkali metals, such as sodium and potassium, alkaline earth metals, such as calcium, and ammonium ions ($^{+}N(R^g)_3R^h$, where each of $R^g$ and $R^h$ independently designates optionally substituted $C_{1-6}$-alkyl, optionally substituted $C_{2-6}$-alkenyl, optionally substituted aryl, or optionally substituted heteroaryl). Pharmaceutically acceptable salts are, e.g., those described in Remington's Pharmaceutical Sciences, 17. Ed. Alfonso R. Gennaro (Ed.), Mack Publishing Company, Easton, Pa., U.S.A., 1985 and more recent editions and in Encyclopedia of Pharmaceutical Technology. Thus, the term "an acid addition salt or a basic salt thereof" used herein is intended to comprise such salts. Furthermore, the oligomers and LNAs as well as any intermediates or starting materials therefor may also be present in hydrate form.

Preparation of Monomers

Figure 34:
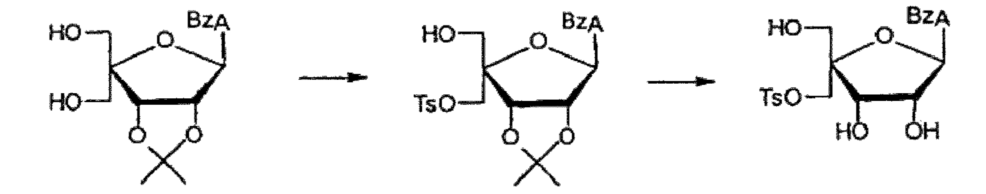
Figure 34:
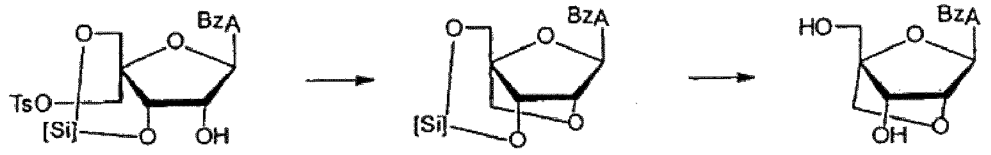

In a preferred embodiment, nucleosides containing an additional 2'-O,4'-C-linked ring were synthesised by the following procedure:

Synthesis of a number of 4'-C-hydroxymethyl nucleosides have been reported earlier (R. D. Youssefyeh, J. P. H. Verheyden and J. G. Moffatt, *J. Org. Chem.,* 1979, 44, 1301; G. H. Jones, M. Taniguchi, D. Tegg and J. G. Moffatt, *J. Org. Chem.,* 1979, 44, 1309; C. O-Yang, H. Y. Wu, E. B. Fraser-Smith and K. A. M. Walker, *Tetrahedron Lett.,* 1992, 33, 37; H. Thrane, J. Fensholdt, M. Regner and J. Wengel, *Tetrahedron,* 1995, 51, 10389; K. D. Nielsen, F. Kirpekar, P. Roepstorff and J. Wengel, *Bioorg. Med. Chem.,* 1995, 3, 1493). For exemplification of synthesis of 2'-O,4'-C-linked bicyclic nucleosides we chose a strategy starting from 4'-C-hydroxymethyl furanose derivative 31. Benzylation, acetylation, and acetolysis followed by another acetylation afforded furanose 33, a key intermediate for nucleoside coupling. Stereoselective reaction with silylated thymine afforded compound 34 which was deacetylated to give nucleoside diol 35. Tosylation followed by base-induced ring closure afforded the 2'-O,4'-C-linked bicyclic nucleoside derivative 36. Debenzylation yielded the unprotected bicyclic nucleoside analogue 37 which was transformed into the 5'-O-4,4'-dimethoxytrityl protected analogue 38 and subsequently into the phosphoramidite derivative 39 for oligonucleotide synthesis. A similar procedure has been used for synthesis of the corresponding uracil, adenine, cytosine and guanine nucleosides as exemplified in the example section. This coupling method is only one of several possible as will be apparent for a person skilled in the art. A strategy starting from a preformed nucleoside is also possible. Thus, for example, conversion of uridine derivative 62 to derivative 44 was successfully accomplished by tosylation, deisopropylidination and base-induced ring-closure. As another example, conversion of nucleoside 67 into nucleoside 61B has been accomplished as depicted in FIG. 34. Conversion of the bicyclic thymine nucleoside 37 into the corresponding 5-methyl-cytosine nucleoside 65 was accomplished by a known reaction sequence using triazole and $POCl_3$ followed by benzoylation and treatment by ammonia. A similar procedure should be applicable for the synthesis of 57C from 44. As another example of possible strategies, coupling of precyclised furanose derivatives already containing an additional ring with nucleobase derivatives is possible. Such a strategy would in addition allow preparation of the corresponding α-nucleoside analogues. When coupling with a protected methyl furanoside of 4-C, 2-O-methylene-D-ribofuranose, we obtained mainly a ring-opened product. However, coupling of 1-O-acetyl furanose 207 or thiophenyl furanose 212 yielded successfully LNA nucleosides with the α-anomers as one product. Incorporation of such α-LNA nucleosides will be possible using the standard oligomerisation techniques (as for the LNA oligomers containing Z) yielding α-LNA oligomers. In addition, a synthetic strategy performing nucleoside coupling using a 4'-C-hydroxymethyl furanose already activated for ring closure (e.g. by containing a mesyl or tosyl group at the 4'-C-hydroxymethyl group), is possible as exemplified by conversion of furanose 78 to nucleoside 79 followed by deprotection and ring closure to give 36. Chemical or enzymatic transglycosylation or anomerisation of appropriate furanose derivatives or nucleosides are yet other possible synthetic strategies. These and other related strategies allow for synthesis of bicyclic nucleosides containing other nucleobases or analogues thereof by either coupling with these nucleobases or analogues, or starting from preformed nucleoside derivatives.

The described examples are meant to be illustrative for the procedures and examples of this invention. The structures of the synthesised compounds were verified using 1D or 2D NMR techniques, e.g. NOE experiments.

An additional embodiment of the present invention is to provide bicyclic nucleosides containing additional rings of different sizes and of different chemical structures. From the methods described it is obvious for a person skilled in the art of organic synthesis that cyclisation of other nucleosides is possible using similar procedures, also of nucleosides containing different C-branches. The person skilled in the art will be able to find inspiration and guidance for the preparation of substituted nucleoside analogue intermediates in the literature, see e.g. WO 96/14329. Regarding rings of different chemical compositions it is clear that using similar procedures or procedures well-established in the field of organic chemistry, synthesis of for example thio analogues of the exemplified oxo analogues is possible as is the synthesis of the corresponding amino analogues (using for example nucleophilic substitution reactions or reductive alkylations).

Figure 35:
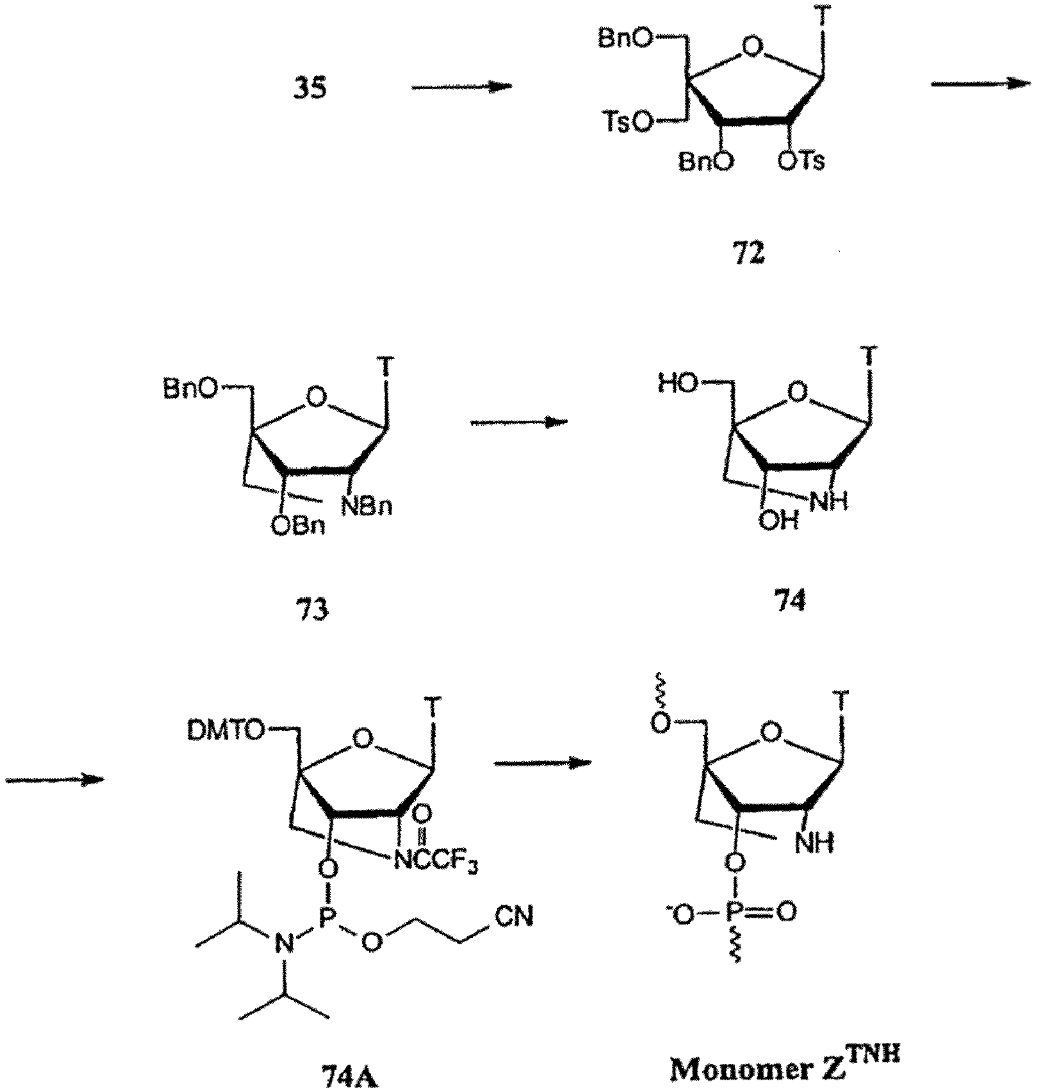
Figure 36:
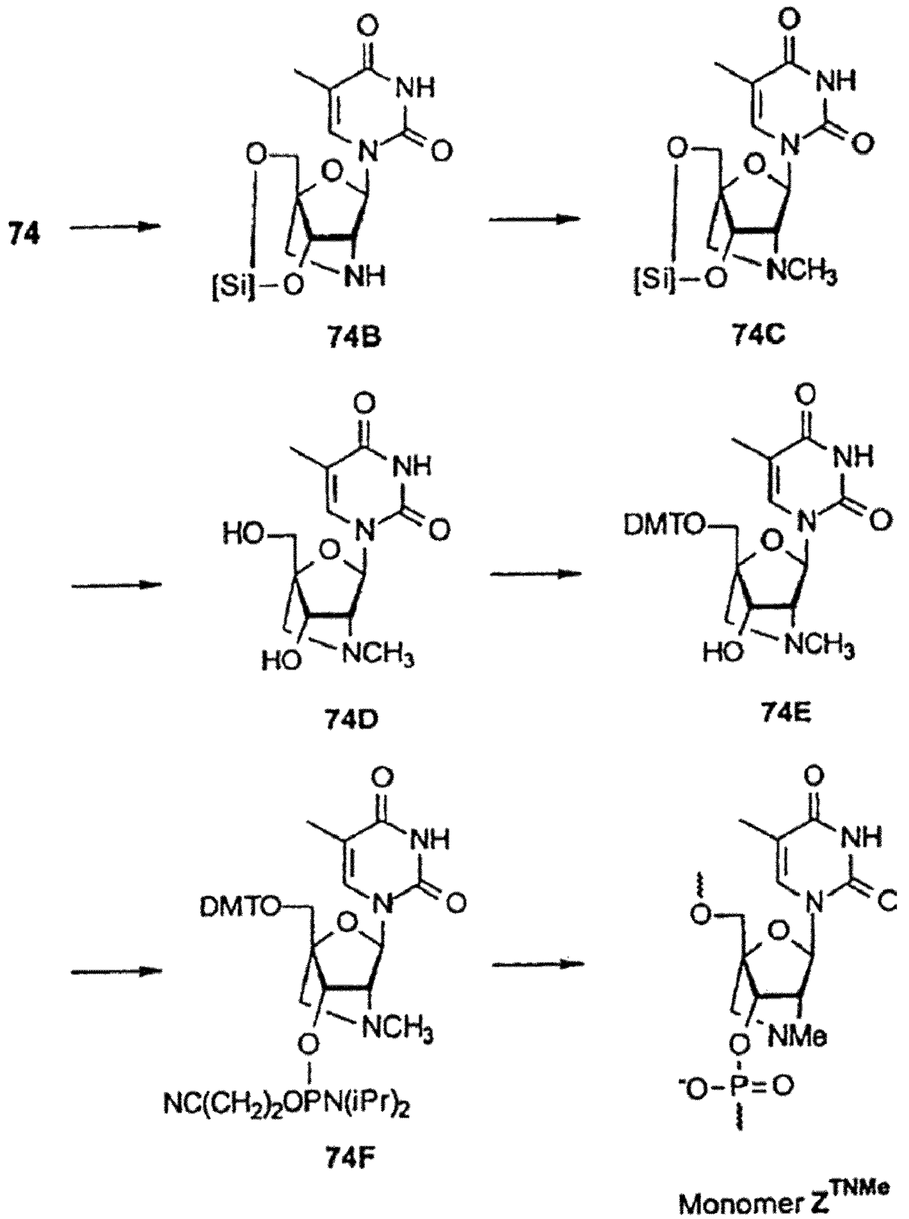

In the example section, synthesis of the amino LNA analogues 73-74F are described. Conversion of 74 and 74D into standard building blocks for oligomerisation was possible by 5'-O-DMT protection and 3'-O-phosphitylation following the standard procedures. For the amino LNA analogue, protection of the 2'-amino functionality is needed for controlled linear oligomerisation. Such protection can be accomplished using standard amino group protection techniques like, e.g., Fmoc, trifluoroacetyl or BOC. Alternatively, an N-alkyl group (e.g. benzyl, methyl, ethyl, propyl or functionalised alkyl) can be kept on during nucleoside transformations and oligomerisation. In FIGS. 35 and 36, strategies using N-trifluoroacetyl and N-methyl derivatives are shown. As outlined in FIG. 37, conversion of nucleoside 75 into the 2'-thio-LNA nucleoside analogue 76D has been successfully performed as has the subsequent syntheses of the phosphoramidite derivative 76F. Compound 76F has the required structure for automated synthesis of 2'-thio-LNA oligonucleotides. The N-trifluoroacetyl 2'-amino-LNA synthon 74A has the required structure for automated synthesis of 2'-amino-LNA oligonucleotides.

Figure 37:
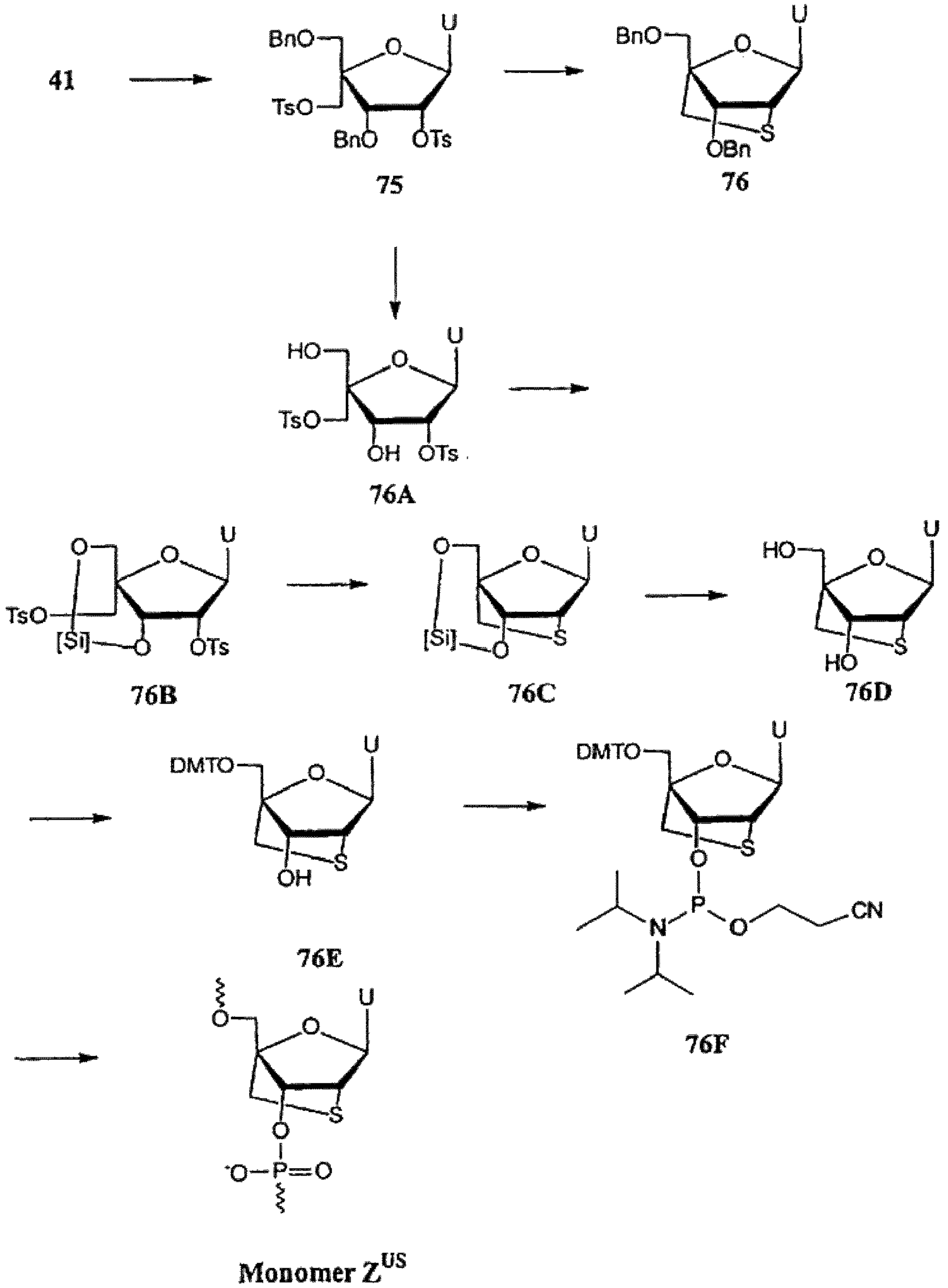
Figure 38:
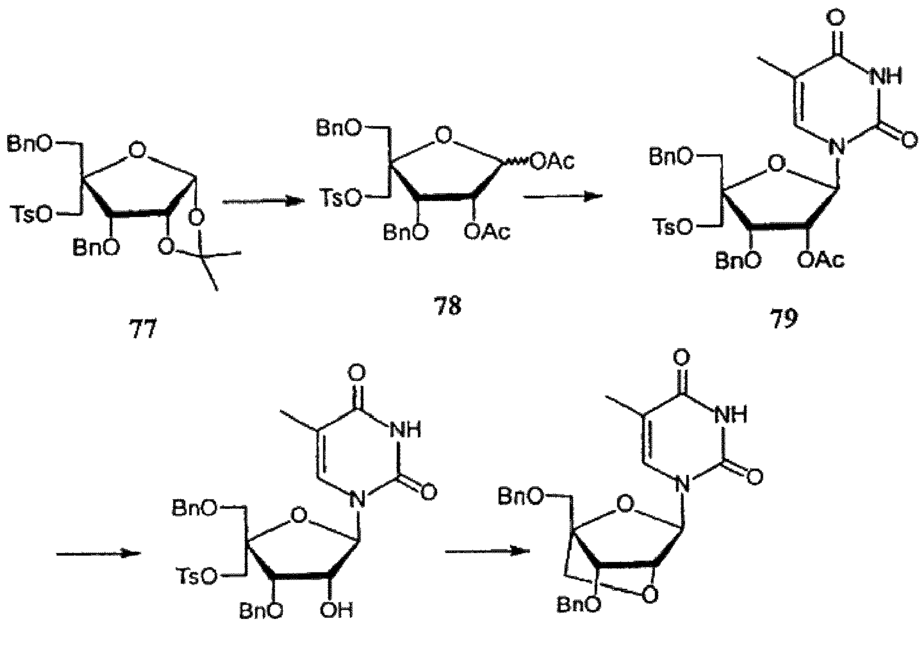
Figure 39:
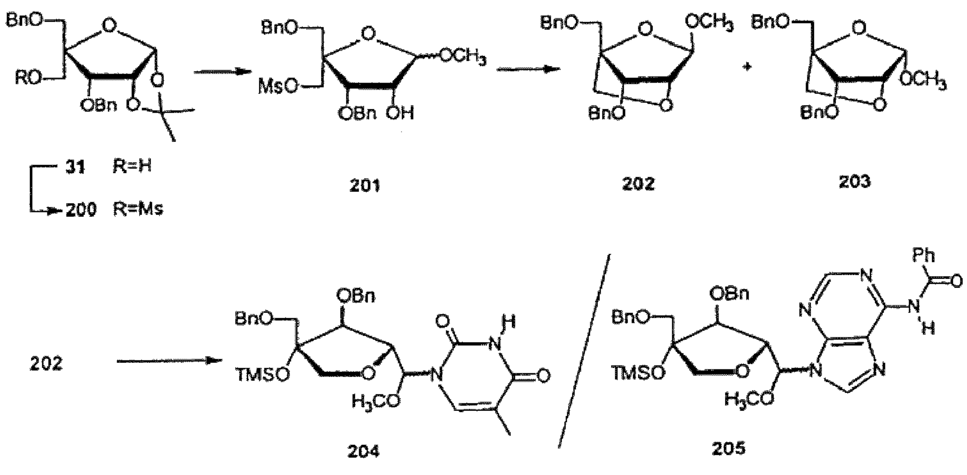
Figure 40:
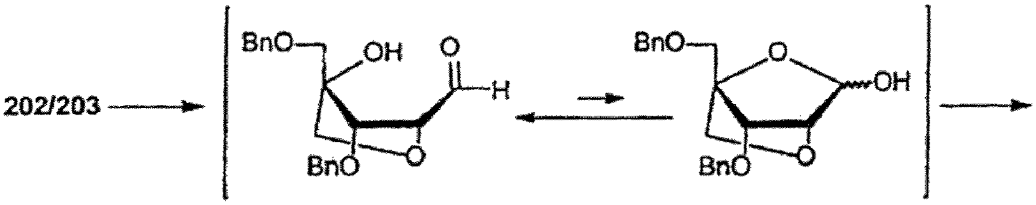
Figure 40:
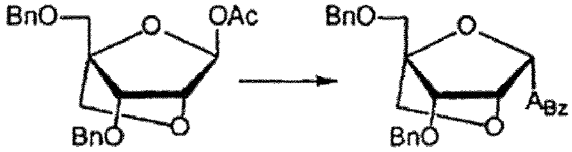
Figure 41:
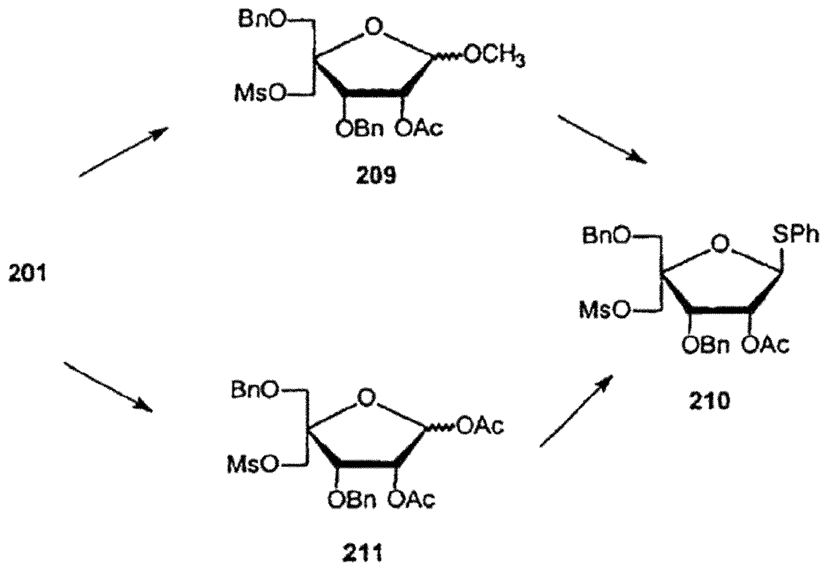
Figure 41:
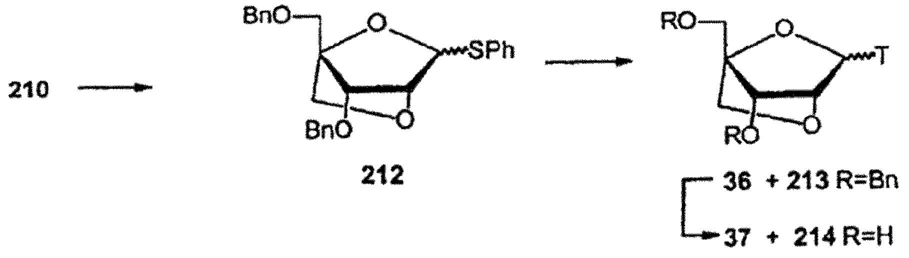

Synthesis of the corresponding cytosine, guanine, and adenine derivatives of the 2'-thio and 2'-amino LNA nucleosides can be accomplished using strategies analogous to those shown in FIGS. 35, 36 and 37. Alternative, the stereochemistry around C-2' can be inverted before cyclisations either by using a conveniently configurated, e.g. an arabino-configurated, furanose synthon, or by inverting the configuration around the C-2' carbon atom starting from a ribo-configurated nucleoside/furanose. Subsequent activation of the 2'-β-OH, e.g. by tosylation, double nucleophilic substitution as in the uracil/thymine example described above, could furnish the desired bicyclic 2'-thio-LNA or 2'-amino-LNA nucleosides. The thus obtained properly protected cytosine, guanine, and adenine analogues can be prepared for oligomerisation using the standard reactions (DMT-protection and phosphitylation) as described above for other examples.

Preparation of Oligomers

Linear-, branched- (M. Grotli and B. S. Sproat, *J. Chem. Soc., Chem. Commun.,* 1995, 495; R. H. E. Hudson and M. J. Damha, *J. Am. Chem. Soc.,* 1993, 115, 2119; M. Von Büren, G. V. Petersen, K. Rasmussen, G. Brandenburg, J. Wengel and F. Kirpekar, *Tetrahedron,* 1995, 51, 8491) and circular- (G. Prakash and E. T. Kool, *J. Am. Chem. Soc.,* 1992, 114, 3523) Oligo- and polynucleotides of the invention may be produced using the polymerisation techniques of nucleic acid chemistry well known to a person of ordinary skill in the art of organic chemistry. Phosphoramidite chemistry (S. L. Beaucage and R. P. Iyer, *Tetrahedron,* 1993, 49, 6123; S. L. Beaucage and R. P. Iyer, *Tetrahedron,* 1992, 48, 2223) was used, but e.g. H-phosphonate chemistry, phosphortriester chemistry or enzymatic synthesis could also be used. Generally, standard coupling conditions and the phosphoramidite approach was used, but for some monomers of the invention longer coupling time, and/or repeated couplings with fresh reagents, and/or use of more concentrated coupling reagents were used. As another possibility, activators more active than 1H-tetrazole could also be used to increase the rate of the coupling reaction. The phosphoramidites 39, 46, 53, 57D, 61D, and 66 all coupled with satisfactory >95% step-wise coupling yields. An all-phosphorothioate LNA oligomer (Table 7) was synthesised using standard procedures. Thus, by exchanging the normal, e.g. iodine/pyridine/$H_2O$, oxidation used for synthesis of phosphordiester oligomers with an oxidation using Beaucage's reagent (commercially available), the phosphorthioate LNA oligomer was efficiently synthesised (stepwise coupling yields >=98%). The 2'-amino-LNA and 2' methylamino-LNA oligonucleotides (Table 9) were efficiently synthesised (step-wise coupling yields 98%) using amidites 74A and 74F. The 2'-thio-LNA oligonucleotides (Table 8) were efficiently synthesised using amidite 76F using the standard phosphoramidite procedures as described above for LNA oligonucleotides. After synthesis of the desired sequence, work up was done using standard conditions (cleavage from solid support and removal of protection groups using 30% ammonia for 55° C. for 5 h). Purification of LNA oligonucleotides was done using disposable reversed phase purification cartridges and/or reversed phase HPLC and/or precipitation from ethanol or butanol. Capillary gel electrophoresis, reversed phase HPLC and MALDI-MS was used to verify the purity of the synthesised oligonucleotide analogues, and to verify that the desired number of bicyclic nucleoside analogues of the invention were incorporated as contemplated.

An additional aspect of the present invention is to furnish procedures for oligonucleotide analogues containing LNA linked by non-natural internucleoside linkages. For example, synthesis of the corresponding phosphorothioate or phosphoramidate analogues is possible using strategies well-established in the field of oligonucleotide chemistry (Protocols for Oligonucleotides and Analogs, vol 20, (Sudhir Agrawal, ed.), Humana Press, 1993, Totowa, N.J.; S. L. Beaucage and R. P. Iyer, *Tetrahedron,* 1993, 49, 6123; S. L. Beaucage and R. P. Iyer, *Tetrahedron,* 1992, 48, 2223; E. Uhlmann and A. Peyman, *Chem. Rev.,* 90, 543).

Thus, generally the present invention also provides the use of an LNA as defined herein for the preparation of an LNA modified oligonucleotides. Is should be understood that LNA modified oligonucleotide may comprise normal nucleosides (i.e. naturally occurring nucleosides such as ribonucleosides and/or deoxyribonucleosides), as well as modified nucleosides different from those defined with the general formula II. In a particularly interesting embodiment, incorporation of LNA modulates the ability of the oligonucleotide to act as a substrate for nucleic acid active enzymes.

Furthermore, solid support materials having immobilised thereto an optionally nucleobase protected and optionally 5'-OH protected LNA are especially interesting as material for the synthesis of LNA modified oligonucleotides where an LNA monomer is included in at the 3' end. In this instance, the solid support material is preferable CPG, e.g. a readily (commercially) available CPG material onto which a 3'-functionalised, optionally nucleobase protected and optionally 5'-OH protected LNA is linked using the conditions stated by the supplier for that particular material. BioGenex Universial CPG Support (BioGenex, U.S.A.) can e.g. be used. The 5'-OH protecting group may, e.g., be a DMT group. 3'-functional group should be selected with due regard to the conditions applicable for the CPG material in question.

Applications

The present invention discloses the surprising finding that various novel derivatives of bicyclic nucleoside monomers (LNAs), when incorporated into oligonucleotides, dramatically increase the affinity of these modified oligonucleotides for both complementary ssDNA and ssRNA compared to the unmodified oligonucleotides. It further discloses the surprising finding that both fully and partly LNA modified oligonucleotides display greatly enhanced hybridisation properties for their complementary nucleic acid sequences. Depending on the application, the use of these LNAs thus offers the intriguing possibility to either greatly increase the affinity of a standard oligonucleotide without compromising specificity (constant size of oligonucleotide) or significantly increase the specificity without compromising affinity (reduction in the size of the oligonucleotide). The present invention also discloses the unexpected finding that LNA modified oligonucleotides, in addition to greatly enhanced hybridisation properties, display many of the useful physicochemical properties of normal DNA and RNA oligonucleotides. Examples given herein include excellent solubility, a response of LNA modified oligonucleotides to salts like sodium chloride and tetramethylammonium chloride which mimic that of the unmodified oligonucleotides, the ability of LNA modified oligonucleotides to act as primers for a variety of polymerases, the ability of LNA modified nucleotides to act as primers in a target amplification reaction using a thermostable DNA polymerase, the ability of LNA modified oligonucleotides to act as a substrate for T4 polynucleotide kinase, the ability of biotinylated LNAs to sequence specifically capture PCR amplicons onto a streptavidine coated solid surface, the ability of immobilised LNA modified oligonucleotides to sequence specifically capture amplicons and very importantly the ability of LNA modified oligonucleotides to sequence specifically target double-stranded DNA by strand invasion. Hence, it is apparent to one of ordinary skills in the art that these novel nucleoside analogues are extremely useful tools to improve the performance in general of oligonucleotide based techniques in therapeutics, diagnostics and molecular biology.

An object of the present invention is to provide monomeric LNAs according to the invention which can be incorporated into oligonucleotides using procedures and equipment well known to one skilled in the art of oligonucleotide synthesis.

Another object of the present invention is to provide fully or partly LNA modified oligonucleotides (oligomers) that are able to hybridise in a sequence specific manner to complementary oligonucleotides forming either duplexes or triplexes of substantially higher affinity than the corresponding complexes formed by unmodified oligonucleotides.

Another object of the present invention is to use LNAs to enhance the specificity of normal oligonucleotides without compromising affinity. This can be achieved by reducing the size (and therefore affinity) of the normal oligonucleotide to an extent that equals the gain in affinity resulting from the incorporation of LNAs.

Another object of the present invention is to provide fully or partly modified oligonucleotides containing both LNAs, normal nucleosides and other nucleoside analogues.

A further object of the present invention is to exploit the high affinity of LNAs to create modified oligonucleotides of extreme affinity that are capable of binding to their target sequences in a dsDNA molecule by way of "strand displacement".

A further object of the invention is to provide different classes of LNAs which, when incorporated into oligonucleotides, differ in their affinity towards their complementary nucleosides. In accordance with the invention this can be achieved by either substituting the normal nucleobases G, A, T, C and U with derivatives having, for example, altered hydrogen bonding possibilities or by using LNAs that differ in their backbone structure. The availability of such different LNAs facilitates exquisite tuning of the affinity of modified oligonucleotides.

Another object of the present invention is to provide LNA modified oligonucleotides which are more resistant to nucleases than their unmodified counterparts.

Another object of the present invention is to provide LNA modified oligonucleotides which can recruit RNAseH.

An additional object of the present invention is to provide LNAs that can act as substrates for DNA and RNA polymerases thereby allowing the analogues to be either incorporated into a growing nucleic acid chain or to act as chain terminators.

A further object of the present invention is to provide LNAs that can act as therapeutic agents. Many examples of therapeutic nucleoside analogues are known and similar derivatives of the nucleoside analogues disclosed herein can be synthesised using the procedures known from the literature (E. De Clercq, *J. Med. Chem.* 1995, 38, 2491; P. Herdewijn and E. De Clercq: Classical Antiviral Agents and Design og New Antiviral Agents. In: A Textbook of Drug Design and Development; Eds. P. Krogsgaard-Larsen, T. Liljefors and U. Madsen; Harwood Academic Publishers, Amsterdam, 1996, p. 425; I. K. Larsen: Anticancer Agents. In: A Textbook of Drug Design and Development; Eds. P. Krogsgaard-Larsen, T. Liljefors and U. Madsen; Harwood Academic Publishers, Amsterdam, 1996, p. 460).

Double-stranded RNA has been demonstrated to posses anti-viral activity and tumour suppressing activity (Sharp et al., Eur. J. Biochem. 230(1): 97-103, 1995, Lengyel-P. et al., Proc. Natl. Acad. Sci. U.S.A., 90(13): 5893-5, 1993, and Laurent-Crawford et al., AIDS Res. Hum. Retroviruses, 8(2): 285-90, 1992). It is likely that double stranded LNAs may mimic the effect of therapeutically active double stranded RNAs and accordingly such double stranded LNAs has a potential as therapeutic drugs.

When used herein, the term "natural nucleic acid" refers to nucleic acids in the broadest sense, like for instance nucleic acids present in intact cells of any origin or vira or nucleic acids released from such sources by chemical or physical means or nucleic acids derived from such primary sources by way of amplification. The natural nucleic acid may be single, double or partly double stranded, and may be a relatively pure species or a mixture of different nucleic acids. It may also be a component of a crude biological sample containing other nucleic acids and other cellular components. On the other hand, the term "synthetic nucleic acids" refers to any nucleic acid produced by chemical synthesis.

The present invention also provides the use of LNA modified oligonucleotides in nucleic acid based therapeutic, diagnostics and molecular biology. The LNA modified oligonucleotides can be used in the detection, identification, capture, characterisation, quantification and fragmentation of natural or synthetic nucleic acids, and as blocking agents for translation and transcription in vivo and in vitro. In many cases it will be of interest to attach various molecules to LNA modified oligonucleotides. Such molecules may be attached to either end of the oligonucleotide or they may be attached at one or more internal positions. Alternatively, they may be attached to the oligonucleotide via spacers attached to the 5' or 3' end. Representative groups of such molecules are DNA intercalators, photochemically active groups, thermochemically active groups, chelating groups, reporter groups, and ligands. Generally all methods for labelling unmodified DNA and RNA oligonucleotides with these molecules can also be used to label LNA modified oligonucleotides. Likewise, all methods used for detecting labelled oligonucleotides generally apply to the corresponding labelled, LNA modified oligonucleotides.

Therapy

The term "strand displacement" relates to a process whereby an oligonucleotide binds to its complementary target sequence in a double stranded DNA or RNA so as to displace the other strand from said target strand.

In an aspect of the present invention, LNA modified oligonucleotides capable of performing "strand displacement" are exploited in the development of novel pharmaceutical drugs based on the "antigene" approach. In contrast to oligonucleotides capable of making triple helices, such "strand displacement" oligonucleotides allow any sequence in a dsDNA to be targeted and at physiological ionic strength and pH.

The "strand displacing" oligonucleotides can also be used advantageously in the antisense approach in cases where the RNA target sequence is inaccessible due to intramolecular hydrogen bonds. Such intramolecular structures may occur in mRNAs and can cause significant problems when attempting to "shut down" the translation of the mRNA by the antisense approach.

Other classes of cellular RNAs, like for instance tRNAs, rRNAs snRNAs and scRNAs, contain intramolecular structures that are important for their function. These classes of highly structured RNAs do not encode proteins but rather (in the form of RNA/protein particles) participate in a range of cellular functions such as mRNA splicing, polyadenylation, translation, editing, maintenance of chromosome end integrity, etc. Due to their high degree of structure, that impairs or even prevent normal oligonucleotides from hybridising efficiently, these classes of RNAs has so far not attracted interest as antisense targets.

The use of high affinity LNA monomers should facilitate the construction of antisense probes of sufficient thermostability to hybridise effectively to such target RNAs. Therefore, in a preferred embodiment, LNA is used to confer sufficient affinity to the oligonucleotide to allow it to hybridise to these RNA classes thereby modulating the qualitative and/or quantitative function of the particles in which the RNAs are found.

In some cases it may be advantageous to down-regulate the expression of a gene whereas in other cases it may be advantageous to activate it. As shown by Møllegaard et al. (Møllegaard, N. E.; Buchardt, O.; Egholm, M.; Nielsen, P. E. *Proc. Natl. Acad. Sci. U.S.A.* 1994, 91, 3892), oligomers capable of "strand displacement" can function as RNA transcriptional activators. In an aspect of the present invention, the LNAs capable of "strand displacement" are used to activate genes of therapeutic interest.

In chemotherapy of numerous viral infections and cancers, nucleosides and nucleoside analogues have proven effective. LNA nucleosides are potentially useful as such nucleoside based drugs.

Various types of double-stranded RNAs inhibit the growth of several types of cancers. Duplexes involving one or more LNA oligonucleotide(s) are potentially useful as such double-stranded drugs.

The invention also concerns a pharmaceutical composition comprising a pharmaceutically active LNA modified oligonucleotide or a pharmaceutically active LNA monomer as defined above in combination with a pharmaceutically acceptable carrier.

Such compositions may be in a form adapted to oral, parenteral (intravenous, intraperitoneal), intramuscular, rectal, intranasal, dermal, vaginal, buccal, ocularly, or pulmonary administration, preferably in a form adapted to oral administration, and such compositions may be prepared in a manner well-known to the person skilled in the art, e.g. as generally described in "Remington's Pharmaceutical Sciences", 17. Ed. Alfonso R. Gennaro (Ed.), Mark Publishing Company, Easton, Pa., U.S.A., 1985 and more recent editions and in the monographs in the "Drugs and the Pharmaceutical Sciences" series, Marcel Dekker.

Diagnostics

Several diagnostic and molecular biology procedures have been developed that utilise panels of different oligonucleotides to simultaneously analyse a target nucleic acid for the presence of a plethora of possible mutations. Typically, the oligonucleotide panels are immobilised in a predetermined pattern on a solid support such that the presence of a particular mutation in the target nucleic acid can be revealed by the position on the solid support where it hybridises. One important prerequisite for the successful use of panels of different oligonucleotides in the analysis of nucleic acids is that they are all specific for their particular target sequence under the single applied hybridisation condition. Since the affinity and specificity of standard oligonucleotides for their complementary target sequences depend heavily on their sequence and size this criteria has been difficult to fulfil so far.

In a preferred embodiment, therefore, LNAs are used as a means to increase affinity and/or specificity of the probes and as a means to equalise the affinity of different oligonucleotides for their complementary sequences. As disclosed herein such affinity modulation can be accomplished by, e.g., replacing selected nucleosides in the oligonucleotide with an LNA carrying a similar nucleobase. As further shown herein, different classes of LNAs exhibit different affinities for their complementary nucleosides. For instance, the 2-3 bridged LNA with the T-nucleobase exhibits less affinity for the A-nucleoside than the corresponding 2-4 bridged LNA. Hence, the use of different classes of LNAs offers an additional level for fine-tuning the affinity of a oligonucleotide.

In another preferred embodiment the high affinity and specificity of LNA modified oligonucleotides is exploited in the sequence specific capture and purification of natural or synthetic nucleic acids. In one aspect, the natural or synthetic nucleic acids are contacted with the LNA modified oligonucleotide immobilised on a solid surface. In this case hybridisation and capture occurs simultaneously. The captured nucleic acids may be, for instance, detected, characterised, quantified or amplified directly on the surface by a variety of methods well known in the art or it may be released from the surface, before such characterisation or amplification occurs, by subjecting the immobilised, modified oligonucleotide and captured nucleic acid to dehybridising conditions, such as for example heat or by using buffers of low ionic strength.

The solid support may be chosen from a wide range of polymer materials such as for instance CPG (controlled pore glass), polypropylene, polystyrene, polycarbonate or polyethylene and it may take a variety of forms such as for instance a tube, a micro-titer plate, a stick, a bead, a filter, etc. The LNA modified oligonucleotide may be immobilised to the solid support via its 5' or 3' end (or via the terminus of linkers attached to the 5' or 3' end) by a variety of chemical or photochemical methods usually employed in the immobilisation of oligonucleotides or by non-covalent coupling such as for instance via binding of a biotinylated LNA modified oligonucleotide to immobilised streptavidin. One preferred method for immobilising LNA modified oligonucleotides on different solid supports is photochemical using a photochemically active anthraquinone covalently attached to the 5' or 3' end of the modified oligonucleotide (optionally via linkers) as described in (WO 96/31557). Thus, the present invention also provide a surface carrying an LNA modified oligonucleotide.

In another aspect the LNA modified oligonucleotide carries a ligand covalently attached to either the 5' or 3' end. In this case the LNA modified oligonucleotide is contacted with the natural or synthetic nucleic acids in solution whereafter the hybrids formed are captured onto a solid support carrying molecules that can specifically bind the ligand.

In still another aspect, LNA modified oligonucleotides capable of performing "strand displacement" are used in the capture of natural and synthetic nucleic acids without prior denaturation. Such modified oligonucleotides are particularly useful in cases where the target sequence is difficult or impossible to access by normal oligonucleotides due to the rapid formation of stable intramolecular structures. Examples of nucleic acids containing such structures are rRNA, tRNA, snRNA and scRNA.

In another preferred embodiment, LNA modified oligonucleotides designed with the purpose of high specificity are used as primers in the sequencing of nucleic acids and as primers in any of the several well known amplification reactions, such as the PCR reaction. As shown herein, the design of the LNA modified oligonucleotides determines whether it will sustain a exponential or linear target amplification. The products of the amplification reaction can be analysed by a variety of methods applicable to the analysis of amplification products generated with normal DNA primers. In the particular case where the LNA modified oligonucleotide primers are designed to sustain a linear amplification the resulting amplicons will carry single stranded ends that can be targeted by complementary probes without denaturation. Such ends could for instance be used to capture amplicons by other complementary LNA modified oligonucleotides attached to a solid surface.

In another aspect, LNA modified oligos capable of "strand displacement" are used as primers in either linear or exponential amplification reactions. The use of such oligos is expected to enhance overall amplicon yields by effectively competing with amplicon re-hybridisation in the later stages of the amplification reaction. Demers, et al. (Nucl. Acid Res. 1995, Vol 23, 3050-3055) discloses the use of high-affinity, non-extendible oligos as a means of increasing the overall yield of a PCR reaction. It is believed that the oligomers elicit these effect by interfering with amplicon re-hybridisation in the later stages of the PCR reaction. It is expected that LNA modified oligos blocked at their 3' end will provide the same advantage. Blocking of the 3' end can be achieved in numerous ways like for instance by exchanging the 3' hydroxyl group with hydrogen or phosphate. Such 3' blocked LNA modified oligos can also be used to selectively amplify closely related nucleic acid sequences in a way similar to that described by Yu et al. (Biotechniques, 1997, 23, 714-716).

In recent years, novel classes of probes that can be used in for example real-time detection of amplicons generated by target amplification reactions have been invented. One such class of probes have been termed "Molecular Beacons". These probes are synthesised as partly self-complementary oligonucleotides containing a fluorophor at one end and a quencher molecule at the other end. When free in solution the probe folds up into a hairpin structure (guided by the self-complimentary regions) which positions the quencher in sufficient closeness to the fluorophor to quench its fluorescent signal. Upon hybridisation to its target nucleic acid, the hairpin opens thereby separating the fluorophor and quencher and giving off a fluorescent signal.

Another class of probes have been termed "Taqman probes". These probes also contain a fluorophor and a quencher molecule. Contrary to the Molecular Beacons, however, the quenchers ability to quench the fluorescent signal from the fluorophor is maintained after hybridisation of the probe to its target sequence. Instead, the fluorescent signal is generated after hybridisation by physical detachment of either the quencher or fluorophor from the probe by the action of the 5' exonuclease activity of a polymerase which has initiated synthesis from a primer located 5' to the binding site of the Taqman probe. High affinity for the target site is an important feature in both types of probes and consequently such probes tends to be fairly large (typically 30 to 40 mers). As a result, significant problems are encountered in the production of high quality probes. In a preferred embodiment, therefore, LNA is used to improve production and subsequent performance of Taqman probes and Molecular Beacons by reducing their size whilst retaining the required affinity.

In a further aspect, LNAs are used to construct new affinity pairs (either fully or partially modified oligonucleotides). The affinity constants can easily be adjusted over a wide range and a vast number of affinity pairs can be designed and synthesised. One part of the affinity pair can be attached to the molecule of interest (e.g. proteins, amplicons, enzymes, polysaccharides, antibodies, haptens, peptides, PNA, etc.) by standard methods, while the other part of the affinity pair can be attached to e.g. a solid support such as beads, membranes, micro-titer plates, sticks, tubes, etc. The solid support may be chosen from a wide range of polymer materials such as for instance polypropylene, polystyrene, polycarbonate or polyethylene. The affinity pairs may be used in selective isolation, purification, capture and detection of a diversity of the target molecules mentioned above.

The principle of capturing an LNA-tagged molecule by ways of interaction with another complementary LNA oligonucleotide (either fully or partially modified) can be used to create an infinite number of novel affinity pairs.

In another preferred embodiment the high affinity and specificity of LNA modified oligonucleotides are exploited in the construction of probes useful in in-situ hybridisation. For instance, LNA could be used to reduce the size of traditional DNA probes whilst maintaining the required affinity thereby increasing the kinetics of the probe and its ability to penetrate the sample specimen. The ability of LNA modified oligonucleotides to "strand invade" double stranded nucleic acid structures are also of considerable advantage in in-situ hybridisation, because it facilitates hybridisation without prior denaturation of the target DNA/RNA.

In another preferred embodiment, LNA modified oligonucleotides to be used in antisense therapeutics are designed with the dual purpose of high affinity and ability to recruit RNAseH. This can be achieved by, for instance, having LNA segments flanking an unmodified central DNA segment.

The present invention also provides a kit for the isolation, purification, amplification, detection, identification, quantification, or capture of natural or synthetic nucleic acids, where the kit comprises a reaction body and one or more LNA modified oligonucleotides (oligomer) as defined herein. The LNA modified oligonucleotides are preferably immobilised onto said reactions body.

The present invention also provides a kit for the isolation, purification, amplification, detection, identification, quantification, or capture of natural or synthetic nucleic acids, where the kit comprises a reaction body and one or more LNAs as defined herein. The LNAs are preferably immobilised onto said reactions body (e.g. by using the immobilising techniques described above).

For the kits according to the invention, the reaction body is preferably a solid support material, e.g. selected from borosilicate glass, soda-lime glass, polystyrene, polycarbonate, polypropylene, polyethylene, polyethyleneglycol terephthalate, polyvinylacetate, polyvinylpyrrolidinone, polymethylmethacrylate and polyvinylchloride, preferably polystyrene and polycarbonate. The reaction body may be in the form of a specimen tube, a vial, a slide, a sheet, a film, a bead, a pellet, a disc, a plate, a ring, a rod, a net, a filter, a tray, a microtitre plate, a stick, or a multi-bladed stick.

The kits are typically accompanied by a written instruction sheet stating the optimal conditions for use of the kit.

The above-mentioned diagnostic and therapeutic aspects of the present invention have been illustrated with the following examples.

Experimental

General

All reagents were obtained from commercial suppliers and were used without further purification. After drying any organic phase using $Na_2SO_4$, filtration was performed. The silica gel (0.040-0.063 mm) used for column chromatography was purchased from Merck. NMR spectra were recorded at 300 MHz or 250 MHz for $^1H$ NMR and 62.9 MHz for $^{13}C$ NMR and at 202.33 MHz for $^{31}P$ NMR. δ-Values are in ppm relative to tetramethylsilane as internal standard ($^1H$ NMR and $^{13}C$ NMR) and relative to 85% $H_3PO_4$ as external standard ($^{31}P$ NMR). Assignments of NMR peaks are given according to standard nucleoside nomenclature. El mass spectra, FAB mass spectra and Plasma Desorption mass spectra were recorded to gain information on the molecular weight of synthesised compounds. Oligonucleotide analogues were synthesised using the phosphoramidite methodology. Purification of 5'-O-DMT-ON or 5'-O-DMT-OFF oligonucleotide analogues was accomplished using disposable reversed phase chromatography cartridges or reversed phase HPLC when necessary. Matrix-assisted laser desorption mass spectra were obtained to verify the molecular weight and monomer composition of representative oligonucleotide samples. Capillary gel electrophoresis was performed to verify the purity of representative oligonucleotide samples.

The specific descriptions below are accompanied by FIGS. 2-41 and Tables 1-10. Unless otherwise stated in the following examples, "LNA" designates the 2'-4'-bridged variant illustrated with the formula Z in FIG. 2.

Preparation of LNA Monomers

EXAMPLE 1

3-C-Allyl-1,2-O-isopropylidene-α-D-ribofuranose (0A). Method 1: A solution of 5-O-t-butyldimethylsilyl-1,2-O-isopropylidene-α-D-ribofuran-3-ulose (Y. Yoshimura, T. Sano, A. Matsuda and T. Ueda, *Chem. Pharm. Bull.,* 1988, 36, 162) (17.8 g, 58.9 mmol) in anhydrous THF (980 $cm^3$) was stirred at 0° C. and 1 M allylmagnesium bromide in anhydrous ether (130 $cm^3$, 130 mmol) was added dropwise. After stirring for 2 h, a saturated aqueous solution of ammonium chloride (800 $cm^3$) was added and the mixture was extracted with dichloromethane (3×400 $cm^3$). The organic phase was washed with brine (3×450 $cm^3$) and dried ($Na_2SO_4$). The solvent was removed under reduced pressure and the residue was dissolved in anhydrous THF (700 $cm^3$). A 1.1 M solution of tetrabutylammonium fluoride in THF (54.4 $cm^3$, 59.8 mmol) was added and the mixture was stirred at room temperature for 1 h and evaporated to dryness. The residue was dissolved in dichloromethane (1700 $cm^3$) and was washed with a saturated aqueous solution of sodium hydrogencarbonate (3×500 $cm^3$) and dried ($Na_2SO_4$). The solvent was removed under reduced pressure and the residue was purified by silica gel column chromatography using dichloromethane/methanol (98:2, v/v) as eluent to give furanose OA as a white solid material (9.42 g, 69%). Method 2: Furanose OA was analogously synthesised from 5-O-t-butyldiphenylsilyl-1,2-O-isopropylidene-α-D-ribofuran-3-ulose (T. F. Tam and B. Fraser-Reid, *J. Chem. Soc., Chem. Commun.,* 1980, 556) (9.5 g, 22.2 mmol) using: anhydrous THF (425 $cm^3$); a 1 M solution of allylmagnesium bromide in anhydrous ether (130 $cm^3$, 130 mmol); a saturated aqueous solution of ammonium chloride (490 $cm^3$); ether for extraction (350+2×160 $cm^3$); brine (2×160 $cm^3$); a 1.1 M solution of tetrabutylammonium fluoride in THF (22.3 $cm^3$, 24.6 mmol); anhydrous THF (400 $cm^3$); dichloromethane (1400 $cm^3$); a saturated aqueous solution of sodium hydrogencarbonate (3×500 $cm^3$); brine (500 $cm^3$) and ($Na_2SO_4$). $\delta_H$ ($(CD_3)_2SO$) 5.84 (1 H, m, 2'-H), 5.65 (1 H, d, J 3.8, 1-H), 5.12 (1H, d, J 6.1, 3'-$H_a$), 5.06 (1H, br s, 3'-$H_b$), 4.76 (1H, s, 3-OH), 4.64 (1H, t, J 5.4, 5-OH), 4.16 (1 H, d, J 3.8, 2-H), 3.84 (1 H, dd, J 2.2, 8.1, 4-H), 3.56 (1 H, ddd, J 2.3, 5.6, 11.8, 5-$H_a$), 3.42 (1 H, m, 5-$H_b$), 2.16 (1 H, dd, J 6.1, 14.3, 1'-$H_a$), 1.98 (1 H, dd, J 8.2, 14.3, 1'-$H_b$), 1.46 (3 H, s, $CH_3$), 1.25 (3 H, s, $CH_3$). $\delta_C$ ($CDCl_3$) 133.5 (C-2'), 117.9 (C-3'), 110.8 ($C(CH_3)_2$), 102.9 (C-1), 82.6, 81.0, 77.7 (C-2, C-3, C-4), 59.4 (C-5), 36.4 (C-1'), 26.4, 26.3 ($CH_3$) (Found: C, 57.4; H, 8.0; $C_{11}H_{18}O_5$ requires C, 57.4; H, 7.9%).

EXAMPLE 2

3-C-Allyl-3,5-di-O-benzyl-1,2-O-isopropylidene-α-D-ribofuranose (0B). A 60% suspension of sodium hydride (4.9 g, 123 mmol) in anhydrous DMF (100 $cm^3$) was stirred at 0° C. and a solution of furanose 0A (9.42 g, 40.9 mmol) in anhydrous DMF (65 $cm^3$) was added dropwise over 45 min. The solution was stirred for 1 h at 50° C. and cooled to 0° C. A mixture of benzyl bromide (14.5 $cm^3$, 121 mmol) and anhydrous DMF (14.5 $cm^3$) was added dropwise and the mixture was stirred at room temperature for 18 h. The reaction mixture was evaporated to dryness and a solution of the residue in dichloromethane (700 $cm^3$) was washed with a saturated aqueous solution of sodium hydrogencarbonate (2×450 $cm^3$) and dried ($Na_2SO_4$). The solvent was removed under reduced pressure and the residue was purified by silica gel column chromatography using petroleum ether/ethylacetate (9:1, v/v) as eluent to give compound 0B as an oil (14.5 g, 86%). $\delta_H$ ($CDCl_3$) 7.39-7.21 (10H, m, Bn), 5.92 (1 H, m, 2'-H), 5.71 (1 H, d, J 3.8, 1-H), 5.17-5.09 (2H, m, 3'-$H_a$, 3'-$H_b$), 4.67 (2 H, m, Bn), 4.60 (1 H, d, J 12.2, Bn), 4.52 (1 H, d, J 12.1, Bn), 4.43 (1 H, m, 4-H), 4.42 (1 H, d, J 3.8, 2-H), 3.73 (1 H, dd, J 3.2, 10.8, 5-$H_a$), 3.66 (1 H, dd, J 7.4, 10.8, 5-$H_b$), 2.50 (1 H, dd, J 7.7, 14.9, 1'-$H_a$), 2.39 (1 H, dd, J 6.5, 14.9, 1'-$H_b$), 1.60 (3 H, s, $CH_3$), 1.34 (3 H, s, $CH_3$). $\delta_C$ ($CDCl_3$) 138.7, 138.1 (Bn), 132.6 (C-2'), 128.3, 128.2, 127.7, 127.5, 127.4, 127.4 (Bn), 118.5 (C-3'), 112.6 ($C(CH_3)_2$), 104.1 (C-1), 86.5, 82.1, 80.4 (C-2, C-3, C-4), 73.4, 68.6 (Bn), 67.0 (C-5), 35.8 (C-1'), 26.8, 26.6 ($CH_3$). FAB-MS m/z 433 $[M+Na]^+$ (Found: C, 73.4; H, 7.4; $C_{25}H_{30}O_5$ requires C, 73.2; H, 7.4%).

EXAMPLE 3

3-C-Allyl-1,2-di-O-acetyl-3,5-di-O-benzyl-D-ribofuranose (0C). A solution of furanose 0B (12.42 g, 30.3 mmol) in 80% aqueous acetic acid (150 $cm^3$) was stirred at 90° C. for 3 h. The solvent was removed under reduced pressure and the residue was coevaporated with ethanol (3×75 $cm^3$), toluene (3×75 $cm^3$) and anhydrous pyridine (2×75 $cm^3$) and redissolved in anhydrous pyridine (60 $cm^3$). Acetic anhydride (46 $cm^3$) was added and the solution was stirred at room temperature for 48 h. A mixture of ice and water (300 $cm^3$) was added and the resulting mixture was extracted with dichloromethane (2×300 $cm^3$). The combined organic phase was washed with a saturated aqueous solution of sodium hydrogencarbonate (3×200 $cm^3$) and dried ($Na_2SO_4$). The solvent was evaporated and the residue was purified using silica gel column chromatography with petroleum ether/ethyl acetate (4:1, v/v) as eluent to give the anomeric mixture 0C (β:α~2:1) as an oil (13.3 g, 97%). $\delta_C$ ($CDCl_3$) 169.7, 169.6 (C═O), 138.7, 138.4, 137.7, 137.6 (Bn), 132.4, 132.2 (C-2'), 128.4 128.4, 128.2, 128.2, 127.8, 127.7, 127.7, 127.6, 127.3, 127.3, 126.9, 126.8 (Bn), 118.5 (C-3'), 99.4, 93.5 (C-1), 84.8, 83.7, 83.2, 82.0, 79.1, 75.5 (C-2, C-3, C-4), 73.7, 73.5, 69.3, 68.7

(Bn), 66.1 (C-5), 35.5, 34.9 (C-1), 21.1, 21.0, 20.7, 20.6 ($CH_3$) (Found: C, 68.7; H, 6.7; $C_{26}H_{30}O_7$ requires C, 68.8; H, 6.6%).

EXAMPLE 4

1-(2-O-Acetyl-3-C-allyl-3,5-di-O-benzyl-β-D-ribofuranosyl)thymine (1). To a stirred solution of the anomeric mixture 0C (β:α-2:1, 11.8 g, 26.0 mmol) (P. Nielsen, H. M. Pfundheller and J. Wengel, *Chem. Commun.,* 1997, 825; P. Nielsen, H. M. Pfundheller, C. E. Olsen and J. Wengel, *J. Chem. Soc., Perkin Trans.* 1, 1997, in the press) and thymine (6.55 g, 52.0 mmol) in anhydrous acetonitrile (250 $cm^3$) was added N,O-bis(trimethylsilyl)acetamide (44.9 $cm^3$, 182 mmol). The reaction mixture was stirred at reflux for 1 h and cooled to 0° C. Trimethylsilyl triflate (8.00 $cm^3$, 44.0 mmol) was added dropwise and the solution was stirred at room temperature for 12 h. An ice-cold saturated aqueous solution of sodium hydrogencarbonate (270 $cm^3$) was added and the mixture was extracted with dichloromethane (3×125 $cm^3$). The organic phase was washed with saturated aqueous solutions of sodium hydrogencarbonate (2×125 $cm^3$) and brine (2×125 $cm^3$) and dried ($Na_2SO_4$). The solvent was removed under reduced pressure and the residue was purified by silica gel column chromatography using dichloromethane/methanol (98:2, v/v) as eluent to give nucleoside 1 as a white solid material (11.6 g, 86%). $\delta_H$ ($CDCl_3$) 8.64 (1H, br s, NH), 7.75 (1 H, d, J 1.1, 6-H), 7.41-7.25 (10 H, m, Bn), 6.43 (1 H, d, J 8.2, 1'-H), 5.88 (1H, m, 2"-H), 5.66 (1 H, d, J 8.2, 2'-H), 5.12 (1 H, s, 3"-$H_a$), 5.07 (1 H, dd, J 1.5, 8.5, 3"-$H_b$), 4.85 (1 H, d, J 11.2, Bn), 4.64 (2 H, s, Bn), 4.63 (1 H, d, J 11.2, Bn), 4.33 (1 H, br s, 4'-H), 3.81 (1 H, dd, J 2.7, 11.1, 5'-$H_a$), 3.65 (1 H, m, 5'-$H_b$), 2.81-2.65 (2 H, m, 1"-$H_a$, 1"-$H_b$), 2.08 (3 H, s, $COCH_3$), 1.52 (3 H, d, J 0.8, $CH_3$). $\delta_C$ ($CDCl_3$) 170.1 (C═O), 163.6 (C-4), 150.9 (C-2), 138.1, 136.6 (Bn), 136.0 (C-6), 131.6 (C-2"), 128.8, 128.4, 128.3, 127.6, 127.5, 127.1 (Bn), 118.5 (C-3"), 111.1 (C-5), 84.2, 83.4, 83.1, 77.4 (C-1', C-2', C-3', C-4'), 73.6, 69.2 (Bn), 65.6 (C-5'), 33.7 (C-1"), 20.8 ($COCH_3$), 11.9 ($CH_3$) (Found: C, 66.8; H, 6.3; N, 5.1. $C_{29}H_{32}N_2O_7$ requires C, 66.9; H, 6.2; N, 5.4%).

EXAMPLE 5

1-(3-C-Allyl-3,5-di-O-benzyl-β-D-ribofuranosyl)thymine (2). To a stirred solution of nucleoside 1 (11.6 g, 22.3 mmol) in methanol (110 $cm^3$) was added sodium methoxide (3.03 g, 55.5 mmol). The reaction mixture was stirred at room temperature for 16 h and neutralised with dilute hydrochloric acid. The solvent was partly evaporated and the residue was dissolved in dichloromethane (2×400 $cm^3$). The organic phase was washed with a saturated aqueous solution of sodium hydrogencarbonate (3×250 $cm^3$) and dried ($Na_2SO_4$). The solvent was removed under reduced pressure to give 2 as a white solid material (10.1 g, 95%). $\delta_H$ ($CDCl_3$) 8.77 (1 H, br s, NH), 7.58 (1 H, d, J 1.2, 6-H), 7.41-7.25 (10 H, m, Bn), 6.14 (1H, m, 2"-H), 6.12 (1 H, d, J 7.8, 1'-H), 5.23 (1 H, m, 3"-$H_a$), 5.17 (1 H, br s, 3"-$H_b$), 4.68 (1 H, d, J 10.8, Bn), 4.59 (2 H, s, Bn), 4.55 (1 H, d, J 10.9, Bn), 4.39 (1 H, br s, 4'-H), 4.26 (1 H, dd J 7.8, 10.7, 2'-H), 3.84 (1 H, dd, J 3.1, 11.0, 5'-$H_a$), 3.58 (1 H, dd, J 1.4, 11.0, 5'-$H_b$), 3.04 (1 H, d, J 10.8, 2'-OH), 2.82-2.78 (2 H, m, 1"-$H_a$, 1"-$H_b$), 1.51 (3 H, d, J 1.0, $CH_3$). $\delta_C$ ($CDCl_3$) 163.5 (C-4), 151.1 (C-2), 137.3, 136.7 (Bn), 136.0 (C-6), 132.1 (C-2"), 128.8, 128.5, 128.3, 127.9, 127.6 (Bn), 118.4 (C-3"), 111.1 (C-5), 87.4, 82.6, 81.1, 79.3 (C-1', C-2', C-3', C-4'), 73.7, 69.8 (Bn), 64.7 (C-5'), 35.1 (C-1"), 11.9 ($CH_3$). (Found: C, 67.8; H, 6.1; N, 5.5. $C_{27}H_{30}N_2O_6$ requires C, 67.8; H, 6.3; N, 5.9%).

EXAMPLE 6

1-(3-C-Allyl-3,5-di-O-benzyl-2-O-methanesulfonyl-β-D-ribofuranosyl)thymine (3). To a stirred solution of nucleoside 2 (3.50 g, 7.31 mmol) in anhydrous pyridine (23 $cm^3$) at 0° C. was added methanesulphonyl chloride (1.69 $cm^3$, 21.89 mmol). The reaction mixture was stirred for 1 h at room temperature, water (100 $cm^3$) was added and extraction was performed using dichloromethane (3×150 $cm^3$). The organic phase was washed with a saturated aqueous solution of sodium hydrogencarbonate (3×200 $cm^3$) and dried ($Na_2SO_4$). The solvent was removed under reduced pressure and the residue purified by silica gel column chromatography using dichloromethane/methanol (99:1) as eluent to give 3 as a white solid material (3.64 g, 89%). $\delta_H$ ($CDCl_3$) 8.95 (1 H, br s, NH), 7.71 (1 H, d, J 1.1, 6-H), 7.39-7.25 (10 H, m, Bn), 6.52 (1 H, d, J 8.0, 1'-H), 5.90 (1H, m, 2"-H), 5.34 (1 H, d, J 7.9, 2'-H), 5.20-5.09 (2 H, m, 3"-$H_a$, 3"-$H_b$), 4.91 (1 H, d, J 11.2, Bn), 4.68 (1 H, d, J 11.3, Bn), 4.64 (2 H, s, Bn), 4.33 (1 H, br s, 4'-H), 3.81 (1 H, dd, J 2.5, 11.1, 5'-$H_a$), 3.73 (1 H, dd, J 1.1, 11.1, 5'-$H_b$), 3.08 (1 H, dd, J 5.5, 5.7, 1"-$H_a$), 2.99 (3 H, s, $CH_3$), 2.68 (1 H, m, 1"-$H_b$), 1.51 (3 H, d, J 0.8, $CH_3$). $\delta_C$ ($CDCl_3$) 163.4 (C-4), 150.8 (C-2), 137.9, 136.3 (Bn), 135.5 (C-6), 131.0 (C-2"), 128.8, 128.3, 127.5, 127.2 (Bn), 119.3 (C-3"), 111.6 (C-5), 84.1, 83.6, 82.4, 82.2 (C-1', C-2', C-3', C-4'), 73.7, 68.9 (Bn), 66.2 (C-5'), 38.7 ($CH_3$), 33.0 (C-1"), 11.9 ($CH_3$) (Found: C, 60.5; H, 5.8; N, 4.9. $C_{28}H_{32}N_2O_8S$ requires C, 60.4; H, 5.8; N, 5.0%).

EXAMPLE 7

1-(3-C-Allyl-3,5-di-O-benzyl-β-D-arabinofuranosyl)thymine (4). A solution of nucleoside 3 (3.59 g, 6.45 mmol) in ethanol (72 $cm^3$), water (72 $cm^3$) and 1 M aqueous sodium hydroxide (20.6 $cm^3$) was stirred under reflux for 18 h. After neutralisation with dilute hydrochloric acid, the solvent was removed under reduced pressure and the residue was dissolved in dichloromethane (3×150 $cm^3$). The organic phase was washed with a saturated aqueous solution of sodium hydrogencarbonate (3×200 $cm^3$) and dried ($Na_2SO_4$). The solvent was removed under reduced pressure and the residue was purified by silica gel column chromatography using dichloromethane/methanol (99:1, v/v) as eluent to give 4 as a white solid material (2.32 g, 74%). $\delta_H$ ($CDCl_3$) 7.60 (1 H, d, J 1.2, 6-H), 7.50-7.23 (10 H, m, Bn), 6.22 (1 H, d, J 2.9, 1'-H), 5.80 (1H, m, 2"-H), 5.15-5.08 (2 H, m, 3"-$H_a$, 3"-$H_b$), 4.86-4.33 (6 H, m, 2×Bn, 2'-H, 4'-H), 3.82-3.71 (2 H, m, 5'-$H_a$, 5'-$H_b$), 2.72 (1 H, m, 1"-$H_a$), 2.52 (1 H, dd, J 7.6, 16.1, 1"-$H_b$), 1.70 (3 H, d, J 0.9, $CH_3$). $\delta_C$ ($CDCl_3$) 165.1 (C-4), 150.4 (C-2), 138.4, 136.8 (Bn), 137.7 (C-6), 132.3 (C-2"), 128.77 128.4, 128.3, 128.0, 127.9, 127.6 (Bn), 118.5, (C-3"), 107.8 (C-5), 88.0, 87.8, 83.7 (C-1', C-3', C-4'), 73.7, 72.9, 69.4 (Bn, C-2'), 64.7 (C-5'), 31.1 (C-1"), 12.4 ($CH_3$) (Found: C, 67.5; H, 6.3; N, 5.3. $C_{27}H_{30}N_2O_6$,$0.25H_2O$ requires C, 67.1; H, 6.4; N, 5.8%).

EXAMPLE 8

1-(3,5-Di-O-benzyl-3-C-(2-hydroxyethyl)-β-D-arabinofuranosyl)thymine (5). To a stirred solution of nucleoside 4 (2.26 g, 4.68 mmol) in THF (12 $cm^3$) and water (12 $cm^3$) was added sodium periodate (3.04 g, 14.2 mmol) and a 2.5% solution of osmium tetraoxide in tert-butanol (w/w, 0.603 $cm^3$, 40 μmol). The solution was stirred at room temperature for 45 min. Water (25 $cm^3$) was added and the solution was extracted with dichloromethane (2×50 $cm^3$). The organic phase was washed with a saturated aqueous solution of sodium hydrogencarbonate (3×30 $cm^3$) and dried ($Na_2SO_4$). The solvent was removed under reduced pressure and the residue was redissolved in THF (12 $cm^3$) and water (12 $cm^3$). The mixture was stirred at room temperature and sodium boronhydride (182 mg, 4.71 mmol) was added. After stirring for 1.5 h, water (25 $cm^3$) was added and the solution was extracted with dichloromethane (2×50 $cm^3$). The organic phase was washed with a saturated aqueous solution of sodium hydrogencarbonate (3×30 $cm^3$) and dried ($Na_2SO_4$). The solvent was removed under reduced pressure and the residue was purified by silica gel column chromatography using dichloromethane/methanol (98:2, v/v) as eluent to give 5 as a white solid material (1.13 g, 49%). $\delta_H$ ($CDCl_3$) 9.29 (1 H, br s, NH), 7.47 (1 H, d, J 1.1, 6-H), 7.38-7.25 (10 H, m, Bn), 6.22 (1 H, d, J 3.4, 1'-H), 4.62 (2 H, s, Bn), 4.60 (1 H, m, 4'-H), 4.46 (2 H, s, Bn), 4.35 (1H, dd, J 3.4, 7.5, 2'-H), 3.83-3.73 (4 H, m, 2×5'-H, 2×2"-H), 2.67 (1 H, br s, OH), 2.07-2.01 (2 H, m, 2×1"-H), 1.77 (3 H, d, J 0.5, $CH_3$). $\delta_C$ ($CDCl_3$) 164.3 (C-4), 150.3 (C-2), 137.6, 137.4 (Bn, C-6), 136.7 (Bn), 128.6, 128.4, 128.2, 127.8, 127.6, 127.3, 127.1 (Bn), 108.4 (C-5), 88.0, 87.7, 81.6, 74.7 (C-1', C-2', C-3', C-4'), 73.7, 69.6 (Bn), 64.6 (C-5'), 57.7 (C-2"), 28.6 (C-1"), 12.4 ($CH_3$). FAB-MS m/z 483 $[M+H]^+$, 505 $[M+Na]^+$ (Found: C, 63.6; H, 6.2; N, 5.4. $C_{26}H_{30}N_2O_7$,$0.5H_2O$ requires C, 63.5; H, 6.4; N, 5.7%).

EXAMPLE 9

(1S,5R,6R,8R)-5-Hydroxy-6-(hydroxymethyl)-8-(thymin-1-yl)-2,7-dioxabicyclo[3.3.0]-octane (6). A solution of nucleoside 5 (1.08 g, 2.20 mmol) in anhydrous pyridine (5.0 $cm^3$) was stirred at 0° C. and a solution of p-toluenesulphonyl chloride (462 mg, 2.47 mmol) in anhydrous pyridine (2.0 $cm^3$) was added dropwise. After stirring at room temperature for 20 h and addition of a mixture of water and ice (70 $cm^3$), extraction was performed with dichloromethane (2×75 $cm^3$). The organic phase was washed with a saturated aqueous solution of sodium hydrogencarbonate (3×50 $cm^3$) and dried ($Na_2SO_4$). The solvent was removed under reduced pressure and the residue was purified by silica gel column chromatography using dichloromethane/methanol (99:1, v/v) as eluent to give an intermediate which after evaporation was dissolved in anhydrous DMF (4.0 $cm^3$). The solution was added dropwise to a stirred suspension of 60% sodium hydride (203 mg, 4.94 mmol) in anhydrous DMF (4.0 $cm^3$) at 0° C. The mixture was stirred for 18 h and water (20 $cm^3$) was added. After neutralisation with hydrochloric acid, dichloromethane (75 $cm^3$) was added. The organic phase was washed with a saturated aqueous solution of sodium hydrogencarbonate (3×50 $cm^3$) and dried ($Na_2SO_4$). The solvent was removed under reduced pressure and the residue was purified by silica gel column chromatography using dichloromethane/methanol (98:2, v/v) as eluent to give a white solid material (858 mg). A solution of this white solid material (846 mg, 1.80 mmol) in ethanol (10.0 $cm^3$) was stirred at room temperature and 20% palladium hydroxide over carbon (400 mg) was added. The mixture was degassed with argon and placed in a hydrogen atmosphere. After stirring for 2 h the mixture was directly purified by silica gel column chromatography using dichloromethane/methanol (97:3, v/v) as eluent to give 6 as a white solid material (444 mg, 82%). $\delta_H$ ($(CD_3)_2SO$) 11.3 (1 H, br s, NH), 7.36 (1 H, d, J 1.1, 6-H), 5.80 (1 H, d, J 4.3, 1'-H), 5.61 (1 H, s, OH), 4.86 (1 H, m, 5'-$H_a$), 3.89 (1 H, d, J 4.2, 2'-H), 3.85 (1 H, m, 2"-$H_a$), 3.83-3.64 (3 H, m, 4'-H, 2"-$H_b$), 2.14 (1 H, m, 1"-$H_a$), 1.81 (1 H, m, 1"-$H_b$), 1.78 (3 H, d, J 1.0, $CH_3$). $\delta_C$ ($CD_3OD$) 166.7 (C-4), 152.2 (C-2), 139.7 (C-6), 110.1 (C-5), 89.4, 89.1, 85.5, 85.2 (C-1', C-2', C-3', C-4'), 71.4 (C-2"), 61.6 (C-5'), 37.0 (C-1"), 12.7 ($CH_3$) (Found: C, 47.4; H, 5.7; N, 9.0. $C_{12}H_{16}N_2O_6$,$H_2O$ requires C, 47.7; H, 6.0; N, 9.3%).

EXAMPLE 10

(1S,5R,6R,8R)-6-(4,4'-Dimethoxytrityloxymethyl)-5-hydroxy-8-(thymin-1-yl)-2,7-dioxabicyclo[3.3.0]nonane (7). A solution of nucleoside 6 (310 mg, 1.09 mmol) in anhydrous pyridine (2.5 $cm^3$) was stirred at room temperature and 4,4'-dimethoxytrityl chloride (593 mg, 1.83 mmol) was added. After stirring for 3 h, additional 4,4'-dimethoxytrityl chloride (100 mg, 0.310 mmol) was added. After stirring for another 2 h, methanol (0.5 $cm^3$) was added and the mixture was evaporated. The residue was dissolved in dichloromethane (5 $cm^3$) and washed with an aqueous saturated solution of sodium hydrogencarbonate (3×5 $cm^3$). The organic phase was dried ($Na_2SO_4$) and evaporated under reduced pressure. The residue was purified by silica gel column chromatography with dichloromethane/methanol (99:1, v/v) as eluent to give 7 as a white solid material (618 mg, 97%). $\delta_H$ ($CDCl_3$) 9.04 (1H, br S, NH), 7.47-7.16 (10 H, m, 6-H, DMT), 6.86-6.82 (4 H, m, DMT), 6.06 (1 H, d, J 4.1, 1'-H), 4.35 (1 H, d, J 4.1, 2'-H), 4.03 (1 H, m, 4'-H), 3.89 (1 H, m, 2"-$H_a$), 3.79 (6 H, s, 2×$OCH_3$), 3.61 (1H, m, 5'-$H_a$), 3.32-3.26 (2H, m, 5'-$H_b$, 2"-$H_b$), 1.94-1.69 (2 H, m, 1"-$H_a$, 1"-$H_b$,), 1.89 (3 H, s, $CH_3$). $\delta_C$ ($CDCl_3$) 163.4 (C-4), 158.6 (DMT), 150.1 (C-2), 144.3 (DMT), 137.2 (C-6), 135.6, 135.3, 129.9, 129.9, 128.9, 128.1, 127.9, 126.9, 125.2, 113.2 (DMT), 109.3 (C-5), 88.7, 87.3, 86.9, 83.5, 81.0 (DMT, C-1', C-2', C-3', C-4'), 69.7 (C-2"), 62.1 (C-5'), 55.1 ($OCH_3$), 36.5 (C-1"), 12.5 ($CH_3$).

EXAMPLE 11

(1S,5R,6R,8R)-5-(2-Cyanoethoxy(diisopropylamino)phosphinoxy)-6-(4,4'-dimethoxytrityloxymethyl)-8-(thymin-1-yl)-2,7-dioxabicyclo[3.3.0]nonane (8). A solution of nucleoside 7 (436 mg, 0.743 mmol) in anhydrous dichloromethane (2.2 $cm^3$) and diisopropylethylamine (0.62 $cm^3$) was stirred at room temperature and 2-cyamoethyl N,N-diisopropylphosphoramidochloridite (0.33 $cm^3$, 1.46 mmol) was added. After stirring for 1.5 h, methanol (0.4 $cm^3$) and ethyl acetate (5 $cm^3$) were added and the mixture was washed with aqueous saturated solutions of sodium hydrogencarbonate (3×5 $cm^3$) and brine (3×5 $cm^3$). The organic phase was dried ($Na_2SO_4$) and evaporated under reduced pressure. The residue was purified by silica gel column chromatography using dichloromethane/-triethylamine (97:3, v/v) as eluent, the solvents were evaporated to give an oil which was dissolved in toluene (1 $cm^3$) and precipitation from hexane at −30° C. yielded 8 as a solid white material (517 mg, 88%). $\delta_p$ ($CDCl_3$) 142.0, 141.9.

EXAMPLE 12

1-(3,5-Di-O-benzyl-3-C-(2-hydroxyethyl)-β-D-ribofuranosyl)thymine (9). To a stirred solution of nucleoside 2 (1.00 g, 2.09 mmol) in THF (5.4 $cm^3$) and water (5.4 $cm^3$) was added sodium periodate (1.34 g, 6.27 mmol) and a 2.5% solution of osmium tetraoxide in tert-butanol (w/w, 0.265 $cm^3$, 19 μmol). The solution was stirred at room temperature for 45 min. Water (25 $cm^3$) was added and the solution was extracted with dichloromethane (2×50 $cm^3$). The organic phase was washed with a saturated aqueous solution of sodium hydrogencarbonate (3×30 $cm^3$) and dried ($Na_2SO_4$). The solvent was removed under reduced pressure and the residue was redissolved in THF (5.4 $cm^3$) and water (5.4 $cm^3$). The mixture was stirred at room temperature and sodium boronhydride (79 mg, 2.08 mmol) was added. After stirring for 1.5 h, water (25 $cm^3$) was added and the solution was extracted with dichloromethane (2×50 $cm^3$). The organic phase was washed with a saturated aqueous solution of sodium hydrogencarbonate (3×30 $cm^3$) and dried ($Na_2SO_4$). The solvent was removed under reduced pressure and the residue was purified by silica gel column chromatography using dichloromethane/methanol (98:2, v/v) as eluent to give nucleoside 9 as a white solid material (488 mg, 48%). $\delta_H$ ($CDCl_3$) 9.14 (1 H, br s, NH), 7.60 (1 H, d, J 1.1, 6-H), 7.40-7.22 (10 H, m, Bn), 6.25 (1 H, d, J 7.7, 1'-H), 4.59 (1 H, d, J 7.1 Bn), 4.49 (1 H, d, J 7.1 Bn), 4.39-3.30 (m, 8H, 4'-H, 2'-H, Bn, 5'-$H_a$, 5'-$H_b$, 2"-$H_a$, 2"-$H_b$), 2.23-2.00 (2 H, m, 1"-$H_a$, 1"-$H_b$), 1.49 (3 H, d, J 0.7, $CH_3$). $\delta_C$ ($CDCl_3$) 163.5 (C-4), 151.2 (C-2), 137.1, 136.5 (Bn), 135.7 (C-6), 128.7, 128.5, 128.2, 127.8, 127.6, 127.2 (Bn), 111.3 (C-5), 87.0, 82.7, 81.1, 78.3 (C-1', C-2', C-3', C-4'), 73.7, 69.6 (Bn), 64.4 (C-5'), 57.0 (C-2"), 32.4 (C-1"), 11.8 ($CH_3$) (Found: C, 63.9; H, 6.3; N, 5.4. $C_{26}H_{30}N_2O_7$,0.25$H_2O$ requires C, 64.1; H 6.3; N, 5.75%).

EXAMPLE 13

1-[3-C-(2-O-t-Butyldimethylsilyloxyethyl)-3,5-di-O-benzyl-βD-ribofuranosyl]thymine (10). A mixture of nucleoside 9 (1.80 g, 3.4 mmol) and t-butyldimethylsilyl chloride (0.585 g, 3.9 mmol) was dissolved in anhydrous pyridine (20 $cm^3$). After 2 h at room temperature the reaction mixture was evaporated to dryness, twice co-evaporated with toluene (2×10 $cm^3$) and re-dissolved in dichloromethane (150 $cm^3$). The solution was washed with a saturated aqueous solution of sodium hydrocarbonate (2×50 $cm^3$) and evaporated to give a foam. This material was purified by preparative silica-gel HPLC using gradient elution (0-3% methanol in dichloromethane, v/v) to give nucleoside 10 as a white solid material (1.86 g, 92%). $\delta_H$ ($CDCl_3$) 7.61 (1H, d, J 1.1, 6-H), 7.35-7.20 (10H, m, Bn), 6.27 (1H, d, J 7.9, 1'-H), 4.65-4.40 (4H, m, Bn, 2'-H), 4.37 (1H, s, Bn), 4.28 (1H, t, J 7.9, 4'-H), 4.35-3.55 (4H, m, 2"-$H_a$, 2"-$H_b$, 5'-$H_a$, 5'-$H_b$), 2.30-2.05 (2H, m, 1"-$H_a$, 1"-$H_b$), 1.46 (3H, s, 5-$CH_3$), 0.90 (9H, m, $CH_3$—C—Si), 0.08 (6H, m, $CH_3$—Si). $\delta_C$ ($CDCl_3$) 163.6 (C-6), 151.0 (C-2), 137.5, 136.6, 135.8 (C-5, Bn), 128.3, 128.1, 127.8, 127.2, 127.1, 126.8, 126.7 (Bn), 110.7 (C-4), 86.8, 82.5, 81.6, 78.3 (C-1', C-2', C-3', C-4'), 73.3, 69.8 (Bn), 64.46 (C-5'), 58.2 (C-2"), 32.9 (C-1"), 25.6, 25.4, 17.9, −3.9, −5.7 (TBDMS), 11.6 ($CH_3$). $FAB^+$-MS: m/z 597.19 $[M+H]^+$, 619.18 $[M+Na]^+$ (Found: C, 64.2; H, 7.4; N, 4.2; $C_{32}H_{44}O_7N_2Si$ requires C, 64.4; H, 7.4; N, 4.7%).

EXAMPLE 14

1-[3-C-(2-t-Butyldimethylsilyloxyethyl)-3,5-di-O-benzyl-β-D-erythro-pentofuran-2-ulosyl]thymine (11). A mixture nucleoside 10 (2.14 g, 3.59 mmol), 1.48 g (3.95 mmol) of pyridinium dichromate (1.48 g, 3.95) and activated 3 A molecular sieve powder (4 g) was suspended in anhydrous dichloromethane (80 $cm^3$). After cooling the mixture to −10° C., acetic anhydride (10 $cm^3$, 98 mmol) was added dropwise under vigorous stirring. The suspension was allowed to warm to room temperature and stirring was continued for 1.5 h whereupon the reaction was quenched by addition of triethylamine (20 $cm^3$). The mixture was diluted with dichloromethane to 300 $cm^3$ and was washed with water (2×200 $cm^3$). The organic phase was evaporated, and the residue purified by flash silica-gel chromatography using a gradient of 1.0, 1.2, 1.3, 1.4, 1.5% methanol in dichloromethane (v/v, total volume 250 $cm^3$ each) to give nucleoside 11 (1.89 g, 84.4%) as a white solid material. $\delta_H$ ($CDCl_3$) 7.35-7.20 (11H, m, Bn, 6-H), 6.40 (1H, s, 1'-H), 4.57 (1H, s, Bn), 4.52 (1H, s, Bn), 4.46 (1H, d, J 11.0, Bn), 4.29 (1H, d, J 11.0, Bn), 4.07 (1H, dd, J' 0.5, 2.2, 4'-H), 3.95-3.70 (4H, m, 2"-$H_a$, 2"-$H_b$, 5'-$H_a$, 5'-$H_b$), 2.05 (1H, m, 1"-$H_a$), 2.42 (1H, m, 1"-$H_b$), 1.42 (3H, d, J 1.1, 5-$CH_3$), 0.86 (9H, s, $CH_3$—C—Si), 0.01 (6H, s, $CH_3$—Si). $\delta_C$ ($CDCl_3$) 202.6 (C-2'), 163.7 (C-4), 151.2 (C-2), 137.7, 136.6, 136.5 (Bn, C-6), 128.7, 128.5, 128.2, 128.1, 127.7, 126.4, 126.3 (Bn), 110.9 (C-5), 84.5, 81.3, 80.2 (C-1', C-3', C-4'), 73.6, 70.4 (Bn), 66.0 (C-5'), 57.6 (C-2"), 27.3 (C-1"), 25.9, 25.7, 18.2, −5.8, −5.9 (TBDMS), 11.7 ($CH_3$). FAB-MS m/z 595.14 $[M+H]^+$ (Found: C, 64.1; H, 6.9; N, 4.5; $C_{32}H_{42}O_7N_2Si$ requires C, 64.6; H, 7.1; N, 4.7%).

EXAMPLE 15

(1S,5R,6R,8R)-1-Hydroxy-5-benzyloxy-6-benzyloxymethyl-8-(thymin-1-yl)-2,7-dioxabicyclo[3.3.0]octane (12). Compound 11 (1.80 g, 30.3 mmol) was dissolved in 0.5% HCl in methanol (w/w, 20 $cm^3$) and the mixture was stirred for 30 min at room temperature. After evaporation to dryness, the residue was dissolved in dichloromethane (100 $cm^3$) and washed with a saturated aqueous solution of sodium hydrogencarbonate (2×40 $cm^3$). The organic phase was evaporated and the residue was purified by flash silica-gel chromatography eluting with 2% methanol in dichloromethane (v/v) to yield nucleoside 12 (1.35 g, 93.5%) as a white solid material. $\delta_H$ ($CDCl_3$) 7.37-7.27 (11H, m, Bn, 6-H), 5.87 (1H, s, 1'-H), 4.71 (2H, s, Bn), 4.64 (1H, d, J 12.0, Bn), 4.56 (1H, d, J 12.0, Bn), 4.36 (1H, t, J 5.7, 4'-H), 4.16 (1H, m, 2"-$H_a$), 3.96 (1H, m, 2"-$H_b$), 3.74 (2H, m, 5'-$H_a$, 5'-$H_b$), 2.35-2.15 (2H, m, 1"-$H_a$, 1"-$H_b$), 1.88 (3H, s, $CH_3$). $\delta_C$ ($CDCl_3$) 163.7 (C-4), 151.4 (C-2), 137.8, 137.3, 136.7 (Bn, C-6), 128.5, 128.4, 128.0, 127.8, 127.5 (Bn), 109.9 (C-5), 108.6 (C-2'), 88.8, 87.1, 80.9 (C-1', C-3', C-4'), 73.6, 68.5, 68.1, 67.9 (C-5', C-2", Bn), 30.9 (C-1"), 12.6 ($CH_3$). FAB-MS: m/z 481.03 $[M+H]^+$, 503.02 $[M+Na]^+$ (Found: C, 64.6; H, 5.8; N, 5.7; $C_{26}H_{28}O_7N_2$ requires C, 65.0; H, 5.9; N, 5.8%).

EXAMPLE 16

(1S,5R,6R,8R)-1,5-Dihydroxy-6-hydroxymethyl-8-(thymin-1-yl)-2,7-dioxabicyclo-[3.3.0]octane (13). Compound 13 was successfully derived from compound 12 by catalytic removal of the benzyl protecting group in the same way as described in preparation of 6. Purification of 13 was accomplished by column silica gel chromatography eluting with gradient concentrations (6 to 14%) of methanol in dichloromethane. Analytical amounts of compound 13 (up to 15 mg) were additionally purified by reverse-phase HPLC at column (10×250 mm) packed by Nucleosil C18 (10 μm). Flow rate: 8 $cm^3$/min; eluent: 0-10% acetonitrile in 60 min. Yield 82%. $\delta_H$ ($CD_3OD$) 7.44 (1H d, J 1.2, 6-H), 5.83 (1H, s, 4.10-3.80 (5H, m, 5'-$H_a$, 2"-$H_a$, 2"-$H_b$, 4'-H), 2.39-2.25 (1H, m, 1"-$H_a$), 2.00-1.90 (1H, m, 1"-$H_b$), 1.87 (3H, d, J 1.2, $CH_3$). $\delta_C$ ($CD_3OD$) 166.3 (C-4), 152.7 (C-2), 139.8 (C-6), 110.0, 109.6 (C-2', C-5), 87.8, 85.8, 84.6 (C-1', C-3', C-4'), 68.8, 61.6 (C-5', C-2"), 35.6 (C-1"), 12.4 ($CH_3$). FAB-MS: m/z 301.03 $[M+H]^+$ (Found: C, 46.6; H, 5.7; N, 8.5; $C_{12}H_{16}O_7N_2$ requires C, 48.0; H, 5.4; N, 9.3%).

EXAMPLE 17

(1S,5R,6R,8R)-5-Benzyloxy-6-benzyloxymethyl-1-methoxy-8-(3-N-methylthymin-1-yl)-2,7-dioxabicyclo [3.3.0]octane (14), (1S,5R,6R,8R)-5-Benzyloxy-6-benzyloxymethyl-1-hydroxy-8-(3-N-methylthymin-1-yl)-2,7- dioxabicyclo[3.3.0]octane (15) and (1S,5R,6R,8R)-5-Benzyloxy-6-benzyloxymethyl-1-methoxy-8-(thymin-1-yl)-2,7-dioxabicyclo[3.3.0]octane (16). A mixture of compound 12 (1.04 g, 2.16 mmol) and sodium hydride (171 mg of a 60% suspension in mineral oil, 4.30 mmol) was dissolved in anhydrous dichloromethane (4 $cm^3$) during 10 min under stirring. Methyl iodide (1 $cm^3$, 16 mmol) was added and the reaction mixture was incubated at 36° C. for 23 h. After evaporation, the residue was purified by silica gel column chromatography eluting with a gradient of 0.4-2.4% methanol in dichloromethane (v/v) to give products 14, 15 and 16 and starting material 12 (212 mg, 20.5%). Compound 14 (47 mg, 4.3%). $\delta_H$ ($CDCl_3$) 7.25-7.37 (11H, m, Bn, 6-H), 6.15 (1H, s, 1'-H), 4.74 (1H, d, J 11.5, Bn), 4.67 (1H, d, J 11.3, Bn), 4.62 (1H, d, J 12.1, Bn), 4.55 (1H, d, J 11.9, Bn), 4.34 (1H, t, J 5.6, 4'-H), 3.99, (1H, m, 2"-$H_a$), 4.22 (1H, m, 2"-$H_b$), 3.72 (2H, m, 5'-$H_a$, 5'-$H_a$), 3.41 (3H, s, $CH_3$—O), 3.35 (3H, s, $CH_3$—$N^3$), 2.27 (1H, m, 1"-$H_a$), 2.41 (1H, m, 1"-$H_b$), 1.93 (3H, s, 5-$CH_3$). $\delta_C$ ($CDCl_3$) 163.3 (C-4), 151.0 (C-2), 138.2, 137.3, 135.7 (Bn, C-6), 128.3, 128.2, 127.8, 127.6, 127.4, 126.9 (Bn), 111.8 (C-5), 108.5 (C-2'), 89.1, 84.8, 79.5 (C-1', C-3', C-4'), 73.5, 68.4, 68.2, 67.3 (Bn, C-5', C-2"), 50.8 ($CH_3$—O), 32.6 (C-1"), 27.9 ($CH_3$—N), 13.2 ($CH_3$). FAB-MS: m/z 508.88 $[M+H]^+$ (Found: C, 65.7; H, 6.9; N, 4.8; $C_{28}H_{32}O_7N_2$ requires C, 66.1; H, 6.3; N, 5.5%). Compound 15 (97 mg, 9.1%). $\delta_H$ ($CDCl_3$) 7.37-7.28 (11H, m, Bn, 6-H), 5.86 (1H, s, 1'-H), 4.72 (2H, s, Bn), 4.64 (1H, d, J 11.9, Bn), 4.58 (1H, d, J 11.9, Bn), 4.37 (1H, t, J 5.6, 4'-H), 4.13 (1H, m, 2"-$H_a$), 3.93 (1H, m, 2"-$H_b$), 3.75 (2H, m, 5'-$H_a$, 5'-$H_b$), 3.34 (1H, s, $CH_3$—N), 2.32-2.16 (2H, m, 1"-$H_a$, 1"-$H_b$), 1.93 (3H, S, $CH_3$). $\delta_C$ ($CDCl_3$) 163.2 (C-4), 151.9 (C-2), 137.5, 137.1, 134.0 (Bn, C-6), 128.4, 128.3, 128.1, 127.9 127.7, 127.6, 127.3 (Bn), 108.8, 108.5 (C-2', C-5), 88.7 (C-1'), 88.0, 81.0 (C-3', C-4'), 73.5, 68.3, 67.9, 67.7 (Bn, C-5', C-2"), 30.6 (C-1"), 27.8 ($CH_3$—N), 13.2 ($CH_3$). FAB-MS m/z 495.28 $[M+H]^+$, 517.24 $[M+Na]^+$. Compound 16 (665 mg, 62.3%). $\delta_H$($CDCl_3$) 7.35-7.25 (11H, m, Bn, 6-H), 6.06 (1H, s, 1'-H), 4.73 (1H, d, J 11.5, Bn), 4.66 (1H, d, J 11.3, Bn), 4.61 (1H, d, J 11.9, Bn), 4.55 (1H, d, J 12.0, Bn), 4.34 (1H, t, J 5.6, 4'-H), 4.20 (1H, m, 2"-$H_a$), 3.98 (1H, m, 2"-$H_b$), 3.72 (2H, m, 5'-$H_a$, 5'-$H_b$), 3.40 (3H, s, $CH_3$—O), 2.45-2.35 (1H, m, 1"-$H_a$), 2.30-2.20 (1H, m, 1"-$H_b$), 1.90 (3H, d, J 1.1, $CH_3$). $\delta_C$ ($CDCl_3$) 163.2 (C-4), 150.1 (C-2), 138.2, 137.9, 137.3 (Bn, C-6), 128.4, 128.2, 127.8, 127.6 127.4, 127.1 (Bn), 110.8 (C-5), 109.3 (C-2'), 89.2, 84.2, 79.6 (C-1', C-3', C-4'), 73.6, 68.5, 68.3, 67.4 (Bn, C-5', C-2"), 50.8 ($CH_3$—O), 32.6 (C-1"), 12.5 ($CH_3$). FAB-MS m/z 495.22 $[M+H]^+$, 517.23 $[M+Na]^+$ (Found: C, 66.2; H, 7.2; N, 4.4; $C_{27}H_{30}O_7N_2$ requires C, 65.6; H, 6.1; N, 5.7%).

EXAMPLE 18

(1S,5R,6R,8R)-5-Hydroxy-6-hydroxymethyl-1-methoxy-8-(thymin-1-yl)-2,7-dioxabicyclo[3.3.0]octane (17). To a solution of nucleoside 16 (1.20 g, 2.43 mmol) in methanol (10 $cm^3$) was added 20% palladium hydroxide over charcoal (250 mg) and the mixture was carefully degassed under reduced pressure. An atmosphere of hydrogen was applied and stirring was continued for 12 h. The catalyst was removed by filtration of the reaction mixture through a glass column (1×8 cm) packed with silica gel in methanol. The column was additionally washed with methanol (20 $cm^3$). All fractions were collected, evaporated to dryness and co-evaporated with petroleum ether to yield a glass-like solid. This residue was purified by silica gel chromatography eluting with a gradient of 5-10% methanol in dichloromethane (v/v). The fractions containing the product were collected, combined and evaporated to dryness. The residue was dissolved in anhydrous methanol (5 $cm^3$) and anhydrous benzene (100 $cm^3$) was added. Lyophilisation yielded nucleoside 17 (0.61 g, 79%) as a white solid material. $\delta_H$ ($CD_3OD$) 7.45 (1H, S, 6-H), 5.93 (1H, s, 1'-H), 4.15-3.81 (5H, m, 5-$H_a$, 5-$H_b$, 2"-$H_a$, 2"-$H_b$, 4'-H), 3.43 (3H, s, $CH_3$—O), 2.47-2.40 (1H, m, 1"-$H_a$), 2.03-1.93 (1H, m, 1"-$H_b$), 1.92 (3H, s, $CH_3$). $\delta_C$ ($CD_3OD$) 164.1 (C-4), 150.1 (C-2), 138.3 (C-6), 109.6 (C-5), 108.3 (C-2'), 84.4, 84.1, 82.4 (C-1', C-3', C-4'), 68.0, 59.5 (C-5', C-2"), 49.6 ($CH_3$—O), 34.0 (C-1"), 10.5 ($CH_3$). FAB-MS m/z 315.13 $[M+H]^+$, 337.09 $[M+Na]^+$ (Found: C, 49.9; H, 5.7; N, 8.2; $C_{13}H_{18}O_7N_2$ requires C, 49.7; H, 5.8; N, 8.9%).

EXAMPLE 19

(1S,5R,6R,8R)-6-(4,4'-Dimethoxytrityloxymethyl)-5-hydroxy-1-methoxy-8-(thymin-1-yl)-2,7-dioxabicyclo[3.3.0]octane (18). A mixture of compound 17 (0.95 g, 3.03 mmol) and 4,4'-dimethoxytrityl chloride (1.54 g, 4.77 mmol) was dissolved in anhydrous pyridine (20 $cm^3$) and stirred for 4 h at room temperature. The reaction mixture was evaporated to give an oily residue which was co-evaporated with toluene (2×20 $cm^3$). Dichloromethane (50 $cm^3$) and a saturated aqueous solution of sodium hydrogencarbonate (50 $cm^3$) were added, the organic phase was separated and evaporated, and the residue purified by silica gel HPLC (the residue was dissolved in the minimum amount of dichloromethane containing 0.5% triethylamine (v/v) and applied to the column equilibrated by the same solvent. The column was washed (ethylacetate:petroleum ether:triethylamine; 15:84.5:0.5 (v/v/v, 1000 $cm^3$) and the product was eluted in a gradient of methanol (C-2%) in dichloromethane containing 0.5% of triethylamine (v/v/v) to give compound 18 (1.71 g, 92.8%) as white solid material. $\delta_H$ ($CDCl_3$) 7.51-7.17 (10H, m, DMT, 6-H), 6.79-6.85 (4H, m, DMT), 6.04 (1H, s, 1'-H), 4.12-3.98 (3H, m, 5-$H_a$, 5'-$H_b$, 4'-H), 3.77 (6H, s, $CH_3$-DMT), 3.49 (3H, s, $CH_3$—O), 3.45-3.32 (2H, m, 2"-$H_a$, 2"-$H_b$), 2.11-2.01 (1H, m, 1"-$H_a$), 1.94-1.87 (1H, m, 1"-$H_b$), 1.93 (3H, s, $CH_3$). $\delta_C$ ($CDCl_3$) 164.2 (C-4), 158.6, 144.7, 135.7, 130.1, 128.2, 127.9, 126.8, 113.2 (DMT), 150.7 (C-2), 137.7 (C-6), 109.8, 109.7 (C-5, C-2'), 86.5, 85.3, 85.0, 81.4 (DMT, C-1', C-3', C-4'), 69.2, 62.4 (C-5', C-2"), 55.2 ($CH_3$-DMT), 51.7 ($CH_3$—O), 35.5 (C-1"), 12.7 ($CH_3$). FAB-MS m/z 617.26 $[M+H]^+$, 639.23 $[M+Na]^+$ (Found: C, 66.4; H, 6.1; N, 4.2; $C_{34}H_{36}O_9N_2$ requires C, 66.2; H, 5.9; N, 4.5%).

EXAMPLE 20

(1S,5R,6R,8R)-5-(2-Cyanoethoxy(diisopropylamino)phosphinoxy)-6-(4,4'-dimethoxytrityloxymethyl)-1-methoxy-8-(thymin-1-yl)-2,7-dioxabicyclo[3.3.0]octane (19). Compound 18 (1.2 g, 1.95 mmol) was dissolved in anhydrous dichloromethane (10 $cm^3$). N,N-Diisopropylethylamine (1.35 $cm^3$, 7.8 mmol) and 2-cyanoethyl-N,N-diisopropylphosphoramidochloridite (0.92 g, 3.9 mmol) were added under stirring at room temperature. After 72 h, the mixture was diluted to 100 $cm^3$ by dichloromethane and washed by a saturated aqueous solution of sodium hydrogencarbonate (50 $cm^3$). The organic phase was evaporated and applied to silica gel HPLC purification using a gradient of eluent B (petroleum ether:dichloromethane:ethyl acetate:pyridine; 45:45:10:0.5; v/v/v) in eluent A (petroleum ether:dichloromethane:pyridine; 50:50:0.5; v/v/v). The fractions containing the product were concentrated, co-evaporated with toluene (10 $cm^3$) and dried under reduced pressure. The residue was dissolved in anhydrous benzene (20 $cm^3$) and precipitated by addition of this solution into anhydrous petroleum ether (400 $cm^3$) under stirring. The resulting white solid was isolated by filtration and dried to give compound 19 (0.96 g, 60.3%). $\delta_p$ ($CDCl_3$) 142.64, 142.52. FAB-MS m/z 817.26 $[M+H]^+$, 839.24 $[M+Na]^+$ (Found: C, 62.8; H, 6.4; N, 6.9; $C_{43}H_{53}O_{10}N_4P$ requires C, 63.2; H, 6.5; N, 6.9%).

EXAMPLE 21

1,2-O-Isopropylidene-3-C-vinyl-α-D-ribofuranose (20). A solution of 5-O-t-butyldimethylsilyl-1,2-O-isopropylidene-α-D-erythro-pent-3-ulofuranose (Y. Yoshimura, T. Sano, A. Matsuda, T. Ueda, *Chem. Pharm. Bull.,* 1988, 36, 162) (6.05 g, 0.020 mol) in anhydrous THF (250 $cm^3$) was stirred at 0° C. and a 1 M solution of vinylmagnesium bromide in ether (44 $cm^3$, 44 mmol) was added dropwise. The reaction mixture was stirred at room temperature for 2 h, whereupon saturated aqueous ammonium chloride (200 $cm^3$) was added, and extraction was performed using dichloromethane (3×300 $cm^3$). The combined extract was washed with brine (3×250 $cm^3$) and dried ($Na_2SO_4$). The solvent was removed and the residue was redissolved in anhydrous THF (225 $cm^3$). To this mixture was added a 1 M solution of tetrabutylammonium fluoride in THF (22 $cm^3$, 22 mmol), stirring at room temperature was continued for 20 min whereupon the mixture was evaporated under reduced pressure. The residue was dissolved in dichloromethane (500 $cm^3$) and washed with a saturated solution of sodium hydrogencarbonate (2×200 $cm^3$). The aqueous phase was extracted using continuous extraction for 12 h and the combined extract was dried ($Na_2SO_4$) and evaporated. The residue was purified by silica gel column chromatography using dichloromethane/methanol (99:1, v/v) as eluent to give furanose 20 as a white solid material (3.24 g, 75%). $\delta_H$ ($CDCl_3$) 5.84 (1H, d, J 3.7, 1-H), 5.74 (1H, dd, J 11.0, 17.2, 1'-H), 5.52 (1H, dd, J 1.6, 17.1, 2'-$H_a$), 5.29 (1H, dd, J 1.3, 11.0, 2'-$H_b$), 4.21 (1H, d, J 3.7, 2-H), 3.98 (1H, t, J 5.7, 4-H), 3.68-3.64 (2H, m, 5-$H_a$, 5-$H_b$), 2.88 (1H, s, 3-OH), 1.99 (1H, t, J 6.3, 5-OH), 1.60 (3H, s, $CH_3$), 1.35 (3H, s, $CH_3$). $\delta_C$ ($CDCl_3$) 133.6 (C-1'), 116.2 (C-2'), 113.0 ($C(CH_3)_2$), 103.8 (C-1), 83.4, 82.4 (C-4, C-2), 79.6 (C-3), 61.3 (C-5), 26.5, 26.4 ($CH_3$).

EXAMPLE 22

3,5-Di-O-benzyl-1,2-O-isopropylidene-3-C-vinyl-α-D-ribofuranose (21). A 60% suspension of sodium hydride (w/w, 1.78 g, 44.5 mmol) in anhydrous DMF (50 $cm^3$) was stirred at 0° C. and a solution of furanose 20 (3.20 g, 14.8 mmol) in anhydrous DMF (35 $cm^3$) was added dropwise over 30 min. The mixture was stirred at 50° C. for 1 h and subsequently cooled to 0° C. A solution of benzyl bromide (5.3 mL, 44.5 mmol) in anhydrous DMF (5.3 $cm^3$) was added dropwise, and the mixture was stirred at room temperature for 20 h. The reaction mixture was evaporated and redissolved in dichloromethane (300 $cm^3$), washed with saturated aqueous sodium hydrogencarbonate (3×200 $cm^3$) and dried ($Na_2SO_4$). The solvents were removed under reduced pressure and the residue was purified by silica gel column chromatography using petroleum ether/ethylacetate (9:1, v/v) as eluent to give furanose 21 as a white solid material (5.36 g, 91%). $\delta_H$ ($CDCl_3$) 7.40-7.26 (10H, m, Bn), 5.90 (1H, d, J 3.6, 1-H), 5.72 (1H, dd, J 11.1, 17.9, 1'-H), 5.41 (1H, dd, J 0.7, 11.1, 2'-$H_a$), 5.30 (1H, dd, J 0.5, 17.8, 2'-$H_b$), 4.70-4.45 (6H, m, Bn, 2-H, 4-H), 3.69 (1H, dd, J 2.6, 10.8, 5-$H_a$), 3.50 (1H, dd, J 7.9, 10.9, 5-$H_b$), 1.64 (3H, s, $CH_3$), 1.40 (3H, s, $CH_3$). $\delta_C$ ($CDCl_3$) 138.6, 138.3 (Bn), 134.5 (C-1'), 128.3-127.4 (Bn), 118.2 (C-2'), 112.9 ($C(CH_3)_2$), 104.7 (C-1), 84.7, 81.1, 81.0 (C-2, C-3, C-4), 73.3 (C-5), 69.4, 67.0 (Bn), 26.8, 26.6 ($CH_3$).

EXAMPLE 23

1,2-Di-O-acetyl-3,5-di-O-benzyl-3-C-vinyl-α,β-D-ribofuranose (22). A solution of furanose 21 (4.40 g, 11.1 mmol) in 80% aqueous acetic acid (50 $cm^3$) was stirred at 90° C. for 8 h. The solvents were removed and the residue was coevaporated with 99% ethanol (3×25 $cm^3$), toluene (3×25 $cm^3$) and anhydrous pyridine (2×25 $cm^3$) and redissolved in anhydrous pyridine (20 $cm^3$). Acetic anhydride (17 $cm^3$) was added and the solution was stirred at room temperature for 48 h. The reaction was quenched with ice-cold water (100 $cm^3$) and extracted with dichloromethane (2×100 $cm^3$). The combined extract was washed with saturated aqueous sodium hydrogencarbonate (3×100 $cm^3$) and dried ($Na_2SO_4$). The solvent was evaporated and the residue was purified by silica gel column chromatography using petroleum ether/ethylacetate (4:1, v/v) as eluent to give furanose 22 as an oil (4.27 g, 87%, α:β~1:1). $\delta_C$ ($CDCl_3$) 169.9, 169.8 (C=O), 139.0, 138.6, 138.0, 137.8 (Bn), 133.3, 132.4 (C-1'), 128.4-126.8 (Bn), 119.6, 119.5 (C-2'), 99.5, 94.0 (C-1), 85.4, 85.0, 84.3, 83.6, 77.7, 73.6, 73.5, 73.3, 70.0, 69.2, 67.5, 67.2 (C-2, C-3, C-4, C-5, Bn), 21.0, 20.9, 20.6, 20.4 ($CH_3$).

EXAMPLE 24

1-(2-O-Acetyl-3,5-di-O-benzyl-3-C-vinyl-β-D-ribofuranosyl)thymine (23). To a stirred solution of compound 22 (4.24 g, 9.6 mmol) and thymine (2.43 g, 19.3 mmol) in anhydrous acetonitrile (100 $cm^3$) was added N,O-bis(trimethylsilyl)acetamide (11.9 $cm^3$, 48.1 mmol). The reaction mixture was stirred at reflux for 30 min. After cooling to 0° C., trimethylsilyl triflate (3.2 $cm^3$, 16.4 mmol) was added dropwise and the solution was stirred for 24 h at room temperature. The reaction was quenched with cold saturated aqueous sodium hydrogencarbonate (100 $cm^3$) and the resulting mixture was extracted with dichloromethane (3×50 $cm^3$). The combined extract was washed with saturated aqueous sodium hydrogencarbonate (2×50 $cm^3$) and brine (2×50 $cm^3$) and dried ($Na_2SO_4$). The extract was evaporated under reduced pressure and the residue was purified by silica gel column chromatography using dichloromethane/methanol (99:1, v/v) as eluent to give nucleoside 23 as a white foam (4.03 g, 83%). $\delta_H$ ($CDCl_3$) 8.78 (1H, br s, NH), 7.75 (1H, s, 6-H), 7.38-7.26 (10 H, m, Bn), 6.49 (1H, d, J 8.1, 1'-H), 5.99-5.88 (2H, m, 2'-H and 1"-H), 5.54-5.48 (2H, m, 2"-$H_a$, 2"-$H_b$), 4.91-4.50 (4H, m, Bn), 4.34 (1H, s, 4'-H), 3.80 (1H, m, 5'-$H_a$), 3.54 (1H, m, 5'-$H_b$), 2.11 (3H, s, $COCH_3$), 1.48 (3H, s, $CH_3$). $\delta_C$ ($CDCl_3$) 170.1 (C=O), 163.8 (C-4), 151.0 (C-2), 138.9, 136.9 (Bn), 136.1 (C-6), 132.0 (C-1"), 128.7, 128.5, 128.2, 127.8, 127.7, 127.5, 127.5, 127.1 (Bn), 120.7 (C-2"), 111.3 (C-5), 85.4 (C-1'), 85.2 (C-3'), 84.3 (C-4'), 76.0 (C-2'), 73.7 (C-5'), 69.3, 67.6 (Bn), 20.6 ($COCH_3$), 11.7 ($CH_3$). Found: C, 66.3; H, 6.0; N, 5.1; $C_{28}H_{30}N_2O_7$ requires C, 66.4; H, 6.0; N, 5.5%.

EXAMPLE 25

1-(3,5-Di-O-benzyl-3-C-vinyl-β-D-ribofuranosyl)thymine (24). To a stirred solution of nucleoside 23 (3.90 g, 7.7 mmol) in anhydrous methanol (40 $cm^3$) was added sodium methoxide (0.83 g, 15.4 mmol). The mixture was stirred at room temperature for 42 h and then neutralised with dilute aqueous hydrochloric acid. The mixture was extracted with dichloromethane (2×150 $cm^3$), and the combined extract was washed with saturated aqueous sodium hydrogencarbonate ($3\times100$ $cm^3$) and dried ($Na_2SO_4$). The solvent was removed under reduced pressure to give nucleoside 24 as a white foam (3.48 g, 97%). $\delta_H$ ($CDCl_3$) 8.89 (1H, br s, NH), 7.60 (1H, d, J 0.9, 6-H), 7.36-7.26 (10H, m, Bn), 6.23 (1H, d, J 7.8, 1'-H), 5.98 (1H, dd, J 11.2, 17.7, 1"-H), 5.66 (1H, d, J 17.7, 2"-$H_a$), 5.55 (1H, d, J 11.5, 2"-$H_b$), 4.75-4.37 (6H, m, 2'-H, 4'-H, Bn), 3.84 (1H, dd, J 2.7, 10.8, 5'-$H_a$), 3.58 (1H, d, J 11.2, 5'-$H_b$), 3.23 (1H, d, J 10.6, 2'-OH), 1.50 (3H, s, $CH_3$). $\delta_C$ ($CDCl_3$) 163.7 (C-4), 151 3 (C-2), 138.0, 136.9 (Bn), 136.0 (C-6), 131.2 (C-1"), 128.8, 128.6, 128.3, 127.8, 127.7, 127.3 (Bn), 120.7 (C-2"), 111.3 (C-5), 87.3 (C-1'), 84.6 (C-3'), 81.4 (C-4'), 78.0 (C-2'), 73.7 (C-5'), 70.0, 66.4 (Bn), 11.8 ($CH_3$). Found: C, 66.8; H, 6.2; N, 5.9; $C_{26}H_{28}N_2O_6$ requires C, 67.2; H, 6.1; N, 6.0%.

EXAMPLE 26

1-(3,5-Di-O-benzyl-2-O-methanesulfonyl-3-C-vinyl-β-D-ribofuranosyl)thymine (25). Nucleoside 24 (2.57 g, 5.53 mmol) was dissolved in anhydrous pyridine (18 $cm^3$) and cooled to 0° C. Methanesulfonyl chloride (1.28 $cm^3$, 16.6 mmol) was added dropwise and the mixture was stirred at room temperature for 30 min. The reaction was quenched with water (5 $cm^3$) and the resulting mixture was extracted with dichloromethane ($3\times80$ $cm^3$). The combined extract was washed with saturated aqueous sodium hydrogencarbonate ($3\times120$ $cm^3$) and dried ($Na_2SO_4$). The solvent was evaporated under reduced pressure and the residue was purified by silica gel column chromatography using dichloromethane/methanol (99:1, v/v) as eluent to give nucleoside 25 as a yellow foam (2.53 g, 84%). $\delta_H$ ($CDCl_3$) 8.92 (1H, br s, NH), 7.71 (1H, d, J 1.4, 6-H), 7.41-7.28 (10H, m, Bn), 6.57 (1H, d, J 7.8, 1'-H), 5.99-5.61 (4H, m, 2'-H, 1"-H and 2"-$H_a$, 2"-$H_b$), 4.86-4.50 (4H, m, Bn), 4.37 (1H, dd, J 1.5, 2.4, 4'-H), 8.82 (1H, dd, J 2.6, 11.0, 5'-$H_a$), 3.55 (1H, dd, J 1.2, 11.0, 5'-$H_b$), 3.02 (3H, s, $CH_3$), 1.47 (3H, d, J 1.1, $CH_3$). $\delta_C$ ($CDCl_3$) 163.7 (C-4), 151.5 (C-2), 138.7, 136.7 (Bn), 135.7 (C-6), 130.9 (C-1"), 128.8, 128.5, 128.4, 127.6, 127.0 (Bn), 121.8 (C-2"), 111.9 (C-5), 85.1 (C-1'), 84.5 (C-3'), 84.0 (C-4'), 80.7 (C-2'), 73.7 (C-5'), 69.2, 67.7 (Bn), 38.9 ($CH_3$), 11.8 ($CH_3$).

EXAMPLE 27

1-(3,5-Di-O-benzyl-3-C-vinyl-β-D-arabinofuranosyl) thymine (26). A solution of nucleoside 25 (2.53 g, 4.66 mmol) in a mixture of ethanol (50 $cm^3$), water (50 $cm^3$) and 1 M aqueous sodium hydroxide (15 $cm^3$) was stirred under reflux for 16 h. The mixture was neutralised using dilute aqueous hydrochloric acid, the solvent was evaporated under reduced pressure, and the residue was extracted with dichloromethane ($3\times120$ $cm^3$). The combined extract was washed with saturated aqueous sodium hydrogencarbonate ($3\times150$ $cm^3$) and dried ($Na_2SO_4$). The solvent was removed under reduced pressure and the residue was purified by silica gel column chromatography using dichloromethane/methanol (99:1) as eluent to give 26 as a white foam (1.61 g, 74%). $\delta_H$ ($CDCl_3$) 9.89 (1H, br s, NH), 7.50 (1H, d, J 1.1, 6-H), 7.41-7.26 (Bn), 6.28 (1H, d, J 2.8, 1'-H), 6.05 (1H, dd, J 11.1, 17.9, 1"-H), 5.58-5.50 (2H, m, 2"-$H_a$, 2"-$H_b$), 4.98 (1H, d, J 9.0, 2'-OH), 4.64-4.31 (6H, m, 2'-H, 4'-H, Bn), 3.73 (2H, m, 5'-$H_a$, 5'-$H_b$), 1.73 (1H, d, J 0.6, $CH_3$). $\delta_C$ ($CDCl_3$) 165.1 (C-4), 150.5 (C-2), 138.4, 138.0, 136.7 (C-6, Bn), 130.4 (C-1"), 128.8, 128.6, 128.5, 128.1, 128.0, 127.8 (Bn), 120.6 (C-2"), 108.1 (C-5), 88.6 (C-1'), 87.9 (C-3'), 87.2 (C-4'), 73.7 (C-2'), 71.8 (C-5'), 69.7, 66.3 (Bn), 12.3 ($CH_3$). Found: C, 66.8; H, 6.2; N, 5.9; $C_{26}H_{28}N_2O_6$ requires C, 67.2; H, 6.1; N, 6.0.

EXAMPLE 28

1-(3,5-Di-O-benzyl-3-C-hydroxymethyl-β-D-arabino-furanosyl)thymine (27). To a solution of nucleoside 26 (2.00 g, 4.31 mmol) in a mixture of THF (15 $cm^3$) and water (15 $cm^3$) was added sodium periodate (2.76 g, 12.9 mmol) and a 2.5% solution of osmium tetraoxide in t-butanol (w/w, 0.54 $cm^3$, 43 μmol). The reaction was stirred at room temperature for 18 h, quenched with water (50 $cm^3$), and the mixture was extracted with dichloromethane ($2\times100$ $cm^3$). The combined extract was washed with saturated aqueous sodium hydrogen carbonate ($3\times75$ $cm^3$), dried ($Na_2SO_4$) and evaporated under reduced pressure. The residue was redissolved in a mixture of THF (15 $cm^3$) and water (15 $cm^3$), and sodium borohydride (488 mg, 12.9 mmol) was added. The reaction mixture was stirred at room temperature for 1 h, water (50 $cm^3$) was added, and the mixture was extracted with dichloromethane ($2\times100$ $cm^3$). The combined organic phase was washed with saturated aqueous sodium hydrogencarbonate ($3\times75$ $cm^3$) and dried ($Na_2SO_4$). The solvent was removed and the residue was purified by silica gel column chromatography using dichloromethane/methanol (98:2, v/v) as eluent to give nucleoside 27 as a white foam (732 mg, 36%). $\delta_H$ ($CDCl_3$) 11.09 (1H, br s, NH), 7.41 (1H, d, J 1.0, 6-H), 7.38-7.26 (Bn), 6.16 (1H, d, J 2.6, 1'-H), 5.12 (1H, d, J 5.4, 2'-OH), 4.66-4.29 (6H, m, 2'-H, 4'-H, Bn), 4.02-3.96 (2H, m, 1"-$H_a$, 1"-$H_b$), 3.90 (1H, dd, J 7.2, 9.7, 5'-$H_a$), 3.79 (1H, dd, J 5.6, 9.7, 5'-$H_b$), 2.49 (1H, t, J 6.4, 1"-OH), 1.68 (3H, d, J 0.6, $CH_3$); $\delta_C$ ($CDCl_3$) 166.1 (C-4), 150.6 (C-2), 139.0, 137.9, 137.0 (C-6, Bn), 128.7, 128.6, 128.4, 128.3, 128.0 (Bn), 107.5 (C-5), 88.2 (C-1'), 88.1 (C-3'), 84.2 (C-4'), 73.7 (C-5'), 72.1 (C-2'), 69.3, 65.4 (Bn), 58.6 (C-1"), 12.3 ($CH_3$).

EXAMPLE 29

(1R,2R,4R,5S)-1-Benzyloxy-2-benzyloxymethyl-4-(thymin-1-yl)-3,6-dioxabicyclo-[3.2.0]heptane (28). A solution of compound 27 (2.26 g, 4.83 mmol) in anhydrous pyridine (20 $cm^3$) was stirred at −40° C. and a solution of methanesulphonyl chloride (0.482 $cm^3$, 4.83 mmol) in anhydrous pyridine (10 $cm^3$) was added. The reaction mixture was stirred at room temperature for 17 h, water (5o $cm^3$) was added, and the mixture was extracted with dichloromethane ($2\times100$ $cm^3$). The combined organic phase was washed with saturated aqueous sodium hydrogencarbonate ($3\times100$ $cm^3$), dried ($Na_2SO_4$) and evaporated under reduced pressure. The residue was purified by silica gel column chromatography using dichloromethane/methanol (99:1, v/v) as eluent to give an intermediate which after evaporation of the solvents was dissolved in anhydrous DMF (15 $cm^3$). This solution was added dropwise to a suspension of 60% sodium hydride (461 mg, 11.5 mmol) in anhydrous DMF (15 $cm^3$) at 0° C. The reaction was stirred at room temperature for 30 min, then quenched with water (60 $cm^3$). After neutralisation using dilute aqueous hydrochloric acid, the mixture was dissolved in dichloromethane (150 $cm^3$), washed with saturated aqueous sodium hydrogencarbonate ($3\times100$ $cm^3$) and dried ($Na_2SO_4$). The solvents were evaporated and the residue was purified by silica gel column chromatography using dichloromethane/methanol (99:1, v/v) as eluent to give nucleoside 28 as a white foam (2.00 g, 93%). $\delta_H$ ($CDCl_3$) 9.13 (1H, br s, NH), 7.55 (1H, d, J 1.4, 6-H), 7.40-7.26 (Bn), 5.99 (1H, d, J 2.5, 1'-H), 5.30 (1H, d, J 2.7, 2'-H), 4.88-4.57 (6H, m, 1"-$H_a$, 1"-$H_b$, Bn), 4.22-4.19 (1H, m, 4'-H), 3.92 (1H, dd, J 6.2, 10.8, 5'-$H_a$), 3.82 (1H, dd, J 3.7, 10.8, 5'-$H_b$), 1.91 (3H, d, J 1.3, $CH_3$). $\delta_C$ ($CDCl_3$) 163.8 (C-4), 150.3 (C-2), 137.6 (C-6), 137.5, 137.0 (Bn), 128.7, 128.6, 128.2, 128.0, 127.8, 127.3

(Bn), 109.8 (C-5), 85.7 (C-3'), 84.1 (C-1'), 83.5 (C-4'), 79.7 (C-1"), 73.9 (C-2'), 73.6 (C-5'), 68.6, 67.8 (Bn), 12.4 ($CH_3$). FAB m/z 451 $[M+H]^+$, 473 $[M+Na]^+$. Found: C, 66.3; H, 5.9; N, 6.1; $C_{25}H_{26}N_2O_6$ requires C, 66.7; H, 5.8; N, 6.2%.

EXAMPLE 30

(1R,2R,4R,5S)-1-Hydroxy-2-hydroxymethyl-4-(thymin-1-yl)-3,6-dioxabicyclo[3.2.0]-heptane (29). To a stirred solution of nucleoside 28 (180 mg, 0.40 mmol) in ethanol (3 $cm^3$) was added 10% palladium hydroxide over carbon (90 mg). The mixture was degassed several times with argon and placed under a hydrogen atmosphere. The reaction mixture was stirred at room temperature for 6 h, then filtered through celite. The filtrate was evaporated under reduced pressure and the residue was purified by silica gel column chromatography using dichloromethane/methanol (96:4, v/v) as eluent to give nucleoside 29 as a white solid material (92 mg, 86%). $\delta_H$ ($CD_3OD$) 7.79 (1H, d, J 1.2, 6-H), 5.91 (1H, d, J 2.5, 1'-H), 4.96 (1H, d, J 2.5, 2'-H), 4.92 (1H, d, J 7.4, 1"-$H_a$), 4.58 (1H, dd, J 0.9, 7.4, 1"-$H_b$), 3.98 (1H, dd, J 7.3, 12.8, 5'-$H_a$), 3.87-3.82 (2H, m, 4'-H, 5'-$H_b$), 3.34 (2H, s, 3'-OH, 5'-OH), 1.87 (3H, d, J 1.3, $CH_3$). $\delta_C$ ($CD_3OD$) 166.5 (C-4), 152.1 (C-2), 140.1 (C-6), 110.1 (C-5), 91.2 (C-2'), 85.1 (C-1'), 84.0 (C-4'), 79.6 (C-3'), 78.6 (C-1"), 61.1 (C-5'), 12.3 ($CH_3$).

EXAMPLE 31

(1R,2R,4R,5S)-1-(2-Cyanoethoxy(diisopropylamino)phosphinoxy)-2-(4,4'-dimethoxytrityloxymethyl)-4-(thymin-1-yl)-3,6-dioxabicyclo[3.2.0]heptane (30). To a solution of diol 29 (250 mg, 0.925 mmol) in anhydrous pyridine (4 $cm^3$) was added 4,4'-dimethoxytrityl chloride (376 mg, 1.11 mmol) and the mixture was stirred at room temperature for 18 h. The reaction was quenched with methanol (1.5 $cm^3$) and the mixture was evaporated under reduced pressure. A solution of the residue in dichloromethane (30 $cm^3$) was washed with saturated aqueous sodium hydrogencarbonate (3×20 $cm^3$), dried ($Na_2SO_4$) and evaporated. The residue was purified by silica gel column chromatography using dichloromethane/methanol (98:2, v/v) as eluent to give an intermediate which was dissolved in anhydrous dichloromethane (7.0 $cm^3$). N,N-Diisopropylethylamine (0.64 $cm^3$, 3.70 mmol) followed by 2-cyanoethyl N,N-diisopropylphosphoramidochloridite (0.41 $cm^3$, 1.85 mmol) were added and the mixture was stirred at room temperature for 25 h. The reaction was quenched with methanol (3 $cm^3$), and the mixture was dissolved in ethylacetate (70 $cm^3$), washed with saturated aqueous sodium hydrogencarbonate (3×50 $cm^3$) and brine (3×50 $cm^3$), dried ($Na_2SO_4$), and was evaporated under reduced pressure. The residue was purified by silica gel column chromatography using petroleum ether/-dichloromethane/ethylacetate/triethylamine (100:45:45:10, v/v/v/v) as eluent. The residue obtained was dissolved in toluene (2 $cm^3$) and precipitated under stirring from petroleum ether at −50° C. After evaporation of the solvents, the residue was coevaporated with anhydrous acetonitrile (4×5 $cm^3$) to give 30 as a white foam (436 mg, 61%). $^{31}P$ NMR ($CDCl_3$) 146.6.

EXAMPLE 32

3,5-Di-O-benzyl-4-C-hydroxymethyl-1,2-O-isopropylidene-α-D-ribofuranose (31). To a solution of 3-O-benzyl-4-C-hydroxymethyl-1,2-O-isopropylidene-α-D-ribofuranose (R. D. Youssefyeh, J. P. H. Verheyden and J. G. Moffatt, *J. Org. Chem.*, 1979, 44, 1301) (20.1 g, 0.064 mol) in anhydrous DMF (100 $cm^3$) at −5° C. was added a suspension of NaH (60% in mineral oil (w/w), four portions during 1 h 30 min, total 2.85 g, 0.075 mol). Benzyl bromide (8.9 $cm^3$, 0.075 mol) was added dropwise and stirring at room temperature was continued for 3 h whereupon ice-cold water (50 $cm^3$) was added. The mixture was extracted with EtOAc (4×100 $cm^3$) and the combined organic phase was dried ($Na_2SO_4$). After evaporation, the residue was purified by silica gel column chromatography eluting with 5% EtOAc in petroleum ether (v/v) to yield compound 31 (18.5 g, 71%). $\delta_C$ ($CDCl_3$) 138.0, 137.4, 128.5, 128.3, 128.0, 127.8, 127.6 (Bn), 113.5 (C$(CH_3)_2$), 104.4 (C-1), 86.5 (C-4), 78.8, 78.6 (Bn), 73.6, 72.6, 71.6 (C-2, C-3, C-5), 63.2, (C-1'), 26.7, 26.1 ($CH_3$).

EXAMPLE 33

4-C-(Acetoxymethyl)-3,5-di-O-benzyl-1,2-O-isopropylidene-α-D-ribofuranose (32). To a solution of furanose 31 (913 mg, 2.28 mmol) in anhydrous pyridine (4.5 $cm^3$) was dropwise added acetic anhydride (1.08 $cm^3$, 11.4 mmol) and the reaction mixture was stirred at room temperature for 3 h. The reaction was quenched by addition of ice-cold water (50 $cm^3$) and extraction was performed with dichloromethane (3×50 $cm^3$). The combined organic phase was washed with a saturated aqueous solution of sodium hydrogencarbonate (2×50 $cm^3$), dried ($Na_2SO_4$) and concentrated under reduced pressure. The residue was purified by silica gel column chromatography using dichloromethane as eluent to give compound 32 as a clear oil (911 mg, 90%). $\delta_H$ ($CDCl_3$) 7.34-7.25 (10 H, m, Bn), 5.77 (1 H, d, J 3.6, 1-H), 4.78-4.27 (8 H, m, Bn, H-$5_a$, H-$5_b$, H-3, H-2), 3.58 (1 H, d, J 10.3, H-$1'_a$), 3.48 (1 H, d, J 10.5, H-$1'_b$), 2.04 (3 H, s, $COCH_3$), 1.64 (3 H, s, $CH_3$), 1.34 (3 H, s, $CH_3$). $\delta_C$ ($CDCl_3$) 171.1 (C=O), 138.2, 137.9, 128.6, 128.1, 128.0, 128.0, 127.8 (Bn), 114.0 (C$(CH_3)_2$), 104.5 (C-1), 85.4 (C-4), 79.3, 78.6 (C-2, C-3), 73.7, 72.7, 71.2 (Bn, C-5), 64.9 (C-1'), 26.7, 26.3 (C$(CH_3)_2$), 21.0 ($COCH_3$). Found: C, 67.0; H, 6.5; $C_{25}H_{30}O_7$,¼$H_2O$ requires C, 67.2; H, 6.9%.

EXAMPLE 34

4-C-(Acetoxymethyl)-1,2-di-O-acetyl-3,5-di-O-benzyl-D-ribofuranose (33). A solution of furanose 32 (830 mg, 1.88 mmol) in 80% acetic acid (10 $cm^3$) was stirred at 90° C. for 4 h. The solvent was removed under reduced pressure and the residue was coevaporated with ethanol (3×5 $cm^3$), toluene (3×5 $cm^3$) and anhydrous pyridine (3×5 $cm^3$), and was redissolved in anhydrous pyridine (3.7 $cm^3$). Acetic anhydride (2.85 $cm^3$) was added and the solution was stirred for 72 h at room temperature. The solution was poured into ice-cold water (20 $cm^3$) and the mixture was extracted with dichloromethane (2×20 $cm^3$). The combined organic phase was washed with a saturated aqueous solution of sodium hydrogencarbonate (2×20 $cm^3$), dried ($Na_2SO_4$) and concentrated under reduced pressure. The residue was purified by silica gel column chromatography using dichloromethane as eluent to give 33 (β:α~1:3) as an clear oil (789 mg, 86%). $\delta_C$ ($CDCl_3$) 171.0, 170.3, 170.0, 169.3 (C=O), 138.1, 137.6, 136.3, 128.9, 128.6, 128.2, 128.0, 128.0, 127.9, 127.7, 124.0 (Bn), 97.8, 97.8 (C-1), 87.0, 85.0, 78.9, 74.5, 74.4, 73.8, 73.6, 72.0, 71.8, 71.0, 70.9, 64.6, 64.4 (C-2, C-3, C-4, Bn, C-5, C-1'), 21.0, 20.8, 20.6 ($COCH_3$). Found: C, 64.2; H, 6.3; $O_{26}H_{30}O_9$ requires C, 64.2; H, 6.2%.

EXAMPLE 35

1-(4-C-(Acetoxymethyl)-2-O-acetyl-3,5-di-O-benzyl-β-D-ribofuranosyl)thymine (34). To a stirred solution of the anomeric mixture 33 (736 mg, 1.51 mmol) and thymine (381 mg, 3.03 mmol) in anhydrous acetonitrile (14.5 $cm^3$) was added N,O-bis(trimethylsilyl)-acetamide (2.61 $cm^3$, 10.6 mmol). The reaction mixture was stirred at reflux for 1 h, then cooled to 0° C. Trimethylsilyl triflate (0.47 $cm^3$, 2.56 mmol) was added dropwise under stirring and the solution was stirred at 65° C. for 2 h. The reaction was quenched with a cold saturated aqueous solution of sodium hydrogen carbonate (15 $cm^3$) and extraction was performed with dichloromethane (3×10 $cm^3$). The combined organic phase was washed with saturated aqueous solutions of sodium hydrogencarbonate (2×10 $cm^3$) and brine (2×10 $cm^3$), and was dried ($Na_2SO_4$). The solvent was removed under reduced pressure and the residue was purified by silica gel column chromatography using dichloromethane/methanol (98:2, v/v) as eluent to give nucleoside 34 as a white solid material (639 mg, 76%). $\delta_H$ ($CDCl_3$) 8.98 (1 H, br s, NH), 7.39-7.26 (11 H, m, Bn, 6-H), 6.22 (1 H, d, J 5.3, 1'-H), 5.42 (1 H, t, J 5.4, 2'-H), 4.63-4.43 (5H, m, 3'-H, Bn), 4.41 (1 H, d, J 12.2, 5'-$H_a$), 4.17 (1 H, d, J 12.1, 5'-$H_b$), 3.76 (1 H, d, J 10.2, 1"-$H_a$), 3.51 (1 H, d, J 10.4, 1"-$H_b$), 2.09 (3 H, s, $COCH_3$), 2.03 (3 H, s, $COCH_3$), 1.53 (3 H, d, J 0.9, $CH_3$). $\delta_C$ ($CDCl_3$) 170.8, 170.4 (C═O), 163.9 (C-4), 150.6 (C-2), 137.4 (C-6) 137.4, 136.1, 128.9, 128.8, 128.4, 128.2, 127.9 (Bn), 111.7 (C-5), 87.2, 87.2, 86.1 (C-1', C-3', C-4'), 77.6 (C-2'), 74.8, 73.9, 71.1, 63.8 (Bn, C-1", C-5'), 20.9, 20.8 ($COCH_3$), 12.0 ($CH_3$). FAB-MS m/z 553 $[M+H]^+$. Found: C, 62.7; H, 5.9; N, 4.7; $C_{29}H_{32}N_2O_9$ requires C, 63.0; H, 5.8; N, 5.1%.

EXAMPLE 36

1-(3,5-Di-O-benzyl-4-C-(hydroxymethyl)-β-D-ribofuranosyl)thymine (35). To a stirred solution of nucleoside 34 (553 mg, 1.05 mmol) in methanol (5.5 $cm^3$) was added sodium methoxide (287 mg, 5.25 mmol). The reaction mixture was stirred at room temperature for 10 min, then neutralised with dilute hydrochloric acid. The solvent was partly evaporated and extraction was performed with dichloromethane (2×20 $cm^3$). The combined organic phase was washed with saturated aqueous sodium hydrogencarbonate (3×20 $cm^3$) and was dried ($Na_2SO_4$). The solvent was removed under reduced pressure to give 35 as a white solid material (476 mg, 97%). $\delta_H$ ($CDCl_3$) 7.47 (1 H, d, J 1.0 6-H), 7.36-7.22 (10 H, m, Bn), 6.07 (1 H, d, J 3.8, 1'-H), 4.87 (1 H, d, J 11.7, Bn), 4.55 (1 H, d, J 11.7, Bn), 4.50-4.32 (4 H, m, Bn, 2'-H, 3'-H), 3.84-3.53 (4 H, m, 5'-$H_a$, 1"-$H_a$, 1"-$H_b$), 1.50 (3 H, d, J 1.1, $CH_3$). $\delta_C$ ($CDCl_3$) 164.3 (C-4), 151.3 (C-2), 137.6 (C-6) 136.4, 136.3, 128.8, 128.6, 128.4, 128.3, 127.9 (Bn), 111.1 (C-5), 91.1, 91.0, 88.1 (C-1', C-3', C-4'), 77.4 (C-2'), 74.8, 73.8, 71.4, 63.2 (Bn, C-5', C-1"), 12.0 ($CH_3$). FAB-MS m/z 491 $[M+Na]^+$. Found: C, 63.4; H, 6.0; N, 5.5; $C_{25}H_{28}N_2O_7$,¼$H_2O$ requires C, 63.5; H, 6.1; N, 5.9%.

EXAMPLE 37

Intermediate 35A. A solution of nucleoside 35 (225 mg, 0.48 mmol) in anhydrous pyridine (1.3 $cm^3$) was stirred at 0° C. and p-toluenesulphonyl chloride (118 mg, 0.62 mmol) was added in small portions. The solution was stirred at room temperature for 16 h and additional p-toluenesulphonyl chloride (36 mg, 0.19 mmol) was added. After stirring for another 4 h and addition of ice-cold water (15 $cm^3$), extraction was performed with dichloromethane (2×15 $cm^3$). The combined organic phase was washed with saturated aqueous sodium hydrogencarbonate (3×15 $cm^3$) and dried ($Na_2SO_4$). The solvent was removed under reduced pressure and the residue was purified by silica gel column chromatography using dichloromethane/methanol (99:1, v/v) as eluent to give a intermediate 35A (140 mg) which was used without further purification in the next step.

EXAMPLE 38

(1S,3R,4R,7S)-7-Benzyloxy-1-benzyloxymethyl-3-(thymin-1-yl)-2,5-dioxabicyclo-[2.2.1]heptane (36). Intermediate 35A (159 mg) was dissolved in anhydrous DMF (0.8 $cm^3$). The solution was added dropwise to a stirred suspension of 60% sodium hydride in mineral oil (w/w, 32 mg, 0.80 mmol) in anhydrous DMF (0.8 $cm^3$) at 0° C. The mixture was stirred at room temperature for 72 h and then concentrated under reduced pressure. The residue was dissolved in dichloromethane (10 $cm^3$), washed with saturated aqueous sodium hydrogencarbonate (3×5 $cm^3$) and dried ($Na_2SO_4$). The solvent was removed under reduced pressure and the residue was purified by silica gel column chromatography using dichloromethane/methanol (99:1, v/v) as eluent to give the bicyclic nucleoside 36 as a white solid material (65.7 mg, 57%). $\delta_H$ ($CDCl_3$) 9.24 (1 H, br s, NH), 7.49 (1 H, s, 6-H), 7.37-7.26 (10 H, m, Bn), 5.65 (1 H, s, 1'-H), 4.70-4.71 (5 H, m, Bn, 2'-H), 4.02-3.79 (5 H, m, 3'-H, 5'-$H_a$, 1"-$H_a$, 1"-$H_b$), 1.63 (3 H, s, $CH_3$). $\delta_C$ ($CDCl_3$) 164.3 (C-4), 150.1 (C-2), 137.7, 137.1 (Bn), 135.0 (C-6), 128.8, 128.7, 128.4, 128.0, 127.9 (Bn), 110.4 (C-5), 87.5, 87.3 (C-1', C-3'), 76.7, 75.8, 73.9, 72.3, 72.1 (Bn, C-5', C-2', C-4'), 64.5 (C-1"), 12.3 ($CH_3$). FAB-MS m/z 451 $[M+H]^+$.

EXAMPLE 39

(1S,3R,4R,7S)-7-Hydroxy-1-hydroxymethyl-3-(thymin-1-yl)-2,5-dioxabicyclo[2.2.1]-heptane (37). A solution of nucleoside 36 (97 mg, 0.215 mmol) in ethanol (1.5 $cm^3$) was stirred at room temperature and 20% palladium hydroxide over carbon (50 mg) was added. The mixture was degassed several times with argon and placed in a hydrogen atmosphere with a balloon. After stirring for 4 h, the mixture was purified by silica gel column chromatography using dichloromethane-methanol (97:3, v/v) as eluent to give nucleoside 37 as a white solid material (57 mg, 98%). $\delta_H$ ($(CD_3)_2SO$) 11.33 (1H, br s, NH), 7.62 (1H, d, J 1.1 Hz, 6-H), 5.65 (1H, d, J 4.4 Hz, 3'-OH), 5.41 (1H, s, 1'-H), 5.19 (1H, t, J 5.6 Hz, 5'-OH), 4.11 (1H, s, 2'-H), 3.91 (1H, d, J 4.2 Hz, 3'-H), 3.82 (1H, d, J 7.7 Hz, 1"-$H_a$), 3.73 (1H, s, H'-$5_a$), 3.76 (1H, s, 5'-$H_b$), 3.63 (1H, d, J 7.7 Hz, 1"-$H_b$), 1.78 (3H, d, J 0.7 Hz, $CH_3$). $\delta_C$ ($CDCl_3$) 166.7 (C-4), 152.1 (C-2), 137.0 (C-6), 110.9 (C-5), 90.5, 88.4 (C-1', C-4'), 80.9, 72.5, 70.4 (C-2', C-3', C-5'), 57.7 (C-1"), 12.6 ($CH_3$). EI-MS m/z 270 $[M]^+$.

EXAMPLE 40

(1R,3R,4R,7S)-1-(4,4'-Dimethoxytrityloxymethyl)-7-hydroxy-3-thymin-1-yl)-2,5-dioxabicyclo[2.2.1]heptane (38). To a solution of nucleoside 37 (1.2 g, 4.44 mmol) in anhydrous pyridine (5 $cm^3$) was added 4,4'-dimethoxytrityl chloride (2.37 g, 7.0 mmol) at 0° C. The solution was stirred at room temperature for 2 h whereupon the reaction was quenched with ice-cold water (10 $cm^3$) and extracted with dichloromethane (3×15 $cm^3$). The combined organic phase was washed with saturated aqueous solutions of sodium hydrogen carbonate (3×10 $cm^3$), brine (2×10 $cm^3$) and dried ($Na_2SO_4$). The solvent was removed under reduced pressure and the residue was purified by silica gel column chromatography using dichloromethane/methanol (98:2, v/v) as eluent to give nucleoside 38 as a white solid material (2.35 g, 93%). $\delta_H$ ($CDCl_3$) 9.89 (1H, br s, NH), 7.64 (1H, s, 6-H), 7.47-7.13

(9H, m, DMT), 6.96-6.80 (4H, m, DMT), 5.56 (1H, s, 1'-H), 4.53 (1H, br s, 2'-H), 4.31 (1H, m, 3'-H), 4.04-3.75 (9H, m, 1"-$H_a$, 1"-$H_b$, 3'-OH, $OCH_3$), 3.50 (2H, br s, $H_b$), 1.65 (3H, s, $CH_3$). $O_c$($CDCl_3$) 164.47 (C-4), 158.66 (DMT), 150.13 (C-2), 144.56, 135.46, 135.35, 134.78, 130.10, 129.14, 128.03, 127.79, 127.05 (C-6, DMT), 113.32, 113.14 (DMT), 110.36 (C-5), 89.17, 88.16, 87.05 (C-1', C-4', DMT), 79.36, 71.81, 70.25, 58.38 (C-2', C-3', C-5', C-1"), 55.22 ($OCH_3$), 12.57 ($CH_3$). FAB-MS m/z 595 $[M+Na]^+$, 573 $[M+H]^+$.

EXAMPLE 41

(1R,3R,4R,7S)-7-(2-Cyanoethoxy(diisopropylamino)phosphinoxy)-1-(4,4'-dimethoxytrityloxymethyl)-3-(thymin-1-yl)-2,5-dioxabicyclo[2.2.1]heptane (39). To a solution of nucleoside 38 (2.21 g, 3.86 mmol) in anhydrous dichloromethane (6 $cm^3$) at room temperature was added N,N-diisopropylethylamine (4 $cm^3$) and 2-cyanoethyl N,N-diisopropylphosphoramidochloridite (1 $cm^3$, 4.48 mmol) and stirring was continued for 1 h. MeOH (2 $cm^3$) was added, and the mixture was diluted with ethyl acetate (10 $cm^3$) and washed successively with saturated aqueous solutions of sodium hydrogencarbonate (3×5 $cm^3$) and brine (3×5 $cm^3$) and was dried ($Na_2SO_4$). The solvent was evaporated under reduced pressure, and the residue was purified by basic alumina column chromatography with dichloromethane/methanol (99:1, v/v) as eluent to give 39 as a white foam. This residue was dissolved in dichloromethane (2 $cm^3$) and the product was precipitated from petroleum ether (100 $cm^3$, cooled to −30° C.) under vigorous stirring. The precipitate was collected by filtration, and was dried to give nucleoside 39 as a white solid material (2.1 g, 70%). $\delta_p$ ($CDCl_3$) 149.06, 148.74. FAB-MS m/z 795 $[M+Na]^+$, 773 $[M+H]^+$.

EXAMPLE 42

1-(2-O-Acetyl-4-C-acetoxymethyl-3,5-di-O-benzyl-β-D-ribofuranosyl)uracil (40). To a stirred solution of the anomeric mixture 33 (3.0 g, 6.17 mmol) and uracil (1.04 g, 9.26 mmol) in anhydrous acetonitrile (65 $cm^3$) was added N,O-bis(trimethylsilyl)acetamide (9.16 $cm^3$, 37.0 mmol). The reaction mixture was stirred for 1 h at room temperature and cooled to 0° C. Trimethylsilyl triflate (1.8 $cm^3$, 10.0 mmol) was added dropwise and the solution was stirred at 60° C. for 2 h. The reaction was quenched by addition of a saturated aqueous solution of sodium hydrogencarbonate (10 $cm^3$) at 0° C. and extraction was performed with dichloromethane (3×20 $cm^3$). The combined organic phase was washed with brine (2×20 $cm^3$) and was dried ($Na_2SO_4$). The solvents were removed under reduced pressure and the residue was purified by silica gel column chromatography using dichloromethane/methanol (99:1, v/v) as eluent to give nucleoside 40 as a white solid material (2.5 g, 75%). $\delta_H$ ($CDCl_3$) 9.57 (1H, br s, NH), 7.63 (1H, d, J 8.2, 6-H), 7.40-7.24 (10H, m, Bn), 6.18 (1H, d, J 4.5, 1'-H), 5.39-5.32 (2H, m, 2'-H, 5-H), 4.61 (1H, d, J 11.6, Bn), 4.49-4.40 (5H, m, 3'-H, Bn, 1"-$H_a$), 4.37 (1H, d, J 12.3, 1"-$H_b$), 3.76 (1H, d, J 10.1, 5-$H_a$), 3.49 (1H, d, J 10.1, 5'-$H_b$), 2.09 (s, 3H, $COCH_3$), 2.04 (3H, s, $COCH_3$). δc ($CDCl_3$) 170.47, 169.94 (C=O), 163.32 (C-4), 150.30 (C-2), 140.24 (C-6), 137.15, 136.95, 128.65, 128.52, 128.32, 128.19, 128.02, 127.77 (Bn), 102.57 (C-5), 87.41, 86.14 (C-1', C-4'), 77.09, 74.84, 74.51, 73.75, 70.60, 63.73 (C-2', C-3', C-5', C-1", Bn), 20.79, 20.68 ($COCH_3$). FAB-MS m/z 539 $[M]^+$.

EXAMPLE 43

1-(3,5-Di-O-benzyl-4-C-hydroxymethyl-β-D-ribofuranosyl)uracil (41). To a stirred solution of nucleoside 40 (2.0 g, 3.7 mmol) in methanol (25 $cm^3$) was added sodium methoxide (0.864 g, 95%, 16.0 mmol). The reaction mixture was stirred at room temperature for 10 min and neutralised with 20% aqueous hydrochloric acid. The solvent was partly evaporated and the residue was extracted with ethyl acetate (3×50 $cm^3$). The combined organic phase was washed with a saturated aqueous solution of sodium hydrogencarbonate (3×20 $cm^3$) and was dried ($Na_2SO_4$). The solvent was removed under reduced pressure and the residue was purified by silica gel column chromatography using dichloromethane/methanol (98.5:1.5, v/v) as eluent to give 41 as a white solid material (1.58 g, 95%). $\delta_H$ ($CDCl_3$) 9.95 (1H, br s, NH), 7.69 (d, J 8.1, 6-H), 7.35-7.17 (10H, m, Bn), 6.02 (1H, d, J 2.3, 1'-H), 5.26 (1H, d, J 8.1, 5-H), 4.80 (1H, d, J 11.7, Bn), 4.47 (1H, d, J 11.7, Bn), 4.45-4.24 (4H, m, Bn, 2'-H, 3'-H), 3.81 (1H, d, J 11.9, 1"-$H_a$), 3.69 (2H, br s, 2'-OH, 1"-OH), 3.67 (2H, m, 5'-$H_a$, 1"-$H_b$), 3.48 (1H, d, J 10.3, 5'-$H_b$). $\delta_C$ ($CDCl_3$) 163.78 (C-4), 150.94 (C-2), 140.61 (C-6), 137.33, 137.22, 128.59, 128.18, 128.01 (Bn), 102.16 (C-5), 91.46, 88.36 (C-1', C-4'), 76.73, 74.66, 73.71, 73.29, 70.81, 62.81 (C-2', C-3', C-5', C-1", Bn). FAB-MS m/z 455 $[M+H]^+$.

EXAMPLE 44

Intermediate 42. A solution of nucleoside 41 (1.38 g, 3.0 mmol), anhydrous pyridine (2 $cm^3$) and anhydrous dichloromethane (6 $cm^3$) was stirred at −10° C. and p-toluenesulfonyl chloride (0.648 g, 3.4 mmol) was added in small portions during 1 h. The solution was stirred at −10° C. for 3 h. The reaction was quenched by addition of ice-cold water (10 $cm^3$) and the mixture was extracted with dichloromethane (3×50 $cm^3$). The combined organic phase was washed with a saturated aqueous solution of sodium hydrogencarbonate (3×20 $cm^3$) and was dried ($Na_2SO_4$). The solvent was removed under reduced pressure and the residue was purified by silica gel column chromatography using dichloromethane/methanol (99:1, v/v) as eluent to give intermediate 42 (0.9 g) which was used without further purification in the next step.

EXAMPLE 45

(1S,3R,4R,7S)-7-Benzyloxy-1-benzyloxymethyl-3-(uracil-1-yl)-2,5-dioxabicyclo[2.2.1]-heptane (43). Compound 42 (0.7 g) was dissolved in anhydrous DMF (3 $cm^3$) and a 60% suspension of sodium hydride (w/w, 0.096 g, 24 mmol) was added in four portions during 10 min at 0° C., and the reaction mixture was stirred at room temperature for 12 h. The reaction was quenched with methanol (10 $cm^3$), and the solvents were removed under reduced pressure. The residue was dissolved in dichloromethane (20 $cm^3$), washed with saturated aqueous sodium hydrogencarbonate (3×6 $cm^3$) and was dried ($Na_2SO_4$). The solvent was removed under reduced pressure and the residue was purified by silica gel column chromatography using dichloromethane/ethanol (99:1, v/v) as eluent to give nucleoside 43 (0.30 g, 60%). $\delta_H$ ($CDCl_3$) 9.21 (1H, br s, NH), 7.70 (1H, d, J 8.2, 6-H), 7.37-7.24 (10H, m, Bn), 5.65 (1H, s, 1'-H), 5.52 (1H, d, J 8.2, 5-H), 4.68-4.45 (5H, m, 2'-H, Bn), 4.02-3.55 (5H, m, 3'-H, 5'-$H_a$, 1"-$H_a$5'-$H_b$, 1"-$H_b$). $\delta_C$ ($CDCl_3$) 163.33 (C-4), 149.73 (C-2), 139.18 (C-6), 137.46, 136.81, 128.58, 128.54, 128.21, 128.10, 127.79, 127.53 (Bn), 101.66 (C-5), 87.49, 87.33 (C-1', C-4'), 76.53, 75.71, 73.77, 72.33, 72.00, 64.35 (C-2', C-3', C-5', C-1", Bn). FAB-MS m/z 459 $[M+Na]^+$.

EXAMPLE 46

(1S,3R,4R,7S)-7-Hydroxy-1-hydroxymethyl-3-(uracil-1-yl)-2,5-dioxabicyclo[2.2.1]-heptane (44). To a solution of compound 43 (0.35 g, 0.8 mmol) in absolute ethanol (2 $cm^3$) was added 20% palladium hydroxide over carbon (0.37 g) and the mixture was degassed several times with hydrogen and stirred under the atmosphere of hydrogen for 4 h. The solvent was removed under reduced pressure and the residue was purified by silica gel column chromatography using dichloramethane/methanol (9:1, v/v) as eluent to give nucleoside 44 as a white solid material (0.16 g, 78%). $\delta_H$ ($CD_3OD$) 7.88 (1H, d, J 8.1, 6-H), 5.69 (1H, d, J 8.1, 5-H), 5.55 (1H, s, 1'-H), 4.28 (1H, s, 2'-H), 4.04 (1H, s, 3'-H), 3.96 (1H, d, J 7.9, 1"-$H_a$), 3.91 (2H, s, 5'-H), 3.76 (1H, d, J 7.9, 1"-$H_b$). $\delta_C$ ($CD_3OD$) 172.95 (C-4), 151.82 (C-2), 141.17 (C-6), 101.97 (C-5), 90.52, 88.50 (C-1', C-4'), 80.88, 72.51, 70.50, 57.77 (C-2', C-3', C-5', C-1"). FAB-MS m/z 257 $[M+H]^+$.

EXAMPLE 47

(1R,3R,4R,7S)-1-(4,4'-Dimethoxytrityloxymethyl)-7-hydroxy-3-(uracil-1-yl)-2,5-dioxabicyclo[2.2.1]heptane (45). To a solution of compound 44 (0.08 g, 0.31 mmol) in anhydrous pyridine (0.5 $cm^3$) was added 4,4'-dimethoxytrityl chloride (0.203 g, 0.6 mmol) at 0° C. and the mixture was stirred at room temperature for 2 h. The reaction was quenched with ice-cold water (10 $cm^3$) and extracted with dichloromethane (3×4 $cm^3$). The combined organic phase was washed with saturated aqueous solutions of sodium hydrogencarbonate (3×3 $cm^3$) and brine (2×3 $cm^3$) and was dried ($Na_2SO_4$). The solvent was removed under reduced pressure and the residue was purified by silica gel column chromatography using dichloromethane/methanol (98:2, v/v) as eluent to give nucleoside 45 as a white solid material (0.12 g, 69%). $\delta_H$ ($CDCl_3$) 9.25 (1H, br s, NH), 7.93 (1H, d, J 7.2, 6-H), 7.50-7.15 (9H, m, DMT), 6.88-6.78 (4H, m, DMT), 5.63 (1H, s, 1'-H), 5.59 (1H, d, J 8.0, 5-H), 4.48 (1H, s, 2'-H), 4.26 (1H, s, 3'-H), 3.88 (1H, d, J 8.1, 1"-$H_a$), 3.85-3.55 (7H, m, 1"-$H_b$, $OCH_3$), 3.58-3.40 (2H, m, 5-$H_a$, 5'-$H_b$). $\delta_C$ ($CDCl_3$) 164.10 (C-4), 158.60 (DMT), 150.45 (C-2), 147.53 (DMT), 144.51 (C-6), 139.72, 135.49, 135.37, 130.20, 129.28, 128.09, 127.85, 127.07 (DMT), 113.39, 113.17 (DMT), 101.79 (C-5), 88.20, 87.10, 86.87 (C-1', C-4', DMT), 79.25, 71.79, 69.70, 58.13 (C-2', C-3', C-5', C-1"), 55.33 ($OCH_3$). FAB-MS m/z 559 $[M+H]^+$.

EXAMPLE 48

(1R,3R,4R,7S)-7-(2-Cyanoethoxy(diisopropylamino) posphinoxy)-1-(4,4'-dimethoxytrityloxymethyl)-3-(uracil-1-yl)-2,5-dioxabicyclo[2.2.1]heptane (46). To a solution of compound 45 (0.07 g, 0.125 mmol) in anhydrous dichloromethane (2 $cm^3$) at room temperature was added N,N-diisopropylethylamine (0.1 $cm^3$) and 2-cyanoethyl N,N-diisopropylphosphoramidochloridite (0.07 $cm^3$, 0.32 mmol). After stirring for 1 h, the reaction was quenched with MeOH (2 $cm^3$), and the resulting mixture was diluted with ethyl acetate (5 $cm^3$) and washed successively with saturated aqueous solutions of sodium hydrogencarbonate (3×2 $cm^3$) and brine (3×2 $cm^3$), and was dried ($Na_2SO_4$). The solvent was evaporated under reduced pressure and the residue was purified by silica gel column chromatography using dichloromethane/methanol (99:1, v/v) as eluent to give a white foam. This foam was dissolved in dichloromethane (2 $cm^3$) and the product was precipitated from petroleum ether (10 $cm^3$, cooled to −30° C.) under vigorous stirring. The precipitate was collected by filtration and was dried to give compound 46 as a white solid material (0.055 g, 58%). $\delta_p$ ($CDCl_3$) 149.18, 149.02.

EXAMPLE 49

9-(2-O-Acetyl-4-C-acetoxymethyl-3,5-di-O-benzyl-β-D-ribofuranosyl)-2-N-isobutyrylguanine (47). To a stirred suspension of the anomeric mixture 33 (1.28 g, 5.6 mmol) and 2-N-isobutyrylguanine (1.8 g, 3.7 mmol) in anhydrous dichloroethane (60 $cm^3$) was added N,O-bis(trimethylsilyl) acetamide (4 $cm^3$, 16.2 mmol). The reaction mixture was stirred at reflux for 1 h. Trimethylsilyl triflate (1.5 mL, 8.28 mmol) was added dropwise at 0° C. and the solution was stirred at reflux for 2 h. The reaction mixture was allowed to cool to room temperature during 1.5 h. After dilution to 250 $cm^3$ by addition of dichloromethane, the mixture was washed with a saturated aqueous solution of sodium hydrogencarbonate (200 $cm^3$) and water (250 $cm^3$). The solvent was removed under reduced pressure and the residue was purified by silica gel column chromatography using 1.25% (200 $cm^3$) and 1.5% (750 $cm^3$) of methanol in dichloromethane (v/v) as eluents to give 2.10 g (87%) of a white solid that according to $^1$H-NMR analysis consisted of three isomers (ratio: 12.5:2.5:1). The main product formed in that conditions is expected to be compound 47 (P. Garner, S. Ramakanth, *J. Org. Chem.* 1988, 53, 1294; H. Vorbruggen, K. Krolikiewicz, B. Bennua, *Chem. Ber.* 1981, 114, 1234). The individual isomers were not isolated and mixture was used for next step. For main product 47: $\delta_H$ ($CDCl_3$) 12.25 (br s, NHCO), 9.25 (br s, NH), 7.91 (s, 8-H) 7.39-7.26 (m, Bn), 6.07 (d, J 4.6, 1'-H), 5.80 (dd, J 5.8, J 4.7, 2'-H), 4.72 (d, J 5.9, 3'-H), 4.59-4.43 (m, Bn, 1"-$H_a$), 4.16 (d, J 12.1, 1"-$H_b$), 3.70 (d, J 10.1, 5'-$H_a$), 3.58 (d, J 10.1, 5'-$H_b$), 2.65 (m, CHCO), 2.05 (s, $COCH_3$), 2.01 (s, $COCH_3$), 1.22 (d, J 6.7, $CH_3CH$), 1.20 (d, J 7.0, $CH_3CH$). $\delta_C$ ($CDCl_3$) 178.3 (COCH), 170.6, 179.8 ($COCH_3$), 155.8, 148.2, 147.6 (guanine), 137.6, 137.2 (guanine, Bn), 128.5, 128.4, 128.2, 128.1, 128.0, 127.8, 127.7 (Bn), 121.2 (guanine), 86.2, 86.0 (C-1', C-4'), 77.8 (C-3'), 74.9, 74.5, 73.7, 70.4 (Bn, C-2', C-5'), 63.5 (C-1"), 36.3 (COCH), 20.8, 20.6 ($COCH_3$), 19.0 ($CH_3CH$). For the mixture: FAB-MS m/z 648 $[M+H]^+$, 670 $[M+Na]^+$. Found: C, 60.8; H, 6.0; N, 10.4; $C_{33}H_{36}N_5O_9$ requires C, 61.3; H, 5.6; N, 10.8%.

EXAMPLE 50

9-(3,5-Di-O-benzyl-4-C-hydroxymethyl-β-D-ribofuranosyl)-2-N-isobutyrylguanine (48). A solution of the mixture described in Example 49 containing compound 47 (2.10 g, 3.25 mmol) in THF/Pyridine/methanol (2:3:4, v/v/v) (40 $cm^3$) was cooled to −10° C. and sodium methoxide (320 mg, 5.93 mmol) was added to the stirred solution. The reaction mixture was stirred at 10° C. for 30 min and neutralised with 2 $cm^3$ of acetic acid. The solvent was evaporated under reduced pressure and the residue was twice extracted in a system of dichloromethane/water (2×100 $cm^3$). The organic fractions were combined and evaporated under reduced pressure. After co-evaporation with toluene, the residue was purified by silica gel column chromatography in a gradient (2-7%) of methanol in dichloromethane (v/v) to give a white solid material (1.62 g). According to $^1$H-NMR it consisted of three isomers (ratio: 13.5:1.5:1). For main product 48: $\delta_H$ ($CD_3OD$) 8.07 (s, 8-H) 7.36-7.20 (m, Bn), 6.05 (d, J 3.9, 1'-H), 4.81 (d, J 11.5, Bn), 4.75 (m, 2'-H), 4.56 (d, J 11.5, Bn), 4.51-4.43 (m, Bn, 3'-H), 3.83 (d, J 11.7, 1"-$H_a$), 3.65 (d, J 11.7, 1"-$H_b$), 3.64 (d, J 10.6, 5'-$H_a$), 3.57 (d, J 10.3, 5'-$H_b$), 2.69 (m, CHCO), 1.20 (6H, d, J 6.8, $CH_3CH$). $\delta_C$ ($CD_3OD$) 181.6 (COCH), 157.3, 150.2, 149.5 (guanine), 139.4, 139.3, 139.0 (guanine, Bn), 129.5, 129.4, 129.3, 129.2, 129.1, 129.0, 128.9, 128.8 (Bn), 121.2 (guanine), 90.7, 89.6 (C-1', C-4'), 79.2 (C-3'), 75.8, 74.5, 74.3, 72.2 (Bn, C-2', C-5'), 63.1

(C-1"), 36.9 (COCH), 19.4 ($CH_3CH$), 19.3 ($CH_3CH$). For the mixture: FAB-MS m/z 564 $[M+H]^+$.

EXAMPLE 51

Intermediate 49. A solution of the mixture described in Example 50 containing 48 (1.6 g) in anhydrous pyridine (6 $cm^3$) was stirred at −20° C. and p-toluenesulphonyl chloride (0.81 g, 4.27 mmol) was added. The solution was stirred for 1 h at −20° C. and for 2 h at −25° C. Then the mixture was diluted to 100 $cm^3$ by addition of dichloromethane and immediately washed with water (2×100 $cm^3$). The organic phase was separated and evaporated under reduced pressure. The residue was purified by silica gel column chromatography using dichloromethane/methanol as eluent (1-2%, v/v) to give intermediate 49 (980 mg). After elution of compound 49 from the column, the starting mixture containing 48 (510 mg) was eluted using 8% methanol in dichloromethane (v/v) as eluent. This material was concentrated, dried under reduced pressure and treated in the same manner as described above to give additionally 252 mg of the intermediate. The intermediate (1.23 g) was purified by silica gel HPLC (PrepPak Cartridge packed by Porasil, 15-20 μm, 125 A, flow rate 60 $cm^3$/min, eluent 0-4% of methanol in dichloromethane (v/v), 120 min). Fractions containing intermediate 49 were pooled and concentrated to give white solid (1.04 g). According to $^1$H-NMR it consisted of two main products, namely 1"-O and 2'-O monotosylated derivatives in a ratio of ~2:1. FAB-MS m/z 718 $[M+H]^+$. Found C, 60.4; H, 5.8; N, 9.3; $C_{36}H_{39}N_5O_9S$ requires C, 60.2; H, 5.5; N, 9.8%.

EXAMPLE 52

(1S,3R,4R,7S)-7-Benzyloxy-1-benzyloxymethyl-3-(2-N-isobutyrylguanin-9-yl)-2,5-dioxabicyclo[2.2.1]heptane (50). To a solution of intermediate 49 (940 mg) in anhydrous THF (20 $cm^3$) was added a 60% suspension of sodium hydride (w/w, 130 mg, 3.25 mmol) and the mixture was stirred for 1 h at room temperature. Acetic acid (0.25 mL) was added and the mixture was concentrated under reduced pressure. The residue was dissolved in dichloromethane (100 $cm^3$) and was washed with water (2×100 $cm^3$). The organic phase was separated and evaporated under reduced pressure. The residue was purified by silica gel column chromatography using methanol/dichloromethane (1-1.5%, v/v) as eluent to give nucleoside 50 as a white solid material (451 mg, 57%). □$_H$ ($CDCl_3$) 12.25 (1H, br s, NHCO), 10.12 (1H, br s, NH), 7.84 (1H, s, 8-H), 7.31-7.15 (10H, m, Bn), 5.72 (1H, s, 1'-H), 4.60-4.46 (5H, m, Bn, 2'-H), 4.14 (1H, s, 3'-H), 4.02 (1H, d, J 7.9, 1"-$H_a$), 3.85 (1H, d, J 7.9, 1"-$H_b$), 3.78 (2H, s, 5'-H), 2.81 (1H, m, CHCO), 1.24 (3H, d, J 6.8, $CH_3CH$), 1.22 (3H, d, J 6.4, $CH_3CH$). $\delta_C$ ($CDCl_3$) 179.5 (COCH), 155.6, 148.1, 147.3 (guanine), 137.3, 136.9, 136.0 (guanine, Bn), 128.4, 128.3, 127.9, 127.8, 127.5, 127.4 (Bn), 121.2 (guanine), 87.1, 86.2 (C-1', C-4'), 77.0 (C-3'), 73.6, 72.5, 72.1 (Bn, C-2', C-5'), 64.9 (C-1"), 36.1 (COCH), 19.0 ($CH_3CH$), 18.9 ($CH_3CH$). FAB-MS m/z 546 $[M+H]^+$. Found: C, 63.3; H, 5.9; N, 12.5; $C_{29}H_{30}N_5O_6$ requires C, 64.0; H, 5.6; N, 12.9%.

Alternative preparation of compound 50. G1AQ. To a suspension of compound 78 (1.5 g, 2.51 mmol), N2-isobutirylguanine (0.93 g, 4.06 mmol) in dry DCM (50 mL) was added BSA (N,O-bistrimethylsilylacetamide; 3.33 mL, 13.5 mmol) and the mixture was refluxed for 2 h. Trimethylsilyl triflate (1.25 mL, 6.9 mmol) was added to the mixture and refluxing was continuing for additional 2 h. The mixture was allowed to cool to room temperature, diluted by 200 mL of DCM and washed by saturated aq. $NaHCO_3$ and water. Chromatography at silica gel column (1-2.5% of $CH_3OH$ in dichloromethane) yielded 1.05 g (55%) of the desired isomer G1AQ and 380 mg of isomers with higher mobility which was converted to G1AQ by repetition of the procedure described above. Ammonium hydroxide (12 mL of 25% aq. solution) was added to a solution of G1AQ (1.05 g in 12 mL of methanol) and the mixture was stirred for 1 hr at room temperature. After concentration, the product was purified by silica gel column chromatography (1-3% $CH_3OH$ in dichloromethane) to give 700 mg G3 as a white solid material. 700 mg of G3 in anhydrous THF (15 mL) was treated with NaH (225 mg of 60% suspension in mineral oil). 30 min later, the reaction was quenched by addition of 1.25 mL of acetic acid, and the mixture was concentrated under reduced pressure. The residue was dissolved in dichloromethane, washed by $NaHCO_3$ and water and purified by silica gel chromatography in gradient 0.5-3% methanol/DCM. Yield 400 mg (75%) of 50.

EXAMPLE 53

(1S,3R,4R,7S)-7-Hydroxy-1-hydroxymethyl-3-(2-N-isobutyrylguanin-9-yl)-2,5-dioxabicyclo[2.2.1]heptane (51). A mixture of nucleoside 50 (717 mg, 1.31 mmol) and 10% palladium over carbon (500 mg) was suspended in methanol (8 $cm^3$) at room temperature. The mixture was degassed several times under reduced pressure and placed under a hydrogen atmosphere. After stirring for 24 h the mixture was purified by silica gel column chromatography using methanol/dichloromethane (8-20%, v/v) as eluent to give nucleoside 51 as a glass-like solid (440 mg, 92%). $\delta_H$ ($CD_3OD$) 8.12 (1H, br s, 8-H), 5.86 (1H, s, 1'-H), 4.50 (1H, s, 2'-H), 4.30 (1H, s, 3'-H), 4.05 (1H, d, J 8.0, 1"-$H_a$), 3.95 (2H, s, 5'-H), 3.87 (1H, d, J 7.9, 1"-$H_b$), 2.74 (1H, m, CHCO), 1.23 (6H, d, J 6.9, $CH_3CH$). $\delta_C$ ($CD_3OD$, signals from the carbohydrate part) 90.2, 87.6 (C-1', C-4'), 81.1 (C-3'), 72.9, 71.3 (C-2', C-5'), 58.2 (C-1"), 37.1 (COCH), 19.5 ($CH_3CH$). FAB-MS m/z 366 $[M+H]^+$.

EXAMPLE 54

(1R,3R,4R,7S)-1-(4,4'-Dimethoxytrityloxymethyl)-7-hydroxy-3-(2-N-isobutyrylguanin-9-yl)-2,5-dioxabicyclo[2.2.1]heptane (52). A mixture of compound 51 (440 mg, 1.21 mmol) and 4,4'-dimethoxytrityl chloride (573 mg, 1.69 mmol) was dissolved in anhydrous pyridine (7 $cm^3$) and was stirred at room temperature for 4 h. The mixture was evaporated under reduced pressure to give an oil. Extraction was performed in a system of dichloromethane/water (1:1, v/v, 40 $cm^3$). The organic phase was separated and concentrated to give a solution in a minimal volume of dichloromethane containing 0.5% of pyridine (v/v) which was applied to a silica gel column equilibrated by the same solvent. The product was eluted in gradient concentrations of methanol (0.6-2%, v/v) in dichloromethane containing 0.5% of pyridine (v/v) to give compound 52 as a white solid material (695 mg, 86%). $\delta_H$ ($CDCl_3$) 12.17 (1H, br s, NHCO), 10.09 (1H, br s, NH), 7.87 (1H, s, 8-H), 7.42-6.72 (13H, m, DMT), 5.69 (1H, s, 1'-H), 4.59 (1H, s, 2'-H), 4.50 (1H, s, 3'-H), 3.98 (1H, d, J 8.1, 1"-$H_a$), 3.69-3.39 (9H, m, DMT, 5'-H, 1"-$H_b$), 2.72 (1H, m, CHCO), 1.17 (6H, d, J 6.8, $CH_3CH$). $\delta_C$ ($CDCl_3$) 179.8 (COCH), 158.8, 144.5, 135.6, 135.5, 130.1, 128.1, 127.7, 126.9, 113.2 (DMT), 155.8, 147.9, 147.5, 137.0, 120.8 (guanine), 87.6, 86.4, 86.1 (C-1', C-4', DMT), 79.7 (C-3'), 72.6, 71.4 (C-2', C-5'), 59.8 (C-1"), 55.2 (DMT), 36.1 (COCH), 19.1, 18.8 ($CH_3CH$). FAB-MS m/z 668 $[M+H]^+$.

EXAMPLE 55

(1R,3R,4R,7S)-7-(2-Cyanoethoxy(diisopropylamino) phosphinoxy)-1-(4,4'-dimethoxytrityloxymethyl)-3-(2-N-isopropyonylguanin-9-yl)-2,5-dioxabicyclo[2.2.1]heptane (53). Compound 52 (670 mg, 1.0 mmol) was at room temperature dissolved in anhydrous dichloromethane (5 $cm^3$) containing N,N-diisopropylethylamine (0.38 $cm^3$, 4 mmol). 2-Cyanoethyl N,N-diisopropylphosphoramidochloridite (0.36 $cm^3$, 2.0 mmol) was added drop-wise with stirring. After 5 h, methanol (2 $cm^3$) was added and the mixture was diluted to 100 $cm^3$ by addition of dichloromethane and washed with a saturated aqueous solution of sodium hydrocarbonate (50 $cm^3$). The organic phase was separated and the solvent was removed by evaporation under reduced pressure. The residue was dissolved in the minimum amount of dichloromethane/petroleum ether (1:1, v/v) containing 0.5% pyridine (v/v) and was applied to a column packed with silica gel equilibrated by the same solvent mixture. The column was washed by dichloromethane/petroleum/pyridine (75:25:0.5, v/v/v, 250 $cm^3$) and the product was eluted using a gradient of methanol in dichloromethane (0-1%, v/v) containing 0.5% pyridine (v/v). The fractions containing the main product were evaporated and co-evaporated with toluene. The residue was dissolved in anhydrous dichloromethane (5 $cm^3$) and precipitated from petroleum ether (100 $cm^3$) to give compound 53 as a white solid material (558 mg, 64%) after filtration and drying. $\delta_p$ ($CDCl_3$) 148.17, 146.07. FAB-MS m/z 868 $[M+1]^+$.

EXAMPLE 56

1-(2-O-Acetyl-4-C-acetoxymethyl-3,5-di-O-benzyl-β-D-ribofuranosyl)-4-N-benzoylcytosine (54). To a stirred solution of the anomeric mixture 33 (4.0 g, 8.22 mmol) and 4-N-benzoylcytosine (2.79 g, 13.0 mmol) was added N,O-bis (trimethylsilyl)acetamide (8.16 $cm^3$, 33.0 mmol). The reaction mixture was stirred for 1 h at room temperature and cooled to 0° C. Trimethylsilyl triflate (3.0 $cm^3$, 16.2 mmol) was added dropwise and the mixture was stirred at 60° C. for 2 h. Saturated aqueous solutions of sodium hydrogencarbonate (3×20 $cm^3$) and brine (2×20 $cm^3$) were successively added, and the separated organic phase was dried ($Na_2SO_4$). The solvent was removed under reduced pressure and the residue was purified by silica gel column chromatography using dichloromethane/methanol (99:1, v/v) as eluent to give compound 54 as a white solid material (3.9 g, 74%). $\delta_H$ ($CDCl_3$), 8.28 (1H, d, J 7.5, 6-H), 7.94-7.90 (2H, m, Bz), 7.65-7.25 (13H, m, Bn, Bz), 7.16 (1H, d, J 7.1, 5-H), 6.22 (1H, d, J 2.8, 1'-H), 5.51 (1H, dd, J 2.8, 5.8, 2'-H), 4.62 (1H, d, J 11.6, Bn), 4.51 (1H, d, J 12.3, 1"-$H_a$), 4.49-4.34 (4H, m, 3'-H, Bn), 4.21 (1H, d, J 12.3, 1"-$H_b$), 3.85 (1H, d, J 10.3, 5'-$H_a$), 3.47 (1H, d, J 10.3, 5'-$H_b$), 2.13 (3H, s, $COCH_3$), 2.06 (3H, s, $COCH_3$). $\delta_C$ ($CDCl_3$) 170.52, 169.61 (C=O), 166.83, 162.27 (C-4, C=O), 154.26 (C-2), 145.26 (C-6), 137.25, 136.93, 133.18, 129.0, 128.75, 128.51, 128.45, 128.18, 128.10, 127.89, 127.71 (Bn, Bz), 96.58 (C-5), 89.42, 86.52 (C-1', C-4'), 76.21, 75.10, 74.17, 73.70, 69.70, 63.97 (C-2', C-3', Bn, C-5', C-1"), 20.82 ($COCH_3$). FAB-MS m/z 664 $[M+Na]^+$, 642 $[M+H]^+$. Found: C, 65.0; H, 5.7; N, 6.5; $C_{35}H_{35}N_3O_9$ requires C, 65.5; H, 5.5; N, 6.5%.

EXAMPLE 57

1-(3,5-Di-O-benzyl-4-C-hydroxymethyl-β-D-ribofuranosyl)-4-N-benzoylcytosine (55). To a stirred solution of nucleoside 54 (3.4 g, 5.3 mmol) in methanol (20 $cm^3$) was added sodium methoxide (0.663 g, 11.66 mmol). The reaction mixture was stirred at room temperature for 10 min and then neutralised with 20% aqueous hydrochloric acid. The solvent was partly evaporated and the residue was extracted with dichloromethane (3×50 $cm^3$). The combined organic phase was washed with a saturated aqueous solution of sodium hydrogencarbonate (3×20 $cm^3$) and was dried ($Na_2SO_4$). The solvent was removed under reduced pressure and the residue was purified by silica gel column chromatography using dichloromethane/methanol (98.5:1.5, v/v) as eluent to give compound 55 as a white solid material (1.6 g, 54%). $\delta_H$ ($CDCl_3$) 9.95 (1H, br s, NH), 8.33 (1H, d, J 7.4, 6-H), 7.98 (2H, m, Bz), 7.60-7.12 (14H, m, Bn, Bz, 5-H), 6.17 (1H, d, J 1.6, 1'-H), 4.78 (1H, d, J 11.8, Bn), 4.48-4.27 (5H, m, Bn, 2'-H, 3'-H), 3.85 (1H, d, J 11.8, 5'-$H_a$), 3.66-3.61 (2H, m, 5'-$H_b$, 1"-$H_a$), 3.47 (1H, d, J 10.4, 1"-$H_b$). $\delta_C$ ($CDCl_3$) 167.5, 162.31 (C-4, C=O), 155.36 (C-2), 145.34 (C-6), 137.49, 137.08, 133.09, 133.01, 128.94, 128.67, 128.48, 128.30, 128.01, 127.90, 127.80 (Bn, Bz), 96.53 (C-5), 93.97, 89.35 (C-1', C-4'), 76.06, 75.28, 73.70, 72.76, 70.26, 62.44 (C-2', C-3', Bn, C-5', C-1"). FAB-MS m/z 558 $[M+H]^+$.

EXAMPLE 58

Intermediate 56. A solution of nucleoside 55 (2.2 g, 3.94 mmol) in anhydrous tetrahydrofuran (60 $cm^3$) was stirred at −20° C. and a suspension of 60% sodium hydride in mineral oil (w/w, 0.252 g, 6.30 mmol) was added in seven portions during 45 min. The solution was stirred for 15 min at −20° C. followed by addition of p-toluenesulfonyl chloride (0.901 g, 4.73 mmol) in small portions. The solution was stirred for 4 h at −20° C. Additional sodium hydride (0.252 g, 6.30 mmol) and p-toluenesulfonyl chloride (0.751 g, 3.93 mmol) was added. The reaction mixture was kept at −20° C. for 48 h. The reaction was quenched by addition of ice-cold water (50 $cm^3$) whereupon extraction was performed with dichloromethane (3×60 $cm^3$). The combined organic phase was washed with a saturated aqueous solution of sodium hydrogencarbonate (3×20 $cm^3$) and dried ($Na_2SO_4$). The solvent was evaporated under reduced pressure and the residue was purified by silica gel column chromatography using dichloromethane/methanol (99:1, v/v) as eluent to give the intermediate 56 (1.80 g).

EXAMPLE 59

(1S,3R,4R,7S)-7-Benzyloxy-1-benzyloxymethyl-3-(4-N-benzoylcytosin-1-yl)-2,5-dioxabicyclo[2.2.1]heptane (57). Intermediate 56 (1.80 g) was dissolved in anhydrous DMF (30.0 $cm^3$) and a 60% suspension of sodium hydride in mineral oil (w/w, 0.16 g, 3.9 mmol) was added in five portions during 30 min at 0° C. The reaction mixture was stirred for 36 h at room temperature. The reaction was quenched by adding ice-cold water (70 $cm^3$) and the resulting mixture was extracted with dichloromethane (3×50 $cm^3$). The combined organic phase was washed with a saturated aqueous solution of sodium hydrogencarbonate (3×30 $cm^3$) and dried ($Na_2SO_4$). The solvents were removed under reduced pressure and the residue was purified by silica gel column chromatography using dichloromethane/methanol (99.5:0.5, v/v) as eluent to give compound 57 as a white solid material (1.08 g, 79%). $\delta_H$ ($CDCl_3$) 8.95 (1H, br s, NH), 8.20 (1H, d, J 7.5, 6-H), 7.95-7.92 (2H, m, Bz), 7.66-7.22 (14H, m, Bn, Bz, 5-H), 5.78 (1H, s, 1'-H), 4.70-4.65 (3H, m, 2'-H, Bn), 4.60 (1H, d, J 11.6, Bn), 4.47 (1H, d, J 11.6, Bn), 4.05-3.78 (5H, m, 3'-H, 5'-$H_a$, 1"-$H_a$, 5'-$H_b$, 1"-$H_b$). $\delta_C$ ($CDCl_3$) 167.0, 162.36 (C-4, C=O), 154.5 (C-2), 144.58 (C-6), 137.46, 136.93, 133.35, 132.93, 129.11, 128.67, 128.50, 128.16, 128.11, 127.68, 127.60 (Bn), 96.35 (C-5), 88.38, 87.67 (C-1', C-4'), 76.14, 75.70, 73.79, 72.27, 72.09, 64.34 (Bn, C-5', C-1", C-2', C-3'). FAB-MS m/z 540 $[M+H]^+$. Found: C, 68.0; H, 5.5; N, 7.5; $C_{31}H_{29}N_3O_6$ requires C, 69.0; H, 5.4; N, 7.8%).

EXAMPLE 60

(1S,3R,4R,7S)-7-Hydroxy-1-hydroxymethyl-3-(cytosin-1-yl)-2,5-dioxabicyclo[2.2.1]-heptane (57A). To a solution of nucleoside 57 (0.3 g, 0.55 mmol) in anhydrous methanol (22 $cm^3$) were added 1,4-cyclohexadiene (5.0 $cm^3$) and 10% palladium on carbon (0.314 g). The mixture was stirred under reflux for 18 h. Additional 10% palladium on carbon (0.380 g) and 1,4-cyclohexadiene (5.5 $cm^3$) were added and the mixture was refluxed for 54 h. The reaction mixture was filtered through a pad of silica gel which was subsequently washed with methanol (1500 $cm^3$). The combined filtrate was evaporated under reduced pressure and the residue was purified by silica gel column chromatography using dichloromethane/methanol (92.5:7.5, v/v) as eluent to give compound 57A as a white solid material (0.051 g, 36%). $\delta_H$ ($(CD_3)_2SO$) 7.73 (1H, d, J 7.7, 6-H), 7.12-7.20 (2H, br s, $NH_2$), 5.74 (1H, d, J 7.7, 5-H), 5.61 (1H, br s, 3'-OH), 5.39 (1H, s, 1'-H), 5.12 (1H, m, 5'-OH), 4.08 (1H, s, 2'-H), 3.80 (1H, d, J 7.7, 1"-$H_a$), 3.81 (1H, s, 3'-H), 3.74 (2H, m, 5'-$H_a$, 5'-$H_b$), 3.63 (1H, d, J 7.7, 1"-$H_b$). $\delta_C$ ($(CD_3)_2SO$) 165.66 (C-4), 154.58 (C-2), 139.68 (C-6), 93.19 (C-5), 88.42, 86.73 (C-1', C-4'), 78.87, 70.85, 68.32, 56.04 (C-2', C-1", C-3', C-5'). FAB-MS m/z 256 $[M+H]^+$.

EXAMPLE 61

Intermediate 57B. To nucleoside 57A (0.030 g, 0.11 mmol) suspended in anhydrous pyridine (2.0 $cm^3$) was added trimethylsilyl chloride (0.14 $cm^3$, 1.17 mmol) and stirring was continued for 1 h at room temperature. Benzoyl chloride (0.07 $cm^3$, 0.58 mmol) was added at 0° C. and the mixture was stirred for 2 h at room temperature. After cooling the reaction mixture to 0° C., water (3.0 $cm^3$) was added. After stirring for 5 min, an aqueous solution of ammonia (1.5 $cm^3$, 32%, w/w) was added and stirring was continued for 30 min at room temperature. The mixture was evaporated under reduced pressure, and the residue was purified by silica gel column chromatography using dichloromethane/methanol (97.5:2.5, v/v) as eluent to give intermediate 57B as white solid material (0.062 g).

EXAMPLE 62

(1R,3R,4R,7S)-1-(4,4'-Dimethoxytrityloxymethyl)-7-hydroxy-3-(4-N-benzoylcytosine-1-yl)-2,5-dioxabicyclo[2.2.1]heptane (57C). To a solution of intermediate 57B (0.042 g, 0.11 mmol) in anhydrous pyridine (1.5 $cm^3$) was added 4,4'-dimethoxytrityl chloride (0.06 g, 0.17 mmol). The reaction mixture was stirred at room temperature for 3.5 h, cooled to 0° C., and a saturated aqueous solution of sodium hydrogencarbonate (20 $cm^3$) was added. Extraction was performed using dichloromethane (3×10 $cm^3$). The combined organic phase was dried ($Na_2SO_4$) and evaporated to dryness under reduced pressure. The residue was purified by silica gel column chromatography using dichloromethane/methanol/pyridine (98.0:1.5:0.5, v/v/v) as eluent to give nucleoside 57C as a white solid material (0.031 g, □63% from 57A). $\delta_H$ ($C_5D_5N$) 12.32 (1H, br s, NHCO), 8.75-7.06 (20H, m, DMT, Bz, H-5, H-6), 6.24 (1H, s, 1'-H), 5.11 (1-H, s, 2'-H), 4.90 (1H, s, 3'-H), 4.38 (1H, d, J 7.6, 1"-$H_a$), 4.10 (1H, d, J 7.6, 1"-$H_b$), 4.02 (1H, d, J 10.6, 5'-$H_a$), 3.87 (1H, d, J 10.6, 5'-$H_b$), 3.77, 3.76 (2×3H, 2×s, 2×$OCH_3$). $\delta_C$ ($C_5D_5N$) 169.00 (NHCO), 164.24 (C-2), 159.39 (DMT), 150.5, 145.62 (DMT), 144.31, 132.89, 130.82, 130.72, 129.09, 128.89, 128.60, 113.96 (DMT), 96.96, 89.01, 87.18, 79.91, 72.56, 70.25 (C-5, C-1', C-4', C-2', C-1", C-3'), 59.51 (C-5'), 55.33 ($OCH_3$). FAB-MS M/Z 662 $[M+H]^+$.

EXAMPLE 63

(1R,3R,4R,7S)-7-(2-Cyanoethoxy(diisopropylamino)phosphinoxy)-1-(4,4'-dimethoxytrityloxymethyl)-3-(4-N-benzoylcytosine-1-yl)-2,5-dioxabicyclo[2.2.1]heptane (57D). To a solution of nucleoside 57C (0.025 g, 0.03 mmol) in anhydrous dichloromethane (1.5 $cm^3$) was added N,N-diisopropylethylamine (0.03 $cm^3$, 0.17 mmol) followed by dropwise addition of 2-cyanoethyl N,N-diisopropylphosphoramidochloridite (0.02 $cm^3$, 0.09 mmol). After stirring for 5 h at room temperature, the reaction mixture was cooled to 0° C., dichloromethane/pyridine (10.0 $cm^3$, 99.5:0.5, v/v) was added, and washing was performed using a saturated aqueous solution of sodium hydrogencarbonate (3×8 $cm^3$). The organic phase was separated, dried ($Na_2SO_4$) and evaporated to dryness under reduced pressure. The residue was purified by silica gel column chromatography using dichloromethane/methanol/pyridine (99.0:0.5:0.5, v/v/v) as eluent to give amidite 57D as a light yellow oil (0.038 g). $\delta_p$ ($CDCl_3$) 147.93.

EXAMPLE 64

9-(2-O-Acetyl-4-C-acetyloxymethyl-3,5-di-O-benzyl-β-D-ribofuranosyl)-6-N-benzoyladenine (58). To a stirred suspension of the anomeric mixture 33 (5.0 g, 10.3 mmol) and 6-N-benzoyladenine (3.76 g, 15.7 mmol) in anhydrous dichloromethane (200 $cm^3$) was added N,O-bis(trimethylsilyl)acetamide (15.54 $cm^3$, 61.8 mmol). The reaction mixture was stirred at reflux for 1 h and then cooled to room temperature. Trimethylsilyl triflate (7.0 $cm^3$, 38.7 mmol) was added dropwise and the mixture was refluxed for 20 h. The reaction mixture was allowed to cool to room temperature and the volume of the mixture was reduced to ¼ under reduced pressure. Dichloromethane (250 $cm^3$) was added, and the solution was washed with a saturated aqueous solution of sodium hydrogencarbonate (3×50 $cm^3$) and water (50 $cm^3$). The organic phase was dried ($Na_2SO_4$) and evaporated under reduced pressure. The residue was purified by silica gel column chromatography using dichloromethane/methanol (99.5:0.5, v/v) as eluent to give nucleoside 58 as white solid material (3.65 g, 52%). $\delta_H$ ($CDCl_3$) 9.25 (1H, br s, NH), 8.71 (1H, s, 8-H), 8.24 (1H, s, 2-H), 8.0 (2H, d, J 7.5, Bz), 7.60-7.23 (13H, m, Bn, Bz), 6.35 (1H, d, J 4.6, 1'-H), 5.99 (1H, dd, J 4.9, 5.3, 2'-H), 4.78 (1H, d, J 5.6, 3'-H), 4.64-4.42 (5H, m, Bn, 1"-$H_a$), 4.25 (1H, d, J 12.1, 1"-$H_b$), 3.72 (1H, d, J 10.1, 5'-$H_a$), 3.56 (1H, d, J 10.1, 5'-$H_b$), 2.07 (3H, s, $COCH_3$), 2.02 (3H, s, $COCH_3$). $\delta_C$ ($CDCl_3$) 170.42, 169.72 ($COCH_3$), 164.60 (NHCO), 152.51 (C-6), 151.45 (C-2), 149.46 (C-4), 141.88 (C-8), 137.04, 137.00, 133.50, 132.60, 128.86, 128.66, 128.53, 128.41, 128.38, 128.18, 128.06, 127.91, 127.88, 127.79, 127.63, 123.26 (Bz, Bn, C-5), 86.38 (C-1'), 86.25 (C-4'), 77.74, 74.74, 74.44, 73.48 (C-2', C-3', 2×Bn), 70.11 (C-1"), 63.42 (C-5'), 20.70, 20.54 ($COCH_3$). FAB-MS m/z 666 $[M+H]^+$.

EXAMPLE 65

9-(3,5-Di-O-benzyl-4-C-hydroxymethyl-β-D-ribofuranosyl)-6-N-benzoyladenine (59). To a stirred solution of nucleoside 58 (4.18 g, 6.28 mmol) in methanol (50 $cm^3$) was added sodium methoxide (0.75 g, 13.8 mmol) at 0° C. The reaction mixture was stirred for 2 h, and ice was added. The mixture was neutralised using a 20% aqueous solution of HCl. Extraction was performed using dichloromethane (3×75 $cm^3$), the organic phase was separated, dried ($Na_2SO_4$) and evaporated under reduced pressure. The residue was purified by silica gel column chromatography using dichloromethane/methanol (98.5:1.5, v/v) as eluent to give nucleoside 59 as a white solid material (2.68 g, 73%). $\delta_H$ ($CDCl_3$) 9.42 (1H, br s, NH), 8.58 (1H, s, H-8), 8.16 (1H, s, 2-H), 7.96 (2H, d, J 7.2, Bz), 7.52-7.08 (13H, m, Bn, Bz), 6.18 (1H, d, J 2.5, 1'-H), 4.85-4.38 (4H, m, Bn, 2'-H, 3'-H), 4.33 (2H, s, Bn) 3.90 (1H, d, J 11.9, 1"-$H_a$), 3.71 (1H, d, J 11.8, 1"-$H_b$), 3.50-3.39 (2H, m, 5-H). $\delta_C$ ($CDCl_3$) 164.98 (NHCO), 152.19 (C-6), 151.00 (C-2), 149.34 (C-4), 142.28 (C-8), 137.32, 137.25, 133.46, 132.70, 128.69, 128.49, 128.40, 128.11, 128.03, 127.94, 127.83, 127.62, (Bz, Bn), 122.92 (C-5), 90.94, 88.75 (C-1', C-4'), 77.65, 74.08, 73.44, 73.20, 71.12, 62.39 (C-1", C-5', C-2', C-3', 2×Bn). FAB-MS m/z 582 $[M+H]^+$. Found: C, 65.6; H, 5.5; N, 11.7; $C_{32}H_{31}N_5O_6$ requires C, 66.1; H, 5.4; N, 12.0%.

EXAMPLE 66

Intermediate 60. A solution of nucleoside 59 (2.43 g, 4.18 mmol) in anhydrous tetrahydrofuran (25 $cm^3$) was stirred at −20° C. and a 60% suspension of sodium hydride in mineral oil (w/w, 0.28 g, 7.0 mmol) was added in four portions during 30 min. After stirring for 1 h, p-toluenesulfonyl chloride (1.34 g, 7.0 mmol) was added in small portions. The mixture was stirred at −10° C. for 15 h. Ice-cold water (50 $cm^3$) was added and extraction was performed with dichloromethane (3×50 $cm^3$). The combined organic phase was washed with a saturated aqueous solution of sodium hydrogencarbonate (2×25 $cm^3$), dried ($Na_2SO_4$) and evaporated under reduced pressure. The residue was purified by silica gel column chromatography using dichloromethane/methanol (99:1, v/v) as eluent to give the intermediate 60 (1.95 g).

EXAMPLE 67

(1S,3R,4R,7S)-7-Benzyloxy-1-benzyloxymethyl-3-(6-N-benzoyladenin-9-yl)-2,5-dioxabicyclo[2.2.1]heptane (61). Intermediate 60 (1.90 g) was dissolved in anhydrous DMF (20 $cm^3$) and a 60% suspension of sodium hydride in mineral oil (w/w, 0.16 g, 3.87 mmol) was added in small portions at 0° C. The mixture was stirred for 10 h at room temperature and then concentrated under reduced pressure. The residue was dissolved in dichloromethane (75 $cm^3$), washed with a saturated aqueous solution of sodium hydrogencarbonate (2×25 $cm^3$), dried ($Na_2SO_4$), and evaporated under reduced pressure. The residue was purified by silica gel column chromatography using dichloromethane/methanol (99:1, v/v) as eluent to give nucleoside 61 as white solid material (1.0 g, ~44% from 59). $\delta_H$ ($CDCl_3$) 8.71 (H, s, 8-H), 8.23 (1H, s, 2-H), 8.02 (2H, m, J 7.0, Bz), 7.99-7.19 (13H, m, Bn, Bz), 6.08 (1H, s, 1'-H), 4.78 (1H, s, 2'-H), 4.61-4.50 (4H, m, 2×Bn), 4.24 (1H, s, 3'-H), 4.12 (1H, d, J 7.8, 1"-$H_a$), 4.00 (1H, d, J 7.9, 1"-$H_b$), 3.85-3.78 (2H, m, 5'-$H_a$, 5'-$H_b$). □$_C$ ($CDCl_3$) 164.61 (NHCO), 152.32 (C-6), 150.61 (C-2), 149.35 (C-4), 140.67 (C-8), 137.24, 136.76, 133.33, 132.66, 128.68, 128.39, 128.29, 127.94, 127.77, 127.51 (Bn, Bz), 123.43 (C-5), 87.14, 86.52 (C-1', C-4'), 77.21, 76.77, 73.56, 72.57, 72.27, 64.65 (C-2', C-3', C-1", 2×Bn, C-5'). FAB-MS m/z 564 $[M+H]^+$. Found: C, 66.2; H, 5.5; N, 11.4; $C_{32}H_{29}N_5O_5$ requires C, 66.2; H, 5.2; N, 12.4%.

EXAMPLE 68

(1S,3R,4R,7S)-7-Hydroxy-1-hydroxymethyl-3-(adenin-9-yl)-2,5-dioxabicyclo[2.2.1]-heptane (61A). To a stirred solution of nucleoside 61 (0.80 g, 1.42 mmol) in anhydrous dichloromethane (30 $cm^3$) at −78° C. was dropwise during 30 min added $BCl_3$ (1 M solution in hexane; 11.36 $cm^3$, 11.36 mmol). The mixture was stirred for 4 h at −78° C., additional $BCl_3$ (1M solution in hexane, 16.0 $cm^3$, 16.0 mmol) was added drop-wise, and the mixture was stirred at −78° C. for 3 h. Then the temperature of the reaction mixture was raised slowly to room temperature and stirring was continued for 30 min. Methanol (25.0 $cm^3$) was added at −78° C., and the mixture was stirred at room temperature for 12 h. The mixture was evaporated under reduced pressure, and the residue was purified by silica gel column chromatography using dichloromethane/methanol (92:8, v/v) as eluent to give nucleoside 61A as a white solid material (0.332 g, 84%). $\delta_H$ ($(CD_3)_2SO$) 8.22 (1H, s, 8-H), 8.15 (1H, s, 2-H), 7.33 (2H, s, $NH_2$), 5.89 (1H, s, 1'-H), 5.83 (1H, d, J 4.2, 3'-OH), 5.14 (1H, t, J 5.9, 5'-OH), 4.14 (1H, s, 2'-H), 4.25 (1H, d, J 4.2, 3'-H), 3.92 (1H, d, J 7.8, 1"-$H_a$), 3.81-3.41 (3H, m, 5'-$H_a$, 1"-$H_b$). $O_c$ ($(CD_3)_2SO$) 155.90 (C-6), 152.64 (C-2), 148.35 (C-4), 137.72 (C-8), 118.94 (C-5), 88.48, 85.17 (C-1', C-4'), 79.09, 71.34, 69.83, 56.51 (C-2', C-3', C-1", C-5'). FAB-MS m/z 280 $[M+H]^+$.

EXAMPLE 69

(1S,3R,4R,7S)-7-Hydroxy-1-hydroxymethyl-3-(6-N-benzoyladenin-9-yl)-2,5-dioxabicyclo[2.2.1]heptane (61B). To a stirred solution of nucleoside 61A (0.32 g, 1.15 mmol) in anhydrous pyridine (1 $cm^3$) was added trimethylsilyl chloride (0.73 $cm^3$, 5.73 mmol) and the mixture was stirred at room temperature for 20 min. Benzoyl chloride (0.67 $cm^3$, 5.73 mmol) was added at 0° C., and the reaction mixture was stirred at room temperature for 2 h. The reaction mixture was cooled to 0° C. and ice-cold water (15.0 cm3) was added. After stirring for 5 min, a 32% (w/w) aqueous solution of ammonia (1.5 $cm^3$) was added and the mixture was stirred for 30 min. The mixture was evaporated to dryness and the residue was dissolved in water (25 $cm^3$). After evaporation of the mixture under reduced pressure, the residue was purified by silica gel chromatography using dichloromethane/methanol (97:3, v/v) as eluent to give nucleoside 61B as a white solid material (0.55 g). FAB-MS m/z 384 $[M+H]^+$.

EXAMPLE 70

(1R,3R,4R,7S)-7-Hydroxy-1-(4,4'-dimethoxytrityloxymethyl)-3-(6-N-benzoyladenin-9-yl)-2,5-dioxabicyclo[2.2.1]heptane (61C). To a stirred solution of compound 61B (0.50 g) in anhydrous pyridine (20 $cm^3$) was added 4,4'-dimethoxytrityl chloride (0.71 g, 2.09 mmol) and 4-N,N-dimethylaminopyridine (DMAP) (0.1 g). After stirring for 2 h at room temperature and for 1 h at 50° C., the reaction mixture was cooled to 0° C. and a saturated aqueous solution of sodium hydrogencarbonate (100 $cm^3$) was added. After extraction using dichloromethane (3×50 $cm^3$), the combined organic phase was dried ($Na_2SO_4$) and evaporated under reduced pressure. The residue was purified by silica gel column chromatography eluting with dichloromethane/methanol/pyridine (98.0:1.5:0.5) to give nucleoside 61C as a white solid material (0.36 g, ~50% from 61A). $\delta_H$ ($C_5D_5N$) 12.52 (NHCO), 9.10 (2H, d, J 7.7, Bz), 8.88 (1H, s, 8-H), 8.50-7.11

(17H, m, DMT, Bz, 2-H), 6.65 (1H, s, H-1'), 5.25 (2H, s, H-2', H-3'), 4.71 (1H, d, J 7.8, 1"-$H_a$), 4.56 (1H, d, J 7.8, 1"-$H_b$), 4.20 (1H, d, J 10.8, 5'-$H_a$), 4.07 (1H, d, J 10.8, 5'-$H_b$), 3.82, 3.81 (2×3H, 2×s, 2×$OCH_3$). $\delta_C$ ($C_5D_5N$) 167.56 (NHCO), 159.24 (C-6), 152.50, 152.08, 151.81, 145.84, 141.45, 136.52, 136.28, 132.55, 130.76, 130.70, 129.32, 128.85, 128.76, 128.46, 127.38, 126.33 (DMT, Bz, C-2, C-4, C-8), 113.84 (C-5), 88.64, 87.20, 86.85, 80.52, 73.13, 72.16, 60.86 (C-1', C-4', DMT, C-2', C-3', C-1", C-5'), 55.24 ($OCH_3$). FAB-MS m/z 686 $[M+H]^+$. Found: C, 68.3; H, 5.0; N, 9.7; $C_{39}H_{35}N_5O_7$ requires C, 68.3; H, 5.1; N, 10.2%).

EXAMPLE 71

(1R,3R,4R,7S)-7-(2-Cyanoethoxy(diisopropylamino) phosphinoxy)-1-(4,4'-dimethoxytrityloxymethyl)-3-(6-N-benzoyladenin-9-yl)-2,5-dioxabicyclo[2.2.1]heptane (61D). To a solution of compound 61C (190 mg, 0.277 mmol) in anhydrous dichloromethane (1.5 $cm^3$) were added N,N-diisopropylethylamine (0.16 $cm^3$, 0.94 mmol) and 2-cyanoethyl N,N-diisopropylphosphoramidochloridite (0.1 $cm^3$, 0.42 mmol) at 0° C. The mixture was allowed to warm to room temperature and stirred for 5 h. The solution was diluted by dichloromethane (50 $cm^3$), washed by a saturated aqueous solution of sodium hydrogencarbonate (2×30 $cm^3$) and evaporated under reduced pressure. The products were isolated by silica gel HPLC (PrepPak cartridge, 25×100 mm, packed by Prep Nova-Pak® HR Silica 6 μm 60 Å; gradient of solution B in solution A (from 0% to 15% during 25 min and from 15% to 100% during another 25 min, solution A: petroleum/dichloromethane/-pyridine, 60/39.6/0.4, v/v/v, solution B: ethylacetate. The fractions containing the two main products (retention times 30-40 min) were joined, concentrated under reduced pressure, co-evaporated with anhydrous toluene (2×40 $cm^3$) and dried overnight in vacuo. The residue was dissolved in anhydrous dichloromethane (4 $cm^3$) and precipitated by adding this solution to anhydrous petroleum ether (80 $cm^3$) under intensive stirring. The precipitate was collected by filtration, washed by petroleum ether (2×20 $cm^3$) and dried under reduced pressure to give compound 61D (178 mg, 73%) as a white solid material. $\delta_p$ ($CD_3CN$) 148.42, 147.93.

EXAMPLE 72

1-(2,3-O-isopropylidene-4-C-(4-toluenesulphonyloxymethyl)-β-D-ribofuranosyl)uridine (62). To a stirred solution of 1-(2,3-O-isopropylidene-4'-C-hydroxymethyl-β-D-ribofuranosyl)uridine (2.0 g, 6.4 mmol) (R. Youssefyeh, D. Tegg, J. P. H. Verheyden, G. H. Jones and J. G. Moffat, *Tetrahedron Lett.,* 1977, 5, 435; G. H. Jones, M. Taniguchi, D. Tegg and J. G. Moffat, *J. Org. Chem.,* 1979, 44, 1309) in anhydrous pyridine (28 $cm^3$) was added p-toluenesulfonyl chloride (1.46 g, 7.3 mmol) dissolved in anhydrous pyridine (10 $cm^3$) at −30° C. After 30 min, the reaction mixture was allowed to reach room temperature and stirring was continued at room temperature for 12 h. The reaction was quenched with methanol (4 $cm^3$), silica gel (2 g) was added and the solvent was removed under reduced pressure. The residue was purified by silica gel column chromatography using a gradient of 0-3% methanol in dichloromethane (v/v) as eluent to give nucleoside 62 as a pale reddish solid material (1.8 g, 60%). $\delta_H$ ($CDCl_3$) 9.80 (1H, br s, NH), 7.80 (2H, d, J 8.3, Ts), 7.46 (1H, d, J 8.1, 6-H), 7.35 (2H, d, J 8.01, Ts), 5.72 (1H, d, J 8.0, 5-H), 5.54 (1H, d, J 3.5, 1'-H), 5.08 (1H, dd, J 3.5, 6.4, 2'-H), 4.94 (1H, d, J 6.4, 3'-H), 4.18 (2H, s, 1"-H), 3.82-3.70 (2H, m, 5'-H), 2.45 (3H, s, Ts), 1.46, 1.29 (6 H, s, $CH_3$). $\delta_C$ ($CDCl_3$) 163.6 (C-4), 150.4 (C-2), 145.2 (C-6), 142.9, 132.5, 129.9, 128.0 (Ts), 114.7 (OCO), 102.6 (C-5), 94.9, 87.6, 83.9, 81.5 (C-4', C-1', C-3', C-2'), 68.7, 63.5 (C-1", C-5'), 26.4, 24.7 ($CH_3$), 21.7 (Ts). FAB-MS m/z 469 $[M+H]^+$.

EXAMPLE 73

1-(4-C-(p-Toluenesulphonyloxymethyl-β-D-ribofuranosyl)uridine (63). Nucleoside 62 (1.33 g, 2.83 mmol) was dissolved in 80% acetic acid (25 $cm^3$) and stirred at 80° C. for 3 h whereupon the solvent was removed under reduced pressure. The residue was coevaporated with ethanol (10 $cm^3$) and purified by silica gel column chromatography using a gradient of 0-2% methanol in dichloromethane (v/v) as eluent to give nucleoside 63 as a white solid material (391 mg, 33%). $\delta_H$ ($CD_3OD$) 7.81 (1H, d, J 8.1, 6-H), 7.77 (1H, d, J 8.4, Ts), 7.40 (2H, d, J 8.6, Ts), 5.74 (1H, d, J 6.6, 1'-H), 5.69 (1H, d, J 8.1, 5-H), 4.17-4.33 (2H, m, 2'-H, 3'-H), 3.67-3.62 (2H, m, 1"-H), 3.26-3.20 (2H, m, 5'-H), 2.43 (3H, s, Ts). $\delta_C$ ($CD_3OD$) 166.0 (C-4), 153.0 (C-2), 146.5 (C-6), 142.5, 130.9, 129.15 (Ts), 103.1 (C-5), 89.0, 87.2 (C-1', C-4'), 75.1, 72.7, 71.3, 63.8 (C-1", C-3', C-2', C-5'), 21.6 (Ts).

EXAMPLE 74

(1S,3R,4R,7S)-7-Hydroxy-1-hydroxymethyl-3-(uracil-1-yl)-2,5-dioxabicyclo[2.2.1]-heptane (44). To a stirred solution of nucleoside 63 (64 mg, 0.14 mmol) in anhydrous DMF (2 $cm^3$) was slowly added sodium hydride (8.4 mg, 21 mmol, 60% suspension in mineral oil, w/w) in anhydrous DMF (2 $cm^3$) at 0° C. The reaction mixture was then heated to 120° C. for 6 h. After quenching the reaction with water (2 $cm^3$), the solvents were removed under reduced pressure and the residue was purified by silica gel column chromatography using a gradient of 5-7% methanol in dichloromethane (v/v) as eluent to give nucleoside 44 as a white solid material (9 mg, 29%). NMR data were in agreement with those reported earlier for compound 44.

EXAMPLE 75

(1S,3R,4R,7S)-7-Acetoxy-1-acetoxymethyl-3-(thymin-1-yl)-2,5-dioxabicyclo[2.2.1]-heptane (64). To a stirred solution of nucleoside 37 (209.8 mg, 0.78 mmol) in anhydrous pyridine (2.5 $cm^3$) was added acetic anhydride (0.3 $cm^3$, 3.23 mmol) and a catalytic amount of DMAP (5 mg). After stirring for 2 h, ethanol was added (4 $cm^3$) and the mixture was evaporated under reduced pressure. The residue was redissolved in dichloromethane and washed with a saturated aqueous solution of sodium hydrogencarbonate (7 $cm^3$). The organic phase was dried ($Na_2SO_4$), and evaporated under reduced pressure. The residue was purified by silica gel column chromatography using dichloromethane/methanol (97:3, v/v) as eluent affording 64 as a white solid material (249 mg, 90%). $\delta_C$ ($CDCl_3$) 169.59, 163.20, 149.50, 133.55, 110.64, 87.05, 85.38, 77.84, 71.70, 71.02, 58.60, 20.62, 20.53, 12.78. FAB-MS m/z 355 $[M+H]^+$.

EXAMPLE 76

(1S,3R,4R,7S)-1-Hydroxymethyl-3-(5-methyl-4-N-benzoylcytosine-1-yl)-7-hydroxy-2,5-dioxabicyclo[2.2.1]heptane (65). To a solution of nucleoside 64 (232.7 mg, 0.66 mmol) in anhydrous acetonitrile (3 $cm^3$) was added a solution of 1,2,4-triazole (420 mg, 6.1 mmol) and $POCl_3$ (0.12 $cm^3$, 1.3 mmol) in anhydrous acetonitrile (5 $cm^3$). The reaction mixture was cooled to 0° C. and anhydrous triethylamine ($0.83\ cm^3$) was added, whereupon the mixture was kept for 90 min at room temperature. Triethylamine ($0.54\ cm^3$) and water ($0.14\ cm^3$) was added, and the reaction mixture was stirred for 10 min and evaporated under reduced pressure. The residue was dissolved in EtOAc and washed with a saturated aqueous solution of sodium hydrogencarbonate ($2\times9\ cm^3$) and water ($9\ cm^3$). The aqueous phase was extracted with dichloromethane ($3\times20\ cm^3$). The combined organic phase was evaporated under reduced pressure and the residue was redissolved in dioxane ($4\ cm^3$), whereupon 32% aqueous ammonia ($0.7\ cm^3$) was added. After stirring for 3 h, the reaction mixture was evaporated under reduced pressure and coevaporated with anhydrous pyridine. The residue was dissolved in anhydrous pyridine ($3.6\ cm^3$) and benzoyl chloride ($0.42\ cm^3$, 3.6 mmol) was added. After stirring for 2 h, the reaction was quenched with water ($1\ cm^3$) and the reaction mixture was evaporated under reduced pressure. The residue was then redissolved in EtOAc and washed with water ($3\times7\ cm^3$). The organic phase was evaporated to dryness under reduced pressure, and the residue was dissolved in pyridine/methanol/water (13:6:1, v/v/v, $14\ cm^3$) at 0° C., and a 2M solution of NaOH in pyridine/methanol/water (13:6:1, v/v/v, $7\ cm^3$) was added. After stirring for 20 min, the reaction mixture was neutralised using a 2M solution of HCl in dioxane, and the reaction mixture was evaporated under reduced pressure. The residue was purified by silica column chromatography using dichloromethane/methanol (95:5, v/v) as eluent to give nucleoside 65 as a yellow foam (94.6 mg, 38%). $\delta_H$ ($CD_3OD$) 8.21 (1H, br, s), 8.02 (1H, m), 7.84-7.9 (1H, m), 7.41-7.58 (4H, m), 5.61 (1H, s), 4.36 (1H, s), 4.10 (1H, s), 3.98 (1H, d, J 8.0), 3.94 (2H, s), 3.78 (1H, d, J 7.9), 2.11 (3H, d, J 1.0). $\delta_C$ ($CD_3OD$, selected signals) 133.66, 132.90, 130.63, 129.50, 129.28, 128.65, 90.71, 88.86, 80.57, 72.47, 70.22, 57.53, 14.01. FAB-MS m/z 374 $[M+H]^+$.

EXAMPLE 77

(1R,3R,4R,7S)-1-(4,4'-Dimethoxytrityloxymethyl)-3-(5-methyl-4-N-benzoylcytosine-1-yl)-7-O-(2-cyanoethoxy(diisopropylamino)phosphinoxy)-2,5-dioxabicyclo[2.2.1]heptane (66). To a stirred solution of nucleoside 65 (82 mg, 0.22 mmol) in anhydrous pyridine ($1.5\ cm^3$) was added 4,4'-dimethoxytrityl chloride (80 mg, 0.24 mmol) and stirring was continued at room temperature for 12 h. Additional 4,4'-dimethoxytrityl chloride (80 mg, 0.24 mmol) was added, and stirring was continued for another 12 h. Methanol ($0.5\ cm^3$) was added and the reaction mixture was evaporated under reduced pressure. The residue was subjected to silica gel column chromatography using dichloromethane/methanol/pyridine (98.5:1.0:0.5, v/v/v). The resulting intermediate (FAB-MS m/z 676) (50.2 mg) was coevaporated with anhydrous acetonitrile and dissolved in anhydrous dichloromethane ($0.62\ cm^3$). N,N-Diisopropylethylamine was added ($0.1\ cm^3$) followed by addition of 2-cyanoethyl N,N-diisopropylphosphoramidochloridite ($0.3\ cm^3$, 0.11 mmol). After stirring for 3 h at room temperature, water ($1\ cm^3$) was added and the resulting mixture was diluted with ethylacetate ($10\ cm^3$), washed with saturated aqueous solutions of sodium hydrogencarbonate ($3\times6\ cm^3$) and brine ($3\times6\ cm^3$). The organic phase was dried ($Na_2SO_4$) and evaporated under reduced pressure. The residue was purified by silica gel column HPLC. Precipitation as described for compound 53 afforded compound 66 as a white solid material (29.5 mg, 0.03 mmol, 14%). $\delta_P$ ($CH_3CN$) 148.46, 147.49.

EXAMPLE 78

9-(4-(Hydroxymethyl)-2,3-O-isopropylidene-β-D-ribofuranosyl)-6-N-benzoyladenine (67). A mixture of oxalyl chloride (0.93 mL, 10.75 mmol) and dichloromethane (25 mL) was cooled to −70° C. Dimethyl sulfoxide (DMSO, 1.7 mL, 22 mmol) was added drop-wise under intensive stirring. The mixture was stirred for 10 min at −70° C. and a solution of 9-(2,3-O-isopropylidene-β-D-ribofuranosyl)-6-N-benzoyladenine (3.4 g, 8.27 mmol) in dimethylsulfoxide/dichloromethane (1:9 v/v, 20 mL) was added during 5 min. The mixture was stirred at −60° C. for 30 min. Triethylamine (7 mL, 50.3 mmol) was added and the mixture was allowed to warm to room temperature. The solution was diluted by dichloromethane (50 mL) and washed by water (3×100 mL). Water fractions were additionally washed by 100 mL of dichloromethane. The organic phase was concentrated to an oily mass, co-evaporated with dioxane (50 mL) and re-dissolved in 30 mL of dioxane. 37% aq. formaldehyde (2.95 mL, 33.4 mmol) and 2M aq. NaOH (8.26 mL) were added; the mixture was stirred at room temperature for 10 min and cooled to 0° C. Sodium borohydride (640 mg, 16.9 mmol) was added and the reaction mixture was allowed to warm to room temperature during 15 min. The reaction was quenched by addition of acetic acid (5 mL) and to the mixture was added dichloromethane and a saturated aqueous solution of sodium hydrogen carbonate (100 mL each). The organic phase was washed with water (100 mL), concentrated in vacuo and the product was isolated by column (2.5×25 cm) silica gel chromatography by the use of 2-3.2% of methanol in dichloromethane (v/v) as eluent. Yield 1.85 g (50.7%) of compound 67 as a white solid material. $\delta_H$ ($CDCl_3$) 8.72 (1H, s), 8.14 (1H, s), 8.03-8.00 (2H, m), 7.60-7.57 (1H, m), 7.56-7.46 (2H, m), 6.00 (1H, d, J 4.9), 5.35 (1H, dd, J 5.8, J" 5.0), 5.13 (1H, d, J 5.8), 3.87-3.78 (4H, m), 1.65 (3H, s), 1.38 (3H, s). $\delta_C$ ($CDCl_3$) 164.8, 152.2, 150.4, 150.2, 142.6, 133.3, 132.9, 128.8, 128.0, 124.1, 114.7, 93.3, 90.2, 83.8, 82.5, 65.3, 62.9, 27.3, 25.1. FAB-MS: m/z 442 $[M+H]^+$, 464 $[M+Na]^+$.

Alternative synthesis of 67. To a solution of 2',3'-O-isopropylideneadenosine (15 g) in anhydrous pyridine (250 mL) was added trimethylsilyl chloride (15.5 mL). The reaction mixture was stirred at room temperature for 20 min and cooled to 0° C. Benzoyl chloride (17 mL) was added dropwise and the mixture was kept at room temperature for 2-3 h. Water (50 mL) and 25% aq. ammonium hydroxide (100 mL) was added and stirring was continued for 3 h. Then the mixture was concentrated under reduced pressure, co-evaporated with toluene (2×200 mL) and dichloromethane (DCM) and saturated sodium hydrogencarbonate was added. The organic phase was evaporated to dryness to give a yellow solid. Recrystallisation from ethanol resulted in 12.5 g (ca 80%) as a white solid intermediate material. Oxalyl chloride (4.68 mL) in dry DCM (120 mL) was cooled to −70° C. DMSO (8.5 mL) was added during intensive stirring. Later (10 min) a solution of the intermediate for which the synthesis is described above (17 g) in 10% DMSO/DCM (100 mL) added dropwise (20 min). The temperature was allowed to increase to −50° C. over a period of 30 min after which the reaction was quenched with triethylamine (35 mL). To the mixture was added DCM (200 ml) which was washed with water (3×200 mL). The intermediate was concentrated in vacuo, co-evaporated with dioxane, and redissolved in dioxane (120 mL). Formaldehyde (37%) and 2 M aq. sodium hydroxide (40 mL) was added and the reaction mixture was stirred for 1 h. The mixture was neutralised with acetic acid (6 mL) and DCM (400 ml) and saturated sodium hydrogencarbonate (400 mL) were added. The organic phase was concentrated. The product 67 was purified by column chromatography (silica gel, 1.5-5.0% methanol/DCM). Yield 8.5 g (46%) of 67. Data were as stated earlier in this example.

EXAMPLE 79

9-(2,3-O-Isopropylidene-4-(p-toluenesulfonyloxymethyl)-β-D-ribofuranosyl)-6-N-benzoyladenine (68) and 9-(4-hydroxymethyl-2,3-O-isopropylidene-5-O-(p-toluenesulfonyl)-β-D-ribofuranosyl)-6-N-benzoyladenine. A mixture of compound 67 (1.95 g, 4.42 mmol) and p-toluenesulfonyl chloride (1.26 g, 6.63 mmol) was dissolved in 10 mL of anhydrous pyridine at 0° C. The reaction mixture was stirred for 4 h and then diluted by dichloromethane (100 mL), washed with water (2×100 mL) and concentrated under reduced pressure. The purification of the mixture by silica gel column (2.5×20 cm) chromatography in a gradient (1-4%) of methanol in dichloromethane allowed isolation of starting material 67 (360 mg, 18.5%) and two structural isomers, namely 68 (less polar isomer; 971 mg, 36.7%) and 9-(4-hydroxymethyl-2,3-O-isopropylidene-5-O-(4'-toluenesulfonyl)-β-D-ribofuranosyl)-$N^6$-benzoyladenine (more polar isomer; 352 mg, 13.1%) as white solid materials. 68: $\delta_H$ ($CDCl_3$) 8.69 (1H, s), 8.11 (1H, s), 8.00 (2H, m), 7.79 (2H, m), 7.58-7.55 (1H, m), 7.50-7.46 (2H, m), 7.34-7.32 (2H, m), 5.88 (1H, d, J 4.9), 5.35 (1H, dd, J 5.8, J" 5.0), 5.13 (1H, d, J 5.8), 3.87-3.78 (4H, m), 1.65 (3H, s), 1.38 (3H, s). $\delta_C$ ($CDCl_3$) 164.7, 152.0, 150.2, 150.1, 144.9, 142.5, 133.2, 132.7, 132.3, 129.6, 128.6, 127.9, 127.8, 123.9, 114.6, 93.1, 87.9, 83.4, 81.6, 68.3, 64.4, 27.1, 25.0, 21.5. FAB-MS: m/z 596 $[M+H]^+$

EXAMPLE 80

9-(4-(p-Toluenesulfonyloxymethyl)-β-D-ribofuranosyl)-6-N-benzoyladenine (69). A solution of compound 68 (940 mg, 1.58 mmol) in 10 mL of 90% aq. trifluoroacetic acid was kept for 30 min at room temperature and concentrated in vacuo to an oily mass. After co-evaporation with methanol (2×20 mL) and toluene (20 mL) the mixture was purified by silica column (2×25 cm) chromatography in a gradient of methanol (2-5.0%) in dichloromethane as eluent to give compound 69 (825 mg, 94%) as white solid material. $\delta_H$ (methanol-$d_4$) 8.67 (1H, s), 8.53 (1H, s), 8.05 (2H, d, J 7.7), 7.75 (2H, d, J 8.2), 7.63 (1H, m), 7.53 (2H, m), 7.32 (2H, d, J 8.0), 5.94 (1H, d, J 7.1), 4.92 (1H, dd, J 7.1, J" 5.3), 4.41 (1H, d, J 5.1), 4.38 (1H, d, J 10.2), 4.28 (1H, d, J 10.2), 3.80 (1H, d, J 12.0), 3.68 (1H, d, J 12.0), 2.35 (3H, s). $\delta_C$ (methanol-$d_4$) 168.2, 152.9, 150.8, 151.2, 146.4, 144.9, 134.7, 134.1, 134.0, 130.8, 129.7, 129.4, 129.1, 125.1, 90.0, 88.4, 75.3, 73.1, 71.1, 64.2, 21.6. FAB-MS: m/z 556 $[M+H]^+$.

EXAMPLE 81

9-(4-(p-Toluenesulfonyloxymethyl)-3,5-O-(tetraisopropyldisiloxane-1,3-diyl)-β-D-ribofuranosyl)-6-N-benzoyladenine (70). To a solution of compound 69 (780 mg, 1.40 mmol) in anhydrous pyridine (7 mL) was added 1,3-dichloro-1,1,3,3-tetraisopropyldisiloxane (500 μL, 1.57 mmol) at 0° C. After stirring for 2 h at 0° C. additional 1,3-dichloro-1,1,3,3-tetraisopropyldisiloxane (50 μL, 0.16 mmol) was added. The reaction mixture was allowed to warm to room temperature, diluted by dichloromethane (100 mL) and washed by water (2×100 mL). The organic phase was concentrated, and the residue was purified by the use of preparative HPLC (PrepPak cartridge, Porasil 15-20 μm 125 Å; eluent: 0-3% of methanol in dichloromethane (v/v) in 120 min; flow rate: 60 ml/min). Concentration in vacuo yielded 870 mg (78%) of compound 70 as a white solid material. $\delta_H$ ($CDCl_3$) 8.65 (1H, s), 8.03 (2H, m), 8.00 (1H, s), 7.83 (2H, d, J 8.4), 7.58 (1H, m), 7.49 (2H, m), 7.34 (2H, d, J 8.4), 5.87 (1H, s), 5.70 (1H, d, J 6.2), 4.68 (1H, d, J 6.2), 4.59 (1H, d, J 10.8), 4.31 (1H, d, J 11.0), 3.91 (2H, s), 2.45 (3H, s), 1.03-0.84 (28H, m). $\delta_C$ ($CDCl_3$) 164.9, 152.2, 150.5, 150.0, 144.7, 142.9, 133.5, 132.9, 132.8, 129.7, 128.8, 128.1, 128.0, 123.6, 90.3, 85.3, 76.0, 75.0, 68.7, 65.2, 21.6, 17.5, 17.4, 17.2, 17.1, 17.0, 16.9, 13.1, 13.0, 12.5, 12.4. FAB-MS: m/z 798 $[M+H]^+$.

EXAMPLE 82

9-(2-O,4-C-Methylene-3,5-O-(tetraisopropyldisiloxa-1,3-diyl)-β-D-ribofuranosyl)-6-N-benzoyladenine (71). A solution of compound 70 (540 mg, 0.68 mmol) in anhydrous THF (20 mL) was cooled to 0° C. and sodium hydride (130 mg of 60% suspension in mineral oil, 3.25 mmol) was added under stirring. The reaction mixture was stirred for 30 min and then neutralised by addition of 750 μL of acetic acid. Dichloromethane (50 mL) was added, the mixture was washed by a saturated aqueous solution of sodium hydrogen carbonate (2×50 mL) and concentrated under reduced pressure. The residue was applied to a silica gel column (2.5×25 cm) and the product was eluted in a gradient concentration (0.5 to 1.2%) of methanol in dichloromethane as eluent to yield compound 71 (356 mg, 84%) as a white foam. $\delta_H$ ($CDCl_3$) 8.77 (1H, s), 8.28 (1H, s), 8.03 (2H, m), 7.59 (1H, m), 7.50 (2H, m), 6.08 (1H, s), 4.86 (1H, s), 4.56 (1H, s), 4.14 (1H, d, J 13.2), 4.06 (1H, d, J 7.7), 3.97 (1H, d, J 13.2), 3.89 (1H, d, J 7.7), 1.12-0.95 (28H, m). $\delta_C$ ($CDCl_3$) 164.8, 152.6, 150.5, 149.6, 140.7, 133.6, 132.7, 128.7, 127.9, 123.1, 89.4, 86.5, 78.9, 71.7, 71.2, 56.7, 17.3, 17.1, 17.0, 16.9, 16.8, 13.3, 13.1, 12.5, 12.2. FAB-MS: m/z 626 $[M+H]^+$.

EXAMPLE 83

7-Hydroxy-1-hydroxymethyl-3-(6-N-benzoyladenin-9-yl)-2,5-dioxabicyclo[2.2.1]-heptane (61B). Triethylamine tris-hydrofluoride (300 μL, 1.84 mmol) was added to a solution of compound 71 (420 mg, 0.067 mmol) in anhydrous THF (7 mL). The reaction mixture was kept at room temperature for 1 h and concentrated to an oil which was purified by silica gel column (2×25 cm) chromatography eluting with 4-10% of methanol in dichloromethane (v/v). Yield 232 mg (92%) of compound 61B as a white solid material. NMR data were identical with those reported earlier for 61B.

EXAMPLE 84

1-(3,5-Di-O-benzyl-4-C-(p-toluenesulphonyloxymethyl)-2-O-p-toluenesulphonyl-β-D-ribofuranosyl)thymine (72). A solution of 1-(3,5-di-O-benzyl-4-C-(hydroxymethyl)-β-D-ribofuranosyl)thymine 35 (1.48 g, 3.16 mmol), DMAP (1.344 g, 0.011 mol) and p-toluenesulphonyl chloride (1.45 g, 7.6 mmol) in dichloromethane (20 ml) was stirred for 3 h at room temperature. The reaction mixture was diluted with dichloromethane (30 ml) and washed with saturated aqueous solutions of sodium hydrogen carbonate (3×20 ml) and sodium chloride (2×25 ml). The organic phase was dried ($Na_2SO_4$), filtered and evaporated under reduced pressure. The residue was subjected to silica gel column chromatography using methanol:dichloromethane (1:99, v/v) as eluent to give nucleoside 72 (1.95 g, 80%) as a white solid material. FAB-MS m/e 776. $\delta_C$ ($CDCl_3$) 162.9, 149.8 (C-2, C-4), 145.8, 145.2 (2×Ts), 136.9, 136.8 (2×Bn), 134.3 (C-6), 132.1, 132.0, 130.0, 129.9, 129.0 128.9, 128.4, 128.3, 128.2, 128.0, 127.7 (2×Ts, 2×Bn), 111.2 (C-5), 85.3, 84.0 (C-1', C-4'), 78.9, 78.3, 75.2, 74.3, 72.7, 69.1 (C-2', C-3', C-5', C-1", 2×Bn), 21.7 (2×$CH_3$), 11.9 ($CH_3$). Anal. Calcd. for $C_{39}H_{40}N_2S_2O_{11}$: C, 60.30; H, 5.19; N, 3.61. Found: C, 59.95; H, 5.11, N 3.81.

EXAMPLE 85

1-(2-Benzylamino-2-deoxy-3,5-di-O-benzyl-2-N,4-C-methylene-β-D-ribofuranosyl)-thymine (73). A solution of 72 (8.6 g, 11.1 mol) in benzyl amine (10 ml) was stirred at 130° C. for 36 h. The reaction mixture was directly subjected to silica gel column chromatography using methanol:dichloromethane (1:99, v/v) as eluent to give nucleoside 73 (1.79 g, 30%) as a white solid material. FAB-MS m/e 540. $\delta_C$ ($CDCl_3$) 163.9, 149.8 (C-2, C-4), 139.2, 137.6, 137.3 (3×Bn), 135.6 (C-6), 128.5, 128.4, 128.3, 128.2, 128.0, 127.7, 127.0 (3×Bn), 109.6 (C-5), 88.2, 86.3 (C-1', C-4'), 76.7, 73.8, 72.0, 66.0, 63.8, 57.9, 57.8 (C-2', C-3', C-5', C-1", 3×Bn), 12.2 ($CH_3$). Anal. Calcd. for $C_{32}H_{33}N_3O_5$×0.5$H_2O$: C, 70.06; H, 6.25; N, 7.66. Found: C, 70.00; H, 6.06; N, 7.50.

EXAMPLE 86

1-(2-Amino-2-deoxy-2-N,4-C-methylene-β-D-ribofuranosyl)thymine (74). To a solution of nucleoside 73 (1.62 g, 0.003 mol) in ethanol (150 ml) was added 20% palladium hydroxide on carbon (3 g) and the suspension was stirred for 5 days under hydrogen. The catalyst was filtered off (silica gel) and washed with methanol (20 ml). The combined filtrate was concentrated under reduced pressure to give a white solid material which was filtered off and washed with methanol: dichloromethane (1:4, v/v) to give a monobenzylated intermediate (0.82 g, 76%). FAB-MS: m/e 360 $(M+H)^+$. $^{13}C$-NMR (DMSO-$d_6$, 250 MHz): 163.7, 149.8 (C-2, C-4), 138.2 (Bn), 134.9 (C-6), 128.2, 127.5, 127.4 (Bn), 107.8 (C-5), 87.8, 87.6 (C-1', C-4'), 72.7, 68.9, 65.9, 61.7, 49.4 (C-2', C-3', C-5', C-1", Bn), 11.9 ($CH_3$). Anal. Calcd. for $C_{18}H_{21}N_3O_5$: C, 60.16; H, 5.89; N, 11.69. Found: C, 59.86; H, 5.61; N, 11.56. A mixture of this intermediate (0.1 g, 0.29 mmol), ammonium formate (0.085 g, 1.35 mmol), 10% palladium on carbon (130 mg) in anhydrous methanol (7 ml) was heated under reflux for 2 h. The catalyst was filtered off (silica gel) and washed with methanol (15 ml) and the combined filtrate was concentrated to dryness under reduced pressure. The residue was subjected to silica gel column chromatography using methanol:dichloromethane (1:9, v/v) as eluent to give title compound 74 (0.053 g, 71%) as a white solid material. FAB-MS m/e 270. $\delta_H$ (DMSO-$d_6$) 11.29 (bs, 1H, NH), 7.73 (d, 1H, J 1.1, 6-H), 5.31 (s, 1H, 1'-H), 5.29 (br s, 1H, 3'-OH), 5.13 (m, 1H, 5'-OH), 3.81 (s, 1H, 3'-H), 3.69 (m, 2H, 5'-H), 3.23 (s, 1H, 2'-H), 2.88 (d, 1H, J 9.8, 1"-$H_a$), 2.55 (d, 1H, J 9.8, 1"-$H_6$), 1.77 (d, 3H, J 0.8, $CH_3$). $\delta_C$ (DMSO-$d_6$) 164.0, 150.1 (C-2, C-4), 135.6 (C-6), 107.8 (C-5), 89.5, 87.9 (C-1', C-4'), 68.7, 61.9, 57.1, 49.4, (C-2', C-3', C-5', C-1"). Anal. Calcd. for $C_{11}H_{16}N_3O_6$×0.5$H_2O$: C, 47.48; H, 5.80; N, 15.10. Found: C, 47.54; H, 5.30; N, 14.79.

Alternative method for conversion of 73 to 74. To a solution of 73 (0.045 g, 0.0834 mmol) in methanol (6 ml) was added 10% Pd on carbon (0.118 g) and—in three portions during 3 h—ammonium formate (0.145 g, 0.0023 mol). The suspension was refluxed for 4.5 h. The catalyst was filtered off (silica gel) and washed with methanol (4×3 ml). The combined filtrate was concentrated and the residue was subjected to column chromatography on silica gel using methanol:dichloromethane (1:9, v/v) as eluent to give nucleoside 74 (0.015 g, 67%). Spectral data were in accordance with data reported earlier in this example for 74.

EXAMPLE 87

1-(2-Amino-2-deoxy-2-N,4-C-methylene-β-N-trifluoroacetyl-8-D-ribofuranosyl)thymine (74-$COCF_3$). To a suspension of nucleoside 74 (0.050 g, 0.186 mmol) in methanol (2 mL) were added DMAP (0.013 mg, 0.106 mmol) and ethyl trifluoroacetate (0.029 mL, 0.242 mmol) and the mixture was stirred at room temperature for 2.5 h. The solvent was removed under reduced pressure and the residue was subjected to column chromatography on silica gel using methanol:dichloromethane (2.5:97.5, v/v) as eluent to give the title nucleoside 74-$COCF_3$ as a white solid material after evaporation of the solvents under reduced pressure (0.055 g, 81%). FAB-MS m/z 366 $[M+H]^+$. $^{13}C$ NMR ($CD_3OD$, 62.9 MHz) δ 166.5, 157.7 (q, $^2J_{C,F}$ 37.5 Hz, $COCF_3$), 157.6 (q, $^2J_{C,F}$ 37.2 Hz, $COCF_3$), 151.8, 136.8, 136.8, 117.6 (d, $^1J_{C,F}$ 287.5 Hz, $CF_3$), 117.5 (d, $^1J_{C,F}$ 286.5 Hz, $CF_3$), 110.8, 110.8, 90.7, 89.3, 87.7, 87.3, 70.1, 68.6, 66.2, 66.2, 64.5, 57.9, 53.3, 12.7. Anal. Calcd. for $C_{13}H_{14}N_3O_6F_3$: C, 42.8; H, 3.9; N, 11.5. Found: C, 42.5; H, 4.0; N, 11.2.

EXAMPLE 88

1-(2-Amino-2-deoxy-5-O-4,4'-dimethoxytrityl-2-N,4-C-methylene-2-N-trifluoroacetyl-β-D-ribofuranosyl)thymine (74-DMT). To a solution of nucleoside 74-$COCF_3$ (0.030 g, 0.082 mmol) in anhydrous pyridine (0.6 mL) at 0° C. was dropwise (during 20 min) added 4,4'-dimethoxytrityl chloride (0.054 g, 0.159 mmol) dissolved in anhydrous pyridine: dichloromethane (0.6 mL, 1:1, v/v) and the mixture was stirred for 10 h at room temperature. A mixture of ice and water was added (5 mL) and the resulting mixture was extracted with dichloromethane (3×5 mL). The combined organic phase was washed with a saturated aqueous solution of sodium hydrogencarbonate (3×2 mL), dried ($Na_2SO_4$) and filtered. The filtrate was evaporated to dryness under reduced pressure and the residue was subjected to column chromatography on silica gel using methanol:dichloromethane:pyridine (1.5:98.0:0.5, v/v/v) as eluent to give nucleoside 74-DMT as a white solid material after evaporation of the solvents under reduced pressure (0.051 g, 93%). FAB-MS m/z 667 $[M]^+$, 668 $[M+H]^+$. FAB-HRMS calcd. for $C_{34}H_{32}N_3O_8F_3^+$: 667.2142. Found: 667.2146. $^{13}C$ NMR($C_5D_5N$, 100.6 MHz) δ 165.1, 165.0, 159.5, 159.5, 151.4, 145.7, 136.3, 136.1, 134.8, 134.6, 130.9, 130.9, 130.9, 128.9, 128.9, 128.7, 128.7, 128.4, 127.7, 123.2, 114.1, 114.1, 114.0, 110.4, 89.4, 87.9, 87.5, 87.4, 87.2. 70.8, 69.0, 66.0, 64.4, 60.5, 60.2, 55.5, 53.6, 53.4, 49.9, 13.2, 13.1.

EXAMPLE 89

1-(2-Amino-3-O-(2-cyanoethoxy(diisopropylamino)phosphino-2-deoxy)-5-O-4,4'-dimethoxytrityl-2-N,4-C-methylene-2-N-trifluoroacetyl-β-D-ribofuranosyl)thymine (74A). To a solution of nucleoside 74-DMT (0.121 g, 0.181 mmol) in anhydrous dichloromethane (2 mL) were added N,N-diisopropylethylamine (0.093 mL, 0.54 mmol) and 2-cyanoethyl N,N-diisopropylphosphoramidochloridite (0.057 mL, 0.26 mmol) at 0° C. and the mixture was stirred for 10 h at room temperature. The mixture was diluted with dichloromethane (20 mL), extracted with a saturated aqueous solution of sodium hydrogencarbonate (3×10 mL), dried ($Na_2SO_4$) and filtered. The filtrate was evaporated to dryness under reduced pressure and the residue was subjected to column chromatography on silica gel using methanol:dichloromethane:pyridine (1.5:98.0:0.5, v/v/v) as eluent to give crude product (0.107 g) after evaporation of the solvents under reduced pressure. The residue was dissolved in anhydrous dichloromethane (1 mL) and by dropwise addition to vigorously stirred petroleum ether (60-80° C., 30 mL) at −30° C., nucleotide 74A precipitated to give a white solid material after filtration (0.090 g, 57%). FAB-MS m/z 868 $[M+H]^+$, 890 $[M+Na]^+$. $^{31}P$ NMR ($CD_3CN$, 121.5 MHz) δ 150.4, 150.2, 148.8, 149.1.

EXAMPLE 90

1-(2-Amino-2-N,4-C-methylene-3,5-O-(tetraisopropyldisiloxane-1,3-diyl)-β-D-ribofuranosyl)thymine (74B). To a solution of nucleoside 74 (0.20 g, 0.74 mmol) in anhydrous pyridine (3 mL) at −15° C. was dropwise (during 3 h) added 1,3-dichloro-1,1,3,3-tetraisopropyldisiloxane (0.305 mL, 0.0011 mol) and the mixture was stirred for 10 h at room temperature. MeOH (3 mL) was added and the mixture was evaporated to dryness under reduced pressure. The residue was subjected to column chromatography on silica gel using methanol:dichloromethane (1:99, v/v) to give nucleoside 74B as a white solid material after evaporation of the solvents under reduced pressure (0.370 mg, 97%). FAB-MS m/z 512 $[M+H]^+$. $^1H$ NMR ($(CD_3)_250$, 400 MHz) δ 11.37 (bs, 1H), 7.48 (s, 1H), 5.32 (s, 1H), 4.06 (d, 1H, J 13.5 Hz), 4.00 (s, 1H), 3.84 (d, 1H, J 13.5 Hz), 3.41 (s, 1H), 2.92 (d, 1H, J 10.2 Hz), 2.64 (d, 1H, J 10.2 Hz), 1.74 (s, 3H), 1.10-0.92 (m, 28 H). $^{13}C$ NMR ($((CD)_3SO_2$, 62.9 MHz) δ 163.8, 149.8, 134.1, 107.9, 89.5, 87.9, 70.1, 61.1, 57.9, 49.3, 17.2, 17.2, 17.0, 16.9, 16.8, 16.7, 12.6, 12.2, 11.7. Anal. Calcd. for $C_{23}H_{41}N_3O_6Si_2$: C, 54.0; H, 8.1; N, 8.2. Found: C, 54.0; H, 8.3; N, 7.8.

EXAMPLE 91

1-(2-Deoxy-2-methylamino-2-N,4-C-methylene-3,5-O-(tetraisopropyldisiloxane-1,3-diyl)-β-D-ribofuranosyl) thymine (74C). To a solution of nucleoside 74B (0.33 g, 0.64 mmol) in anhydrous THF:dichloromethane (4:1, v/v) at −10° C. was dropwise (during 30 min) added 1,8-diazabicyclo [5.4.0]undec-7-ene (DBU, 0.125 mL, 0.836 mmol) and methyl iodide (0.05 mL, 0.79 mmol) and the mixture was stirred for 48 h at 10° C. Additional DBU (0.05 mL, 0.33 mmol) and methyl iodide (0.020 mL, 0.32 mmol) was dropwise (during 15 min) added to the reaction mixture and stirring at 10° C. was continued for 24 h. The mixture was evaporated to dryness under reduced pressure and the residue was subjected to column chromatography on silica gel using methanol:dichloromethane (1:99, v/v) as eluent to give nucleoside 74C as a white solid material after evaporation of the solvents (0.25 g, 74%). FAB-MS m/z 526 $[M+H]^+$. $^1H$ NMR ($CDCl_3$, 400 MHz) δ 8.19 (bs, 1H), 7.65 (d, 1H, J 1.3 Hz), 5.59 (s, 1H), 4.11 (s, 1H), 4.05 (d, 1H, J 13.2 Hz), 3.87 (d, 1H, J 13.2 Hz), 3.44 (s, 1H), 2.98 (d, 1H, J 9.5 Hz), 2.71 (d, 1H, J 9.5 Hz), 2.72 (s, 3H), 1.91 (d, 1H, J 1.1 Hz), 1.12-0.96 (m, 28H). $^{13}C$ NMR ($CDCl_3$, 62.9 MHz) δ 163.7, 149.6, 135.2, 109.7, 90.9, 85.7, 71.4, 67.3, 58.6, 58.2, 41.2, 17.5, 17.4, 17.3, 17.2, 17.1, 16.9, 13.3, 13.1, 13.0, 12.6, 12.1. Anal. Calcd. for $C_{24}H_{44}N_3O_6Si_2$,$0.25H_2O$: C, 54.4; H, 8.3; N, 7.9. Found: C, 54.4; H, 8.1; N, 7.7.

EXAMPLE 92

1-(2-Deoxy-2-methylamino-2-N,4-C-methylene-β-D-ribofuranosyl)thymine (74D). To a solution of nucleoside 74C (0.40 g, 0.76 mmol) in THF at room temperature was added a solution of tetrabutylammonium fluoride in THF (1.0 M, 2.2 mL, 2.2 mmol) and the reaction mixture was stirred for 20 min whereupon pyridine:water:methanol (6 mL, 3:1:1, v/v/v) was added. The mixture was added to Dowex 50×200 resin (2.2 g, $H^+$ (pyridinium) form, 100-200 mesh) suspended in pyridine:water:methanol (6 mL, 3:1:1, v/v/v) and the resulting mixture was stirred for 20 min. After filtration, the residue was washed with pyridine:water:methanol (3×3 mL, 3:1:1, v/v/v) and the combined filtrate was evaporated to dryness under reduced pressure to give an oily residue after coevaporation with methanol (2×5 mL). Column chromatography on silica gel using methanol:dichloromethane (1:49, v/v) as eluent gave nucleoside 74D as a white solid material after evaporation of the solvents under reduced pressure (0.17 g, 79%). FAB-MS m/z 284 $[M+H]^+$. FAB-HRMS calcd. for $C_{12}H_{18}N_3O_5^+$: 284.12465. Found: 284.12402. $^1H$ NMR ($(CD_3)_2SO$, 400 MHz) δ 11.3 (bs, 1H, NH), 7.70 (d, 1H, J 1.1 Hz, 6-H), 5.50 (s, 1H, 1'-H), 5.26 (d, 1H, J 4.9 Hz, 3'-OH), 5.12 (t, 1H, J 5.7 Hz, 5'-OH), 3.87 (d, 1H, J 4.8 Hz, 3'-H), 3.67 (d, 2H, J 5.5 Hz, 5'-H), 3.12 (s, 1H, 2'-H), 2.87 (d, 1H, J 9.3 Hz, 5"-$H_a$), 2.56 (s, 3H, $NCH_3$), 2.52-2.49 (1H, m, 5"-$H_b$), 1.77 (s, 3H, $CH_3$). $^1H$ NMR ($CD_3OD$, 400 MHz) δ 7.80 (d, 1H, J 1.3 Hz, 6-H), 5.71 (s, 1H, 1'-H), 4.07 (s, 1H, 3'-H), 3.83 (s, 2H, 5'-H), 3.36 (s, 1H, 2'-H), 3.08 (d, 1H, J 9.9 Hz, 5"-$H_a$), 2.68 (s, 3H, $NCH_3$), 2.57 (d, 1H, J 9.9 Hz, 5"-$H_b$), 1.88 (d, 3H, J 1.1 Hz, $CH_3$). $^{13}C$ NMR ($CD_3OD$, 62.9 MHz) δ 166.6, 151.9, 137.4, 110.4, 91.3, 85.2, 71.4, 69.1, 59.4, 58.7, 40.2, 12.2.

EXAMPLE 93

1-(2-Deoxy-5-O-4,4'-dimethoxyfrityl-2-methylamino-2-N,4-C-methylene-β-D-ribofuranosyl)thymine (74E). To a solution of nucleoside 74D (0.135 g, 0.477 mmol) in anhydrous pyridine (1.5 mL) at 0° C. was dropwise (during 20 min) added a solution of 4,4'-dimethoxytrityl chloride (0.238 g, 0.702 mmol) in anhydrous pyridine:dichloromethane (1.0 mL, 1:1, v/v) and the resulting mixture was stirred for 10 h at RT. A mixture of ice and water was added (5 mL) and the mixture was extracted with dichloromethane (3×10 mL). The combined organic phase was washed with a saturated aqueous solution of sodium hydrogencarbonate (3×5 mL), dried ($Na_2SO_4$) and filtered. The filtrate was evaporated to dryness under reduced pressure and the residue was subjected to column chromatography on silica gel using methanol:dichloromethane:pyridine (1:98:1, v/v/v) as eluent to give nucleoside 74E as a white solid material after evaporation of the solvents under reduced pressure (0.20 g, 72%). FAB-MS m/z 586 $[M+H]^+$. $^1H$ NMR($C_5D_5N$, 400 MHz) δ 13.2 (bs, 1H), 7.98 (d, 1H, J 1.3 Hz), 7.98-7.00 (m, 13H), 6.12 (s, 1H), 4.78 (d, 1H, J 3.7 Hz), 3.88-3.79 (m, 4H), 3.71 (s, 3H), 3.71 (s, 3H), 3.29 (d, 1H, J 9.3 Hz), 2.84 (d, 1H, J 9.3 Hz), 2.81 (s, 3H), 1.85 (d, 3H, J 0.9 Hz). $^{13}C$ NMR($C_5D_5N$, 62.9 MHz) δ 165.1, 159.2, 151.4, 145.9, 136.5, 136.4, 130.8, 130.7, 128.7, 128.4, 127.4, 113.8, 109.6, 89.8, 86.8, 85.1, 72.0, 68.7, 60.9, 59.4, 55.2, 40.1, 13.1. Anal. Calcd. for $C_{33}H_{35}N_3O_7$,$0.25H_2O$: C, 67.2; H, 6.1; N, 7.1. Found: C, 67.2; H, 6.2; N, 6.9.

EXAMPLE 94

1-(3-O-(2-Cyanoethoxy(diisopropylamino)phosphino)-5-O-4,4'-dimethoxytrityl-2-methylmino-2-N,4-C-methylene-2-deoxy-β-D-ribofuranosyl)thymine (74F). To a solution of nucleoside 74E (0.130 g, 0.222 mmol) in anhydrous dichloromethane (2 mL) at 0° C. were added N,N-diisopropylethylamine (0.088 mL, 0.514 mmol) and 2-cyanoethyl N,N-diisopropylphosphoramidochloridite (0.065 mL, 0.291 mmol) and the mixture was stirred for 10 h at room temperature. Dichloromethane (30 mL) was added and the mixture was extracted with a saturated aqueous solution of sodium hydrogencarbonate (3×10 mL), dried ($Na_2SO_4$) and filtered. The filtrate was evaporated to dryness under reduced pressure and the residue was subjected to column chromatography on silica gel using methanol:dichloromethane:pyridine (0.5:98.5:1.0, v/v/v) as eluent to give crude product (0.120 g) after evaporation of the solvents under reduced pressure. The residue was dissolved in anhydrous dichloromethane (1 mL) and by dropwise addition to vigorously stirred petroleum ether (60-80° C., 30 mL) at −30° C., nucleotide 74F precipitated to give a white solid material after filtration (0.090 g, 52%). $^{31}P$ NMR ($CD_3CN$, 121.5 MHz) δ 147.7.

EXAMPLE 95

1-(3,5-Di-O-benzyl-4-C-(p-toluenesulphonyloxymethyl)-2-O-p-toluenesulphonyl-δ-D-ribofuranosyl)uracil (75). To a stirred solution of 1-(3,5-di-O-benzyl-4-C-hydroxymethyl-β-D-ribofuranosyl)uracil 41 (3.55 g, 7.81 mmol) in dichloromethane (50 $cm^3$) were added DMAP (3.82 g) and p-toluenesulphonyl chloride (4.47 g, 23.5 mmol) at room temperature. Stirring was continued for 2 h, and dichloromethane (100 $cm^3$) was added. The reaction mixture was washed with a saturated aqueous solution of sodium hydrogen carbonate (2×75 $cm^3$) and dried ($Na_2SO_4$). The organic phase was evaporated under reduced pressure and the residue was purified by silica gel column chromatography using dichloromethane/-methanol (99.5:0.5, v/v) as eluent to give nucleoside 75 (4.65 g, 78%) as a white solid material. $\delta_H$ ($CDCl_3$) 8.49 (1H, br s, NH), 7.67 (1H, d, J 8.3, 6-H), 7.51-7.03 (18H, m, Bn, Ts), 6.0 (1H, d, J 7.6, 1'-H), 5.05 (1H, m, 2'-H), 4.91 (2H, m, 5-H, Bn), 4.56 (2H, m, Bn), 4.42 (1H, d, J 10.4, Bn), 4.31 (1H, d, J 4.9, 3'-H), 4.05 (2H, m, 1"-H), 3.75-3.64 (2H, m, 5'-H), 2.41 (3H, s, $CH_3$), 2.34 (3H, s, $CH_3$). $\delta_C$ ($CDCl_3$) 162.2 (C-4), 149.5 (C-2), 146.0, 145.3 (Ts), 139.0 (C-6), 136.7, 131.9, 130.0, 129.9, 128.9, 128.7, 128.5, 128.4, 128.3, 128.2, 128.0, 127.6 (Bn, Ts) 102.7 (C-5), 85.5 (1'-C), 84.4 (4'-C), 79.2, 78.3, 75.1, 74.3, 72.4, 69.1 (Bn, 3'-C, 2'-C, 5'-C, 1"-C), 21.7, 21.6 (Ts). FAB-MS m/z 763. Found: C, 61.2; H, 4.4; N, 3.3; $C_{38}H_{38}N_2O_{11}S_2$ requires C, 59.8; H, 5.0; N, 3.6.

EXAMPLE 96

1-(2-Deoxy-3,5-di-O-benzyl-2-S,4-C-methylene-2-mercapto-β-D-ribofuranosyl)thymine (76). To a stirred solution of nucleoside 75 (3.70 g, 4.86 mmol) in DMF (40 $cm^3$) was added potassium thioacetate (0.83 g, 7.28 mmol). The mixture was stirred and heated at 110° C. for 80 h. After evaporation under reduced pressure, $H_2O$ (100 $cm^3$) was added. Extraction was performed with dichloromethane (4×50 $cm^3$) and the combined organic phase was dried ($Na_2SO_4$), filtered and evaporated under reduced pressure. The residue was purified by silica gel chromatography using dichloromethane/methanol (99.6:0.4, v/v) as eluent to give nucleoside 76 (1.65 g, 75%) as a white solid material. $\delta_H$ ($CDCl_3$) 9.08 (1H, br s, NH), 7.98 (1H, d, J 8.1, 6-H), 7.39-7.20 (10H, m, Bn), 5.85 (1H, s, 1'-H), 5.26 (1H, d, J 8.1, 5-H), 4.61 (1H, d J 11.4, 5'-H), 4.56 (2H, s, Bn), 4.45 (1H, d, J 11.4, Bn), 4.14 (1H, d, J 1.7, 3'-H), 3.82 (2H, m, Bn), 3.72 (1H, d, J 1.9, 2'-H), 3.02 (1H, d, J 9.9, 1"-$H_a$), 2.78 (1H, d, J 9.9, 1"-$H_b$). $\delta_C$ ($CDCl_3$) 163.4 (C-4), 150.0 (C-2), 139.9 (C-6), 137.2, 136.8, 128.6, 128.5, 128.2, 127.9, 127.7 (Bn), 100.8 (C-5), 90.8, 88.8 (C-1', C-4'), 76.5, 73.8, 72.0, 70.0 (2×Bn, C-3', C-5'), 49.52 (C-2'), 35.63 (C-1"). FAB-MS m/z 453. Found: C, 63.4; H, 5.1; N, 5.9; $C_{24}H_{24}N_2O_5S$ requires C, 63.7; H, 5.3; N, 6.1.

EXAMPLE 97

1-(2-O-p-Toluenesulfonyl-4-C-(p-toluenesulfonyloxymethyl)-β-D-ribofuranosyl)uracil (76A). To a solution of compound 75 (0.80 g, 1.0 mmol) in absolute ethanol (2 $cm^3$) was added 20% palladium hydroxide over carbon (0.80 g) and the mixture was degassed several times with hydrogen and stirring was continued under hydrogen for 48 h. The catalyst was filtered off and the filtrate was evaporated under reduced pressure. The residue was purified by silica gel column chromatography using dichloromethane/methanol (99:1, v/v) as eluent to give nucleoside 76A (0.30 g, 49%) as a white solid material. $\delta_H$ ($CD_3OD$) 7.67 (4H, m), 7.45 (1H, d, J 8.2 Hz), 7.34 (4H, m), 5.86 (1H, d, J 8.0 Hz), 5.40 (1H, d, J 8.1 Hz), 4.95 (1H, m), 4.35 (1H, d, J 5.0 Hz), 4.17 (2H, m), 3.61 (2H, s), 2.40 (6H, s). $\delta_C$ ($CD_3OD$) 165.4, 151.6, 147.5, 146.6, 141.3, 134.0, 133.8, 131.4, 130.9, 129.2, 128.9, 103.7, 88.0, 85.4, 80.7, 72.4, 71.0, 64.3, 21.7, 21.6. FAB-MS m/z 583 $[M+H]^+$.

EXAMPLE 98

1-(3,5-O-(Tetraisopropyldisiloxa-1,3-diyl)-2-O-p-toluenesulfonyl-4-C-(p-toluenesulfonyloxymethyl)-β-D-ribofuranosyl)uracil (76B). To a stirred solution of nucleoside 76A (0.27 g, 0.46 mmol) in anhydrous pyridine (4 $cm^3$) was added 1,3-dichloro-1,1,3,3-tetraisopropyldisiloxane (0.22 $cm^3$, 0.70 mmol). After stirring for 48 h, the mixture was cooled to 0° C. and a saturated aqueous solution of sodium hydrogen carbonate (15 $cm^3$) was added. The mixture was extracted with dichloromethane (3×10 $cm^3$) and the combined organic phase was dried ($Na_2SO_4$) and filtered. The solvent was evaporated under reduced pressure and the residue was purified by silica gel chromatography using dichloromethane/methanol (99.5:0.5, v/v) as eluent to give nucleoside 76B (0.37 g, 97%) as a white solid material. $\delta_H$ ($CDCl_3$) 8.70 (1H, br s), 7.80 (4H, m), 7.36 (4H, m), 6.98 (1H, d, J 8.1 Hz), 5.64 (1H, d, J 8.0 Hz), 5.18 (2H, m), 4.98 (1H, d, J 7.0 Hz), 4.39-4.32 (2H, m), 3.92-3.76 (2H, s), 2.45 (6H, s), 1.27-0.66 (28H, m). $\delta_C$ ($CDCl_3$) 162.9, 149.3, 145.6, 144.8, 143.9, 132.9, 130.1, 129.9, 128.2, 128.1, 102.2, 94.6, 84.7, 80.4, 72.8, 67.8, 64.6, 21.7, 17.3, 17.2, 17.1, 16.9, 16.8, 13.1, 12.8, 12.3. FAB-MS m/z 825 $[M+H]^+$.

EXAMPLE 99

1-(2-Deoxy-2-mercapto-2-S,4-C-methylene-3,5-O-(tetraisopropyldisiloxa-1,3-diyl)-β-D-ribofuranosyl)uracil (76C). To a stirred solution of nucleoside 76B (0.26 g, 0.32 mmol) in DMF (5 $cm^3$) was added potassium thioacetate (0.054 g, 0.47 mmol). The reaction mixture was stirred at 110° C. for 20 h. After evaporation of the mixture under reduced pressure, $H_2O$ (20 $cm^3$) was added. Extraction was performed with dichloromethane (3×10 $cm^3$) and the combined organic phase was dried ($Na_2SO_4$), filtered and evaporated under reduced pressure. The residue was purified by silica gel column chromatography using dichloromethane/methanol (99.25:0.75, v/v) as eluent to give nucleoside 76C (0.125 g, 77%) as a white solid material. $\delta_H$ ($CDCl_3$) 8.55 (1H, br s), 8.02 (1H, d, J 8.1 Hz), 5.82 (1H, s, 1'-H), 5.65 (1H, d, J 8.1 Hz), 4.37 (1H, d, J 2.1 Hz), 4.10 (1H, d, J 13.2 Hz), 3.90 (1H, d, J 13.1 Hz), 3.53 (1H, d, J 2.1 Hz), 2.92 (1H, d, J 10.1 Hz), 2.74 (1H, d, J 10.0 Hz), 1.30-0.80 (28H, m). $\delta_C$ ($CDCl_3$) 163.2, 149.8, 139.6, 100.9, 91.4, 90.7, 71.5, 59.8, 51.5, 34.4, 17.5, 17.3, 17.1, 16.9, 15.5, 13.6, 13.3, 13.1, 12.9, 12.3. FAB-MS m/z 515 $[M+H]^+$.

EXAMPLE 100

1-(2-Deoxy-2-mercapto-2-S,4-C-methylene-β-D-ribofuranosyl)uracil (76D). To a stirred solution of nucleoside 76C (25 mg, 0.049 mmol) in THF (1.0 $cm^3$) was added a solution of tetrabutylammonium fluoride (0.20 $cm^3$ of a 1M solution in THF, 0.20 mmol) at 0° C. After stirring the mixture at 0° C. for 1 h, $H_2O$ (5 $cm^3$) was added and the mixture was evaporated. The residue was purified by silica gel column chromatography using dichloromethane/-methanol (97:3, v/v) as eluent to give nucleoside 76D (9.0 mg, 69%) as a white solid material. $\delta_H$ ($CD_3OD$) 8.19 (1H, d, J 8.1 Hz, 6-H), 5.77 (1H, s, 1'-H), 5.65 (1H, d, J 8.1 Hz, 5-H), 4.31 (1H, d, J 2.1 Hz, 3'-H), 3.86 (2H, s, 5'-H), 3.53 (1H, d, J 2.2 Hz, 2'-H), 2.93 (1H, d, J 10.3 Hz, 1"-$H_a$), 2.73 (1H, d, J 10.3 Hz, 1"-$H_b$). $\delta_C$ ($CD_3OD$) 166.5, 152.0, 141.7, 101.2, 92.1, 92.0, 71.4, 59.9, 53.6, 35.4. FAB-MS m/z 273 $[M+H]^+$.

EXAMPLE 101

1-(2-Deoxy-5-O-(4,4'-dimethoxytrityl)-2-mercapto-2-S,4-C-methylene-β-D-ribofuranosyl)uracil (76E). To a solution of 76D (0.2 g, 0.37 mmol) in anhydrous pyridine (5 $cm^3$) was added 4,4'-dimethoxytrityl chloride (0.186 g, 0.55 mmol) at room temperature. The solution was stirred for 5 h whereupon the reaction mixture was cooled to 0° C. A saturated aqueous solution of sodium hydrogen carbonate (30 $cm^3$) was added and the resulting mixture was extracted with dichloromethane (3×50 $cm^3$). The combined organic phase was separated and dried ($Na_2SO_4$). The solvent was removed under reduced pressure and the residue was purified by silica gel column chromatography with dichloromethane/methanol/pyridine (98.5:1.0:0.5 v/v) as eluent to give nucleoside 76E as a white brownish solid material (0.175 g, 83%). $\delta_C$ ($CDCl_3$) 164.5, 159.4, 151.6, 145.7, 139.9, 136.4, 136.0, 135.6, 130.9, 130.8, 128.8, 128.5, 128.4, 127.5, 127.4, 122.7, 113.9, 101.5, 91.7, 90.2, 87.6, 71.8, 61.9, 55.3, 53.7, 36.2, 30.6. FAB-MS m/z 574 $[M]^+$, 575 $[M+H]^+$ (Found: C, 65.2; H, 5.4; N, 5.0; $C_{31}H_{30}N_2O_7S$ requires C, 64.8; H, 5.3; N, 4.9%).

EXAMPLE 102

1-(3-O-(2-Cyanoethoxy(diisopropylamino)phosphino)-(2-deoxy-5-O-(4,4'-dimethoxytrityl)-2-mercapto-2-S,4-C-methylene-β-D-ribofuranosyl)uracil (76F). To a solution of 76E (0.160 g, 0.28 mmol) in anhydrous dichloromethane (2 $cm^3$) at 0° C. were added N,N-diisopropylethylamine (0.27 $cm^3$) and 2-cyanoethyl N,N-diisopropylphosphoramidochloridite (97 mg, 0.42 mmol). Stirring was continued at room temperature for 5 h. The reaction mixture was cooled to 0° C. and a saturated aqueous solutions of sodium hydrogen carbonate (30 $cm^3$) was added. Extraction was performed using dichloromethane (3×20 $cm^3$) and the combined organic phase was dried ($Na_2SO_4$) and evaporated to dryness under reduced pressure. The residue was purified by silica gel column chromatography using dichloromethane/methanol/pyridine (99:0.5:0:5 v/v) as eluent to give a white foam. This residue was dissolved in dichloromethane (2 $cm^3$) and the product was precipitated from light petroleum (100 $cm^3$, cooled to −40° C.) under vigorous stirring. The precipitate was collected by filtration, and was finally dried to give nucleoside 76F as a white solid material (95 mg, 44%). $\delta_p$ ($CDCl_3$) 148.9, 149.0.

EXAMPLE 103

3,5-Di-O-benzyl-1,2-O-isopropylidene-4-C-(p-toulenesulfonyloxymethyl)-β-D-ribofuranose (77). A solution of 3,5-di-O-benzyl-4-C-hydroxymethyl-1,2-O-isopropylidene-β-D-ribofuranose 31 (15.38 g, 38.4 mmol), anhydrous pyridine (20 $cm^3$) and anhydrous dichloromethane (80 ml) was stirred at −5° C. p-Toulenesulphonyl chloride (8.75 g, 46.0 mmol) dissolved in anhydrous dichloromethane (8 $cm^3$) was added during 15 min. The solution was stirred at room temperature for 17 h. The reaction was quenched with ice-cold $H_2O$ (200 $cm^3$). Extraction was performed with dichloromethane (5×150 $cm^3$) and the combined organic phase was washed with saturated aqueous solutions of sodium hydrogen carbonate (3×100 $cm^3$) and brine (3×100 $cm^3$), dried ($Na_2SO_4$), filtered and evaporated under reduced pressure. The residue was purified by silica gel column chromatography using dichloromethane:methanol (98.5:1.5, v/v) as eluent to give 77 as a clear oil (17.4 g, 82%). $\delta_H$ ($CDCl_3$) 7.79-7.19 (14H, m, Bn), 5.66 (1H, d, J 3.6, 1-H), 4.69-4.20 (8H, m, Bn, 5-$H_a$, 5-$H_b$, 3-H, 2-H), 3.53 (1H, d, J 10.3, 1'-$H_a$), 3.46 (1H, d, J 10.3, 1'-$H_b$), 2.40 (3H, s, $CH_3$), 1.29 (3H, s, $CH_3$), 1.26 (3H, s, $CH_3$). $\delta_C$ ($CDCl_3$) 144.6, 137.9, 137.3, 133.0, 129.8, 128.4, 128.3, 128.1, 128.0, 127.9, 127.7, 127.6 (aromatic), 113.6 ($C(CH_3)_2$), 104.2, (C-1), 84.7 (C-4), 79.0, 78.7, 73.7, 72.7, 70.7, 70.2, (Bn, C-2, C-3, C-5, C-1'), 26.3, 26.0 ($C(CH_3)_2$), 21.6 ($CH_3$). FAB-MS m/z 555 $[M+H]^+$. (Found: C, 64.8; H, 6.2; $C_{30}H_{34}O_8S$ requires C, 64.9; H, 6.1%).

EXAMPLE 104

1,2-Di-O-acetyl-3,5-di-O-benzyl-4-C-(p-toluenesulfonyloxymethyl)-α,β-D-ribofuranose (78). A solution of furanose 77 (17.4 g, 31.4 mmol) in 80% acetic acid (250 $cm^3$) was stirred at 60° C. for 20 h. The solvent was removed in vacuo and the residue was coevaporated with toluene (3×20 $cm^3$). The residue was redissolved in anhydrous pyridine (100 $cm^3$). Acetic anhydride (14.2 $cm^3$) was added and the solution was stirred for 15 h at room temperature. The reaction was quenched by addition of ice-cold $H_2O$ (200 $cm^3$), and the mixture was extracted with dichloromethane (4×150 $cm^3$). The combined organic phase was washed with saturated aqueous solutions of sodium hydrogen carbonate (2×125 $cm^3$) and brine (3×150 $cm^3$), dried ($Na_2SO_4$), filtered and evaporated under reduced pressure. The residue was purified by silica gel column chromatography using dichloromethane:—methanol (98.5:1.5, v/v) as eluent to give 78 (α,β~1:1) as a clear oil (13.5 g, 72%). $\delta_C$ ($CDCl_3$) 169.8, 169.6, 69.4, 168.8 (C═O), 144.7, 137.7, 137.5, 132.8, 129.7, 129.6, 128.5, 128.4, 128.3, 128.2, 128.0, 127.8, 127.7, 127.6 (Bn), 97.4, 94.2 (C-1), 86.4, 84.2 (C-4), 78.9, 77.5, 74.5, 74.1, 73.7, 73.5, 71.8, 70.6, 70.5, 69.6, 69.5 (Bn, C-2, C-3, C-1'), 21.6, 21.0, 20.8, 20.6, 20.4 ($COCH_3$, $C(CH_3)_2$). FAB-MS m/z 599 $[M+H]^+$.

Alternative Procedure for the Preparation of Compound 78.

3-O-Benzyl-1,2:5,6-di-O-isopropylidene-α-D-glucofuranose (30B). To a solution of 1,2:5,6-Di-O-isopropylidene-α-D-allofuranose (30A) (obtained from Pfanstiehl Laboratories Inc.) (40 g) in dimethylformamide at 0° C. was added sodium hydride in smaller portions. The reaction mixture was stirred for 1 h, benzyl bromide was added drop wise over a period of 1 h. The reaction mixture was stirred at room temperature for 16 h. Methanol was added to quench the reaction and dimethylformamide was removed under pressure. The syrup was extracted with ethyl acetate and washed with brine. Evaporation of the ethyl acetate layer yielded a semisolid (93%). Homogeneous by TLC.

3-O-Benzyl-1,2-O-isopropylidene-α-D-glucofuranose (30C). Partial hydrolysis of 30B (50 g) was achieved in 75% acetic acid in a period of 20 h. Concentration to a smaller volume and extraction with ethyl acetate yielded 30C, 40 g, (90%). Homogeneous by TLC.

3-O-Benzyl-1,2-O-isopropylidene-α-D-ribo-pentodialdofuranose (30D). A solution of 30C (40 g) in water/methanol (1:1) was slowly added with stirring to a solution of sodium periodate in water at 0° C. The reaction was stirred for 2 h, ethylene glycol was added and the mixture was extracted with ethyl acetate. The dried extract was evaporated to yield 30D, 32 g, (89%). Homogeneous by TLC. In this step addition of methanol is essential for the completion of the reaction.

3-O-Benzyl-4-(hydroxymethyl)-1,2-O-isopropylidene-α-D-erythro-pentofuranose (30E). Aqueous 37% formaldehyde and 1N sodium hydroxide were added at 0° C. to a stirred solution of 30D (32 g) in water and tetrahydrofuran (1:1), the reaction was continued for 16 h, extracted in ethyl acetate and washed with brine. Evaporation of the organic layer afforded a syrup which crystallised from ether/petroleum ether as white solid, 23 g, the filtrate was an oil which solidified as a low melting solid, 10 g, total yield of 30E, 92%. [23 g (white solid was 99% pure by TLC), 10 g of low melting solid (had faster moving impurities by TLC, approximately 75% pure)]. In this step addition of tetrahydrofuran is very important for the time and reaction completion.

3,5-Di-O-benzyl-4-C-hydroxymethyl-1,2-O-isopropylidene-α-D-ribofuranose (31). Benzylation of 30E (20 g) with NaH 60% and BnBr at −10° C. yielded a mixture of two isomers. Flash column chromatography afforded 31 as the major isomer, 14 g, (54%). Homogeneous by TLC.

3,5-Di-O-benzyl-1,2-O-isopropylidene-4-C-tosyl-α-D-ribofuranose (77). A solution of 31 (12.5 g) in pyridine at 0° C. was treated with p-toluenesulphonyl chloride and the reaction was continued at room temperature for 14-16 h. Removal of pyridine, extraction with methylene chloride and saturated bicarbonate solution afforded 77, 14 g, (80%). Homogeneous by TLC.

1,2-di-O-acetyl-3,5-di-O-benzyl-4-C-tosyl-D-ribofuranose (78). Hydrolysis of 77 (14 g) was done in 75% acetic acid at 65° C. for 18 h. The solvent was removed under pressure and the residue was treated with ethanol (3×100), toluene (3×50) and anhydrous pyridine (2×50). (This compound 78 crystallised from petroleum ether as fine white solid.) The residue was taken in dry pyridine and treated with acetic anhydride at room temperature for 8 h. Extraction with ethyl acetate and saturated bicarbonate followed by washing with brine afforded 78 as a mixture of α and β anomers, 12 g, (83%). A direct comparison with an authentic sample of 78 (TLC, HPLC, NMR) confirmed its identity and purity.

EXAMPLE 105

1-(2-O-Acetyl-3,5-di-O-benzyl-4-C-(p-toulenesulfonyloxymethyl)-β-D-ribofuranosyl)-thymine (79). To a stirred solution of the anomeric mixture 78 (12.8 g, 21.4 mmol) and thymine (5.38 g, 42.7 mmol) in anhydrous acetonitrile (182 $cm^3$) was added N,O-bis(trimethylsilyl)acetamide (31.68 ml, 128.23 mmol). The reaction mixture was stirred for 1 h at room temperature, and stirring was continued at 60° C. for 1.5 h. After cooling to 0° C., trimethylsilyl triflate (6.57 ml, 30.33 mmol) was added dropwise, and the mixture was stirred at 60° C. for 10 h. The reaction mixture was neutralised with an ice-cold saturated aqueous solution of sodium hydrogen carbonate (90 mL). The reaction mixture was filtered, and the filtrate was concentrated under reduced pressure to half volume. Extraction was performed using dichloromethane (4×200 $cm^3$). The combined organic phase was washed with saturated aqueous solutions of sodium hydrogen carbonate (3×150 $cm^3$) and brine (3×150 ml), dried ($Na_2SO_4$), filtered and evaporated under reduced pressure. The residue was purified by silica gel column chromatography using dichloromethane:methanol (99:1 to 98:2, v/v) as eluent to give nucleoside 79 as a white solid material (13.1 g, 92%). $\delta_H$ ($CDCl_3$) 9.04 (s, 1H, NH), 7.73-7.19 (15H, m, 6-H, aromatic), 5.94 (1H, d, J 5.5, 1'-H), 5.37 (1H, d, J 5.6, 2'-H), 4.57-4.40 (5H, m, 3'-H, 5'-$H_a$, 5'-$H_b$, Bn), 4.14 (2H, s, Bn), 3.75 (1H, d, J 10.2, 1"-$H_a$), 3.57 (1H, d, J 10.2, 1"-$H_b$), 2.41 (3H, s, $CH_3C_6H_5$), 2.02 (3H, s, $COCH_3$), 1.54 (3H, s, $CH_3$). $\delta_C$ ($CDCl_3$) 169.8 (C═O), 163.5 (C-4), 150.2 (C-2), 145.0, 136.8, 135.6, 132.1, 129.7, 128.5, 128.0, 127.9, 127.8, 127.5 (aromatic), 113.5 (C-5), 86.8, 85.3, 77.6, 74.6, 74.3, 73.6, 70.8, 68.8 (Bn, C-1', C-3', C-2', C-4'), 21.3 ($CH_3$), 20.5 ($COCH_3$), 11.8 ($CH_3$).

FAB-MS m/z 665 $[M+H]^+$ (Found C, 61.2; H, 5.3; N, 4.1; S, 4.7, $C_{34}H_{36}O_{10}N_2S$ requires C, 61.4; H, 5.4; N, 4.2; S, 4.8).

EXAMPLE 106

1-(3,5-Di-O-benzyl-4-C-(p-toulenesulfonyloxymethyl)-β-D-ribofuranosyl)thymine (80). Nucleoside 79 (13.1 g, 19.7 mmol) was dissolved in a solution of ammonia in methanol (200 $cm^3$, prepared by diluting saturated methanolic ammonia with an equal volume of methanol) and stirred at room temperature for 4 h. The reaction mixture was subsequently evaporated, and the residue was dissolved in dichloromethane (400 $cm^3$). The organic phase was washed with brine (3×150 $cm^3$), dried ($Na_2SO_4$), filtered and evaporated under reduced pressure. The residue was purified by silica gel column chromatography using dichloromethane:methanol (99.5:0.5, v/v) as eluent to give nucleoside 80 as a white solid material (10.7 g, 87%). $\delta_H$ ($CDCl_3$) 9.66 (s, 1H, NH), 7.71-7.21 (15H, m, 6-H, aromatic), 5.72 (1H, d, J 5.1, 1'-H), 4.75, 4.55 (2H, each d, J 11.5, Bn), 4.51 (2H, s, Bn), 4.37 (1H, t, J 5.4, 2'-H), 4.30-4.12 (3H, m, Bn), 3.76 (1H, d, J 10.2, 1"-$H_a$), 3.59 (1H, d, J 10.2, 1"-$H_b$), 2.39 (3H, s, $CH_3C_6H_5$), 1.48 (3H, s, $CH_3$). $\delta_C$ ($CDCl_3$) 163.8 (C-4), 150.9 (C-2), 145.0, 137.0, 136.9, 135.9, 132.3, 129.8, 128.7, 128.6, 128.2, 128.1, 128.0, 127.6 (aromatic), 111.0 (C-5), 89.6, 85.3, 78.4, 74.5, 73.8, 71.1, 69.7, (Bn, C-1', C-3', C-2', C-4', C-1"), 21.6 ($CH_3$), 12.0 ($CH_3$). FAB-MS m/z 623 $[M+H]^+$ (Found C, 61.5; H, 5.2; N, 4.4; S, 5.2, $C_{32}H_{34}O_9N_2S$ requires C, 61.7; H, 5.4; N, 4.5; S, 5.1).

EXAMPLE 107

(1S,3R,4R,7S)-7-Benzyloxy-1-benzoyloxymethyl-3-(thymin-1-yl)-2,5-dioxabicyclo-[2.2.1]heptane (36). To a stirred solution of nucleoside 80 (10.65 g, 17.1 mmol) in anhydrous DMF (150 $cm^3$) was added a 60% suspension of sodium hydride in mineral oil (0.9 g, 22.2 mmol) in small portions at 0° C. The mixture was stirred at 0° C. for 15 h whereupon additional 60% sodium hydride (0.205 g, 5.12 mmol) was added, and the reaction mixture was stirred for additional 22 h at 0° C. Methanol (20 $cm^3$) was added and the reaction mixture was subsequently concentrated under reduced pressure to half volume. Ice-cold $H_2O$ (300 $cm^3$) was added and extraction was performed with dichloromethane (5×150 $cm^3$). The combined organic phase was washed with saturated aqueous solutions of sodium hydrogen carbonate (3×40 $cm^3$) and brine (3×40 $cm^3$), dried ($Na_2SO_4$), filtered and evaporated under reduced pressure. The residue was purified by silica gel column chromatography using dichloromethane:methanol (99.5:0.5, v/v) as eluent to give nucleoside 36 as a white solid material (7.1 g, 92%). Spectral data were in accordance with data given earlier for 36 (Found C, 66.2; H, 5.8; N, 6.1; $C_{25}H_{26}N_2O_6$ requires C, 66.6; H, 5.8; N, 6.2).

EXAMPLE 108

3,5-Di-O-benzyl-1,2-O-isopropylidene-4-C-methanesulfonyloxymethyl-α-D-ribofuranose (200). To a stirred solution of furanose 31 (2.16 g, 5.39 mmol) in anhydrous pyridine (3 mL) at 0° C. was added dropwise methanesulfonyl chloride (0.61 mL, 16.0 mmol). The reaction mixture was stirred for 20 min at room temperature, quenched with ice-cold water (300 mL) and extracted with dichloromethane (2×300 mL). The combined extracts were washed with saturated aqueous sodium hydrogen carbonate (300 mL) and then dried ($MgSO_4$). The solvent was removed by distillation under reduced pressure and the residue was purified by chromatography over silica gel with dichloromethane as eluent to give the product 200 as a clear oil (2.55 g, 99%); $^1H$ NMR ($CDCl_3$): δ 7.37-7.24 (10 H, m, Bn), 5.78 (1 H, d, J 3.8 Hz, H-1), 4.85 (1 H, d, J 11.7 Hz, Bn), 4.73 (1 H, d, J 11.9 Hz, Bn), 4.64 (1 H, dd, J 4.0, 5.3 Hz, H-2), 4.54 (1 H, d, J 11.9 Hz, H-5'), 4.52 (1 H, d, J 11.9 Hz, Bn), 4.46 (1 H, d, J 11.9 Hz, H-5'), 4.41 (1 H, d, J 11.8 Hz, Bn), 3.60 (1 H, d, J 10.4 Hz, H-5), 3.50 (1 H, d, J 10.5 Hz, H-5), 3.06 (3 H, s, $SO_2CH_3$), 1.68 (3 H, s, $CH_3$), 1.34 (3 H, s, $CH_3$); $^{13}C$ NMR ($CDCl_3$): δ 137.79, 137.31, 128.54, 128.48, 128.16, 128.01, 127.87, 127.79 (Bn), 113.66 ($C(CH_3)_2$), 104.46 (C-1), 84.88 (C-4), 78.48, 78.41 (C-2, C-3), 73.65, 72.63, 70.78, 70.16 (Bn, C-5, C-5'), 37.84 ($SO_2CH_3$), 26.20 ($CH_3$), 25.69 ($CH_3$); MS FAB: 501 (M+Na, 100%). Found: C, 60.37; H, 6.29; S, 6.53; $C_{24}H_{30}O_8S$ requires C, 60.24; H, 6.32; S, 6.70%.

EXAMPLE 109

Methyl 3,5-di-O-benzyl-4-C-methanesulfonyloxymethyl-α-D-ribofuranoside (201). A solution of furanose 200 (1.133 g, 2.37 mmol) in methanolic hydrochloric acid (20% w/w, 31.7 mL) and water (4.4 mL) was stirred at room temperature for 2 h. After neutralisation with sodium hydrogen carbonate (s), the solution was extracted with dichloromethane (2×150 mL). The combined extracts were washed with water (150 mL) and then dried ($MgSO_4$). The solvent was removed by distillation under reduced pressure and the residue purified by chromatography over silica gel with dichloromethane:methanol (99:1) as eluent to give the product 201 (β:α~2:1) as a clear oil (1.018 g, 95%); $^1H$ NMR ($CDCl_3$): δ 7.39-7.22 (m, Bn), 4.86 (br s, Bn), 4.69-3.99 (m, Bn, H-5', H-1, H-2, H-3), 3.68 (d, J 8.9 Hz, H-5'), 3.51 (d, J 9.8 Hz, H-5'), 3.46 (s, $OCH_3$ β), 3.34 (d, J 9.1 Hz, H-5 β), 3.32 (d, J 9.7 Hz, H-5'), 3.28 (s, $OCH_3$ β), 2.97 (3 H, s, $SO_2CH_3$ β), 2.93 (3 H, s, $SO_2CH_3$ α); $^{13}C$ NMR ($CDCl_3$): δ 137.74, 136.98, 128.70, 128.64, 128.58, 128.56, 128.37, 128.21, 128.15, 128.09, 127.98, 127.86, 127.83 (Bn), 107.54 (C-1 β), 103.39 (C-1 α), 84.65, 83.18, 81.90, 78.87 (C-4, C-3), 75.04, 74.07, 73.73, 73.70, 73.38, 72.56, 72.11, 70.85, 70.55, 70.20 (C-2, Bn, C-5, C-5'), 55.90 ($OCH_3$ α), 54.96 ($OCH_3$ β), 37.18 ($SO_2CH_3$ β), 37.07 ($SO_2CH_3$ α); MS FAB: 475 (M+Na, 25%). Found: C, 58.40; H, 6.33; $C_{24}H_{30}O_8S$ requires C, 58.39; H, 6.24%.

EXAMPLE 110

(3R)- and (3S)-(1S,4R,7S)-7-Benzyloxy-1-benzyloxymethyl-3-methoxy-2,5-dioxabicyclo[2.2.1]heptane (202 and 203). A solution of 201 (3.32 g, 7.34 mmol) in anhydrous DMF (25 mL) was stirred at 0° C. and a 60% oil dispersion of sodium hydride (700 mg, 16.9 mmol) was added. The mixture was stirred at room temperature for 90 min, quenched with water (300 mL) and extracted with diethyl ether (2×300 mL). The combined extract was washed with water (200 mL) and dried ($MgSO_4$). The solvent was removed under reduced pressure and the residue was purified by chromatography over silica gel with dichloromethane as eluent to give the two products 202 and 203 as clear oils (1.571 g, 60% and 0.777 g, 30% respectively). (1S,3R,4R,7S)-7-Benzyloxy-1-benzyloxymethyl-3-methoxy-2,5-dioxabicyclo[2.2.1]heptane (202). $^1H$ NMR ($CDCl_3$): δ 7.36-7.26 (10 H, m, Bn), 4.81 (1 H, s, H-1), 4.65 (1 H, d, J 11.9 Hz, Bn), 4.61 (2 H, s, Bn), 4.56 (1 H, d, J 11.9 Hz, Bn), 4.11 (1 H, s, H-2), 4.09 (1 H, s, H-3), 4.01 (1 H, d, J 7.5 Hz, H-5'), 3.80-3.77 (3 H, m, H-5', H-5), 3.39 (3 H, s, $OCH_3$); $^{13}C$ NMR ($CDCl_3$): δ 138.05, 137.36, 128.47, 128.44, 127.88, 127.73, 127.63 (Bn), 104.97 (C-1), 85.13 (C-4), 79.16 (C-3), 77.18 (C-2), 73.64 (Bn), 72.26, 72.10 (Bn, C-5'), 66.50 (C-5), 55.34 ($OCH_3$); MS FAB: 379 (M+Na, 28%). Found: C, 70.55; H, 6.97; $C_{21}H_{24}O_5$ requires C, 70.77; H, 6.79%. (1S,3R,4R,7S)-7-Benzyloxy-1-benzyloxymethyl-3-methoxy-2,5-dioxabicyclo[2.2.1]heptane (203). $^1H$ NMR ($CDCl_3$): δ 7.36-7.26 (10 H, m, Bn), 5.00 (1 H, s, H-1), 4.67-4.54 (4 H, m, Bn), 4.18 (1H, s, H-2), 3.99 (1 H, s, H-3), 3.99-3.90 (2 H, m, H-5'), 3.75-3.68 (2 H, m, H-5), 3.49 (3 H, s, $OCH_3$); $^{13}C$ NMR ($CDCl_3$): δ 137.83, 137.53, 128.51, 128.48, 127.96, 127.82, 127.71, 127.62 (Bn), 104.05 (C-1), 88.44 (C-4), 79.54 (C-3), 77.16 (C-2), 73.68 (Bn), 72.61 (C-5'), 72.24 (Bn), 65.73 (C-5), 56.20 ($OCH_3$); MS FAB: 379 (M+Na, 100%).

EXAMPLE 111

(1R,2S,3S)-2-Benzyloxy-3-benzyloxymethyl-1-(methoxy(thymin-1-yl)methyl)-3-trimethylsilyloxytetrahydrofuran (204). A solution of 202 (216 mg, 0.606 mmol) and thymine (153 mg, 1.22 mmol) in anhydrous acetonitrile (9.3 mL) was added BSA (N,O-bis(trimethylsilyl)acetamide, 0.90 mL, 3.6 mmol) and stirred under reflux for 15 min. The solution was cooled to 0° C. and trimethylsilyl triflate (0.153 mL, 0.777 mmol) was added dropwise. After stirring at room temperature for 18 h and at 60° C. for 24 h, the reaction was quenched with a saturated aqueous solution of sodium hydrogen carbonate (20 mL), and extraction was performed using dichloromethane (2×50 mL). The combined extract was washed with a saturated aqueous solution of sodium hydrogen carbonate (50 mL) and dried ($MgSO_4$). The solvent was removed under reduced pressure and the residue was purified by chromatography over silica gel with dichloromethane: methanol (98:2) as eluent to give the product 204 (mixture of diastereomers ~1.7:1) as a solid (196 mg, 67%). $^1H$ NMR ($CDCl_3$): δ 7.36-7.14 (m, Bn, H-6), 5.77 (1 H, d, J 7.9 Hz, H-1'), 5.57 (1 H, d, J 5.8 Hz, H-1'), 4.68-4.43 (m, Bn, H-2'), 4.12-3.68 (m, H-5', H-5', H-3'), 3.32 (s, $OCH_3$), 3.24 (s, $OCH_3$), 1.93 (d, J 0.9 Hz, $CH_3$), 1.86 (d, J 1.1 Hz, $CH_3$), 0.14 (s, $Si(CH_3)_3$), 0.12 (s, $Si(CH_3)_3$); $^{13}C$ NMR ($CDCl_3$): δ 163.68, 163.55 (C-4), 151.58, 151.07 (C-2), 137.84, 137.74, 137.32 (Bn), 135.93, 135.10 (C-6), 128.57, 128.42, 128.41, 128.10, 127.95, 127.85, 127.77, 127.74 (Bn), 111.38, 111.01 (C-5), 86.89, 85.61, 85.40, 84.72, 83.40, 83.31, 82.10 (C-1', C-2', C-3', C-4'), 75.20, 73.98, 73.62, 73.59, 72.55, 72.13, 71.04, 70.74 (Bn, C-5', C-5''), 56.82, 56.54 ($OCH_3$), 12.47, 12.38 ($CH_3$), 1.72, 1.69 ($Si(CH_3)_3$); MS FAB: 555 (M+H, 65%), 577 (M+Na, 70%). Found: C, 62.76; H, 6.88; N, 4.94; $C_{29}H_{38}N_2O_7Si$ requires C, 62.79; H, 6.90; N, 5.05%.

EXAMPLE 112

(1R,2S,3S)-2-Benzyloxy-3-benzyloxymethyl-1-(methoxy(6-N-benzoyladenin-9-yl)-methyl)-3-trimethylsilyloxytetrahydrofuran (205). A solution of 202 (240 mg, 0.673 mmol) and 6-N-benzoyladenine (301 mg, 1.26 mmol) in anhydrous acetonitrile (8.2 mL) was added BSA (0.67 mL, 2.7 mmol) and stirred at room temperature for 1 h. The solution was cooled to 0° C. and trimethylsilyl triflate (0.25 mL, 1.33 mmol) was added dropwise. After stirring at 65° C. for 18 h, the reaction was quenched with a saturated aqueous solution of sodium hydrogen carbonate (50 mL), extracted with dichloromethane (2×50 mL). The combined extract was dried ($MgSO_4$). The solvent was removed under reduced pressure and the residue was purified by chromatography over silica gel with dichloromethane:methanol (98:2) as eluent to give the product 205 (mixture of diastereomers ~1.8:1) as a solid (185 mg, 41%). $^1$H NMR ($CDCl_3$): δ 8.78 (s, H-8), 8.21 (s, H-2), 8.17 (s, H-2), 8.03-8.00 (m, Bz), 7.61-7.49 (m, Bz), 7.36-7.23 (m, Bn), 7.07-7.04 (m, Bz), 5.85 (1 H, d, J 7.9 Hz, H-1'), 5.76 (1 H, d, J 6.0 Hz, H-1'), 4.74-4.40 (m, Bn, H-2'), 4.22-3.62 (m, H-5', H-5', H-3'), 3.33 (s, $OCH_3$), 3.24 (s, $OCH_3$), 0.15 (s, $Si(CH_3)_3$), 0.14 (s, $Si(CH_3)_3$); $^{13}$C NMR ($CDCl_3$): δ 164.68 (HNC═O), 153.17, 152.99 (C-6), 149.47 (C-2), 141.82, 141.66 (C-8), 137.74, 137.71, 137.65 (Bn), 133.87, 132.87, 132.78 (Bz), 128.97, 128.93, 128.45, 128.42, 128.38, 128.14, 127.97, 127.88, 127.82, 127.78 (Bn, Bz), 123.66, 122.85 (C-5), 86.41, 86.23, 85.70, 85.24, 84.78, 83.73, 83.58, 82.79 (C-1', C-2', C-3', C-4'), 75.32, 74.55, 73.61, 72.18, 71.98, 70.85, 70.59 (Bn, C-5□, C-5□□), 57.23, 57.04 ($OCH_3$), 1.78 ($Si(CH_3)_3$); MS FAB: 668 (M+H, 50%), 690 (M+Na, 100%). Found: C, 64.07; H, 6.01; N, 9.94; $C_{29}H_{38}N_2O_7Si$,0.5$H_2O$ requires C, 63.88; H, 6.25; N, 10.34%.

EXAMPLE 113

(1R,2R,3R)-2-Benzyloxy-3-benzyloxymethyl-3-hydroxytetrahydrofurfural (206). A solution of 202/203 (252 mg, 0.707 mmol) in 80% acetic acid (3.8 mL) was stirred at 90° C. for 2 h whereupon the solvent was removed by distillation under reduced pressure. The residue was coevaporated in toluene (3×10 mL) to give the product 206 as an oil (242 mg, 100%). $^1$H NMR ($CDCl_3$): δ 9.66 (1 H, d, J 0.8 Hz, H-1), 7.36-7.25 (10 H, m, Bn), 4.68 (1 H, d, J 11.9 Hz, Bn), 4.60-4.39 (5 H, m, Bn, H-2, H-3), 3.98-3.92 (2 H, m, H-5), 3.85 (1 H, d, J 9.3 Hz, H-5'), 3.52 (1 H, d, J 9.2 Hz, H-5'); $^{13}$C NMR ($CDCl_3$): δ 203.64 (C-1), 137.39, 137.19, 128.61, 128.54, 128.29, 128.12, 127.87, 127.83 (Bn), 87.17, 87.05 (C-4, C-2), 80.98 (C-3), 75.00, 73.70, 71.86 (Bn, C-5'), 67.84 (C-5); MS FAB: 707 (2×M+Na, 100%).

EXAMPLE 114

(1S,3S,4R,7S)-3-Acetoxy-7-benzyloxy-1-benzyloxymethyl-2,5-dioxabicyclo[2.2.1]-heptane (207). To a stirred solution of 206 (230 mg, 0.672 mmol) in anhydrous pyridine (2.0 mL) was added acetic anhydride (0.18 mL, 1.91 mmol). The reaction mixture was stirred for 23 h at room temperature, water (0.13 mL) was added, and the solvent was removed by distillation under reduced pressure. The residue was coevaporated in toluene (3×10 mL) and purified by chromatography over silica gel with dichloromethane:methanol (99:1) as eluent to give the product 207 as an clear oil (56.7 mg, 23%); $^1$H NMR ($CDCl_3$): δ 7.38-7.26 (10 H, m, Bn), 6.00 (1 H, s, H-1), 4.68 (1 H, d, J 12.0 Hz, Bn), 4.62 (1 H, d, J 12.2 Hz, Bn), 4.60 (1 H, d, J 12.4 Hz, Bn), 4.56 (1 H, d, J 12.2 Hz, Bn), 4.17 (1 H, s, H-2), 4.14 (1 H, s, H-3), 4.01 (1 H, d, J 7.7 Hz, H-5'), 3.81-3.78 (3 H, m, H-5', H-5), 20.06 (3 H, s, $COCH_3$); $^{13}$C NMR ($CDCl_3$): δ 169.18 (C═O), 137.92, 137.48, 128.52, 128.45, 128.03, 127.77, 127.73, 127.68 (Bn), 95.95 (C-1), 86.49 (C-4), 78.27, 76.58 (C-3, C-2), 73.65 (Bn), 72.26, 71.96 (Bn, C-5'), 65.49 (C-5), 20.98 ($COCH_3$); MS FAB: 407 (M+Na, 55%). Found: C, 68.80; H, 6.11; $C_{22}H_{24}O_6$ requires C, 68.74; H, 6.29%.

EXAMPLE 115

(1S,3S,4R,7S)-3-(6-N-Benzoyladenin-9-yl)-7-benzyloxy-1-benzyloxymethyl-2,5-dioxabicyclo[2.2.1]heptane (208). A solution of furanose 207 (167 mg, 0.434 mmol) and 6-N-benzoyladenine (194 mg, 0.813 mmol) in anhydrous acetonitrile (5.3 mL) was added BSA (0.43 mL, 1.76 mmol) and stirred at room temperature for 1 h. The solution was cooled to 0° C. and trimethylsilyl triflate (0.16 mL, 0.86 mmol) was added dropwise. After stirring at 65° C. for 2 h, the reaction was quenched with a saturated aqueous solution of sodium hydrogen carbonate (40 mL) and the mixture was extracted with dichloromethane (2×50 mL). The combined extract was dried ($MgSO_4$). The solvent was removed under reduced pressure and the residue was purified by chromatography over silica gel with dichloromethane:methanol (98:2) as eluent to give the product 208 as a solid (111 mg, 45%); $^1$H NMR ($CDCl_3$): δ 8.82 (1 H, s, H-8), 8.14 (1 H, s, H-2), 7.59-7.26 (15 H, m, Bz, Bn), 6.74 (1 H, s, H-1'), 4.92 (1 H, s, H-2'), 4.74-4.39 (4 H, m, Bn), 4.42 (1 H, s, H-3'), 4.19-4.10 (2 H, m, H-5''), 3.92 (1 H, d, J 11.8 Hz, H-5'), 3.88 (1 H, d, J 11.5 Hz, H-5'); MS FAB: 564 (M+H, 100%).

EXAMPLE 116

Methyl 2-O-acetyl-3,5-di-O-benzyl-4-C-methanesulfonyloxymethyl-D-ribofuranoside (209). To a stirred solution of 201 (687 mg, 1.52 mmol) in anhydrous pyridine (4 mL) at 0° C. was added dropwise acetic anhydride (0.43 mL, 4.56 mmol). The reaction mixture was stirred for 2 days at room temperature, quenched with saturated aqueous sodium hydrogen carbonate (75 mL) and extracted with dichloromethane (150+75 mL). The combined extract was dried ($MgSO_4$), the solvent was removed by distillation under reduced pressure and the residue was purified by chromatography over silica gel with dichloromethane as eluent to give the product 209 as a clear oil (β:α~3:1, 750 mg, 100%); MS FAB: 463 (M−$OCH_3$, 100%), 517 (M+Na, 28%); Found: C, 58.53; H, 6.16; $C_{24}H_{30}O_9S$ requires C, 58.29; H, 6.11%. Methyl 2-O-acetyl-3,5-di-O-benzyl-4-C-methanesulfonyloxymethyl-β-D-ribofuranoside (209□). $^1$H NMR ($CDCl_3$): δ 7.36-7.18 (10 H, m, Bn), 5.27 (1 H, d, J 4.9 Hz, H-2), 4.88 (1 H, s, H-1), 4.55-4.44 (6 H, m, H-5', Bn), 4.35 (1 H, d, J 5.0 Hz, H-3), 3.73 (1 H, d, J 9.2 Hz, H-5), 3.38 (1 H, d, J 9.3 Hz, H-5), 3.30 (3 H, s, $OCH_3$), 2.95 (3 H, s, $SO_2CH_3$), 2.11 (3 H, s, $OCCH_3$); $^{13}$C NMR ($CDCl_3$): δ 169.91 (C═O), 137.83, 137.28, 128.49, 128.44, 127.99, 127.87, 127.77 (Bn), 105.40 (C-1), 82.65, 81.05, 74.55, 73.62, 73.56, 71.86, 70.22 (C-2, C-3, C-4, C-5, C-5', Bn), 55.03 ($OCH_3$), 37.14 ($SO_2CH_3$), 20.73 ($OCCH_3$). Methyl 2-O-acetyl-3,5-di-O-benzyl-4-C-methanesulfonyloxymethyl-□-D-ribofuranoside (209β). $^1$H NMR ($CDCl_3$): δ 7.36-7.18 (10 H, m, Bn), 5.09 (1 H, d, J 4.5 Hz, H-1), 4.95 (1 H, dd, J 4.5, 6.8 Hz, H-2), 4.65-4.44 (6 H, m, H-5', Bn), 4.27 (1 H, d, J 6.6 Hz, H-3), 3.49 (1 H, d, J 9.9 Hz, H-5), 3.46 (3 H, s, $OCH_3$), 3.36 (1 H, d, J 9.9 Hz, H-5), 2.92 (3 H, s, $SO_2CH_3$), 2.14 (3 H, s, $OCCH_3$); $^{13}$C NMR ($CDCl_3$): δ 170.41 (C═O), 137.59, 137.28, 128.56, 128.51, 128.49, 128.44, 127.98, 127.88 (Bn), 102.35 (C-1), 84.25, 77.53, 74.66, 73.67, 72.12, 70.39, 70.28 (C-2, C-3, C-4, C-5, C-5', Bn), 56.07 ($OCH_3$), 36.94 ($SO_2CH_3$), 20.63 ($OCCH_3$).

EXAMPLE 117

Phenyl 2-O-acetyl-3,5-di-O-benzyl-4-C-methanesulfonyloxymethyl-1-thio-β-D-ribofuranoside (210). Method a. A stirred solution of 209 (738 mg, 1.49 mmol) in anhydrous dichloromethane (6.4 mL) was added phenylthiotrimethylsilane (2.42 mL, 12.8 mmol) and cooled to 0° C. Trimethylsilyl triflate (0.67 mL, 3.67 mmol) was added dropwise and the solution was stirred at room temperature for 4 h. The reaction was quenched with a saturated aqueous solution of sodium hydrogen carbonate (100 mL) and extracted with dichloromethane (2×200 mL). The combined extract was dried ($MgSO_4$) and the solvent removed by distillation under reduced pressure. The residue was purified by chromatography over silica gel with dichloromethane as eluent to give the product 210 as a clear oil (564 mg, 66%) and unreacted starting material (191 mg, 26%); Method b. A stirred solution of 211 (86 mg, 0.165 mmol) in anhydrous dichloromethane (0.49 mL) was added phenylthiotrimethylsilane (0.16 mL, 0.825 mmol) and cooled to 0° C. Trimethylsilyl triflate (0.037 mL, 0.206 mmol) was added and the solution was stirred at room temperature for 2 h. The reaction was quenched with a saturated aqueous solution of sodium hydrogen carbonate (15 mL) and the resulting mixture was extracted with dichloromethane (2×25 mL). The combined extract was dried ($MgSO_4$) and the solvent removed by distillation under reduced pressure. The residue was purified by chromatography over silica gel with dichloromethane as eluent to give the product 210 as a clear oil (75 mg, 79%); $^1$H NMR ($CDCl_3$): δ 7.47-7.19 (15 H, m, Bn, SPh), 5.48 (1 H, d, J 3.6 Hz, H-2), 5.34 (1 H, dd, J 3.7, 5.2 Hz, H-1), 4.54-4.36 (7 H, m, H-3, H-5□, Bn), 3.66 (1 H, d, J 9.7 Hz, H-5), 3.48 (1 H, d, J 9.5 Hz, H-5), 2.89 (3 H, s, $SO_2CH_3$), 2.09 (3 H, s, $OCCH_3$); $^{13}$C NMR ($CDCl_3$): δ 169.93 (C═O), 137.69, 137.08, 132.65, 132.45, 129.15, 128.53, 128.52, 128.18, 128.14, 128.08, 127.91, 127.85 (Bn, SPh), 87.99, 84.35, 80.34, 75.33, 74.20, 73.67, 70.83, 69.34 (C-1, C-2, C-3, C-4, C-5, C-5', Bn), 37.27 ($SO_2CH_3$), 20.68 ($OCCH_3$); MS FAB: 463 (M−SPh, 100%), 595 (M+Na, 24%); Found: C, 61.17; H, 5.55; $C_{29}H_{32}O_8S_2$ requires C, 60.82; H, 5.63%.

EXAMPLE 118

1,2-Di-O-acetyl-3,5-di-O-benzyl-4-C-methanesulphonyloxymethyl-D-ribofuranose (211). A solution of 201 (150 mg; 0.313 mmol) in 80% aqueous acetic acid (1.5 mL) was stirred at 90° C. for 3 h. The solvent was removed by distillation under reduced pressure and the residue was coevaporated in ethanol (3×5 mL), toluene (3×5 mL) and pyridine (2×5 mL). The residue was redissolved in anhydrous pyridine (0.62 mL) and added acetic anhydride (0.47 mL) and the solution was stirred at room temperature for 16 h. The reaction was quenched with water (50 mL) and the resulting mixture extracted with dichloromethane (2×50 mL). The combined extract was washed with an aqueous saturated solution of sodium hydrogen carbonate (50 mL) and dried ($MgSO_4$). The solvent was evaporated and the residue purified on column chromatography over silica gel with dichloromethane as eluent to give the product 211 as an oil (99 mg, 60%); $^1$H NMR ($CDCl_3$): δ 7.39-7.21 (m, Bn), 6.38 (d, J 4.6 Hz, H-1 β), 6.15 (s, H-1 α), 5.35 (d, J 4.9 Hz, H-2 α), 5.17 (dd, J 6.3, 4.9 Hz, H-2 β), 4.69-4.23 (m, H-3, Bn), 3.64 (d, J 9.7 Hz, H-5 α), 3.52 (d, J 10.1 Hz, H-2 β), 3.45 (d, J 9.7 Hz, H-5 α), 3.39 (d, J 9.9 Hz, H-2 β), 2.99 (s, $SO_2CH_3$ α), 2.96 (s, $SO_2CH_3$ β), 2.14, 2.13, 2.06, 1.90 (4×s, $COCH_3$); $^{13}$C NMR ($CDCl_3$): δ 169.68, 169.00 (C═O), 137.68, 137.05, 128.60, 128.55, 128.50, 128.21, 128.12, 128.04, 127.94, 127.82, 127.79 (Bn), 99.35 (C-1 α), 94.24 (C-1 β), 86.36 (C-4 β), 84.28 (C-4 α), 79.15, 77.47, 74.58, 74.06, 73.73, 73.56, 71.67, 70.57, 70.19, 69.84 (Bn, C-2, C-3, C-5, C-5'), 37.61 ($SO_2CH_3$ β), 37.48 ($SO_2CH_3$ α), 21.07, 20.74, 20.63, 20.39 ($COCH_3$); MS FAB: 545 (M+Na, 13%). Found: C, 57.70; H, 5.56; $C_{25}H_{30}O_{10}S$ requires C, 57.46; H, 5.79%.

EXAMPLE 119

(3R)- and (3S)-(1S,4R,7S)-7-Benzyloxy-1-benzyloxymethyl-3-phenylthio-2,5-dioxabicyclo[2.2.1]heptane (212). A solution of 210 (553 mg, 0.966 mmol) in methanol saturated with ammonia (35 mL) was stirred at room temperature for 2 h whereupon the solvent removed by distillation under reduced pressure. The residue was redissolved in anhydrous DMF (3.5 mL) and the solution stirred at 0° C. A 60% suspension of sodium hydride (118 mg, 2.88 mmol) was added and the mixture stirred at room temperature for 12 h. The reaction was quenched with a saturated aqueous solution of sodium hydrogen carbonate (100 mL) and the resulting mixture was extracted with dichloromethane (2×100 mL). The combined extract was dried ($MgSO_4$) and the solvent was removed by distillation under reduced pressure. The residue was purified by chromatography over silica gel with dichloromethane as eluent to give the product 212 as a clear oil (404 mg, 96%). MS FAB: 435 (M+H, 35%), 457 (M+Na, 16%); Found: C, 71.76; H, 6.18; $C_{26}H_{26}O_4S$ requires C, 71.86; H, 6.03%. (1S,3R,4R,7S)-7-Benzyloxy-1-benzyloxymethyl-3-phenylthio-2,5-dioxabicyclo[2.2.1]heptane (212β). $^1$H NMR ($CDCl_3$): δ 7.46-7.26 (15 H, m, Bn, SPh), 5.35 (1 H, s, H-1), 4.68-4.56 (4 H, m, Bn), 4.31 (1 H, s, H-2), 4.10 (1 H, s, H-3), 4.09 (1 H, d, J 7.3 Hz, H-5'), 3.93 (1 H, d, J 7.8 Hz, H-5'), 3.79 (2 H, m, H-5); $^{13}$C NMR ($CDCl_3$): δ 138.03, 137.45, 133.42, 132.36, 129.19, 128.55, 128.46, 128.05, 127.84, 127.83, 127.76 (Bn, SPh), 89.96 (C-1), 87.18 (C-4), 79.71 (C-2), 79.40 (C-3), 73.64 (Bn), 73.23 (C-5'), 72.30 (Bn), 66.31 (C-5). (1S,3S,4R,7S)-7-Benzyloxy-1-benzyloxymethyl-3-phenylthio-2,5-dioxabicyclo[2.2.1]heptane (212α). $^1$H NMR ($CDCl_3$): δ 7.52-7.19 (15 H, m, Bn, SPh), 5.52 (1 H, s, H-1), 4.70-4.50 (4 H, m, Bn), 4.41 (1 H, s, H-2), 4.18 (1 H, d, J 7.8 Hz, H-5'), 4.08 (1 H, d, J 8.4 Hz, H-5'), 4.07 (1 H, s, H-3), 3.78 (1 H, d, J 11.3 Hz, H-5), 3.72 (1 H, d, J 11.5 Hz, H-5); $^{13}$C NMR ($CDCl_3$): δ 137.89, 137.46, 135.29, 130.93, 129.13, 128.99, 128.57, 128.48, 127.81, 127.76, 127.58, 126.95 (Bn, SPh), 91.87 (C-1), 88.59 (C-4), 80.07, 79.14 (C-2, C-3), 73.65, 73.40, 72.04 (Bn, C-5'), 65.62 (C-5).

EXAMPLE 120

(3R)- and (3S)-(1S,4R,7S)-7-Benzyloxy-1-benzyloxymethyl-3-(thymin-1-yl)-2,5-dioxabicyclo[2.2.1]heptane (36+213). Thymine (175 mg, 1.38 mmol) was stirred in hexamethyldisilazane (6.8 mL) at reflux and ammonium sulphate (5 mg) was added. After stirring for 16 h, the clear solution was cooled to 40° C. and the solvent was removed by distillation under reduced pressure. To the residue was added a solution of 212 (201 mg, 0.463 mmol) in anhydrous dichloromethane (4.6 mL) and 4 Å molecular sieves (180 mg). After stirring at room temperature for 10 min, NBS (107 mg, 0.602 mmol) was added and the mixture stirred for another 30 min. The reaction was quenched with a saturated aqueous solution of sodium thiosulphate (25 mL) and the resulting mixture was extracted with dichloromethane (2×50 mL). The combined extract was dried ($MgSO_4$) and evaporated, and the residue was purified on column chromatography over silica gel with dichloromethane:methanol (97:3) as eluent to give the product 36+213 and as an anomeric mixture (β:α~1:2) (127 mg, 61%); $^1$H NMR ($CDCl_3$): δ 7.49 (d, J 0.9 Hz, H-6 β), 7.46 (d, J 1.0 Hz, H-6 α), 7.39-7.25 (m, Bn), 5.94 (s, H-1' α), 5.64 (s, H-1' β), 4.71-4.50 (m, Bn, H-2'), 4.23 (s, H-3' α), 4.16 (d, J 8.6 Hz, H-5" α), 4.09-3.78 (m, H-5', H-5", H-3' β), 1.94 (d, J 0.9 Hz, $CH_3$ α), 1.62 (d, J 1.2 Hz, $CH_3$ β); MS FAB: 551 (M+H, 96%).

EXAMPLE 121

(3R)- and (3S)-(1S,4R,7S)-7-Hydroxy-1-hydroxymethyl-3-(thymin-1-yl)-2,5-dioxabicyclo[2.2.1]heptane (37+214).

A solution of 36+213 (175 mg, 0.39 mmol) in ethanol (2.7 mL) was stirred at room temperature and 20% palladium hydroxide over carbon (50 mg) was added. The mixture was degassed several times with argon and placed under a hydrogen atmosphere. After stirring for 18 h, the mixture was purified on column chromatography over silica gel with dichloromethane:methanol (95:5) as eluent to give a mixture of 37 and 214 (1:1.2) (26 mg, 25%); $^1H$ NMR ($CD_3OD$): δ 7.78 (d, J 1.3 Hz, H-6 α), 7.73 (d, J 1.2 Hz, H-6 β), 5.88 (s, H-1' α), 5.53 (s, H-1' β), 4.38 (s, H-2' α), 4.34 (s, H-3' α 4.26 (s, H-2' β), 4.08-3.69 (m, H-5', H-5", H-3' β), 1.92 (d, J 1.2 Hz, $CH_3$ α), 1.88 (d, J 1.1 Hz, $CH_3$ β); $^{13}C$ NMR ($CD_3OD$): δ 138.00 (C-6 α), 136.96 (C-6 β), 110.80 (C-5 β), 110.08 (C-5 α), 92.49, 89.01 (C-4', C-1' α), 90.46, 88.37 (C-4', C-1' β), 80.89, 74.27, 73.34 (C-2', C-3', C-5' α), 80.59, 72.47, 70.39 (C-2', C-3', C-5' β), 59.29 (C-5" α), 57.61 (C-5" β), 12.52 ($CH_3$ α), 12.39 ($CH_3$ β); MS EI: 270 ($M^{+\cdot}$ 100%).

Preparation of LNA Phosphoramidites

EXAMPLE 122

4-N-Benzoyl-LNA-C[(1R,3R,4R,7S)-3-(4-N-benzoylcytosine-1-yl)-1-(hydroxymethyl)-7-hydroxy-2,5-dioxabicyclo{2.2.1}heptane]. LNA-C (formula Z) was taken in absolute ethanol and heated at reflux. To the refluxing solution, benzoic anhydride (2 equivalents) was added and the reaction was followed by HPLC (Eluant: 20% acetonitrile in 0.1 M TEAA, pH 7.0, flow rate: 1 ml/min., Novapak C-18 analytical column). Additional anhydride was added at 0.5-2 h intervals till no more increase in product was observed by HPLC. Reaction mixture was concentrated on rotavap. Residue was repeatedly washed with ether, filtered and dried to give an off white solid. Yield: 45%.

General method for dimethoxytritylation of base protected LNA nucleosides (LNA-$C^{BZ}$, LNA-T, LNA-$G^{iBu}$, LNA-$A^{Bz}$). Base protected LNA-nucleoside was coevaporated with pyridine (2×) and was stirred with dimethoxytrityl chloride (1.5 equivalents) in pyridine (~10 ml/g of nucleoside). The reaction was followed by HPLC (50% acetonitrile in 0.1M TEAA, pH 7.0, for 5 min., 50-100% acetonitrile in 10 min. and 100% acetonitrile for 5 min., flow rate: 1 ml/min., Novapak C-18 column). When >95% of the starting material had reacted, reaction mixture was cooled in ice. Reaction was quenched by addition of cold saturated $NaHCO_3$ (~15 ml×vol. of pyridine). The mixture was extracted with dichloromethane (3× half the vol. of sodium bicarbonate). Organic extractions were combined, dried over anhydrous sodium sulfate, filtered and concentrated on rotavap. Residue was dried in vacuo and purified by silica gel chromatography using 0.5% pyridine and 0-2% methanol in dichloromethane as eluant. Fractions containing pure products were combined and concentrated on rotavap. Residue was coevaporated with anhydrous acetonitrile (3×) and dried in vacuo.

General method for phosphitylation of protected LNA nucleosides. Base protected dimethoxytrityl-LNA nucleoside was coevaporated with anhydrous dichloromethane (2×) and was taken in anhydrous dichloromethane (10 ml/g of nucleoside for A, G &T and ~30 ml/g for C). To this bis (diisopropylamino)(2-cyanoethyl)phosphite (1.05-1.10 equivalent), followed by tetrazole (0.95 equivalent) were added. Mixture was stirred at room temperature and reaction was followed by HPLC (70% acetonitrile in 0.1M TEAA, pH 7, 2 min., 70-100% acetonitrile in 8 min., and 100% acetonitrile in 5 min., flow rate: 1 ml/min., Novapak C-18 column). Once the reaction had proceeded to >90% and no more increase in amidite formation was observed upon further stirring, the mixture was cooled in ice. It was diluted with dichloromethane (~15-20 times the original volume) and washed with cold saturated sodium bicarbonate (2×) followed by cold brine (1×). Organic layer was dried over anhydrous sodium sulfate, filtered and concentrated on rotavap. Residue was coevaporated with anhydrous acetonitrile (3×) and dried in vacuo overnight. HPLC purity ranged from 93-98%.

Preparation of LNA nucleoside 5'-triphosphates

EXAMPLE 123

Synthesis of LNA nucleoside 5'-triphosphates. (*Tetrahedron Letters* 1988, 29 4525). In a 13×100 mm polypropylene tube, nucleosides 37, 44, 51, 4-N-benzoylated 57A or 61B (93.8 μmol) was suspended in 1 mL pyridine (dried by $CaH_2$). The solution was evaporated in a speedvac, under high vacuum, to dryness. The residue was twice resuspended in acetonitrile (dried by $CaH_2$) and evaporated to dryness. The nucleoside was suspended in 313 μL trimethyl phosphate (dried by 4 Å molecular sieves), to which 30.1 mg Proton Sponge™ (1.5 equivalents) were added. The mixture was sealed, vortexed, and cooled to 0° C. $POCl_3$ (9.8 μL, 1.1 equivalent) was added with vortexing. The reaction was allowed to proceed at 0° C. for 2.5 hours. During this interval, 469 μmols sodium pyrophosphate (5 equivalents) were dissolved in 5 mL water and passed through 5 mL Dow $50H^+$ ion exchange resin. When the effluent turned acidic, it was collected in 220 μL tributylamine and evaporated to a syrup. The TBA pyrophosphate was coevaporated three times with dry acetonitrile. Finally, the dried pyrophosphate was dissolved in 1.3 mL DMF (4 Å sieves). After 2.5 hours reaction time, the TBA pyrophosphate and 130 μL tributylamine were added to the nucleoside solution with vigorous vortexing. After 1 minute, the reaction was quenched by adding 3 mL 0.1 M triethylammonium acetate, pH 7.5. Assay by Mono Q chromatography showed 49% nucleoside 5'-triphosphate. The reaction mixture was diluted to 100 mL with water and adsorbed onto a Q Sepharose ion exchange column, washed with water, and eluted with a linear gradient of 0 to 700 mM NaCl in 5 mM sodium phosphate, pH 7.5. Fractions containing triphosphate were assayed by Mono Q ion exchange chromatography. Fractions containing triphosphate were pooled and concentrated to the point of NaCl saturation. The product was desalted on a $C_{18}$ cartridge. The triphosphate was quantitated by UV spectroscopy and adjusted to 10 mM solution. Yields were 17-44%. LNA nucleosides prepared by this method were, U, T, A, G, and C.

Preparation of LNA Modified Oligonucleotides

EXAMPLE 124

Synthesis of oligonucleotides containing LNAs of formula V, X, Y and $Z^T$, $Z^U$, $Z^G$, $Z^C$, $Z^A$, $Z^{MeC}$. The bicyclic nucleoside 3'-O-phosphoramidite analogues 8, 19, 30, 39, 46, 53, 57D, 61D, and 66 as well as commercial 3'-O-phosphoramidites were used to synthesise example LNA oligonucleotides of the invention (0.2 to 5 μmol scale) containing one or more of the LNAs of types V, X, Y and $Z^T$, $Z^U$, $Z^G$, $Z^C$, $Z^A$, and $Z^{MeC}$. The purity and composition of the synthesised LNA oligonucleotides was verified by capillary gel electrophoresis, and/or HPLC and/or MALDI-MS. In general, satisfactory coupling efficiencies were obtained for all the monomers. The best coupling efficiencies (~95-100%) were obtained for LNAs 39, 46, 53, 57D, 61D, and 66 (leading to LNA monomers of formula Z) giving very satisfactory results when synthesising fully modified LNA oligonucleotides or when incorporating LNAs in otherwise unmodified DNA or RNA stands or LNAs into an all-phosphorothioate oligonucleotide. LNA oligonucleotides were dissolved in pure water and the concentration determined as $OD_{260}$. Solubilities in all cases were excellent. For plain DNA/RNA synthesis and partially modified LNA oligomers, a standard CPG support or a polystyrene support, was used. For the synthesis of fully modified LNA oligomers (e.g. 5'-d(GTGATATGC)-3'), a BioGenex Universial CPG Support (BioGenex, U.S.A.) was used, or LNA derivatised supports were used.)

EXAMPLE 125

Synthesis of phosphorothioate LNA oligonucleotides. The all-phosphorothioate LNA (Table 7) was synthesised on an automated DNA synthesiser using similar conditions as those described earlier (Example 124). Beaucages' reagent was used as sulphurising agent. The stepwise coupling yields were >98%. After completion of the syntheses, deprotection and cleavage from the solid support was effected using concentrated ammonia (55° C., 14 h).

EXAMPLE 126

Synthesis of 2'-Thio-LNA oligonucleotides. The 2'-thio-LNA oligonucleotides (containing monomer $U^S$ (formula Z (thio-variant) of FIG. 2), FIG. 37, Table 8) were synthesised on an automated DNA synthesiser using standard conditions (Example 124). The step-wise coupling yield for amidite 76F was approximately 85% (12 min couplings; improved purity of amidite 76F is expected to result in increased coupling yield). After completion of the syntheses, deprotection and cleavage from the solid support was effected using concentrated ammonia (55° C., 8 h).

EXAMPLE 127

Synthesis of 2'-Amino-LNA oligonucleotides. By procedures similar to those described in Example 126, 2'-Amino-LNA oligonucleotides (containing monomer $T^{NH}$ and monomer $T_{NMe}$ (formula Z (amino variants) of FIG. 2), FIGS. 35 and 36) was efficiently obtained on an automated DNA synthesiser using amidites 74A and 74F (≧98% stepwise coupling yields).

EXAMPLE 128

Fluorescein-labeling of LNA oligomers. LNA oligomers (formula Z of FIG. 2) AL16 (5'-d(TGTGTGAAATTGTTAT)-3' (SEQ ID NO:1); LNA nucleotides in bold) and AL17 (5'-d(ATAAAGTGTAAAG)-3' (SEQ ID NO:2); LNA nucleotides in bold) were successfully labeled with fluorescein using the FluoroAmp T4 Kinase Green Oligonucleotide Labeling System as described by the manufacturer (Promega). Briefly, 16 nmol of either LNA-oligomer AL16 or AL17 was 5'-thiophosphate labelled in a 50 μl reaction buffer containing T4 kinase and γ-S-ATP. The reactions were incubated for 2 h at 37° C. The thiophosphorylated LNA oligos were precipitated by the addition of 5 μl of oligonucleotide precipitant (Promega) and 165 μl of ice cold (−20° C.) 95% ethanol. After centrifugation the pellets were washed once with 500 μl of ice cold (−20° C.) 70% ethanol and redissolved in 25 μl of PBSE buffer. Freshly prepared 5-maleimide-fluorescein solution (50 μg in 5 μl DMSO) were added to the thiophosphorylated LNA oligos and the reaction mixtures incubated at 68° C. for 30 min. Additional 5-maleimide-fluorescein (50 μg in 5 μl DMSO) were added to each LNA oligo and the reaction mixtures incubated for an additional 60 min. After incubation 10 μl of oligonucleotide precipitant was added to each reaction mixture followed by 180 μl ice-cold (−20° C.) and 100 μl N,N-dimethylformamide. The fluorescein labeled LNA oligos were isolated by centrifugation followed by aspiration of the supernatant. The fluorescein labelled LNA-oligomers were purified by reversed-phase HPLC as follows: column Delta-Pack C-18, 300 A, 0.4×30 cm; eluent 0-50% acetonitrile in 0.04 M triethylammonium buffer (pH 7.0); flow rate 1.5 ml/min. The fractions containing LNA-oligos were pooled and evaporated under reduced pressure (oil pump and speed-vac system) during 12 h.

Hybridisation Data

EXAMPLE 129

Figure 2:
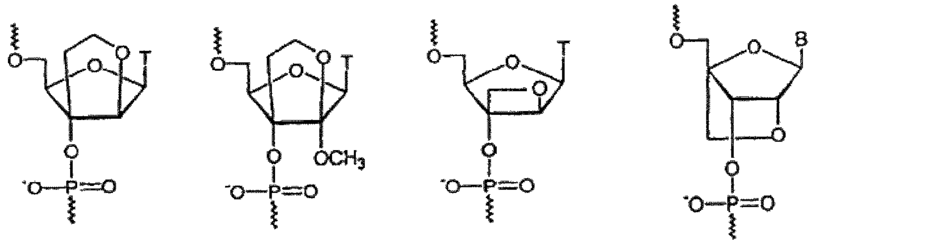
FIG. 2 illustrates nucleotide/nucleoside analogues of the invention.

Thermostability of oligonucleotides containing monomers of formula V, X, Y and $Z^T$, $Z^U$, $Z^G$, $Z^C$, $Z^A$, $Z^{MeC}$. The thermostability of the LNA modified oligonucleotides were determined spectrophotometrically using a spectrophotometer equipped with a thermoregulated Peltier element. Hybridisation mixtures of 1 ml were prepared containing either of 3 different buffers (10 mM $Na_2HPO_4$, pH 7.0, 100 mM NaCl, 0.1 mM EDTA; 10 mM $Na_2HPO_4$ pH 7.0, 0.1 mM EDTA; 3M tetramethylammoniumchlorid (TMAC), 10 mM $Na_2HPO_4$, pH 7.0, 0.1 mM EDTA) and equimolar (1 μM or 1.5 μM) amounts of the different LNA modified oligonucleotides and their complementary or mismatched DNA or RNA oligonucleotides. Identical hybridisation mixtures using the unmodified oligonucleotides were prepared as references. The $T_m$'s were obtained as the first derivative of the melting curves. Tables 1-4 summarise the results (LNAs are marked with bold). FIG. 2 illustrates the monomeric LNAs used. The nomenclature V, X, Y and $Z^T$, $Z^U$, $Z^G$, $Z^C$, $Z^A$, $Z^{MeC}$ refer to structures V, X, Y and Z of FIG. 2. In the tables, the nucleobases of the LNA monomers are indicated. Furthermore, for the thio and amino variants of the LNA structure Z of the last two tables, the nomenclature used is, e.g., $Z^{TS}$ and $Z^{TNH}$, respectively.

LNAs containing structure Z were particularly thoroughly examined (see Table 1). When three $Z^T$ residues were incorporated into an oligonucleotide of mixed sequence the $T_m$'s obtained in NaCl buffer with both complementary DNA (10) and RNA (16) oligonucleotides were substantially higher (RNA: roughly 7° C. and DNA: roughly 5° C. per modification) than the $T_m$ of the corresponding duplexes with unmodified oligonucleotides (1 and 8). Similar results were obtained with LNAs containing two $Z^T$ residues and either one $Z^G$ (21 and 24B) or $Z^U$ (25), $Z^C$ (69), $Z^{MeC}$ (65), and $Z^A$ (58) residues. When mismatches were introduced into the target RNA or DNA oligonucleotides the $T_m$ of the LNA modified oligonucleotides in all cases dropped significantly (11-15A and 17; 18-20 and 22-24A; 26-31; 57 and 59-60; 63-64 and 66, and 67), unambiguously demonstrating that the LNA modified oligonucleotides hybridise to their target sequences obeying the Watson-Crick hydrogen bonding rules. In all cases the drop in $T_m$ of the LNA modified oligonucleotides upon introduction of mismatches was equal to or greater than that of the corresponding unmodified oligonucleotides (2-7 and 9; 33-38), showing that the LNA modified oligonucleotide are at least as specific as their natural counterparts. A lowering of the ionic strength of the hybridisation buffer (from 10 mM $Na_2HPO_4$, pH 7.0, 100 mM NaCl, 0.1 mM EDTA to 10 mM $Na_2HPO_4$ pH 7.0, 0.1 mM EDTA) lowers the $T_m$ of the LNA modified oligonucleotides for their complementary DNA oligos (40,41) or RNA oligonucleotides (40A, 41A). A similar effect is observed with the unmodified oligonucleotides and its complementary DNA oligo (39) or RNA oligo (39A).

Addition of 3M tetramethylammoniumchlorid (TMAC) to the hybridisation buffer significantly increases the $T_m$ of the LNA modified oligonucleotide for their complementary DNA oligos (10,21,25). Moreover, TMAC levels out the differences in the $T_m$'s of the different oligonucleotides which is observed in the NaCl buffer (lowest $T_m$ in the NaCl buffer 44° C. and highest 49° C. as opposed to 56° C. and 57° C. in TMAC). Introduction of mismatches substantially decreases the $T_m$ of the LNA modified oligonucleotides for their DNA targets (11-13, 18-20, and 26-28). A similar picture emerges with the unmodified reference oligonucleotides (1-4 and 32-35)

The data with the low salt buffer shows that LNA modified oligonucleotides exhibit a sensitivity to the ionic strength of the hybridisation buffer similar to normal oligonucleotides. From the $T_m$ data with the TMAC buffer we infer that TMAC exhibits a $T_m$ equalising effect on LNA modified oligonucleotides similar to the effect observed with normal DNA oligonucleotides. LNA modified oligonucleotides retain their exquisite specificity in both hybridisation buffers.

The fully modified LNA oligonucleotide containing all four monomers (71 and 75), the almost fully modified LNA oligonucleotide (except for a 3'-terminal DNA nucleoside) containing both $Z^G$ and $Z^T$ (41 and 41A) and the partly modified oligonucleotide containing a central block of $Z^T$ and $Z^G$ (40 and 40A) also exhibit substantially increased affinity compared to the unmodified control oligonucleotide (39 and 39A; 1 and 8). This shows that LNAs of formula Z are very useful in the production of both fully and partly modified oligomers. We note that the almost fully modified oligomer (41 and 41A) exhibits an unprecedented high affinity for both complementory RNA (>93° C.) and DNA (83° C.). A similar extreme affinity (for both RNA and DNA) was observed with the almost fully modified LNA oligomer containing exclusively $Z^T$ (Table 1: 52 and 53) and the fully modified LNA oligomer (71 and 75). The affinity of the partly modified poly-T oligonucleotide depended on the positions and the number of $Z^T$ monomers incorporated (44-51). Whereas the $T_m$'s with RNA targets (45, 47, 49 and 51) in all cases were higher than the corresponding unmodified oligonucleotides (43) one gave a lower $T_m$ with the DNA target (46). Since mixed sequence oligonucleotide containing 3 $Z^T$ residues exhibited a substantially increased affinity for their DNA (10) and RNA target (16) compared to the unmodified reference oligonucleotides (1 and 8) this suggests that other binding motifs than Watson-Crick (such as for example the Hoogsteen binding motif) are open to poly-T oligonucleotides and that these binding motifs are somewhat sensitive to the precise architecture of the modified oligonucleotide. In all cases introduction of single base mismatches into the complex between the fully $Z^T$ modified poly-T oligonucleotide and a DNA target (54-56) resulted in a significant drop in $T_m$.

Oligonucleotides containing either LNAs of structures V (Table 2), X (Table 3) and Y (Table 4) were analysed in the context of fully and partly modified poly-T sequences. The fully modified oligonucleotides of structure V and Y exhibited an increase in $T_m$ (albeit much lower than the $Z^T$ modified oligonucleotides) with both RNA (Table 2, 14 and Table 4, 14) and DNA targets (Table 2, 13, and Table 4, 13) compared to the unmodified oligonucleotides (Table 1, 42 and 43). The partly modified oligonucleotides containing monomers of structure V and Y behaved similarly to partly modified oligonucleotides containing $Z^T$ and probably this is due to the homopolymer nature of the sequence as outlined above. Oligonucleotides containing $X^T$ in all cases exhibited a much reduced $T_m$ compared to the reference DNA oligonucleotides.

EXAMPLE 130

A fully modified LNA oligonucleotide form stable hybrids with complementary DNA in both the anti-parallel and the parallel orientation. A full modified LNA oligonucleotide was hybridised to its complementary DNA in both the anti-parallel and the parallel orientation. Hybridisation solutions (1 mL) contained 10 mM $Na_2HPO_4$ (pH 7), 100 mM NaCl and 0.1 mM EDTA and 1 μM of each of the two oligonucleotides. As shown in Table 1 both the anti-parallel (71) and the parallel binding orientation (77) produces stable duplexes. The anti-parallel is clearly the most stable of the two. However, even the parallel duplex is significantly more stable than the corresponding anti-parallel duplex of the unmodified DNA oligonucleotides (Table 1, 1).

EXAMPLE 131

LNA monomers can be used to increase the affinity of RNA oligomers for their complementary nucleic acids. The thermostability of complexes between a 9-mer RNA oligonucleotide containing 3 LNA-T monomers ($Z^T$) and the complementary DNA or RNA oligonucleotides were measured spectrophotometrically. Hybridisation solutions (1 ml) containing 10 mM $Na_2HPO_4$, pH 7.0, 100 mM NaCl, 0.1 mM EDTA and 1 μM of each of the two oligonucleotides. Identical hybridisation mixtures using the unmodified RNA oligonucleotides were measured as references. As shown in Table 5 the LNA modified RNA oligonucleotide hybridises to both its complementary DNA (1) and RNA (3) oligonucleotide. As previously observed for LNA modified DNA oligonucleotides, the binding affinity of the LNA modified RNA oligonucleotide is strongest to the RNA complement (3). In both cases the affinity of the LNA modified RNA oligonucleotide is substantially higher than that of the unmodified controls (2 and 4). Table 5 also shows that the specificity towards both DNA and RNA targets are retained in LNA modified RNA oligonucleotides.

EXAMPLE 132

LNA-LNA base pairing. RNA or DNA oligonucleotides containing three $Z^T$ LNA monomers or an oligonucleotide composed entirely of LNA Z monomers were hybridised to complementary unmodified DNA oligonucleotides or DNA oligonucleotides containing three $Z^A$ LNA monomers and the $T_m$ of the hybrids were measured spectrophotometrically. Hybridisation solutions (1 ml) contained 10 mM $Na_2HPO_4$, pH 7.0, 100 mM NaCl and 0.1 mM EDTA and 1 μM of each of the two oligonucleotides. As shown in Table 6 all the LNA modified oligonucleotides hybridises to the complementary, unmodified DNA oligonucleotides (2 and 3) as well as the complementary LNA modified oligonucleotides (4, 5 and 6). As observed previously the presence of LNA monomers in one strand of a hybrid (2 and 3) increases the $T_M$ significantly compared to the unmodified control hybrid (1). The presence of LNA-LNA base pairs in the hybrid increases the $T_M$ even further (4 and 5) Moreover, a highly stable hybrid can be formed between a fully modified LNA oligonucleotide and a partly LNA-$Z^A$ modified DNA oligonucleotide (6). This constitutes the first example of LNA-LNA base pairs in a hybrid.

EXAMPLE 133

An LNA all-phosphoromonothioate oligonucleotide display relatively less decreased thermostability towards complementary DNA and RNA than the corresponsing all-phosphorothioate DNA oligonucleotide. The thermostability of an all-phosphoromonothioate DNA oligonucleotide containing three $Z^T$ LNA monomers (LNA oligonucleotide) and the corresponding all-phosphoromonothioate reference DNA oligonucleotide towards complementary DNA and RNA was evaluated under the same conditions as described in Example 132, however without EDTA (Table 7). It was observed that the LNA all-phosphoromonothioate oligonucleotide containing three LNA $Z^T$ monomers displayed only weakly decreased thermostability (Table 7, 3 and 4) when compared to the corresponding reference LNA oligonucleotide (Table 1, 10 and 16). The corresponding all-phosphoromonothioate DNA oligonucleotide (Table 7, 1 and 2) displayed significantly decreased thermostability when compared to the corresponding reference DNA oligonucleotide (Table 1, 1 and 8). This has important possible implications on the use of all- or partially phosphoromonothioate LNA oligonucleotides in antisense and other therapeutic applications. Thus, the compatibility of LNA monomers and unmodified monomers in an phosphoromonothioate oligonucleotide has been demonstrated. It can be anticipated that such constructs will display both Rnase H activity and nuclease resistance in addition to the LNA enhanced hybridisation characteristics.

EXAMPLE 134

2'-Thio-LNA display nucleic acid recognition properties comparable with those of LNA (Monomer Z). The hybridisation conditions were as described in Example 132, however without EDTA. The results for the 2'-thio-LNAs (Table 8) clearly indicate a positive effect on the thermal stability of duplexes towards both DNA and RNA by the introduction of 2'-thio-LNA monomer $U^S$ (The monomers correspond to formula Z of FIG. 2 where the methyleneoxy bridge has been substituted with a methylenethio bridge). This effect ($\Delta T_m$~+5° C./modification towards DNA; $\Delta T_m$~+8° C./modification towards RNA) is comparable with that observed for parent LNA. The picture is complicated by the simultaneous introduction of two modifications (the 2'-thio functionality and uracil instead of thymine). However, as we have earlier observed identical melting temperatures for the LNA thymine and uracil monomers, and as the references containing 2'-deoxyuridine instead of thymidine, if anything, would be expected to display lower $T_m$ values, the comparison is relevant.

EXAMPLE 135

2'-Amino-LNA (Monomer $Z^{TNH}$) and 2'-Methylamino-LNA (Monomer $Z^{TNMe}$) display nucleic acid recognition properties comparable with those of parent LNA (Monomer Z). The hybridisation conditions were as described in Example 132, however without EDTA. The melting results for the 2'-amino-LNAs (Table 9) clearly indicate a positive effect on the thermal stability of duplexes towards DNA and RNA by introduction of either 2'-amino-LNA monomers $T^{NH}$ or $T^{NMe}$ (The monomers correspond to formula Z of FIG. 2 where the methyleneoxy bridge has been substituted with a methyleneamino bridge or methylene-(N-methyl)amino bridge, respectively). This effect ($\Delta T_m$~+3° C./modification towards DNA and $\Delta T_m$~+6 to +8° C./modification towards RNA) is comparable to that of parent LNA. It is noteworthy, that the increased thermal affinity is also observed with an oligo composed of a mixture of 2'-alkylamino-LNA monomers and nonalkylated 2'-amino-LNA monomers.

LNA and LNA Modified Oligonucleotides as a Substrates for Enzymes

EXAMPLE 136

3'-Exonucleolytic stability of oligomers 5'-$V^T{}_{13}$T and 5'-$Z^T{}_{13}$T. A solution of oligonucleotides (0.2 OD) in 2 ml of the following buffer (0.1 M Tris-HCl, pH 8.6, 0.1 M NaCl, 14 mM $MgCl_2$) was digested at 25° C. with 1.2 U SVPDE (snake venom phosphodiesterase). During digestion, the increase in absorbance at 260 nm was followed. Whereas the unmodified control $T_{14}$ was fully degraded after 10 min of degradation, 5-$Z^T{}_{13}$T and 5'-$V^T{}_{13}$T remained intact for 60 min.

EXAMPLE 137

Figure 6:
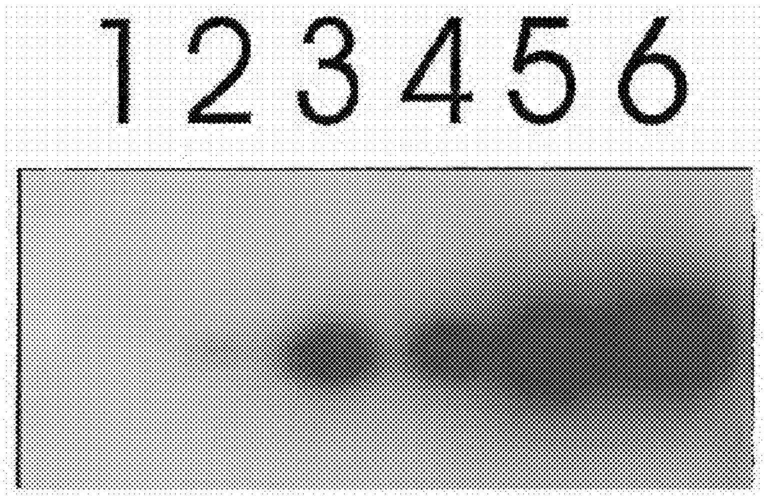
FIG. 6 illustrates that LNA modified oligonucleotides can act as substrates for T4 polynucleotide kinase.

LNA modified oligos as substrates for T4 polynucleotide kinase. 20 pmoles of each primer (FP2: 5'-GGTG-GTTTGTTTG-3' (SEQ ID NO:3); DNA probe), (AL2: 5'-GGTGGTTTGTTTG-3' (SEQ ID NO:4), LNA nucleosides in bold) and (AL3: 5'-GGTGGTTTGTTTG-3' (SEQ ID NO:5), LNA nucleosides in bold) was mixed with T4 polynucleotide Kinase (5 Units; New England Biolabs) and 6 µl $\gamma^{32P}$ ATP (3000 Ci/mmol, Amersham) in a buffer containing 70 mM Tris-HCl (pH 7.6), 10 mM $MgCl_2$, 5 mM dithiotretiol (final volume 20 µl). The samples were incubated 40 min at 37° C. and afterwards heated to 65° C. for 5 min. To each of the reactions were added 2 µl of tRNA (1 µg/µl), 29 µl of a 3M ammonium acetate and 100 µl of ethanol. The reactions were incubated at −20° C. for 30 min. and the labelled oligos were precipitated by centrifugation at 15000 g for 30 min. The pellet was resuspended in 20 µl $H_2O$. The samples (1 µl) were mixed with a loading buffer (formamide (pH 8.0), 0.1% xylene cyanol FF, 0.1% bromophenol blue and 10 mM EDTA) and electrophoresed on a denaturing polyacrylamide gel (16% acrylamide/bisacrylamide solution, 7 M urea, 1×TBE and 0.1 mM EDTA) in a TBE running buffer (90 mM Tris-HCl (pH 8.3), 90 mM boric acid and 2.5 mM disodium EDTA-2 $H_2O$). The gel was dried on a gel dryer (BioRad model 583) and autoradiographed to a X-ray film (CL-XPosure film, Pierce 34075) for 20 min. The result is shown in FIG. 6 (FP2: lane 1 and 2; AL2: lane 3 and 4; AL3: lane 5 and 6). Three conclusions can be drawn on the basis of this experiment. Firstly, it can be concluded that partly and fully LNA modified oligos are excellent mimics of natural nucleic acid in their ability to act as substrate for a nucleic acid specific enzyme like polynucleotide kinase. Secondly, it can be concluded that LNA modified oligos can be efficiently precipitated by procedures normally employed to precipitate standard nucleic acids. In fact, the relative signal intencities of the unmodified (lane 1,2), partly (lane 3,4) and fully modified oligos (lane 5,6) in the autoradiogram suggests that the more LNA nucleosides a standard DNA oligo contains the more efficiently it can be precipitated by salt/alcohol procedures. Thirdly, the similar positions of the signal in the autoradiogram of the unmodified, partly and fully modified oligos shows that incorporation of LNA nucleosides into a DNA oligo does not alter its electrophoretic mobility in polyacrylamide gels.

EXAMPLE 138

3'-End labelling of LNA-containing oligonucleotides with terminal deoxynucleotidyl transferase. Oligonucleotides containing LNA monomers were 3' end-labelled using the enzyme terminal deoxynucleotidyl transferase. The sequence and extent of LNA modification were as follows (where LNA monomers are in bold):

Control 5' GGT GGT TTG TTT G 3' (SEQ ID NO: 6)

(1) 5' GGT GGT TTG TTT G 3' (SEQ ID NO: 7)

(2) 5' GGT GGT TTG TTT G 3' (SEQ ID NO: 8)

(3) 5' GGT GGT TTG TTT G 3' (SEQ ID NO: 9)

Oligonucleotide (50 pmol) was incubated with 250 μCi [α-$^{32}$P]ddATP (3000 Ci/mmol) and 100 Units terminal deoxynucleotidyl transferase in 250 μl 100 mM cacodylate buffer pH 7.2, 2 mM $CoCl_2$ and 0.2 mM 2-mercaptoethanol at 37° C. for 2 hours. The reaction was then stopped by adding formamide loading buffer and heating to 100° C. for 5 min before placing on ice. Samples (0.2 pmol) were run on a 19% acrylamide gel containing 7M urea and the percentage incorporation of radioactivity into the oligonucleotide bands was quantified by means of a phosphorimager (Molecular Dynamics). The results show incorporation of radioactivity in all cases, including the oligonucleotide with a high LNA content: Control 94.9%, (1) 39.7%, (2) 83.7%, (3) 31.7%. We conclude that LNA modified oligos are substrates for the TdT enzyme.

EXAMPLE 139

The ability of terminal deoxynucleotidyl transferase (TdT) to tail LNA modified oligonucleotides depends on the design of the oligomer. The following 15mer primers and a mixture of 8 to 32 base oligonucleotide markers were 5' end labelled with [γ$^{33}$P] ATP and T4 polynucleotide kinase (where LNA monomers are in bold):

P1 5'-TGC ATG TGC TGG AGA-3' (SEQ ID NO: 10)

P2 5'-GC ATG TGC TGG AGA T-3' (SEQ ID NO: 11)

PZ1 5'-TGC ATG TGC TGG AGA-3' (SEQ ID NO: 12)

PZ2 5'-GC ATG TGC TGG AGA T-3' (SEQ ID NO: 13)

Figure 22:
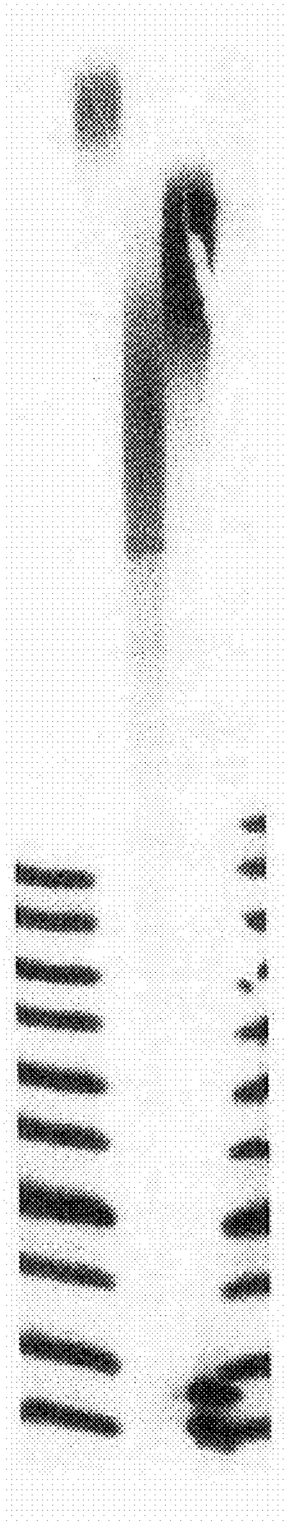
FIG. 22 illustrates the ability of terminal deoxynucleotidyl transferase (TdT) to tail LNA modified oligonucleotides.

Reactions were boiled for 5 min after labelling to remove any PNK activity. Four picomoles of each labelled primer, 25 U terminal deoxynucleotidyl transferase and 16 μM dATP were incubated in 25 μl 100 mM cacodylate buffer pH 7.2, 2 mM $CoCl_2$ and 0.2 mM 2-mercapto-ethanol for 90 min at 37° C. The reactions were stopped by the addition of formamide stop solution and the reaction products run on a 19% polyacrylamide 7 M urea gel with the labelled markers. Autoradiography using Biomax film was carried out on the dry gel. As shown in FIG. 22, P1 (lane 2), P2 (lane 4) and PZ1 (lane 3) all gave a tail estimated at greater than 70 bases long on the basis of the 8-32 base marker (lanes 1 and 6). Primer PZ2 (lane 5) was not extended under these reaction conditions. We conclude that the TdT enzyme will tolerate LNA monomers within the oligonucleotide, but not at the extreme 3' end.

EXAMPLE 140

Figure 10:
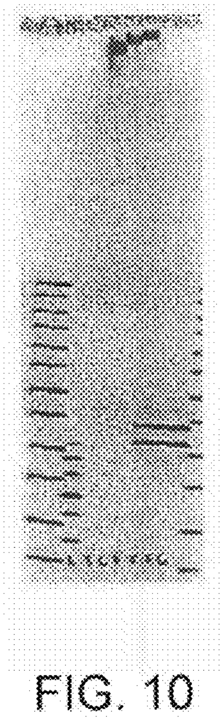
FIG. 10 illustrates that LNA-thymidine-5'-triphosphate (LNA-TTP) can act as a substrate for terminal deoxynucleotidyl transferase (TdT).

LNA-thymidine-5'-triphosphate (LNA-TTP) as a substrate for terminal deoxynucleotidyl transferase (TdT). In order to test the ability of the triphosphate of LNA-TTP (Example 123) to be accepted by terminal deoxynucleotidyl transferase as a substrate, an oligonucleotide tailing reaction was performed. A 15mer primer (sequence: 5'-TGC ATG TGC TGG AGA-3') (SEQ ID NO:14) and a mixture of 8 to 32 base oligonucleotide markers were 5' end labelled with [γ$^{33}$P] ATP and T4 polynucleotide kinase. Reactions were boiled for 5 min after labelling to remove any PNK activity. Four picomoles of the labelled primer, 25 U terminal deoxynucleotidyl transferase and 32, 64 or 128 μM dTTP or LNA-TTP were incubated in 25 μl 100 mM cacodylate buffer pH 7.2, 2 mM $CoCl_2$ and 0.2 mM 2-mercaptoethanol for 90 min at 37° C. The reactions were stopped by the addition of formamide stop solution and the reaction products run on a 19% polyacrylamide 7M urea gel with the labelled markers. Autoradiography using Biomax film was carried out on the dry gel. As shown in FIG. 10, reactions with either 32 μM dTTP (lane B), 64 μM dTTP (lane C) or 128 μM dTTP (lane D) all produced tailed oligonucleotides which on the basis on the 8-32 oligonucleotide marker (outermost left and right lanes) were estimated at greater than 100 nucleotides. The LNA-TTP reactions (32 μM dTTP (lane E), 64 μM dTTP (lane F) or 128 μM dTTP (lane G)) all resulted in the primer being extended by one base and ~50% of this being extended by a further base. This result is very similar to that obtained with ribonucleotides and TdT. We conclude that LNA derived triphosphates can be recognised and incorporated into a DNA oligonucleotide by the TdT enzyme. This latter finding that LNA-TTP can bind to the polymerase underscores the possibility of successfully using LNA-monomer derivatives as nucleoside drugs.

EXAMPLE 141

Exonuclease free Klenow fragment DNA polymerase I can incorporate LNA Adenosine, Cytosine, Guanosine and Uridine-5'-triphosphates (LNA ATP, LNA CTP, LNA GTP, LNA UTP) into a DNA strand. A primer extension assay was used to evaluate the LNA NTP's (see Example 123), ribonucleotides, as substrates for exonuclease free Klenow fragment DNA polymerase I (EFK). The assay used a $^{33}$P 5' end labelled 15mer primer hybridised to one of four different 24mer templates. The sequences of the primer and templates are (LNA monomer in bold):

Primer 5' TGCATGTGCTGGAGA 3' (SEQ ID NO: 15)

Template 1 3' ACGTACACGACCTCTACCTTGCTA 5' (SEQ ID NO: 16)

Template 2 3' ACGTACACGACCTCTCTTGATCAG 5' (SEQ ID NO: 17)

Template 3 3' ACGTACACGACCTCTTGGCTAGTC 5' (SEQ ID NO: 18)

Template 4 3' ACGTACACGACCTCTGAACTAGTC 5' (SEQ ID NO: 19)

One picomole $^{33}$P labelled primer was hybridised to 2 picomoles of template in ×2 Klenow buffer. To this was added either 4 μM dNTPαS or 500 μM LNA NTP or a mixture of 4 μM dNTPαS and 500 μM LNA NTP. Two units of EFK DNA polymerase was added to each reaction. 2 mU inorganic pyrophosphatase was added to each of the reactions. Primer plus template plus enzyme controls were also carried out. All reactions were carried out in a total volume of 20 μl. The reactions were incubated at 37° C. for 3 min. Reactions were then stopped by the addition of 10 μl formamide EDTA stop solution. Reaction products were separated on a 19% polyacrylamide 7M urea gel and the product fragments sized by comparison with a $^{33}P$ labelled 8 to 32 base oligonucleotide ladder after exposure to Kodak Biomax autoradiography film.

Figure 20:
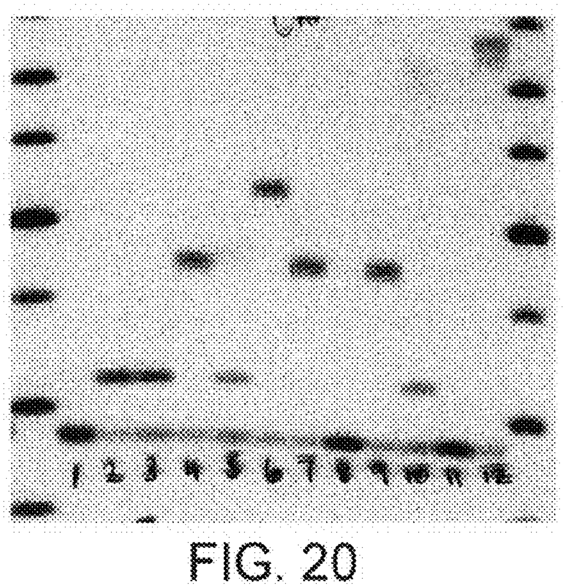
FIGS. 20 and 21 illustrate that exonuclease free Klenow fragment DNA polymerase I can incorporate LNA Adenosine, Cytosine, Guanosine and Uridine-5'-triphosphates into a DNA strand.

FIG. 20 shows the result with LNA-UTP using template 1. The tracks (1-12) correspond to the following reactions: Incorporation of LNA UTP by EFK. Lane 1—Primer, template and enzyme. Lane 2—plus dTTPαS. Lane 3—plus LNA UTP. Lane 4—plus dTTPαS and dGTPαS. Lane 5—plus LNA UTP and dGTPαS. Lane 6—plus dATPαS, dGTPαS and dTTPαS. Lane 7—plus LNA UTP, dCTPαS, dGTPαS and dTTPαS. Lane 8—plus dGTPαS. Lane 9—plus dCTPαS, dGTPαS and dTTPαS. Lane 10—plus LNA UTP, dATPαS, dCTPαS and dGTPαS. Lane 11—plus dATPαS, dCTPαS and dGTPαS. Lane 12- all 4 dNTPαS. The lanes either side show the 8-32 base oligonucleotide markers used for sizing the products.

As is evident from FIG. 20, LNA UTP is specifically incorporated as a "T". Further extension from an LNA UTP terminated 3' end with dNTPαS is very slow.

Figure 21:
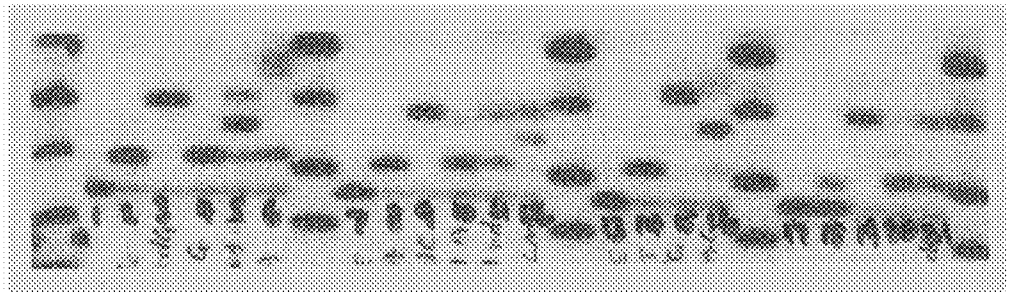

FIG. 21 shows the result with LNA-ATP, LNA CTP, and LNA GTP using template 2-4. The tracks (1-21) correspond to the following reactions: Lanes 1, 7, 13 and 17—primer, template and enzyme. Lane 2—plus dGTPαS. Lane 3—plus dATPαS and dGTPαS. Lane 4—plus LNA GTP. Lane 5—plus dGTPαS and LNA ATP. Lane 6—plus LNA ATP and LNA GTP. Lane 8—plus dATPαS. Lane 9—plus dATPαS and dCTPαS. Lane 10—plus LNA ATP. Lane 11—plus dCTPαS and LNA ATP. Lane 12—plus dATPαS and LNA CTP. Lane 14—plus dTTPαS. Lane 15—plus dGTPαS and dTTPαS. Lane 16—plus dTTPαS and LNA GTP. Lane 18—plus dCTPαS. Lane 19—plus dCTPαS and dTTPαS. Lane 20—plus LNA CTP. Lane 21—dTTPαS and LNA CTP. The lanes either side show the 8-32 base oligonucleotide markers used for sizing the products.

The experiments using template 2 (track 1-6), show that LNA GTP is able to produce the +1 product with efficient extension of the primer (track 4). The addition of dGTPαS and LNA ATP results in mainly the +2 product (track 5). This is from the incorporation of dGTPαS to give the +1 product followed by extension with LNA ATP. There is evidence of a small amount of +3 product from the consecutive incorporation of LNA ATP. The experiments using Template 3 (tracks 7-12) show that LNA ATP is efficiently incorporated to give the +1 product (track 10). Extension of this product with dCTPαS is slow (track 11). The addition of dATPαS and LNA CTP results in the +2 and +3 products (track 12). The absence of any significant +1 product shows that the addition of the first LNA CTP is efficient, but that the addition of the second LNA CTP is slow. The results from experiments on Templates 1 (tracks 13-16) and 4 (tracks 17-21) show similar trends to those on the other templates. LNA CTP is efficiently incorporated to give the +1 product on Template 4 (track 20). Extension of this product by dTTPαS is again slow (track 21). The addition of LNA GTP and dTTPαS to reactions on Template 1 results in the +2 product (track 16). Again this shows that the addition of a single LNA triphosphate is quite efficient, but that the addition of consecutive LNA triphosphates is slow.

EXAMPLE 142

LNA monomers can be used to enhance the resistance of an oligonucleotide to digestion by exonuclease III. In order to test the resistance of the LNA containing oligonucleotides to Exonuclease III degradation the following reaction was performed. The following 15mer primers and 8 to 32 base oligonucleotide markers were 5' end labelled with [$\gamma^{33}P$] ATP and T4 polynucleotide kinase (LNA monomer in bold):

P2 5'-GC ATG TGC TGG AGA T-3' (SEQ ID NO: 20)

PZ2 5'-GC ATG TGC TGG AGA T-3' (SEQ ID NO: 21)

Reactions were boiled for 5 min after labelling to remove any PNK activity. 8 picomoles of each primer was hybridised to 25 pmoles Template (sequence: 3'-ACG TAC ACG ACC TCT ACC TTG CTA-5' (SEQ ID NO:22)) in x2 Klenow buffer. 10 Units of Exonuclease III was added to each of the reactions. Controls were also set up which had 1 μl water added in place of the enzyme. The reactions were incubated at 37° C. for 5 min. The reactions were stopped by the addition of 10 μl formamide/EDTA stop solution. The reactions were heated at 95° C. for 3 min before loading onto a 19% polyacrylamide 7M urea gel. The gel was fixed in 10% acetic acid/10% methanol before transferring to 3 MM paper and drying. The dried gel was exposed to a phosphor screen for 3 hours. The phosphor screen was analysed on the Molecular Dynamics Storm 860 instrument using ImageQuant software. The phosphor screen analysis showed that in the absence of the enzyme the P2 full length band was 99% of the signal and PZ2 full length band was 96% of the signal. In the presence of the enzyme only 20% of the P2 full length product was left after the 5 minute incubation. However, 62% of the full length PZ2 product remained after the same treatment. This shows that a single LNA monomer at the 3' end of an oligonucleotide can enhance the resistance to degradation by exonuclease III.

PCR Applications

EXAMPLE 143

LNA monomers can be used to significantly increase the performance of biotinylated-DNA oligos in the sequence specific capture of PCR amplicons in a MTP format. Two DIG labelled amplicons from pUC19 were generated by PCR amplification as follows:

PCR Reaction Mixture for Amplicon 1

1 μl pUC19 (1 ng/μl),

1 μl reverse primer (5'-AACAGCTATGACCATG-3') (SEQ ID NO:23) (20 μM),

1 μl forward primer (5'-GTAAAACGACGGCCAGT-3') (SEQ ID NO:24) (20 μM),

10 μl dUTP-mix (2 mM dATP, 2 mM dCTP, 2 mM dGTP and 6 mM dUTP), 1.5 μl DIG-11-dUTP (1 mM)

10 μl 10× Taq buffer (Boehringer Mannheim incl $MgCl_2$)

1 μl Taq polymerase (Boehringer Mannheim) 5 U/μl $H_2O$ ad 100 μl

PCR Reaction Mixture for Amplicon 2

1 μl pUC19 (1 ng/μl), 0.4 μl primer 3 (5'-GATAGGTGCCTCACTGAT-3') (SEQ ID NO:25) (50 μM), 0.4 μl primer 4 (5'-GTCGTTCGCTCCAAGCTG-3') (SEQ ID NO:26) (50 μM), 10 μl dUTP-mix (2 mM dATP, 2 mM dCTP, 2 mM dGTP and 6 mM dUTP), 1.5 μl DIG-11-dUTP (1 mM)

10 μl 10× Taq buffer (Boehringer Mannheim incl $MgCl_2$)

1 μl Taq polymerase (Boehringer Mannheim) 5 U/μl $H_2O$ ad 100 μl

PCR reaction: (Cycler: Perkin Elmer 9600) 94° C. 5 min; add polymerase; 94° C. 1 min, 45° C. 1 min, 70° C. 2 min (29 cycles) 72° C. 10 min.

10 μl from each PCR reaction was analysed on a standard agarose gel and the expected fragments of approximately 100 bp and 500 bp were observed.

Figure 3:
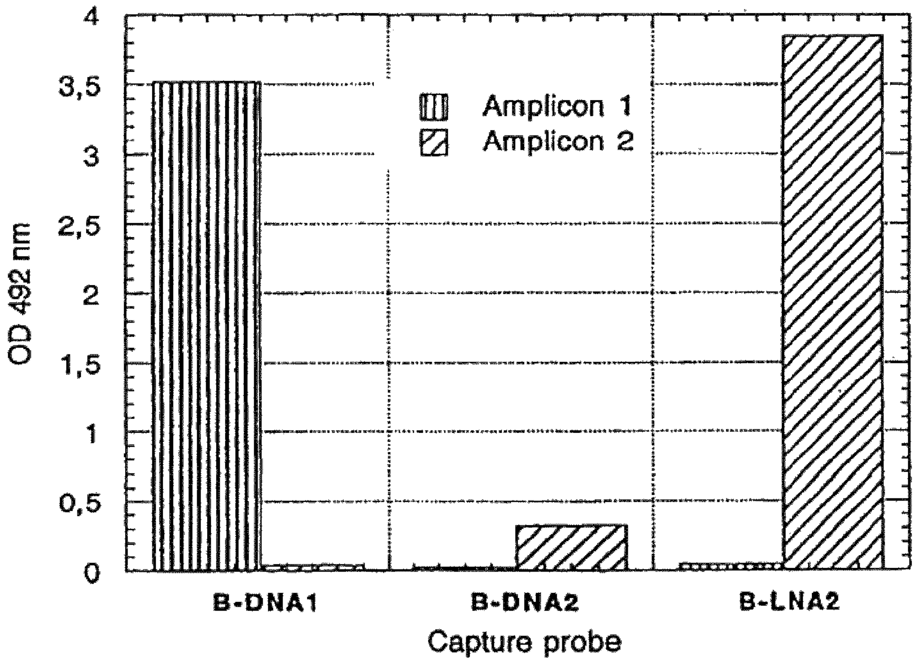
FIG. 3 illustrates the performance of LNA modified oligonucleotides in the sequence specific capture of PCR amplicons.
Figure 4A:
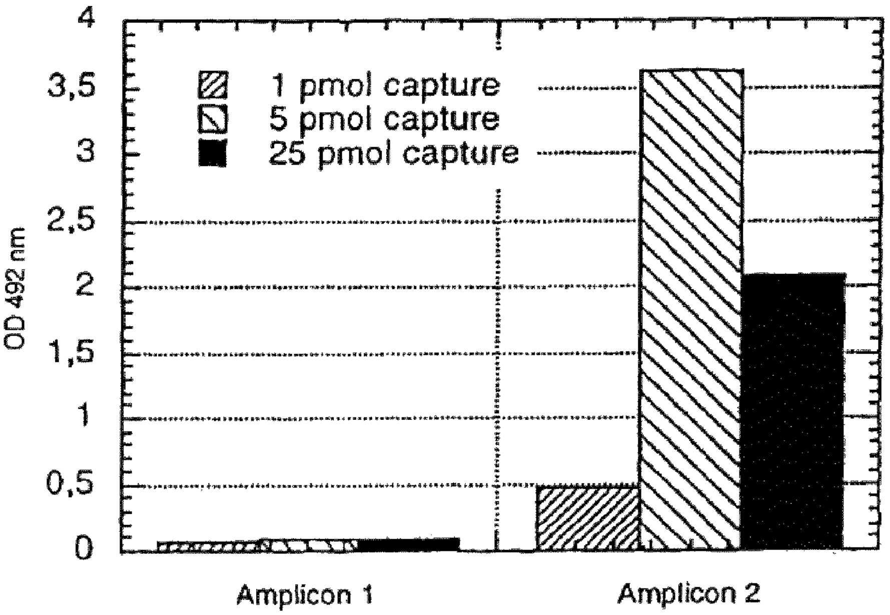
FIGS. 4A and 4B illustrate that LNA modified oligonucleotides are able to capture its cognate PCR amplicon by strand invasion.
Figure 4B:
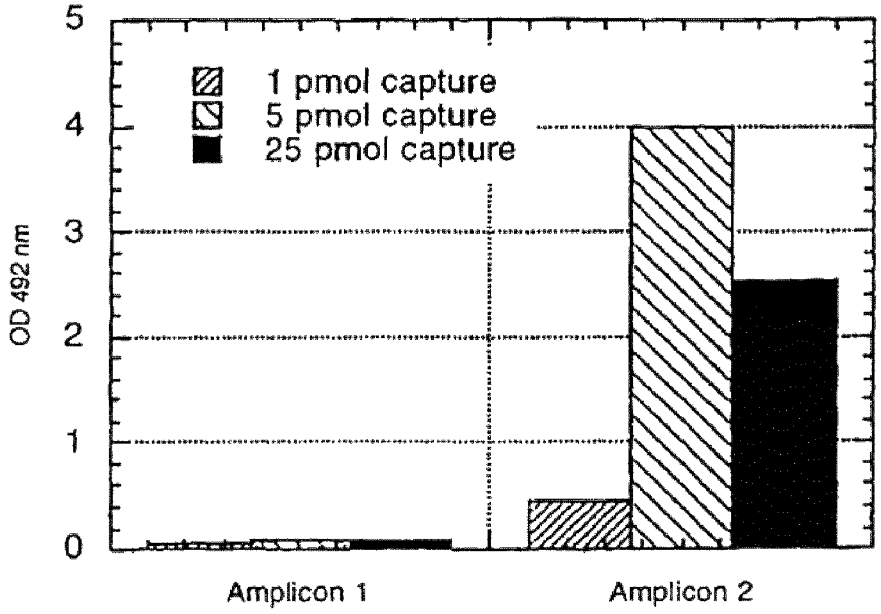

10 μl of DIG-labelled amplicon 1 or amplicon 2 was mixed with 5 pmol of 5' biotinylated capture probe in 1×SSC (0.15 M NaCl, 15 mM citrate, pH 7.0) in a total volume of 450 μl. The following capture probes were used: B-DNA1 (biotin-ATGCCTGCAGGTCGAC-3' (SEQ ID NO:27); DNA probe specific for amplicon 1), B-DNA2 (biotin-GGTGGTTTGTTTG-3' (SEQ ID NO:28); DNA probe specific for amplicon 2) and B-LNA2 (biotin-GGTG-GTTTGTTTG-3' (SEQ ID NO:29), LNA nucleosides in bold; LNA probe specific for amplicon 2). Reactions were heated to 95° C. for 5 min in order to denature amplicons and allowed to cool at 25° C. for 15 min to facilitate hybridisation between the probe and the target amplicon strand. After hybridisation 190 μl of each reaction were transferred to a streptavidin coated micro plate (Pierce, cat. no. 15124) and incubated for one hour at 37° C. After washing the plate with phosphate buffered saline (PBST, 0.15 M Nat, pH 7.2, 0.05% Tween 20, 3×300 μl), 200 μl of peroxidase labelled anti- DIG antibodies were added (Boehringer Mannheim, diluted 1:1000 in PBST). Plates were incubated for 30 min at 37° C. and washed (PBST, 3×300 μl). Wells were assayed for peroxidase activity by adding 100 μl of substrate solution (0.1 M citrate-phosphate buffer pH 5.0, 0.66 mg/ml ortho-phenylenediamine dihydrochloride, 0.012% $H_2O_2$). The reaction was stopped after 8 min by adding 100 μl $H_2SO_4$ (0.5 M) and the absorbance at 492 nm was read in a micro plate reader. As shown in FIG. 3, the unmodified bio-DNAs capture probes (B-DNA1 and B-DNA2) both behave as expected, i.e. they each capture only their target PCR amplicon. Compared to the B-DNA1 probe the B-DNA2 probe is rather inefficient in capturing its cognate amplicon. The capture efficiency of the B-DNA2 probe, however, can be dramatically improved by substituting 12 of its 13 DNA nucleosides by the corresponding LNA nucleosides. As shown in FIG. 3 the use of the B-LNA2 probe in place of the B-DNA2 probe leads to a more that 10 fold increase in the sensitivity of the assay. At the same time the B-LNA2 retains the ability of the un-modified B-DNA2 to efficiently discriminate between the related and non-related amplicon, underscoring the excellent specificity of LNA-oligos. We conclude that 1) biotin covalently attached to an LNA modified oligo retains its ability to bind to streptavidin, 2) that LNA modified oligos works efficiently in a MTP based amplicon capture assay and that 3) LNA offers a means to dramatically improve the performance of standard DNA oligos in the affinity capture of PCR amplicons.

EXAMPLE 144

An LNA substituted oligo is able to capture its cognate PCR amplicon by strand invasion. Two identical sets of 10 μl reactions of amplicon 1 or 2 (prepared as in Example 143) were mixed with either 1, 5 or 25 pmol of the B-LNA2 capture probe (biotin-GGTGGTTTGTTTG-3' (SEQ ID NO:30), LNA nucleosides in bold; probe specific for amplicon 2) in 1×SSC (0.15 M NaCl, 15 mM citrate, pH 7.0) in a total volume of 450 μl. One set of reactions were heated to 95° C. for 5 min in order to denature amplicons and allowed to cool to 25° C. to facilitate hybridisation between the probe and the target amplicon strand. The other set of reactions were left without denaturation. From each of the reactions 190 μl were transferred to a streptavidin coated micro plate (Pierce, cat. no. 15124) and incubated for one hour at 37° C. After washing the plate with phosphate buffered saline (PBST, 0.15 M $N^+$, pH 7.2, 0.05% Tween 20, 3×300 μl), 200 μl of peroxidase labelled anti- DIG antibodies were added (Boehringer Mannheim, diluted 1:1000 in PBST). Plates were incubated for 30 min at 37° C. and washed (PBST, 3×300 μl). Wells were assayed for peroxidase activity by adding 100 μl of substrate solution (0.1 M citrate-phosphate buffer pH 5.0, 0.66 mg/ml ortho-pheylenediamine dihydrochloride, 0.012% $H_2O_2$). The reaction was stopped after 10 min by adding 100 μl $H_2SO_4$ (0.5 M) and the absorbance at 492 nm was read in a micro plate reader. When amplicons are denaturated prior to hybridisation with the capture probe (FIG. 4A) we observe an efficient and sequence specific amplicon capture similar to that shown in Example 143. Increasing the concentration of the B-LNA2 from 1 to 5 pmol leads to an increase in capture efficiency. A further increase to 25 pmol of probe results in a decreased signal. This observation is consistent with saturation of the available biotin binding sites on the streptavidin MTP. When amplicons are not denaturated prior to hybridisation with the capture probe (FIG. 4B) we also observe an efficient and sequence specific amplicon capture. In fact, the data shows that amplicon capture without denaturation are as effective and specific as amplicon capture with denaturation. This strongly indicates that the Bio-LNA2 probe is capable of binding to its target sequence by strand invasion. To our knowledge, this constitutes the first example ever of sequence specific targeting of dsDNA under physiological salt conditions by a mixed purine/pyrimidine probe. Aside from its potential to significantly simplify a range of basic research and DNA diagnostic procedures this unexpected property of LNA modified oligos can be foreseen to be of major importance in the development of efficient new drugs by the antisense, and in particular anti-gene approach.

EXAMPLE 145

Figure 5:
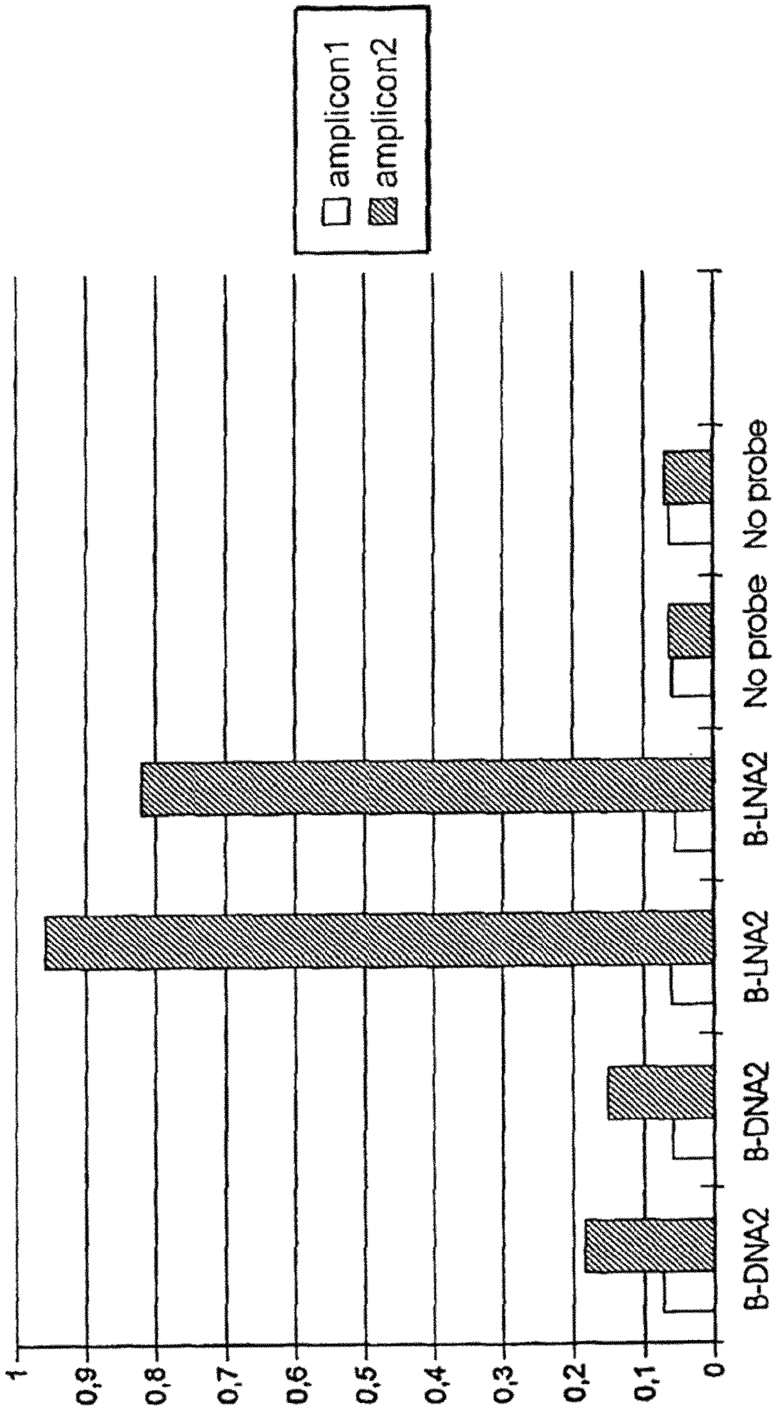
FIG. 5 illustrates that LNA modified oligonucleotides, immobilised on a solid surface, function efficiently in the sequence specific capture of a PCR amplicon.

An LNA substituted oligo, immobilised on a solid surface function efficiently in the sequence specific capture of a PCR amplicon. Wells of a streptavidin coated micro-titer plate (Boehringer Mannheim) were incubated for 1 hour with either 5 pmol of the B-DNA2 probe (biotin-GGTG-GTTTGTTTG-3' (SEQ ID NO:31); DNA probe specific for amplicon 2) or the B-LNA2 probe (biotin-GGTG-GTTTGTTTG-3' (SEQ ID NO:32), LNA nucleosides in bold; LNA probe specific for amplicon 2) in a total volume of 100 μl 1×SSC (0.15 M NaCl, 15 mM citrate, pH 7.0). In total, four wells were incubated with the B-DNA2 probe, four wells with the B-LNA2 probe and four wells were incubated with buffer alone. After incubation the wells were washed three times with 1×SSC. DIG-labelled amplicon1 (60 μl) or amplicon2 (60 μl) (prepared as in Example 143) were mixed with 540 μl of 1×SSC, heat denaturated at 95° C. for 5 min., and transferred (100 μl) to the micro plate wells. Two of the wells containing either B-DNA2, B-LNA2 or no capture probe received amplicon1 and two of the wells containing B-DNA2, B-LNA2 or no capture probe received amplicon2. After 1 hour at 37° C. the plate was washed 3 times with phosphate buffered saline (PBST, 0.15 M $Na^+$, pH 7.2, 0.05% Tween 20, 3×300 μl) and 200 μl of peroxidase labelled anti- DIG antibodies were added (Boehringer Mannheim, diluted 1:1000 in PBST). Plates were incubated for 30 min at 37° C. and washed 3 times with 300 μl PBST. Wells were assayed for peroxidase activity by adding 100 μl of substrate solution (0.1 M citrate-phosphate buffer pH 5.0, 0.66 mg/ml ortho-phenylenediamine dihydrochloride, 0.012% $H_2O_2$). The reaction was stopped after 6 min by adding 100 μl $H_2SO_4$ (0.5 M) and the absorbance at 492 nm was read in a micro plate reader. As shown in FIG. 5, the LNA modified capture probe (B-LNA2) captures its specific amplicon (amplicon2) very efficiently and significantly better (approx. five fold increase in sensitivity) than the corresponding unmodified DNA capture probe (B-DNA2). No signal is obtained when the B-LNA2 probe is incubated with the unrelated amplicon (amplicon1) underscoring the exquisite specificity of the B-LNA2 probe. We conclude that LNA modified oligos function efficiently in the sequence specific capture of PCR amplicons when immobilised on a solid surface. We further conclude that the use of LNA modified oligos in place of standard DNA oligos provide for a better signal to noise ratio. Thus, LNA offers a means to significantly improve the performance of current DNA based assays that utilises immobilised capture probes, like for instance the array format wherein multiple immobilised probes are used to simultaneously detect the occurrence of several different target sequences in a sample.

EXAMPLE 146

Fully mixed LNA monomers can be used to significantly increase the performance of immobilised biotinylated-DNA oligos in the sequence specific capture of PCR amplicons in a MTP format. Three DIG labelled amplicons from Nras sequence (ref.: Nucleic Acid Research, 1985, Vol. 13, No. 14, p 52-55) were generated by PCR amplification as follows:

PCR primers:

Forward primer: 5'-CCAGCTCTCAGTAGTTTAGTACA-3' (SEQ ID NO:33) bases 701-723 according to the NAR reference.

910 by reverse primer: 5'-GTAGAGCTTTCTGGTATGA-CACA-3' (SEQ ID NO:34) bases 1612-1590 (reverse sequence according to NAR ref.).

600 by reverse primer: 5'-TAAGTCACAGACGTATCTCA-GAC-3' (SEQ ID NO:35) bases 1331-1308 (reverse sequence according to NAR ref.).

200 by reverse primer: 5'-CTCTGTTTCAGACATGAACT-GCT-3' (SEQ ID NO:36) bases 909-886 (reverse sequence according to NAR ref.).

Figure 23A:
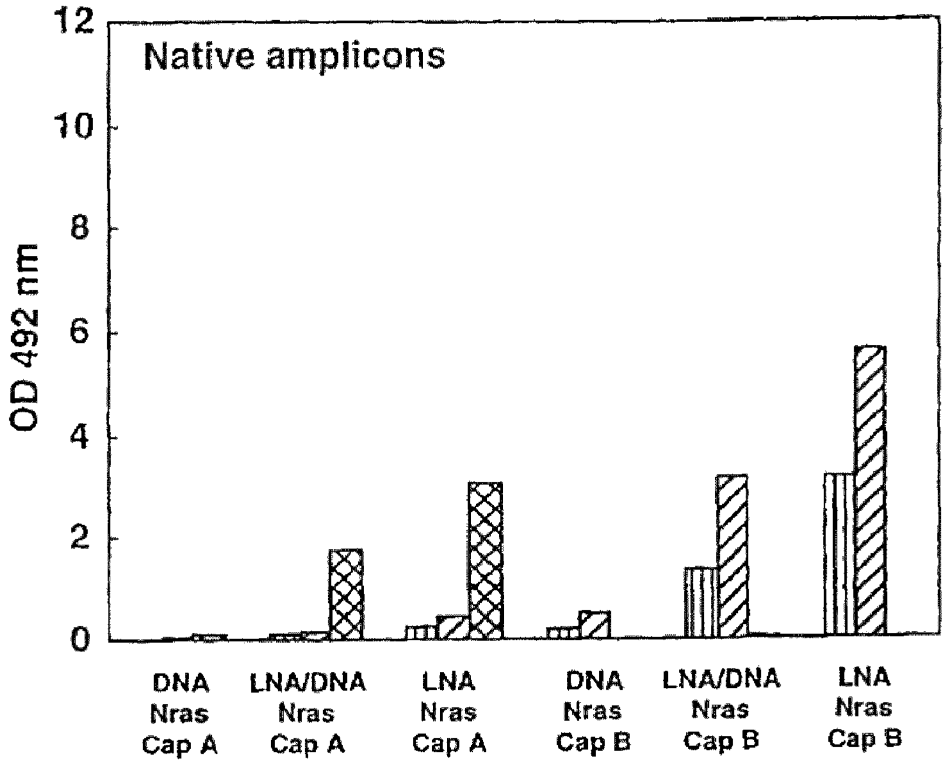
FIGS. 23A and 23B illustrate that fully mixed LNA monomers can be used to significantly increase the performance of immobilised biotinylated-DNA oligos in the sequence specific capture of PCR amplicons.
Figure 23B:
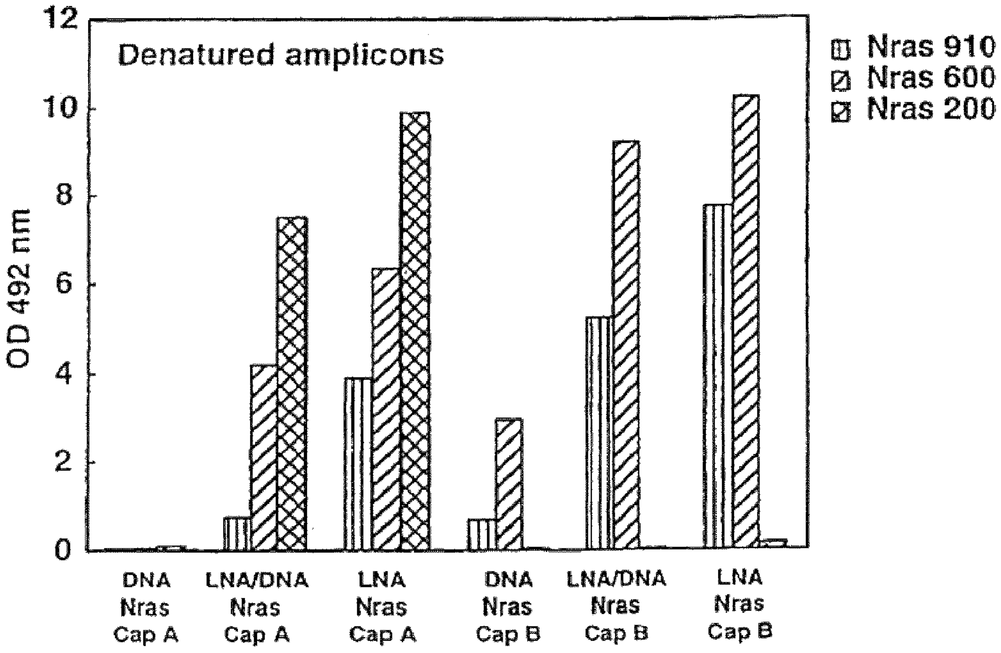
Figure 24:
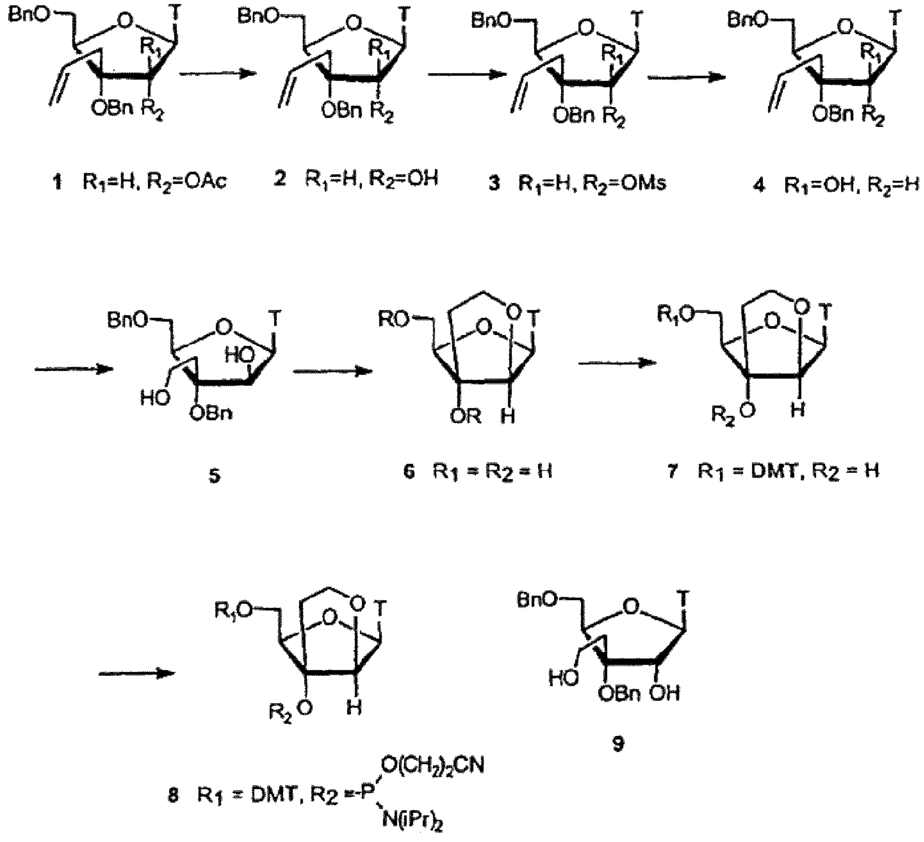
FIGS. 24 to 41 illustrates possible synthetic routes towards the LNA monomers of the invention.
Figure 25:
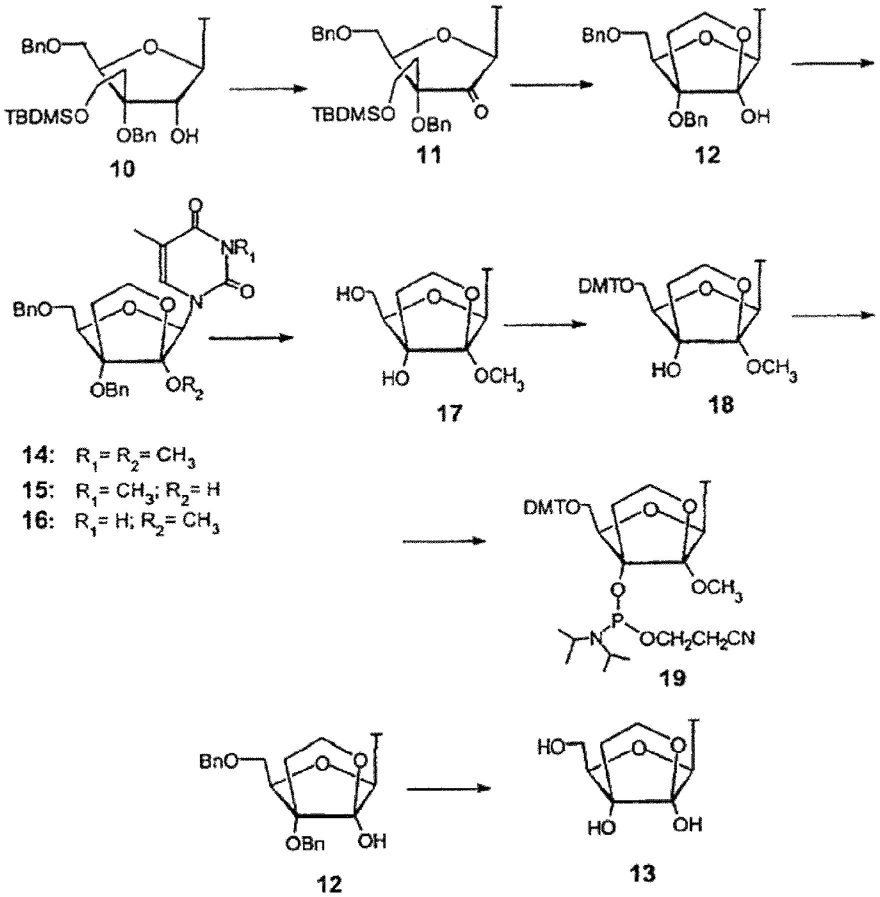
Figure 26:
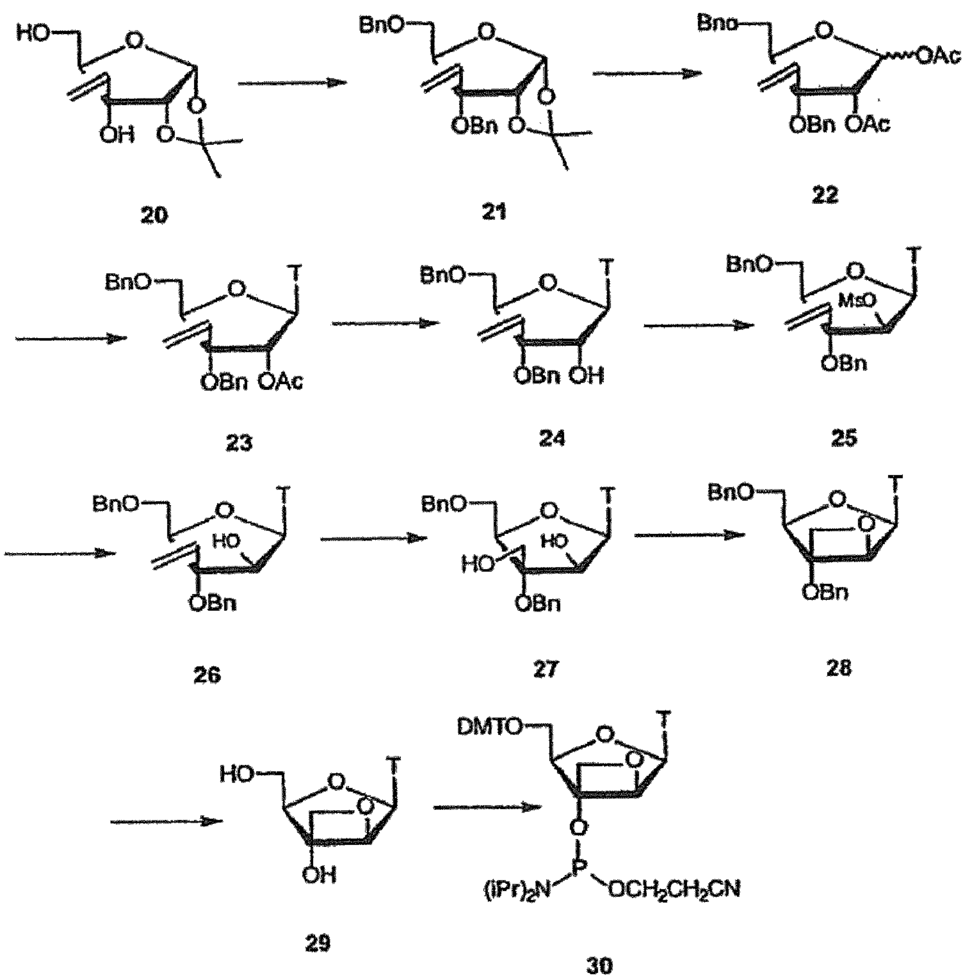
Figure 27:
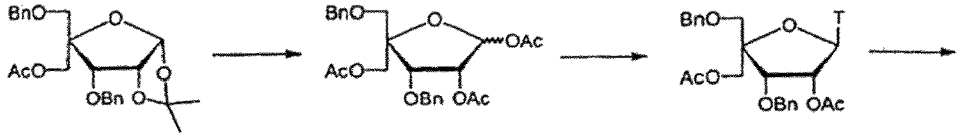
Figure 27:
Figure 27:
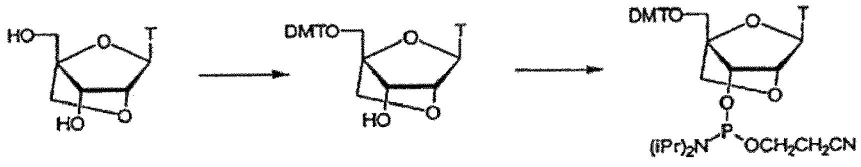
Figure 28:
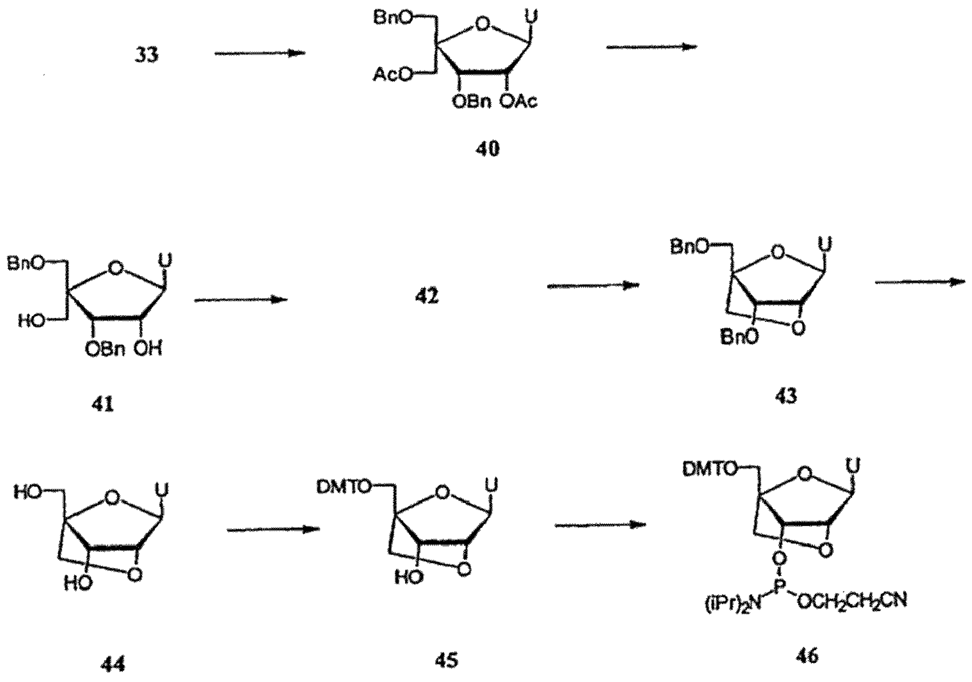
Figure 29:
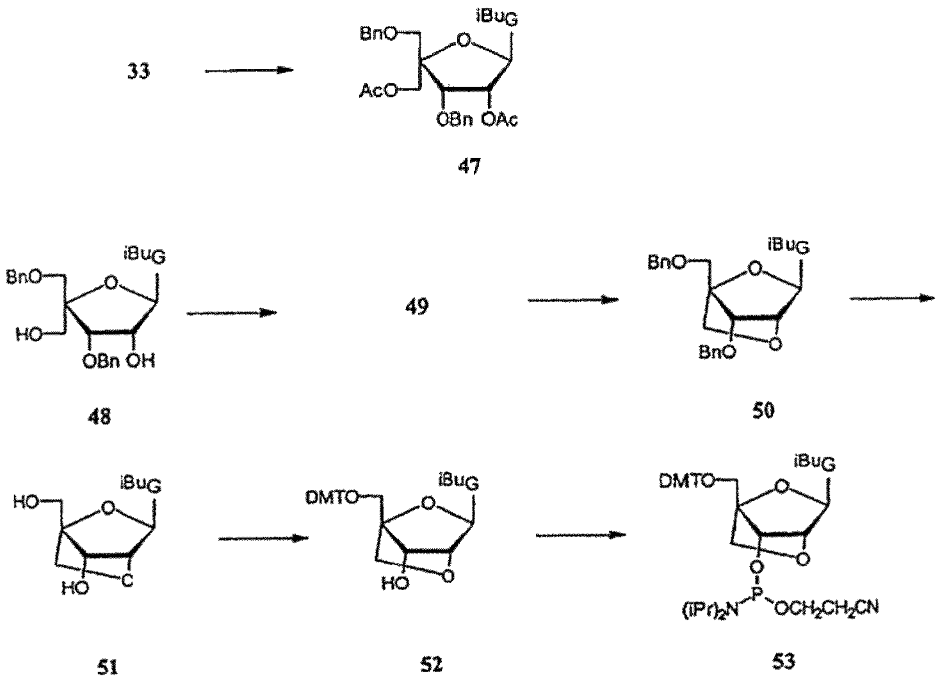
Figure 30:
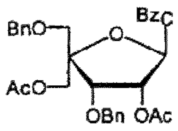
Figure 30:
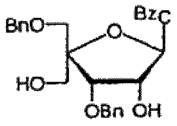
Figure 30:
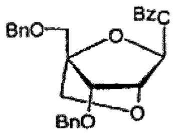
Figure 30:
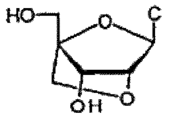
Figure 30:
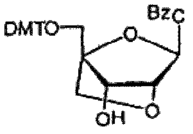
Figure 30:
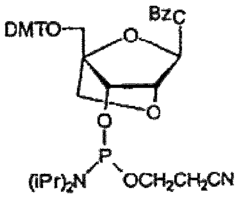
Figure 31:
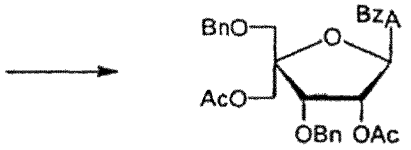
Figure 31:
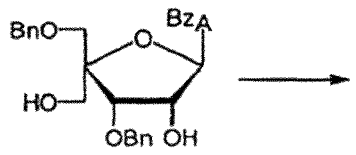
Figure 31:
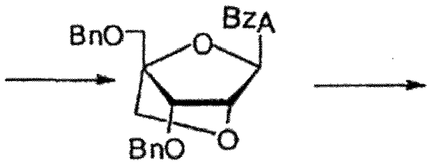
Figure 31:
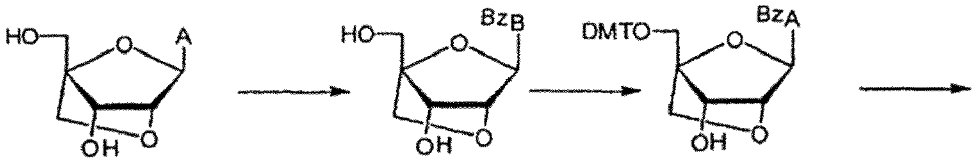
Figure 31:
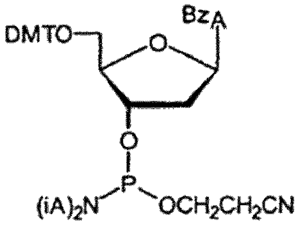
Figure 32:
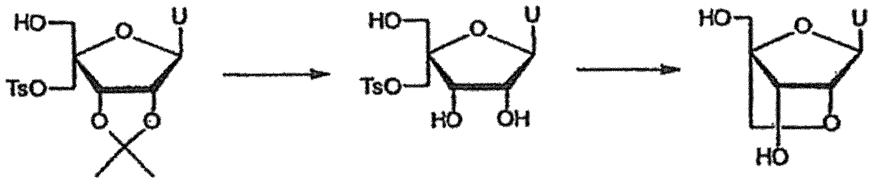
Figure 33:
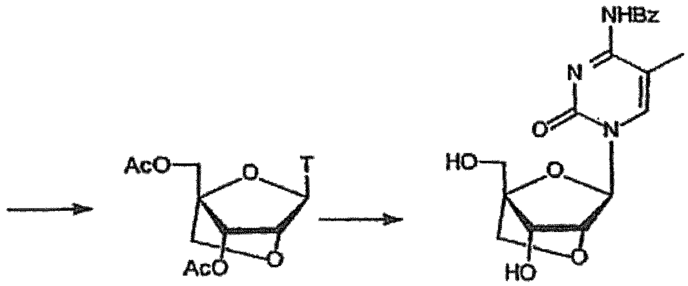
Figure 33:
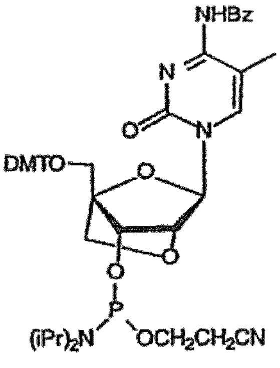

PCR reaction mixture for Nras amplicons: 2.3 μl human placental genomic DNA (440 ng/μl), 50 μl 10×PCR buffer (without $MgCl_2$ Perkin Elmer), 30 μl 25 mM $MgCl_2$, 50 μl dNTP-mix (2 mM dATP, dCTP, dGTP and 1.8 mM dTTP), 10 μl 1 mM Dig-11-dUTP, 10 μl 25 μM forward primer, 10 μl 25 μM reverse primer, 5 μl 5 U/μl AmpliTaq Gold (Perkin Elmer) and water ad 500 μl. PCR reaction: The above mixture was made for all the Nras PCR products. The only difference being reverse primer 910 bp, 600 bp or 200 bp added once at a time. The PCR mixtures were aliquoted into ten PCR tubes each and cycled in a Perkin Elmer 9600 at the following conditions: 95° C. 3 min; 55° C. 2 min, 72° C. 3 min, 95° C. 1 min (30 cycles); 55° C. 2 min, 72° C. 10 min and 4° C. soak. 10 μl from each PCR reaction was analysed on a standard agarose gel and the expected fragments of approximately 910 bp, 600 bp and 200 bp were observed. Assay conditions: Wells of a streptavidin coated micro-titer plate (Boehringer Mannheim; binding capacity of 20 pmol biotin per well) were incubated for 1 hour in 5×SSCT (0.75 M NaCl, 75 mM citrate, pH 7.0, 0.1% Tween 20) at 37° C. with either 1 pmol of DNA Nras Cap A (biotin-5'-TTCCACAGCACAA-3') (SEQ ID NO:37), LNA/DNA Nras Cap A (biotin-5'-TTCCACAGCA-CAA-3') (SEQ ID NO:38), LNA Nras Cap A (biotin-5'-TTC-CACAGCACAA-3') (SEQ ID NO:39), DNA Nras Cap B (biotin-5'-AGAGCCGATAACA-3') (SEQ ID NO:40), LNA/DNA Nras Cap B (biotin-5'-AGAGCCGATAACA-3') (SEQ ID NO:41) or LNA Nras Cap B (biotin-5'-AGAGC-CGATAACA-3') (SEQ ID NO:42); LNA nucleosides in bold. The Nras Cap A capture probes capture amplicons Nras 910, Nras 600 and Nras 200. Nras Cap B capture probes capture specific amplicons Nras 910 and Nras 600. After incubation with the different capture probes, the wells were washed in 5×SSCT and 5 μl native or denatured (95° C. 5 min and 10 min on ice) DIG-labelled amplicons (Nras 910, Nras 600 or Nras 200) in 95 μl 1×SSCT (0.15 M NaCl, 15 mM citrate, pH 7.0, 0.1% Tween 20) were added per well and incubated for 1 hour at 37° C. The wells were washed three times in phosphate buffered saline (1×PBST, 0.15 M $N^+$, pH 7.2, 0.05% Tween 20) and incubated 30 min at 37° C. with 200 μl peroxidase labelled anti-DIG antibodies (Boehringer Mannheim, diluted 1:1000 in 1×PBST). Finally the wells were washed three times in 1×PBST and assayed for peroxidase activity by adding 100 μl of substrate solution (0.1 M citrate-phosphate buffer pH 5.0, 0.66 mg/ml ortho-phenylenediamine dihydrochloride, 0.012% $H_2O_2$) the reaction was stopped after 9 min by adding 100 μl 0.5 M $H_2SO_4$ and diluted 4 times in $H_2SO_4$ before the absorbance at 492 nm was read in a micro-titer plate reader. As shown in FIG. 23A, capture probes spiked with 12 LNA nucleosides (LNA Nras Cap A and LNA Cap B) capture very efficiently the specific amplicons without prior denaturation (native amplicons). Capture probes spiked with 4 LNA nucleosides (LNA/DNA Nras Cap A and LNA/DNA Nras Cap B) capture the same amplicons with a lower efficiency and the DNA capture probes (DNA Nras Cap A and DNA Nras Cap B) do not capture the specific amplicons at all. The control amplicon, Nras 200, are not captured by the LNA Cap B or the LNA/DNA Nras Cap B probes demonstrating the exquisite specificity of the LNA spiked capture probes. FIG. 23B shows the same experiment performed with denatured amplicons. Essentially the same picture emerges with the essential difference that capture efficiencies are generally increased. We conclude that LNA modified oligos containing mixed LNA nucleosides (A, T, G or C LNA nucleosides) function efficiently in sequence specific capture of PCR amplicons when immobilised on a solid surface. We further conclude that LNA offers a means to construct capture probes that will function efficiently in amplicon capture without prior denaturation i.e. capture by strand displacement. This ability facilitates a significant simplification of current amplicon detection formats based on DNA.

EXAMPLE 147

Figure 7:
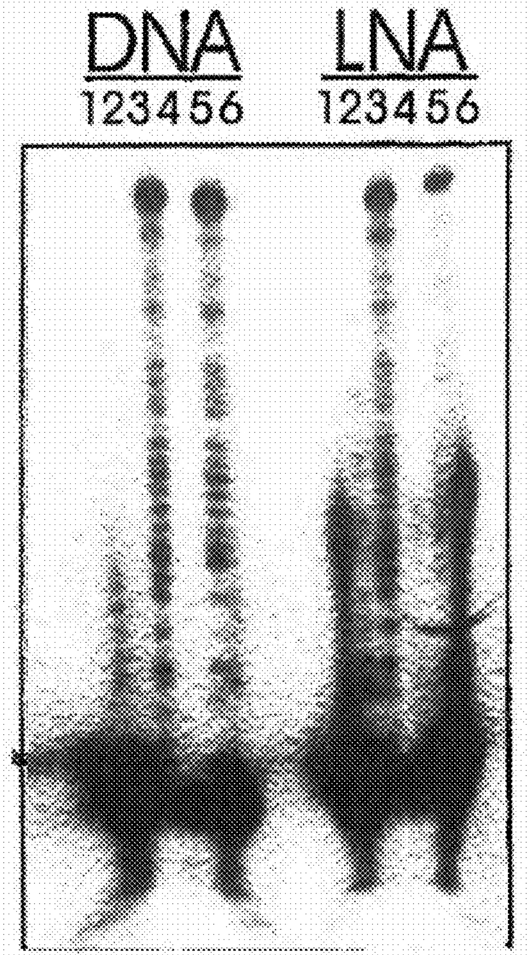
FIG. 7 illustrates that LNA modified oligonucleotides can function as primers for nucleic acid polymerases.

LNA modified oligos function as primers for nucleic acid polymerases. The ability of an LNA modified oligo (5'-GGTGGTTTGTTTG-3' (SEQ ID NO:43), LNA nucleosides in bold) to serve as primer in template dependent, enzymatic elongation were investigated with 3 different classes of polymerases. A reverse transcriptase M-MuLV (Boehringer Mannheim) which can use both RNA and DNA as template, the Klenow polymerase which is representative of standard DNA polymerases and a thermostable polymerase, BM-TAQ (Boehringer Mannheim). As control the extension reactions were conducted using the identical unmodified DNA primer (5'-GGTGGTTTGTTTG-3') (SEQ ID NO:44). The LNA and DNA primers were labelled with $^{32}P$-γ-ATP as previously described in Example 137. A 50mer DNA oligo (5''-AAAAATCGACGCTCAAGTCAGAAAAG-CATCTCACAAACAAAC-AAACCACC-3') (SEQ ID NO:45) was used as template. The reaction with M-MuLV (Boehringer Mannheim) contained 2 μl of either labelled LNA-primer or DNA primer (10 μM), 2 μl of DNA template (10 μM), 2 μl of 2 mM dNTP, 2 μl of 10× buffer (500 mM Tris-HCl, 300 mM KCl, 60 mM $MgCl_2$, 100 mM DTT, pH 8.3 (37° C.)), 1 μl of enzyme (20 U/μl) and water to 20 μl. The reactions were incubated at 37° C. for 60 min. The reaction with Klenow polymerase (USB) contained 2 μl of either labelled LNA or DNA primer (10 μM), 2 μl of DNA template (10 μM), 2 μl of 2 mM dNTP, 2 μl of 10× buffer (100 mM Tris-HCl, 50 mM $MgCl_2$, 75 mM DTT, pH 7.5), 1 μl of enzyme (10 U/μl) and water to 20 μl. The reactions were incubated at 37° C. for 60 min. The reaction with BM-Taq (Boehringer Mannheim) contained 2 μl of either labelled LNA or DNA-primer (10 μM), 2 μl of DNA template (10 μM), 2 μl of 2 mM dNTP, 2 μl of 10× buffer (100 mM Tris-HCl, 15 mM $MgCl_2$, 50 mM KCL, pH 8.3), 1 μl of enzyme (5 U/μl) and water to 20 μl. The reactions were incubated at a starting temperature of 37° C. and ramped at 1° C./min to 60° C. where they were maintained for 30 min. At the end of the incubation period the reactions were stopped by the addition of 10 μl of loading buffer (0.25% (w/v) bromophenol blue, 0.25% (w/v) xylene cyanol, 80% (v/v) formamid). The samples were heated to 95° C. for 1 min., placed on ice and 2 μl was loaded onto a 8% sequencing polyacrylamide gel and electrophoresed on a Life Technologies Inc. BRL model 52. After electrophoresis the gel was dried on the glass plate and subjected to autoradiography (X-ray film: Kodak X-Omat AR). As shown in FIG. 7, clear and similar extension products are observed with both the LNA and DNA primer when either the Klenow polymerase (lanes 3) or the BM-Taq polymerase (lanes 5) is used. When M-MuLV reverse transcriptase is used (lanes 2) an extension product can be detected only in the case of the LNA-primer. The labelled LNA and DNA primer that have not been subjected to enzymatic elongation are present in lanes 1, 4 and 6. We conclude that the incorporation of LNA nucleosides into standard DNA oligos does not prevent recognition of the oligo/template duplex by nucleic acid polymerases. We further conclude that LNA modified oligos act as efficiently as primers as unmodified DNA oligos.

EXAMPLE 148

Figure 8:
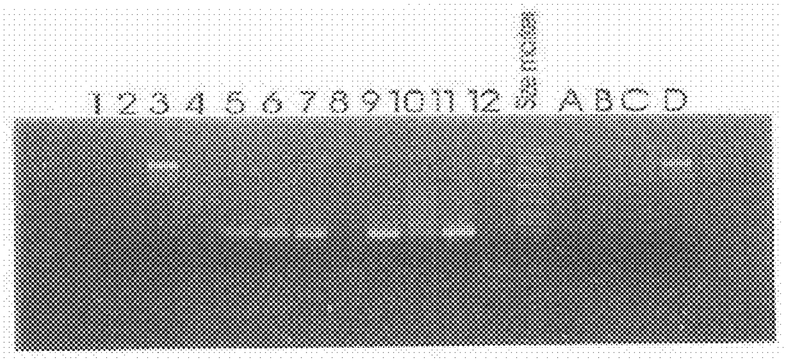
FIG. 8 illustrates that LNA modified oligonucleotides can functions as primers in target amplification processes.

LNA modified oligo functions as primers in target amplification processes. The ability of LNA modified oligos to act as primers in PCR amplification was analysed with three oligos differing only in the number of LNA nucleosides they contained: 4 LNA nucleosides (AL2 primer: 5'-GGTG-GTTTGTTTG-3' (SEQ ID NO:46), LNA nucleosides in bold), 1 LNA nucleoside (AL10 primer: 5'-GGTG-GTTTGTTTG-3' (SEQ ID NO:47), LNA nucleoside in bold) and no LNA nucleoside (FP2 primer: 5'-GGTG-GTTTGTTTG-3') (SEQ ID NO:48). The PCR reactions (1000 contained either no template (control), 0.01 ng, 0.1 ng or 1 ng of template (pUC19 plasmid), 0.2 μM reverse primer (5'-GTGGTTCGCTCCAAGCTG-3') (SEQ ID NO:49), 0.2 μM of either the AL2, AL10 or FP2 forward primer, 200 μM of dATP, dGTP, dCTP and dTTP, 10 mM Tris-HCl pH 8.3, 1.5 mM $MgCl_2$, 50 mM KCl and 2.5 U of the BM-Taq polymerase. A total of 50 cycles each consisting of 94° C. 1 min.-45° C. 1 min.-72° C. 1.5 min. were conducted (with an additional 2.5 U of Taq polymerase added after the first 30 cycles) on a Techne Genius thermocycler. After the final cycle the reactions were incubated at 72° C. 3 min. and then at 4° C. overnight. To 30 μl of each reaction was added 6 μl of loading buffer (0.25% (w/v) bromophenol blue and 40% (v/v) glycerol) and the samples (together with a Amplisize™ size marker) were loaded onto a 2% agarose gel and electrophoresed for 45 min. at 150V. Finally, the gel was stained with ethidiumbromid and photographed. As shown in FIG. 8 the PCR reactions using the unmodified forward primer FP2 and unmodified reverse primer generates detectable amplicons of the correct sizes with all amounts of template used (lane 9: 0.01 ng template, lane 10: 0.1 ng and lane 11: 1 ng). No signal is obtained in the control reaction without template (lane 12). When the FP2 forward primer is replaced by the primer containing 1 central LNA nucleoside (AL10) amplicons are also detected with all amounts of template used (lane 5: 0.01 ng, lane 6: 0.1 ng and lane 7: 1 ng). This clearly indicates that the AL10 primer sustains an exponential amplification. i.e. the AL10 primer can be both extended and used as template in its entirety. Again, the control reaction without template (lane 8) does not produce an amplicon. When the FP2 forward primer is replaced by the primer containing 4 central LNA nucleosides (AL2), amplicons of the correct size cannot be detected in any of the reactions. (lane 1: 0.01 ng template, lane 2: 0.1 ng, lane 3: 1 ng and lane 4: no template). With the highest concentration of template (1 ng), however, a high molecular weight band appears in the gel (lane 3). This, however, is an artefact of the RP1 primer as indicated by the control reaction wherein each of the primers AL2 (lane A), AL10 (lane B), FP2 (lane C) and RP1 (lane D) were tested for their ability to produce an amplicon with the highest amount of template (1 ng). Since AL2 was shown to act as a primer in Example 147, the absence of detectable amplicons strongly indicates that it lacks the ability to act as a template, i.e. the block of 4 consecutive LNA nucleosides blocks the advance of the polymerase thereby turning the reaction into a linear amplification (the product of which would not be detectable by the experimental set-up used). We conclude that LNA modified oligos can be used as primers in PCR amplification. We further conclude that the degree of amplification (graded from fully exponential to linear amplification) can be controlled by the design of the LNA modified oligo. We note that the possibility to block the advance of the polymerase by incorporating LNA nucleosides into the primer facilitates the generation of amplicons carrying single stranded ends. Such ends are readily accessible to hybridisation without denaturation of the amplicon and this feature could be useful in many applications.

EXAMPLE 149

Figure 9:
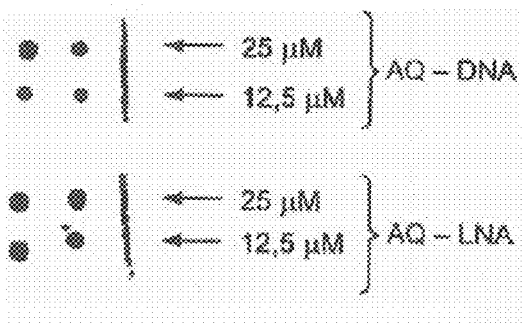
FIG. 9 illustrates that LNA modified oligonucleotides carrying a 5' anthraquinone can be covalently immobilised on a solid support by irradiation and that the immobilised oligomer is efficient in the capture of a complementary DNA oligo.

An LNA modified oligomer carrying a 5'anthraquinone can be covalently immobilised on a solid support by irradiation and the immobilised oligomer is efficient in the capture of a complementary DNA oligo. Either 25 pmol/μl or 12.5 pmol/μl of an anthraquinone DNA oligo (5'-AQ-CAG CAG TCG ACA GAG-3') (SEQ ID NO:50) or an anthraquinone LNA modified DNA oligo (5'-AQ-CAG CAG TCG ACA GAG-3' (SEQ ID NO:51); LNA monomer is underlined) was spotted (1 μl/spot) in 0.2 M LiCl on a polycarbonate slide (Nunc). The oligos were irradiated for 15 min with soft UV light. After irradiation the slide was washed three times in Milli-Q water and air-dried. 25 ml of 0.5 pmol/μl of complimentary biotinylated oligomer (5'-biotin- CTC TGT CGA CTG CTG-3') (SEQ ID NO:52) was hybridised to the immobilised oligomers in 5×SSCT (75 mM Citrate, 0.75 M NaCl, pH 7.0, 0.1% Tween 20) at 50° C. for 2 hours. After washing four times with 1×SSCT and one time phosphate buffered saline (PBST, 0.15 M $Na^+$, pH 7.2, 0.05% Tween 20), 25 ml PBST containing 0.06 μg/mlstreptavidin conjugated horse radish peroxidase and 1 μg/ml streptavidin were added to the slide. The slide was incubated for 30 min and washed 4 times with 25 ml PBST. The slide was visualised by using chemiluminescent substrate (SuperSignal; Pierce) as described by the manufacturer and X-ray film (CL-XPosure film, Pierce 34075). As shown in FIG. 9 both the AQ-DNA oligo and the AQ-LNA modified DNA oligo yields a clearly detectable signal. We conclude that anthraquinone linked LNA modified DNA oligos can be efficiently attached to a solid surface by irradiation and that oligos attached in this ways are able to hybridise to their complementary target DNA oligos.

EXAMPLE 150

Hybridisation and detection on an array with different LNA modified Cy3-labelled 8mers. Slide preparation: Glass slides were aminosilanised using a 10% solution of amino propyl triethoxy silane in acetone followed by washing in acetone. The following oligonucleotides were spotted out onto the slides:

| Oligo used | Oligo sequence | Pens 1 + 2 + 3 | Sequence cf. probes |
|---|---|---|---|
| Seq. 3 | 5'-GTA TGG AG-3' | 1 pmol/µl | 1 internal mismatch |
| Seq. 6 | 5'-GTA TGA AG-3' | 1 pmol/µl | match |

Ten repeat spots, approximately 1 nl each spot, were performed for each oligonucleotide from each pen on each of 12 slides.

Probes (LNA monomers in bold):

a) Seq. No. aZ1     5'-Cy3-CTT CAT AC-3' b) Seq. No. aZ2     5'-Cy3-CTT CAT AC-3' c) Seq. No. aZ3     5'-Cy3-CTT CAT AC-3' d) Seq. No. 16      5'-Cy3-CTT CAT AC-3'

Slides and Conditions for Hybridisation:
Slides 1, 2 and 3 hybridised with aZ1 probe @ 300 fmol/µl, 30 fmol/µl, 3 fmol/µl
Slides 4, 5 and 6 hybridised with aZ2 probe @ 300 fmol/µl, 30 fmol/µl, 3 fmol/µl
Slides 7, 8 and 9 hybridised with aZ3 probe @ 300 fmol/µl, 30 fmol/µl, 3 fmol/µl
Slides 10, 11 and 12 hybridised with seq. 16 probe @ 300 fmol/µl, 30 fmol/µl, 3 fmol/µl A probe diluted in 30 µl hybridisation buffer (5×SSC, 7% sodium lauryl sarcosine) was pipetted along the length of each slide, covered with a coverslip, and placed into a plastic box on top of a plastic insert, which was lying on a paper towel wetted with water. Boxes were covered with aluminium foil to keep light out, and incubated at +4° C. overnight.

Slide Washes: Coverslips were removed and the slides inserted in racks (6 slides per rack) which were placed in glass slide dishes, wrapped in foil:

| Slide Number | Wash buffer (4° C.) | Wash time | Probe sequence |
|---|---|---|---|
| 1, 2, 3 | 5 × SSC, 0.1% Tween-20 | 2 × 5 min | Seq. No. aZ1 |
| 4, 5, 6 | 5 × SSC, 0.1% Tween-20 | 2 × 5 min | Seq. No. aZ2 |
| 7, 8, 9 | 5 × SSC, 0.1% Tween-20 | 2 × 5 min | Seq. No. aZ3 |
| 10, 11, 12 | 5 × SSC, 0.1% Tween-20 | 2 × 5 min | Seq. No. 16 |

After washing, slides were blow-dried and scanned. The fluorescence was imaged on a slide scanner and the data analysed from ImageQuant software (Molecular Dynamics).

Figure 11:
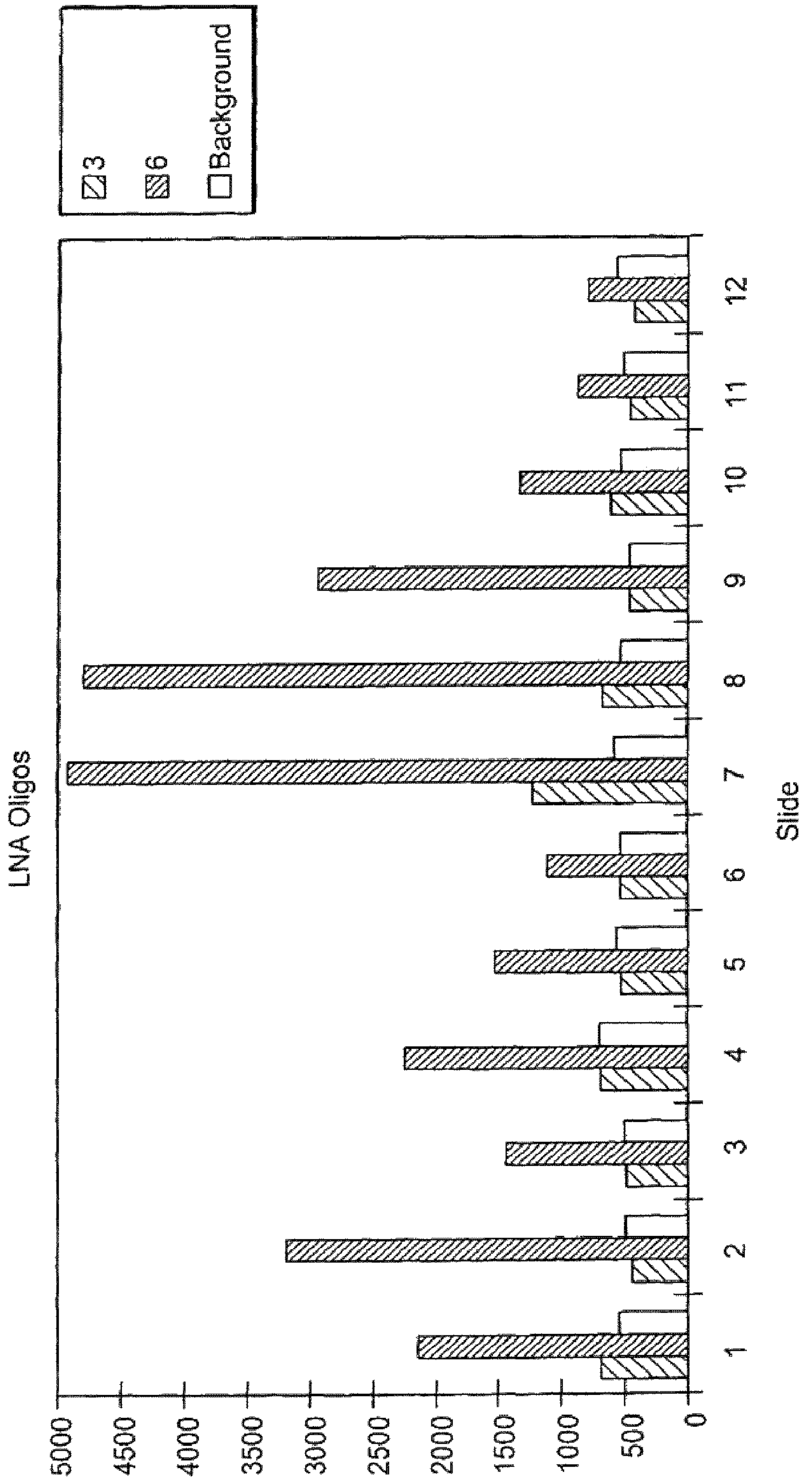
FIG. 11 illustrates hybridisation and detection on an array with different LNA modified Cy3-labelled 8mers.

As shown in FIG. 11, no binding of the Cy3 labelled probes is observed to the mismatched oligo 3 with either the unmodified probe (slide 10-12), single LNA modified probe aZ1 (slide 1-3) single LNA modified probe aZ2 (slide 4-6) or triple LNA modified probe aZ3 (slide 7-9) (i.e. the obtained signal with the mismatched oligo 3 is comparable to the background signal). With complementary oligo 6, specific signals are observed in all cases. The intensity of these signals clearly correlates with the number of LNAs present in the probes and with the concentration of the probes. Each LNA T residue approximately increased the signal strength by about a factor of 2 over that of the normal DNA oligo probe, i.e. aZ1 and aZ2=2× signal of sequence 16, and aZ3=8× signal of sequence 16. The match/mismatch discrimination is good with the LNA T base replacements, and with the increased signal strength, the mismatch discriminations appear to be easier.

EXAMPLE 151

Hybridisation and detection of end mismatches on an array with LNA modified Cy3-labelled 8mers. Slide preparation: Glass slides were aminosilanised using a 10% solution of amino propyl triethoxy silane in acetone followed by washing in acetone. The following oligonucleotides were spotted out at 1 pmol/µl onto the slides:

| Seq No. 9   | 5'-GTGTGGAG-3' |
| Seq No. 15  | 5'-GTGTGGAA-3' |
| Seq No. 131 | 5'-GTGTGGAT-3' |
| Seq No. 132 | 5'-GTGTGGAC-3' |
| Seq No. 133 | 5'-ATGTGGAA-3' |
| Seq No. 134 | 5'-CTGTGGAA-3' |
| Seq No. 135 | 5'-TTGTGGAA-3' |

Ten repeat spots, approximately 1 nl each spot, were performed for each oligonucleotide from each of 6 pens on each of 12 slides.

Probes (LNA monomers in bold):

DNA
Probe No. 1:      5'-Cy3-TTCCACAC-3'

Probe No. 2:      5'-Cy3-GTCCACAC-3'

Probe No. 3:      5'-Cy3-ATCCACAC-3'

Probe No. 4:      5'-Cy3-CTCCACAC-3'

Probe No. 5:      5'-Cy3-TTCCACAT-3'

Probe No. 6:      5'-Cy3-TTCCACAG-3'

LNA
Probe No. 35Z-1:  5'-Cy3-TTCCACAC-3'

Probe No. 35Z-2:  5'-Cy3-GTCCACAC-3'

Probe No. 35Z-3:  5'-Cy3-ATCCACAC-3'

Probe No. 35Z-4:  5'-Cy3-CTCCACAC-3'

Probe No. 35Z-5:  5'-Cy3-TTCCACAT-3'

Probe No. 35Z-6:  5'-Cy3-TTCCACAG-3'

Probes with LNA monomers are prefixed with 35Z- as part of the sequence number. Specific LNA monomers are indicated in italics/bold and are situated at the 3' and 5' ends of the LNA oligos.

Slides and conditions for hybridisation: Each probe sequence was hybridised on a separate slide, and all probe concentrations were 1 fmol/μl. Each probe was diluted in hybridisation buffer (5×SSC, 7% sodium lauryl sarcosine), of which 30 μl was pipetted along the length of each slide, covered with a coverslip, and placed into a plastic box on top of a plastic insert, which was lying on a paper towel wetted with water. Boxes were covered with aluminium foil to keep light out, and incubated at +4° C. overnight.

Slide Washes: Coverslips were removed and the slides inserted in racks (8 slides per rack) which were placed in glass slide dishes, wrapped in foil. All slides were washed in 5×SSC for 2×5 min at +4° C. After washing, slides were blow-dried and scanned. The fluorescence was imaged on a slide scanner and the data analyzed from ImageQuant software (Molecular Dynamics).

Figure 12:
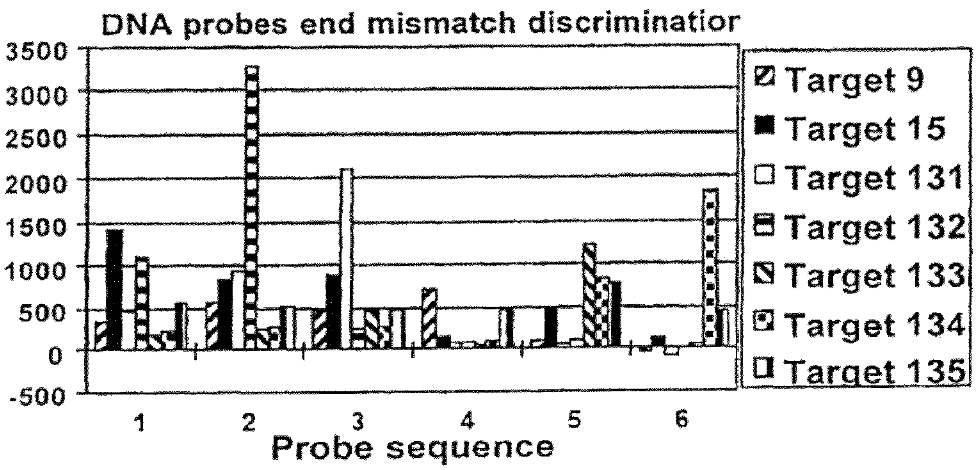
FIGS. 12 and 13 illustrate hybridisation and detection of end mismatches on an array with LNA modified Cy3-labelled 8mers.
Figure 13:
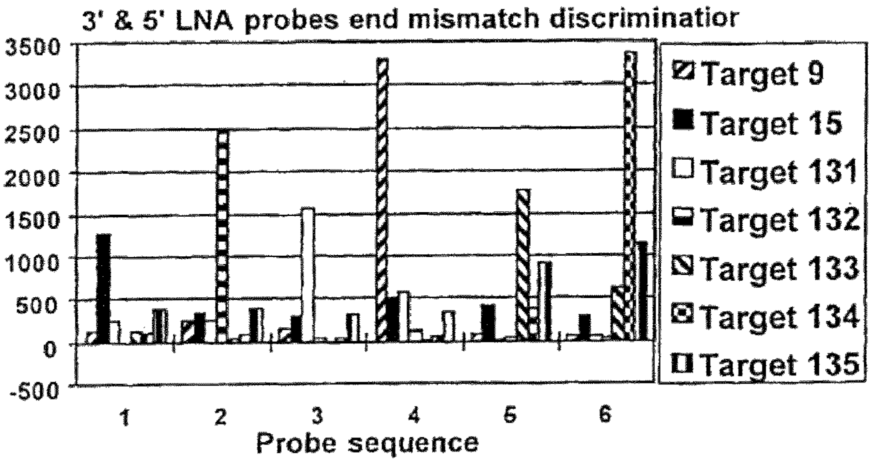

Conclusions: As shown in FIGS. 12 and 13, probes containing LNA nucleosides at their 5' and 3' ends are in the majority of cases significantly better in discriminating between matched and mismatched target sequences than their corresponding unmodified oligonucleotides.

For DNA oligos, C=T mismatches were the most difficult to distinguish, for example, where probe sequence 1 hybridised to target sequence 132 and where probe sequence 5 hybridised to target sequence 134. Other mismatches were visible such as T=T and G=T mismatches, but these spots were less intense, for example where probe sequences 5 and 6 respectively hybridised to target sequence 135. The LNA oligos, significantly reduced these C=T and T=T mismatch spot intensites, to comparable levels to other mismatches. The relative spot intensities of probe sequences 1, 2 and 3 were similar for the DNA and LNA oligos. However, with probe sequences 4, 5 and 6, the LNA oligos gave a significantly increased spot intensity when hybridised to their match target sequences 9, 133 and 134 respectively.

EXAMPLE 152

Hybridization and detection of end mismatches on an array with AT and all LNA modified Cy3-labelled 8mers. Slide preparation: Glass slides were aminosilanized using a 10% solution of amino propyl triethoxy silane in acetone followed by washing in acetone. The following oligonucleotides were spotted out at 1 pmol/μl onto the slides:

| | |
|---|---|
| Seq No. 9 | 5'-GTGTGGAG-3' |
| Seq No. 15 | 5'-GTGTGGAA-3' |
| Seq No. 131 | 5'-GTGTGGAT-3' |
| Seq No. 132 | 5'-GTGTGGAC-3' |
| Seq No. 133 | 5'-ATGTGGAA-3' |
| Seq No. 134 | 5'-CTGTGGAA-3' |
| Seq No. 135 | 5'-TTGTGGAA-3' |

Ten repeat spots, approximately 1 nl each spot, were performed for each oligonucleotide from each of 6 pens on each of 36 slides.

Probes: (LNA monomers in bold):

DNA:

| | |
|---|---|
| Probe No. 1: | 5'-Cy3-TTCCACAC-3' |
| Probe No. 2: | 5'-Cy3-GTCCACAC-3' |
| Probe No. 3: | 5'-Cy3-ATCCACAC-3' |
| Probe No. 4: | 5'-Cy3-CTCCACAC-3' |
| Probe No. 5: | 5'-Cy3-TTCCACAT-3' |
| Probe No. 6: | 5'-Cy3-TTCCACAG-3' |

AT LNA:

| | |
|---|---|
| Probe No. ATZ-1: | 5'-Cy3-**TT**CC**A**C**A**C-3' |
| Probe No. ATZ-2: | 5'-Cy3-G**T**CC**A**C**A**C-3' |
| Probe No. ATZ-3: | 5'-Cy3-**AT**CC**A**C**A**C-3' |
| Probe No. ATZ-4: | 5'-Cy3-C**T**CC**A**C**A**C-3' |
| Probe No. ATZ-5: | 5'-Cy3-**TT**CC**A**C**AT**-3' |
| Probe No. ATZ-6: | 5'-Cy3-**TT**CC**A**C**A**G-3' |

All LNA:

| | |
|---|---|
| Probe No. AIIZ-1: | 5'-Cy3-**TTCCACAC**-3' |
| Probe No. AIIZ-2: | 5'-Cy3-**GTCCACAC**-3' |
| Probe No. AIIZ-3: | 5'-Cy3-**ATCCACAC**-3' |
| Probe No. AIIZ-4: | 5'-Cy3-**CTCCACAC**-3' |
| Probe No. AIIZ-5: | 5'-Cy3-**TTCCACAT**-3' |
| Probe No. AIIZ-6: | 5'-Cy3-**TTCCACAG**-3' |

Probes with LNA monomers are prefixed with ATZ- or AIIZ- as part of the sequence number. Specific LNA monomers are indicated in italics for the LNA oligos.

Slides and conditions for hybridization: Each probe sequence was hybridized on a separate slide, and all probe concentrations were 1 fmol/μl. Each probe was diluted in hybridization buffer (5×SSC, 7% sodium lauryl sarcosine), of which 30 μl was pipetted along the length of each slide, covered with a coverslip, and placed into a plastic box on top of a plastic insert, which was lying on a paper towel wetted with water. Boxes were covered with aluminium foil to keep light out, and incubated at room temperature overnight.

Slide Washes: Coverslips were removed and the slides inserted in racks (9 slides per rack) which were placed in glass slide dishes, wrapped in foil. All slides were washed in 5×SSC for 2×5 minutes at RT. After washing, slides were blow-dried and scanned. The fluorescence was imaged on a slide scanner and the data analyzed from ImageQuant software (Molecular Dynamics).

Figure 15A:
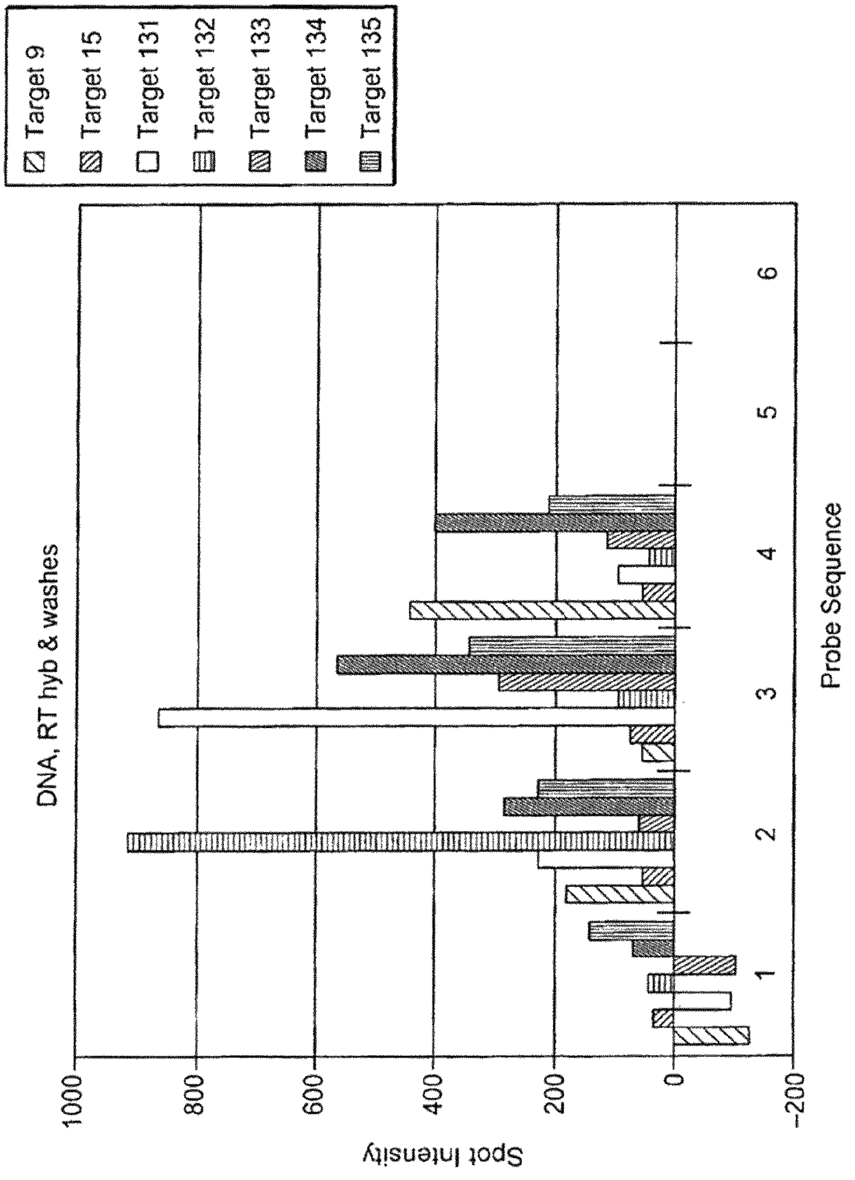
FIGS. 15A, 15B, and 15C illustrate Hybridization and detection of end mismatches on an array with AT and all LNA modified Cy3-labelled 8mers.
Figure 15B:
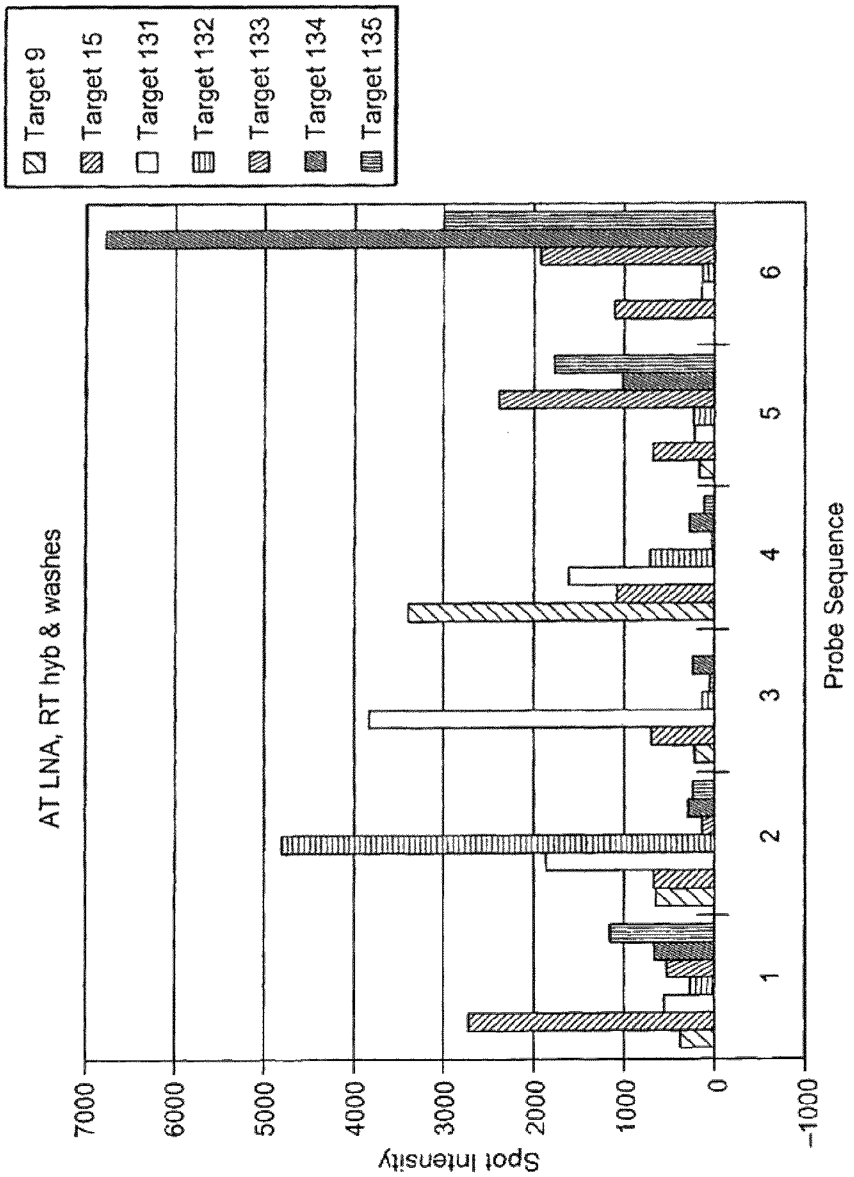
Figure 15C:
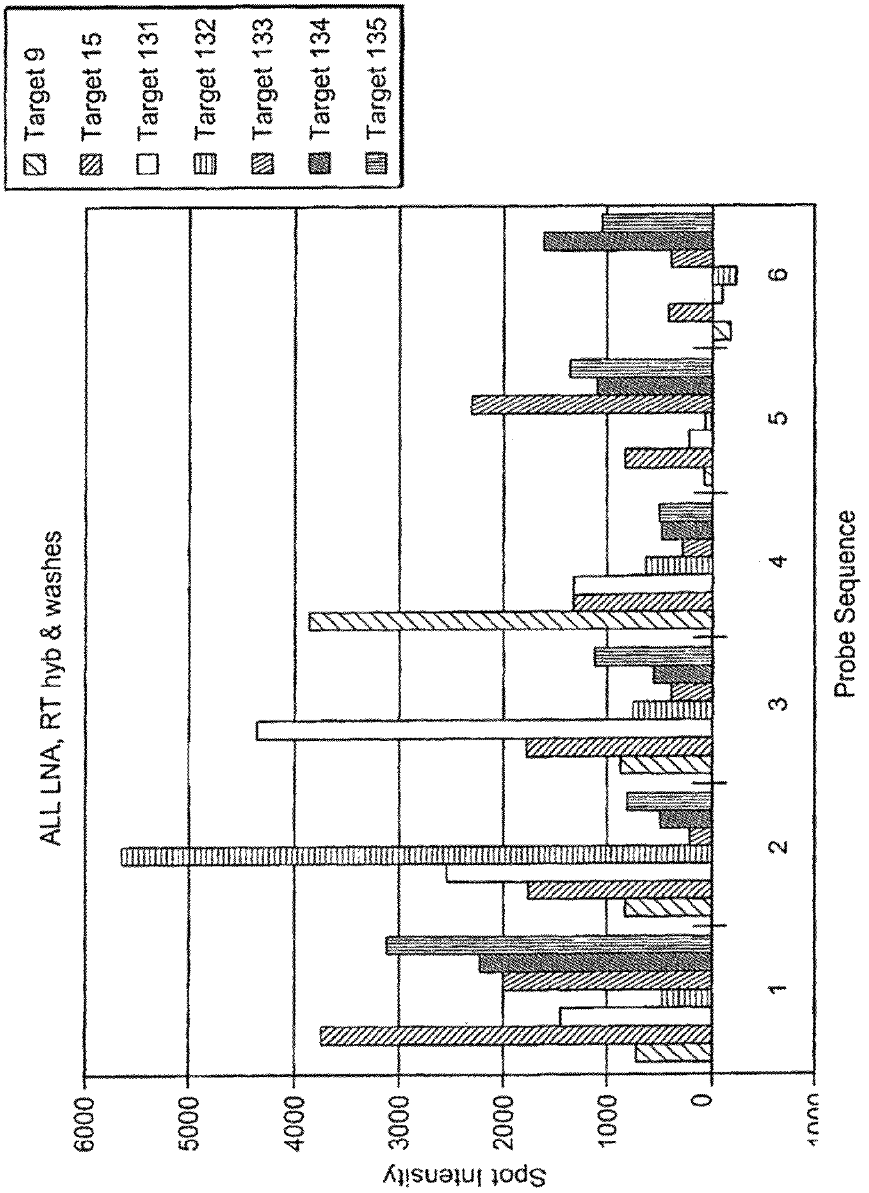

Conclusion: As shown in FIGS. 15A, 15B and 15C, The average intensity of DNA hybridization at room temperature was about 10% of the intensity achieved with the AT or all LNA modified oligos. No spots were seen on slides hybridized with DNA probes 5 and 6. These conditions were therefore not optimal for the DNA probes. However, the match/mismatch discrimination is very good with the LNA nucleoside replacements at the A and T bases. The stringency for the all LNA oligos may not be great enough as the match/mismatch discrimination was not as good as for the AT LNA oligos.

The oligos with LNA modifications worked very well, and the mismatches that were the most difficult to discriminate were;

Probe 1 to target 135=CT mismatch
Probe 2 to target 131=GT mismatch
Probe 3 to target 15=AA mismatch
Probe 4 to target 131=CT mismatch
Probe 5 to target 135=TT mismatch
Probe 6 to target 135=GT mismatch
Probe 6 to target 133=GA mismatch The AT LNA oligos gave good discrimination where these mismatch spot intensities were typically at the most 50% of the intensity of the match spots. For these mismatches, the all LNA oligos gave mismatch spot intensities about 50 to 70% of the match spot intensities. Overall, LNA modifications allows the use of higher temperatures for hybridizations and washes, and end mismatches can be discriminated. These results are at least as good as those from DNA probes hybridised at 4° C. (see example 151).

EXAMPLE 153

Use of [$\alpha^{33}$P] ddNTP's and ThermoSequenase™ DNA Polymerase to Sequence DNA Templates Containing LNA T Monomers. Radiolabelled terminator sequencing reactions were set up in order to test the ability of the LNA T monomer to be accepted as a template for DNA polymerases. The 15mer primer (sequence: 5'-TGC ATG TGC TGG AGA-3') (SEQ ID NO:53) was used to prime the following short oligonucleotide sequences (LNA monomer in bold):

```
Template 1  3'-ACG TAC ACG ACC TCT ACC TTG CTA-5'  (SEQ ID NO: 54)

TemplateTZ1 3'-ACG TAC ACG ACC TCT ACC TTG CTA-5'  (SEQ ID NO: 55)
```

The following reaction mixes were made:

Template 1 Mix:
2 μl ×16 ThermoSequenase Buffer
6 μl Primer 2 pmole/μl
6 μl Template 1 1 pmole/μl
4 μl Water
2μl ThermoSequenase DNA Polymerase (4U/μl)
20 μl Total volume Template TZ1 Mix
2 μl ×16 ThermoSequenase Buffer
6 μl Primer 2 pmole/μl
6 μl Template TZ1 1 pmole/μl
4 μl Water
2μl ThermoSequenase DNA Polymerase (4U/μl)
20 μl Total volume 2 μl Nucleotide mix (7.5 μM each dNTP) was added to each of 8 Eppendorf tubes. 0.5 μl [$\alpha^{33}$P] ddATP was added to tubes 1 and 5. 0.5 μl [$\alpha^{33}$P] ddCTP was added to tubes 2 and 6. 0.5 μl [$\alpha^{33}$P] ddGTP was added to Tubes 3 and 7. 0.5 μl [$\alpha^{33}$P] ddTTP was added to tubes 4 and 8. 4.5 μl of Template 1 mix was added to each of tubes 1-4. 4.5 μl of Template TZ1 mix was added to each of tubes 5-8. All the reactions were incubated at 60° C. for 3 min. The reactions were stopped by the addition of 4 μl formamide/EDTA stop solution. Reactions were heated at 95° C. for 3 min before loading onto a 19% polyacrylamide 7M urea gel. The gel was fixed in 10% acetic acid 10% methanol before transferring to 3 MM paper and drying. The dried gel was exposed to Kodak Biomax autoradiography film.

Figure 18:
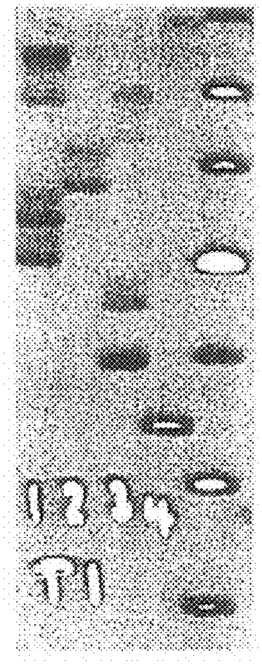
FIGS. 18 and 19 illustrate the use of $[\alpha^{33}P]$ ddNTP's and ThermoSequenase™ DNA Polymerase to sequence DNA templates containing LNA T monomers.
Figure 19:
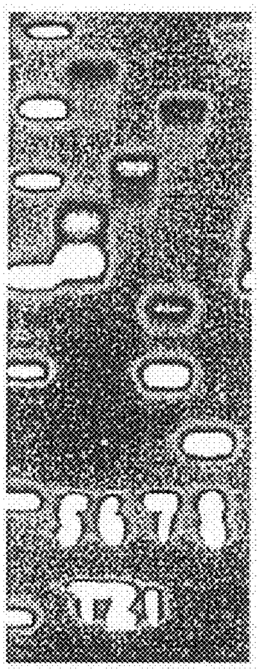

The results are depicted in FIG. 18 (track 1-4) and FIG. 19 (5-8). The tracks correspond to the following reactions: (FIG. 18): Lane 1—ddATP track. Lane 2—ddCTP track. Lane 3—ddGTP track, Lane 4—ddTTP track. Lane 5—8-32 base oligo markers; FIG. 19: Lane A—8-32 base oligo markers. Lane 5—ddATP track. Lane 6—ddCTP track. Lane 7—ddGTP track. Lane 8—ddTTP track.

As is evident from FIGS. 18 and 19, the full sequence of both templates can easily be read from the autorad. The sequence is 5'-TGG AAC GTA-3' which corresponds to the template sequence 3'-ACC TTG CTA-5'. This shows that a single LNA T monomer can act as a template for DNA polymerases. The LNA T monomer is specifically copied as "T" with ddATP being incorporated.

Therapeutic Applications

EXAMPLE 154

LNA modified oligos can be transferred into cells. Experiment with radiolabelled LNA oligos. 10 μmol of a oligodeoxynucleotide (ODN) (ODN#10: 5'-TTA ACG TAG GTG CTG GAC TTG TCG CTG TTG TAC TT-3' (SEQ ID NO:56), a 35-mer complementary to human Cathepsin D) and 10 pmoles of two LNA oligos: AL16 (5'-d(TGT GTG AAA TTG TTA T)-3' (SEQ ID NO:57), LNA nucleosides in bold) and AL17 (5'-d(ATA AAG TGT AAA G)-3' (SEQ ID NO:58), LNA nucleosides in bold) were mixed with T4 polynucleotide Kinase (10 units, BRL cat. no. 510-8004SA), 5 μl gamma-$^{32}$P-ATP 5000 Ci/mmol, 10 uCi/μl (Amersham) in kinase buffer (50 mM Tris/HCl pH 7, 6, 10 mM $MgCl_2$, 5 mM DTT, 0.1 mM EDTA). The samples were incubated for 45 min at 37° C. and afterwards heated to 68° C. for 10 min, and then moved to +0° C. Unincorporated nucleotides were removed by passage over Chroma Spin TE-10 columns (Clontech cat. no. K1320-1). The yields were $5\times10^5$ cpm/μl, $2\times10^5$ cpm/μl and $0.8\times10^5$ cpm/μl for ODN#10, AL16 and AL17, respectively. MCF-7 human breast cancer cells originally obtained from the Human Cell Culture Bank (Mason Research Institute, Rockville) were cultured in DME/F12 culture medium (1:1) supplemented with 1% heat inactivated fetal calf serum (Gibco BRL), 6 ng/ml bovine insulin (Novo) and 2.5 mM glutamax (Life Technologies) in 25 $cm^2$ cell culture flasks (Nunclon, NUNC) and incubated in a hunified incubator at 37° C., 5% $CO_2$, 20% $O_2$, 75% $N_2$. The MCF-7 cells were approximately 40% confluent at the time of the experiment. A small amount (less than 0.1 μmol) of the kinased oligos were mixed with 1.5 μg pEGFP-NI plasmid (Clontech cat. no. 60851) and mixed with 100 μl diluted FuGENE6 transfection agent (Boehringer Mannheim cat no. 1 814 443), dilution: 5 μl FuGENE6 in 95 μl DME/F12 culture medium without serum. The FuGENE6/DNA/oligo-mixture were added directly to the culture medium (5 ml) of adherent growing MCF-7 cells and incubated with the cells for 18 hours, closely following the manufacturers directions. Three types of experiments were set up. 1) ODN#10+pEGFP-NI; 2) AL16+pEGFP-NI; 3) AL17+pEGFP-NI. Cellular uptake of DNA/LNA material were studied by removing FuGENE6/DNA/oligo-mixture containing medium (an aliquot was transferred to a scintillator vial). Cells were rinced once with phosphate buffered saline (PBS), fresh culture medium was added and cells inspected by fluorescence microscopy. Approximately 30% of the transfected cells contained green fluorescent material, indicating that approximately 30% of the cells have taken up the pEGFP-NI plasmid and expressed the green fluorescent protein coded by this plasmid. Following fluorescence microscopy the adherent MCF-7 cells were removed from the culture flasks. Briefly, the culture medium was removed, then cells were rinsed with a solution of 0.25% trypsin (Gibco BRL) 1 mM EDTA in PBS (without $Mg^{2+}$ and $Ca^{2+}$), 1 ml trypsin/EDTA was added and cells were incubated 10 min at 37° C. During the incubation the cells loosened and were easily resuspended and transferred to scintillator vials. The cells were then completely dissolved by addition of 10 ml Optifluor scintillation coctail (Packard cat. no. 6013199), and the vials were counted in a Wallac 1409 scintillation counter. The results were as follows: 1) ODN#10+pEGFP-NI: approximately 1.4% of the added radioactivity were associated with cellular material; 2) AL16+pEGFP-NI: approximately 0.8% of the added radioactivity were associated with cellular material; and 3) AL17+pEGFP-NI: approximately 0.4% of the added radioactivity were associated with cellular material. We conclude that 0.4-0.8% of the added LNA oligos were taken up by the cells.

EXAMPLE 155

LNA is efficiently delivered to living human MCF-7 breast cancer cells. To increase the efficiency of LNA-uptake by human MCF-7 cells different transfection agents were tested with various concentrations of 5'FITC-labelled LNAs and DNA. The oligonucleotides described in the table below were tested.

TABLE

Oligonucleotides tested

| Name | Sequence (LNA monomers in bold) | Characteristics |
|---|---|---|
| AL16 | 5'-**TGT GTG AAA TTG TTA** T-3' (SEQ ID NO: 59) | LNA, enzym. FITC-labeled |
| AL17 | 5'-**ATA AAG TGT AAA** G-3' (SEQ ID NO: 60) | LNA, enzym. FITC-labeled |
| EQ3009-01 | 5'-**TGC CTG CAG GTC GAC** T-3' (SEQ ID NO: 61) | LNA-FITC-labeled |
| EQ3008-01 | 5'-TGC CTG CAG GTC GAC T-3' (SEQ ID NO: 62) | DNA-FITC-labeled |

Figure 16:
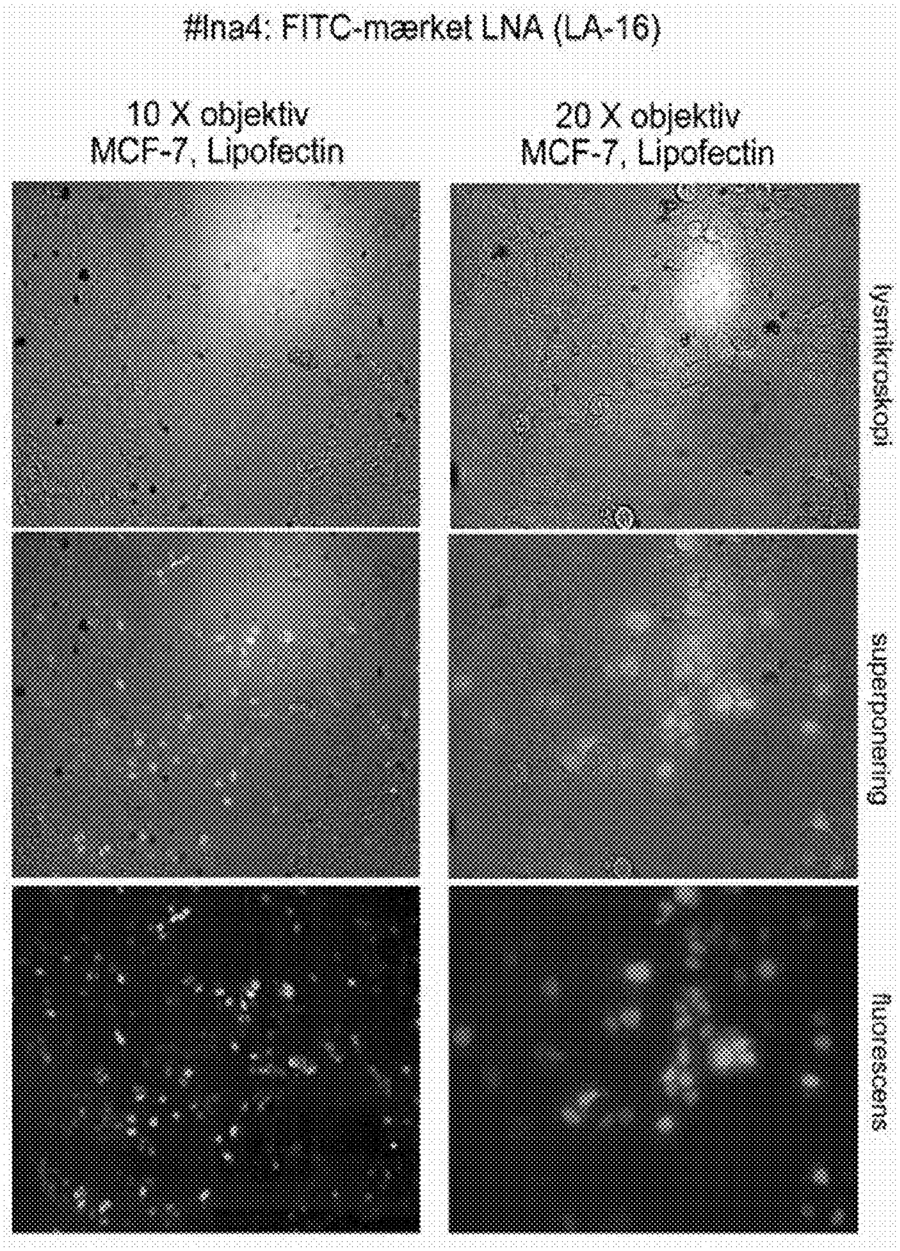
FIGS. 16 and 17 illustrate that LNA can be delivered to living human MCF-7 breast cancer cells.
Figure 17:
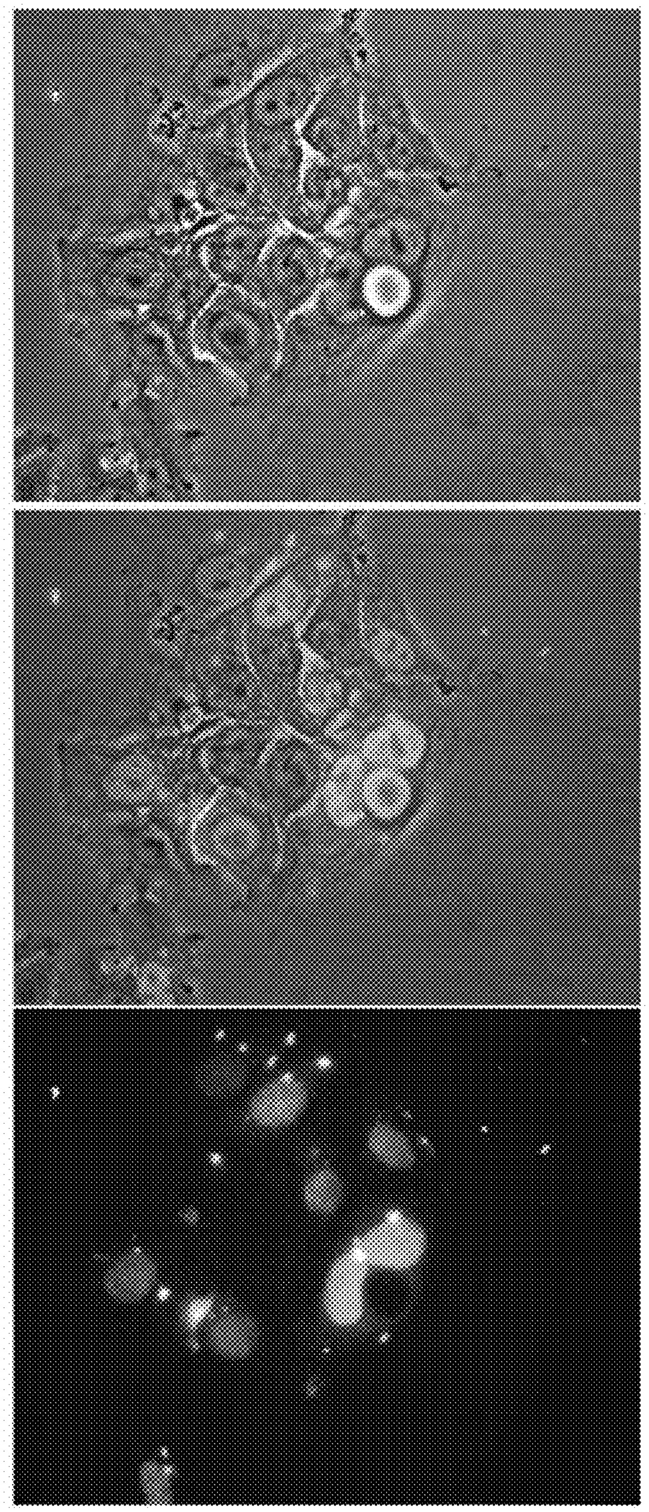

AL16 and AL17 were enzymatically labelled with FITC as described in Example 128. EQ3009-01 and EQ3008-01 were labelled with FITC by standard solid phase chemistry. Three transfection agents were tested: FuGENE-6 (Boehringer Mannheim cat. no. 1 814 443), SuperFect (Quiagen cat. no. 301305) and Lipofectin (GibcoBRL cat. no. 18292-011). Human MCF-7 breast cancer cells were cultured as described previously (Example 154). Three days before the experiments the cells were seeded at a cell density of approx. 0.8×$10^4$ cells per $cm^2$. Depending on the type of experiment the MCF-7 cells were seeded in standard T25 flasks (Nunc, LifeTechnologies cat. no. 163371A), 24 wells multidish (Nunc, LifeTechnologies cat. no. 143982A) or slide flasks (Nunc, LifeTechnologies cat. no. 170920A). The experiments were performed when cells were 30-40% confluent. Cellular uptake of LNA and DNA was studied at serum-free conditions, i.e. the normal serum containing DME/F12 medium was removed and replaced with DME/F12 without serum before the transfection-mixture was added to the cells. Under these conditions SuperFect proved to be toxic to the MCF-7 cells. Transfection mixtures consisting of SuperFect and either plasmid DNA (pEGFP-N1, Clontech cat. no. 6085-1), oligo DNA or oligo LNA was equally toxic to MCF-7 cells. In contrast to SuperFect, FuGene6 and Lipofectin worked well with plasmid DNA (pEGFP-N1). However, only lipofectin was capable of efficient delivery of oligonucleotides to living MCF-7. Briefly, efficient delivery of FITC-labelled LNA and DNA to MCF-7 cells was obtained by culturing the cells in DME/F12 with 1% FCS to approx. 40% confluence. The Lipofectin reagent was then diluted 40× in DME/F12 medium without serum and combined with the oligo to a concentration of 750 nM oligo. The oligo-Lipofectin complex was allowed to form for 15 min at r.t., and further diluted with serum-free medium to at final concentration of 250 nM oligo, 0.8 ug/ml Lipofectin. Then, the medium was removed from the cells and replaced with the medium containing oligo-Lipofectin complex. The cells were incubated at 37° C. for 6 hours, rinsed once with DME/F12 medium without serum and incubated for a further 18 hours in DME/F12 with 1% FCS at 37° C. The result of the experiment was evaluated either directly on living cells in culture flasks or in 24 wells multidishes or on cells cultured in slide flasks and fixed in 4% ice-cold PFA. In all cases a Leica DMRB fluorescence microscope equipped with a high resolution CCD camera was used. The result with living cells is shown in FIG. 16 and the result with fixed cells cultured in slide flask is shown in FIG. 17. Both the cells in FIGS. 16 and 17 was transfected with the FITC-labelled AL16 LNA molecule. By counting total number of cells and green fluorescent cells in several fields we observe that FITC-labelled AL16 LNA was transfected into approximately 35% of the MCF-7 cells. Importantly, we saw that the LNA predominantly was localised in the nuclei of the cells (FIG. 17). This is noteworthy, since nuclear uptake of fluorescent oligos correlates with their antisense activity (Stein C. A. et al. (1997) Making sense of antisense: A debate. In HMS Beagle: A BioMedNet Publication (http://hmsbeagle.com/06/cutedge/overwiev.htm)). Increasing the amount of oligo and lipofectin up to a final concentration of 1250 nM oligo and 4 ug/ml lipofectin only increased the percentage of green fluorescent cells marginally. Increasing the concentration even further was toxic for the cells. Similar results were obtained with the other LNAs and the FITC-labelled oligo DNA (see the table above). We conclude that: 1) LNA can be efficiently delivered to living MCF-7 breast cancer cells by Lipofectin-mediated transfection. 2) A consistent high fraction, 30% or more of cells, is transfected using a final concentration of 250 nM LNA, 0.8 ug Lipofectin pr. ml growth medium without serum. Increasing the concentrations of LNA and Lipofectin up to 5 times only increased the transfection yield marginally. 3) The procedure transfected the LNA into the nuclei of the cells, which according to literature is a good indication that such transfected LNAs may exhibit antisense effects on cells.

EXAMPLE 156

LNA modified oligos can be transferred into cells. Experiment with fluorescein labelled LNA oligos. Two LNA oligos: AL16 (5'-TGT GTG AAA TTG TTA T-3' (SEQ ID NO:63), LNA nucleosides in bold) and AL17 (5'-ATA AAG TGT AAA G-3' (SEQ ID NO:64), LNA nucleosides in bold) were labeled with fluorescein as described in Example 128. MCF-7 human breast cancer cells were cultured as described in Example 154. Three types of experiments were set up. 1) approximately 1.5 μg FITC-labelled AL16; 2) approximately 1.5 μg FITC-labelled AL17; and 3) approximately 0.75 μg FITC-labelled AL16 and 0.75 μg pRSVβgal plasmid (a plasmid expressing the bacterial lac Z gene coded enzyme β-galactosidase, Tulchinsky et. al. (1992) PNAS, 89, 9146-50). The two LNA oligos and the LNA-plasmid mix were mixed with FuGENE6 and added to MCF-7 cells as described in Example 154. After incubation for 18 hours cellular uptake of the LNA oligos were assessed by fluorescence microscopy of the cell cultures. A part of the treated cells contained green fluorescent material (see FIG. 16), indicating that cells take up the fluorescein labelled LNA. The fluorescein labelled AL16 appeared superior to fluorescein labelled AL17 in this respect. After fluorescence microscopy the culture medium were removed from the cells treated both with fluorescein labelled AL16 and pRSVβgal. The cells were washed once with PBS, fixed in 2% (v/v) formaldehyde, 0.2% (v/v) glutaraldehyde at 4° C. for 5 min and β-galactosidase containing cells were stained blue with X-gal (5-bromo-4-chloro-3-indoyl β-D-galactopyranosid) which turns from colorless to blue in the presence of β-galactosidase activity. The X-gal staining showed that the pRSVβgal effectively had been transferred into cells. We conclude that the fluorescein LNA oligos were taken up by the cells.

EXAMPLE 157

LNA modified oligos are relatively stable under cell culture conditions. Following fluorescence microscopy as described in Example 156 cells treated only with the fluorescein labelled AL16 LNA were allowed to incubate for an additional 3 days. During this period of time the number of green fluorescent cells appeared unaltered. We conclude that fluorescein labelled LNA oligos has a good stability under the conditions prevailing in cell culture.

EXAMPLE 158

Figure 14:
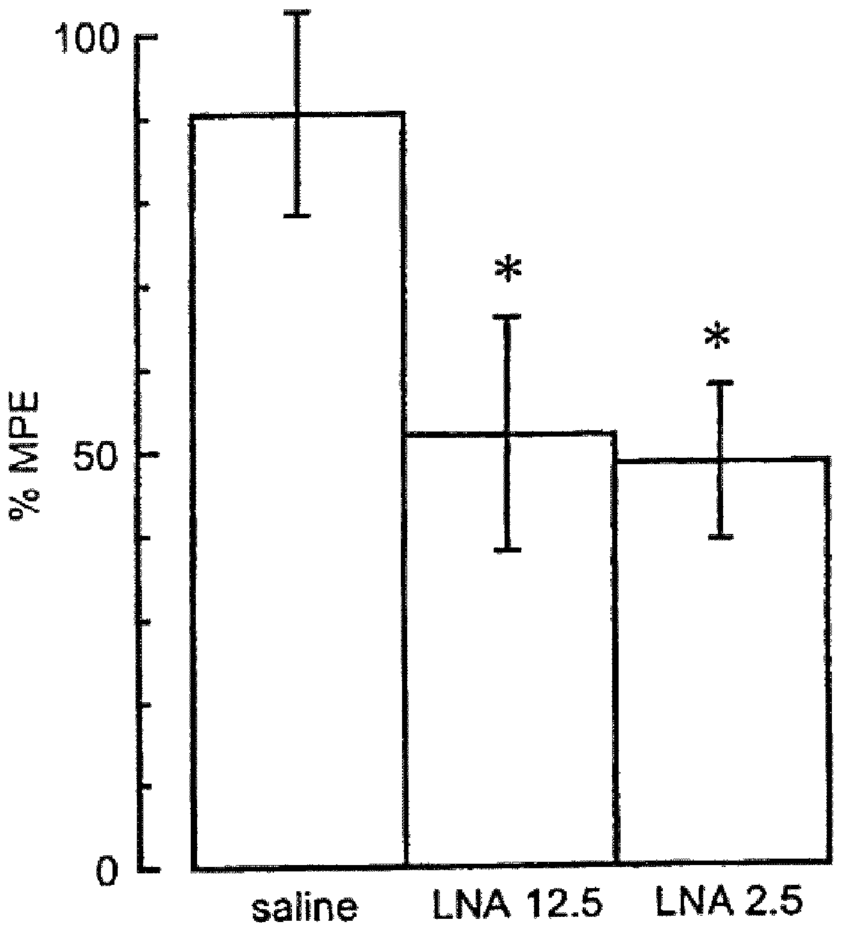
FIG. 14 illustrates blockade by LNA of [D-Ala2]deltorphin-induced antinociception in the warm water tail flick test in conscious rats.

Blockade by Antisense Locked Nucleic Acids (LNA) of [D-Ala2]Deltorphin-Induced Antinociception in the Warm Water Tail Flick Test in Conscious Rats. Male Sprague-Dawley rats (300 g) were implanted with an intrathecal (i.th). polyethylene catheter and allowed to recover for at least 5 days before start of injections (including controls). The antisense LNA compounds (12.5 and 2.5 μg per injection) were administered in a 5 μl volume twice-daily (08.00 and 17.00 h) for 3 days. No signs of non-specific effects or toxicity could be detected, as shown by observations of locomotor behavior and measurements of body weight. The day after the last injection the rats were injected with [D-Ala2]deltorphin (60 μg, i.th) and tested in the warm water (52° C.) tail flick test for δ opioid receptor-mediated antinociception. Data are presented in FIG. 14 as medians based on 6-8 animals per group (data converted to percent maximum possible response, % MPE). Statistical analyses were performed by means of Kruskal-Wallis 1-way ANOVA by ranks, followed by comparisons of treatments versus control. As shown in FIG. 14, deltorphin produced a robust antinociceptive effect in saline-treated controls. This response was statistically significantly suppressed in both antisense LNA groups (12.5 and 2.5 μg) as compared with saline-treated controls.

LNA Solid Supports

EXAMPLE 159

General method for DMT-LNA nucleoside succinates. Base protected DMT-LNA nucleoside and succinic anhydride (1.5 equivalents) were taken in anhydrous ethylene dichloride (~10 ml/g of nucleoside). To the mixture, triethylamine (2 equivalents) was added and the mixture was stirred at room temperature. Reaction was followed by HPLC (conditions same as for tritylation). After complete reaction (>95%), reaction mixture was concentrated, coevaporated with ethylene dichloride and acetonitrile, and dried in vacuo to remove triethylamine. Residue was dissolved in ethylene dichloride or ethyl acetate (~100 ml/g of starting nucleoside), washed with cold 10% citric acid (3×80 ml/g) and cold water (3×80 ml/g). Organic layer was dried over anhydrous sodium sulfate, filtered and concentrated with or without addition of 1-2 equivalents of triethylamine. Residual solid was coevaporated with anhydrous acetonitrile (2-3×) and dried in vacuo to give pure product as white solid.

General method for LNA nucleoside supports. Base protected DMT-LNA-nucleoside succinate (free acid or triethylammonium salt, 65 micromol/g of support), amino derivatised support (Primer Support™ 30HL, 160 micromol amino groups/g of support), DMAP (3 mg/g of support) and 1-(3-[dimethylamino]propyl)-3-ethylcarbodimide hydrochloride (80 mg/g of support) were taken in anhydrous pyridine (6 ml/g of support). To this mixture, triethylamine (16 microliter/g of support) was added and the mixture was kept on a shaker at 150 rpm overnight. Support was filtered, washed with methanol (3×10 ml/g of support) and dichloromethane (3×10 ml/g of support). After air drying, support was dried in vacuo for 0.5 h. To this 6% DMAP in anhydrous acetonitrile (Cap A, ~3 ml/g of support) and a mixture of 20% acetic anhydride/30% 2,4,6-collidine/50% acetonitrile (Cap B, ~3 ml/g of support) were added. The micture was kept on shaker for 5 h. Support was filtered, washed with anhydrous dichloromethane (2×10 ml/g of support) and dried as above. It was resuspended in a mixture of Cap A and Cap B (total vol. 6 ml/g of support) and kept on shaker overnight. Support was filtered, washed with methanol (6×10 ml/g of support), dichloromethane (3×10 ml/g of support) and dried in air. It was further dried in vacuo for 5-6 h. Loading was determined by dimethoxytrityl assay and was found to be approx. 40 μmol/g.

EXAMPLE 160

First Strand cDNA Synthesis Using Poly dT Primers Containing LNA T monomers. Reactions were set up in order to test the ability of poly dT primers containing LNA T residues to prime $1^{st}$ strand cDNA synthesis. The following poly dT primers were tested (LNA monomers are in bold):

RTZ1 5'-TTT TTT TTT TTT TT-3' (SEQ ID NO: 65)

RTZ2 5'-TTT TTT TTT TTT TT-3' (SEQ ID NO: 66)

RTZ3 5'-TTT TTT TTT TTT TT-3' (SEQ ID NO: 67)

RTZ4 5'-TTT TTT TTT TTT TT-3' (SEQ ID NO: 68)

RTZ5 5'-TTT TTT TTT T-3' (SEQ ID NO: 69)

Anchored poly dT primer from RPK0140 kit Cy Dye cDNA labelling kit (Amersham Pharmacia Biotech) was as a control.

Reactions were set up as follows for each of the primers above:

1 μl *Arabidopsis* mRNA 0.5μg/μl
2 μl poly dT primer 8 pmoles/μl
4 μl ×5 AMV Reverse Transcriptase buffer
1μl Water
8 μl Total volume This mix was then heated to 75° C. for 3 min and then allowed to cool at room temperature for at least 10 min.

The following was then added to each of the reactions:

1 μl 80 mM Sodium Pyrophosphate
1 μl Human Placental Ribonuclease Inhibitor 20U/μl
7 μl 0.5 mM dNTP solution
2 μl [$\alpha^{33}$P] dATP 10mCi/ml3000Ci/mmole
1μl AMV Reverse Transcriptase 20U/μl
20 μl Total volume The reactions were incubated at 42° C. for 2 hours. The reactions were then heated at 95° C. for 3 min before loading onto a 6% polyacrylamide 7M urea gel. The gel was fixed in 10% acetic acid/10% methanol before transferring to 3 MM paper and drying. The dried gel was exposed to Kodak Biomax autoradiography film overnight.

The autoradiograph clearly showed that the LNA containing oligonucleotide primers RTZ1-4 were able to efficiently prime cDNA synthesis. The amount and intensity of the cDNA products produced in these reactions was equal to that produced with the anchored poly dT control oligonucleotide. RTZ 5 did produce some cDNA, but the yield was significantly lower than that produced with the control oligo primer.

EXAMPLE 161

LNA-modified oligonucleotides covalently attached to Separose beads function efficiently in the sequence specific capture of RNA molecules. Three oligos were synthesised by chemistry (Amy Mueller) for evaluation in poly (rA) binding.

$NH_2$(T8)-T Control $NH_2$(T15)-T Control (SEQ ID NO:70)

$NH_2$(LNA-T8)-T Test 200 nmol of each oligo were coupled to 50 mg of prepared CNBr-activated Separose 4B (Pharmacia) per booklet instructions. Unreacted binding sites on the resin were blocked in 100 nM Tris pH 8.0.

Table of Oligo Binding Data

| Steps | T9 oligo $A_{260}$ units | T16 oligos $A_{260}$ units | LNA T9 oligo $A_{260}$ units | No oligo Control |
|---|---|---|---|---|
| Oligo reacted | 14.7 (200 nM) | 26.0 (200 nM) | 14.7 (200 nM) | 0 |
| Unbound oligo | 5.50 | 10.43 | 4.20 | — |
| ∴Bound oligo | 9.20 | 15.57 | 10.50 | — |
| % Bound | 62.6% | 59.9% | 71.4% | — |

Oligo bound resins were divided into two portions (~25 mg resin each) for poly (rA) binding analysis in duplicate. Poly (rA) Pharmacia #27-4110-01 (dissolved at 28.2 $A_{260}$ units/ml in binding buffer) was used for binding. Five (5) $A_{260}$ units were bound to duplicate 25 mg portions of each oligo bound resin per SOP QC 5543. Unbound "breakthrough" poly (rA) was quantitated by $A_{260}$ absorbance and used to calculate bound. The fate of the bound poly (rA) was tracked through Low salt buffer wash and several elutions. As shown in Table 10 both the LNA and DNA coated beads function efficiently in the capture of poly (rA) target molecules. The LNA coated beads, however, bind the poly (rA) target much more tightly than the DNA coated beads as evidenced by the poly (rA) elution profiles of the different beads. We conclude that 1) an LNA T9 oligo is efficient in the capture of RNA molecules containing a stretch of A residues and that 2) the captured RNA molecules are bound much more tightly to the LNA T9 oligo beads than to the control DNA T9 and DNA T16 oligo.

TABLE 1

| Monomer Z | | | | | |
|---|---|---|---|---|---|
| Oligo | Target | $T_m$ No. | $T_m$ (° C.) $Na_2HPO_4$/EDTA | $T_m$ (° C.) $Na_2HPO_4$/NaCl/EDTA | $T_m$ (° C.) $Na_2HPO_4$/TMAC |
| 5'-d(GTGATATGC)-3' | 5'-d(GCATATCAC)-3' | 1 | | 28 | 42 |
| | 5'-d(GCATTTCAC)-3' | 2 | | 12 | 31 |
| | 5'-d(GCATGTCAC)-3' | 3 | | 19 | 23 |
| | 5'-d(GCATCTCAC)-3' | 4 | | 11 | 30 |
| | 5'-d(GCATAACAC)-3' | 5 | | 12 | |
| | 5'-d(GCATAGCAC)-3' | 6 | | <10 | |
| | 5'-d(GCATACCAC)-3' | 7 | | <10 | |
| | 5'-(GCAUAUCAC)-3' | 8 | | 28 | |
| | 5'-(GCAUCUCAC)-3' | 9 | | 10 | |
| 5'-d(G**T**GA**T**A**T**GC)-3' | 5'-d(GCATATCAC)-3' | 10 | | 44 | 56 |
| | 5'-d(GCATTTCAC)-3' | 11 | | 27 | 43 |
| | 5'-d(GCATGTCAC)-3' | 12 | | 30 | 43 |
| | 5'-d(GCATCTCAC)-3' | 13 | | 23 | 38 |
| | 5'-d(GCATAACAC)-3' | 14 | | 28 | |

TABLE 1-continued

| Monomer Z | | | | | |
|---|---|---|---|---|---|
| Oligo | Target | $T_m$ No. | $T_m$ (° C.) $Na_2HPO_4$/EDTA | $T_m$ (° C.) $Na_2HPO_4$/NaCl/EDTA | $T_m$ (° C.) $Na_2HPO_4$/TMAC |
| | 5'-d(GCATAGCAC)-3' | 15 | | 28 | |
| | 5'-d(GCATACCAC)-3' | 15A | | 29 | |
| | 5'-(GCAUAUCAC)-3' | 16 | | 50 | |
| | 5'-(GCAUCUCAC)-3' | 17 | | 33 | |
| 5'-d(G**T**GA**G**A**T**GC)-3' | 5'-d(GCATATCAC)-3' | 18 | | 26 | 39 |
| | 5'-d(GCATTTCAC)-3' | 19 | | 33 | 44 |
| | 5'-d(GCATGTCAC)-3' | 20 | | 28 | 38 |
| | 5'-d(GCATCTCAC)-3' | 21 | | 49 | 57 |
| | 5'-d(GCATAACAC)-3' | 22 | | <15 | |
| | 5'-d(GCATAGCAC)-3' | 23 | | <15 | |
| | 5'-d(GCATACCAC)-3' | 24 | | <15 | |
| | 5'-(GCAUAUCAC)-3' | 24A | | 34 | |
| | 5'-(GCAUCUCAC)-3' | 24B | | 59 | |
| 5'-d(G**T**GA**U**A**T**GC)-3' | 5'-d(GCATATCAC)-3' | 25 | | 44 | 56 |
| | 5'-d(GCATTTCAC)-3' | 26 | | 25 | 44 |
| | 5'-d(GCATGTCAC)-3' | 27 | | 32 | 43 |
| | 5'-d(GCATCTCAC)-3' | 28 | | 24 | 37 |
| | 5'-d(GCATAACAC)-3' | 29 | | 27 | |
| | 5'-d(GCATAGCAC)-3' | 30 | | 28 | |
| | 5'-d(GCATACCAC)-3' | 31 | | 20 | |
| 5'-d(GTGAGATGC)-3' | 5'-d(GCATATCAC)-3' | 32 | | 17 | 34 |
| | 5'-d(GCATTTCAC)-3' | 33 | | 16 | 30 |
| | 5'-d(GCATGTCAC)-3' | 34 | | 15 | 28 |
| | 5'-d(GCATCTCAC)-3' | 35 | | 33 | 44 |
| | 5'-d(GCATAACAC)-3' | 36 | | 9.0 | |
| | 5'-d(GCATAGCAC)-3' | 37 | | <5 | |
| | 5'-d(GCATACCAC)-3' | 38 | | <5 | |
| | 5'-(GCAUCUCAC)-3' | 38A | | 33 | |
| 5'-d(GGTGGTTTGTTTG)-3' (SEQ ID NO: 71) | 5'-d(CAAACAAACCACA)-3' (SEQ ID NO: 72) | 39 | 31 | 47 | 55 |
| | 5'-(CAAACAAACCACA)-3' (SEQ ID NO: 73) | 39A | 32 | 52 | |
| 5'-d(GGTGG**TTTG**TTTG)-3' (SEQ ID NO: 74) | 5'-d(CAAACAAACCACA)-3' (SEQ ID NO: 75) | 40 | 40 | 57 | 67 |
| | 5'-(CAAACAAACCACA)-3' (SEQ ID NO: 76) | 40A | 50 | 70 | |
| d(**GGTGGTTTGTTT**G)-3' (SEQ ID NO: 77) | 5'-d(CAAACAAACCACA)-3' (SEQ ID NO: 78) | 41 | 67 | 83 | >90 |
| | 5'-(CAAACAAACCACA)-3' (SEQ ID NO: 79) | 41A | 85 | >93 | |
| 5'-d(TTTTTTTTTTTTTT)-3' (SEQ ID NO: 80) | 5'-d(AAAAAAAAAAAAAA)-3' (SEQ ID NO: 81) | 42 | | 36 | |
| | 5'-(AAAAAAAAAAAAAA)-3' (SEQ ID NO: 82) | 43 | | 32 | |
| 5'-d(TTTTTT**T**TTTTTTT)-3' (SEQ ID NO: 83) | 5'-d(AAAAAAAAAAAAAA)-3' (SEQ ID NO: 84) | 44 | | 36 | |
| | 5'-(AAAAAAAAAAAAAA)-3' (SEQ ID NO: 85) | 45 | | 32 | |
| 5'-d(TTTTTTT**TT**TTTTT)-3' (SEQ ID NO: 86) | 5'-d(AAAAAAAAAAAAAA)-3' (SEQ ID NO: 87) | 46 | | 34 | |
| | 5'-(AAAAAAAAAAAAAA)-3' (SEQ ID NO: 88) | 47 | | 40 | |
| 5'-d(TTTTT**TTTT**TTTTT)-3' (SEQ ID NO: 89) | 5'-d(AAAAAAAAAAAAAA)-3' (SEQ ID NO: 90) | 48 | | 42 | |
| | 5'-(AAAAAAAAAAAAAA)-3' (SEQ ID NO: 91) | 49 | | 52 | |
| 5'-d(TTTT**T**T**T**T**T**T**T**TTT)-3' (SEQ ID NO: 92) | 5'-d(AAAAAAAAAAAAAA)-3' (SEQ ID NO: 93) | 50 | | 47 | |
| | 5'-(AAAAAAAAAAAAAA)-3' (SEQ ID NO: 94) | 51 | | 53 | |
| 5'-d(**TTTTTTTTT**T)-3' (SEQ ID NO: 95) | 5'-d(AAAAAAAAAAAAAA)-3' (SEQ ID NO: 96) | 52 | | 80 | |
| | 5'-(AAAAAAAAAAAAAA)-3' (SEQ ID NO: 97) | 53 | | 70 | |
| | 5'-d(AAAACAAAA)-3' | 54 | | 63 | |
| | 5'-d(AAAAGAAAA)-3' | 55 | | 55 | |
| | 5'-d(AAAATAAAA)-3' | 56 | | 65 | |
| 5'-d(G**T**GA**A**A**T**GC)-3' | 5'-d(GCATATCAC)-3' | 57 | | 26 | |
| | 5'-d(GCATTTCAC)-3' | 58 | | 45 | |
| | 5'-d(GCATGTCAC)-3' | 59 | | 23 | |
| | 5'-d(GCATCTCAC)-3' | 60 | | 25 | |
| 5'-d(GTGA$^{Me}$CATGC)-3' | 5'-d(GCATATCAC)-3' | 61 | | <15 | |
| 5'-d(G**T**GA$^{Me}$**C**A**T**GC)-3' | 5'-d(GCATATCAC)-3' | 63 | | 32 | |
| | 5'-d(GCATTTCAC)-3' | 64 | | 27 | |

TABLE 1-continued

| Monomer Z | | | | | |
|---|---|---|---|---|---|
| Oligo | Target | $T_m$ No. | $T_m$ (° C.) $Na_2HPO_4$/ EDTA | $T_m$ (° C.) $Na_2HPO_4$/ NaCl/EDTA | $T_m$ (° C.) $Na_2HPO_4$/ TMAC |
| 5'-d(GCATGTCAC)-3' | | 65 | | 53 | |
| | 5'-d(GCATCTCAC)-3' | 66 | | 32 | |
| 5'-d(G**T**GA**C**A**T**GC)-3' | 5'-d(GCATATCAC)-3' | 67 | | 32 | |
| | 5'-d(GCATGTCAC)-3' | 69 | | 52 | |
| 5'-d(**GTGATATG**$^{Me}$**C**)-3' | 5'-d(GCATATCAC)-3' | 71 | | 64 | |
| | 5'-d(GCATGTCAC)-3' | 73 | | 52 | |
| | 5'-(GCAUAUCAC)-3' | 75 | | 74 | |
| | 5'-(GCAUCUCAC)-3' | 76 | | 60 | |
| | 5'-d(CACTATACG)-3' | 77 | | 40 | |
| 5'-d(G**T**G**TTTT**GC)-3' | 5'-d(GCAAAACAC)-3' | 78 | | 52 | |

TABLE 2

| Monomer V | | | | | |
|---|---|---|---|---|---|
| Oligo | Target | $T_m$ No. | $T_m$ (° C.) $Na_2HPO_4$/ EDTA | $T_m$ (° C.) $Na_2HPO_4$/ NaCl/EDTA | $T_m$ (° C.) $Na_2HPO_4$/ TMAC |
| 5'-d(TTTTTTT**T**TTTTTT)-3' | 5'-d(AAAAAAAAAAAAAA)-3' (SEQ ID NO: 99) | | | 32 | |
| (SEQ ID NO: 98) | 5'-(AAAAAAAAAAAAAA)-3' (SEQ ID NO: 100) | | | 27 | |
| 5'-d(TTTTTT**TT**TTTTTT)-3' | 5'-d(AAAAAAAAAAAAAA)-3' (SEQ ID NO: 102) | | | 31 | |
| (SEQ ID NO: 101) | 5'-(AAAAAAAAAAAAAA)-3' (SEQ ID NO: 103) | | | 28 | |
| 5'-d(TTTTTT**T**T**T**TTTTT)-3' | 5'-d(AAAAAAAAAAAAAA)-3' (SEQ ID NO: 105) | | | 30 | |
| (SEQ ID NO: 104) | 5'-(AAAAAAAAAAAAAA)-3' (SEQ ID NO: 106) | | | 23 | |
| 5'-d(TTTTT**TTTT**TTTTT)-3' | 5'-d(AAAAAAAAAAAAAA)-3' (SEQ ID NO: 108) | | | 23 | |
| (SEQ ID NO: 107) | 5'-(AAAAAAAAAAAAAA)-3' (SEQ ID NO: 109) | | | 31 | |
| 5'-d(TTTT**T**T**T**T**T**T**T**TTT)-3' | 5'-d(AAAAAAAAAAAAAA)-3' (SEQ ID NO: 111) | | | 23 | |
| (SEQ ID NO: 110) | 5'-(AAAAAAAAAAAAAA)-3' (SEQ ID NO: 112) | | | 16 | |
| 5'-d(**TTTTTTTTTTTTT**T)-3' | 5'-d(AAAAAAAAAAAAAA)-3' (SEQ ID NO: 114) | | | <10 | |
| (SEQ ID NO: 113) | 5'-(AAAAAAAAAAAAAA)-3' (SEQ ID NO: 115) | | | 42 | |
| | 5'-(AAAAAAGAAAAAAA)-3' (SEQ ID NO: 116) | | | 37 | |
| 5'-d(G**T**GA**T**A**T**GC)-3' | 5'-d(GCATATCAC)-3' | | | 26 | |
| | 5'-(GCAUAUCAC)-3' | | | 27 | |

TABLE 3

| Monomer X | | | | | |
|---|---|---|---|---|---|
| Oligo | Target | $T_m$ No. | $T_m$ (° C.) $Na_2HPO_4$/ EDTA | $T_m$ (° C.) $Na_2HPO_4$/ NaCl/EDTA | $T_m$ (° C.) $Na_2HPO_4$/ TMAC |
| 5'-d(TTTTTTT**T**TTTTTT)-3' | 5'-d(AAAAAAAAAAAAAA)-3' (SEQ ID NO: 118) | | | 23 | |
| (SEQ ID NO: 117) | 5'-(AAAAAAAAAAAAAA)-3' (SEQ ID NO: 119) | | | 23 | |
| 5'-d(TTTTTT**TT**TTTTTT)-3' | 5'-d(AAAAAAAAAAAAAA)-3' (SEQ ID NO: 121) | | | 19 | |
| (SEQ ID NO: 120) | 5'-(AAAAAAAAAAAAAA)-3' (SEQ ID NO: 122) | | | 23 | |
| 5'-d(TTTTTT**T**T**T**TTTTT)-3' | 5'-d(AAAAAAAAAAAAAA)-3' (SEQ ID NO: 124) | | | 9 | |
| (SEQ ID NO: 123) | 5'-(AAAAAAAAAAAAAA)-3' (SEQ ID NO: 125) | | | 15 | |

TABLE 3-continued

| Monomer X | | | | | |
|---|---|---|---|---|---|
| Oligo | Target | $T_m$ No. | $T_m$ (° C.) $Na_2HPO_4$/ EDTA | $T_m$ (° C.) $Na_2HPO_4$/ NaCl/EDTA | $T_m$ (° C.) $Na_2HPO_4$/ TMAC |
| 5'-d(TTTTT**TTTT**TTTTT)-3' | 5'-d(AAAAAAAAAAAAAA)-3' (SEQ ID NO: 127) | | | 5 | |
| (SEQ ID NO: 126) | 5'-(AAAAAAAAAAAAAA)-3' (SEQ ID NO: 128) | | | 14 | |

TABLE 4

| Monomer Y | | | | | |
|---|---|---|---|---|---|
| Oligo | Target | $T_m$ No. | $T_m$ (° C.) $Na_2HPO_4$/ EDTA | $T_m$ (° C.) $Na_2HPO_4$/ NaCl/EDTA | $T_m$ (° C.) $Na_2HPO_4$/ TMAC |
| 5'-d(TTTTTTT**T**TTTTTT)-3' | 5'-d(AAAAAAAAAAAAAA)-3' (SEQ ID NO: 130: | | | 36 | |
| (SEQ ID NO: 129) | 5'-(AAAAAAAAAAAAAA)-3' (SEQ ID NO: 131) | | | 37 | |
| 5'-d(TTTTTT**TT**TTTTTT)-3' | 5'-d(AAAAAAAAAAAAAA)-3' (SEQ ID NO: 133) | | | 35 | |
| (SEQ ID NO: 132) | 5'-(AAAAAAAAAAAAAA)-3' (SEQ ID NO: 134) | | | 37 | |
| 5'-d(TTTTTT**T**T**T**TTTTT)-3' | 5'-d(AAAAAAAAAAAAAA)-3' (SEQ ID NO: 136) | | | 35 | |
| (SEQ ID NO: 135) | 5'-(AAAAAAAAAAAAAA)-3' (SEQ ID NO: 137) | | | 36 | |
| 5'-d(TTTTT**TTTT**TTTTT)-3' | 5'-d(AAAAAAAAAAAAAA)-3' (SEQ ID NO: 139) | | | 32 | |
| (SEQ ID NO: 138) | 5'-(AAAAAAAAAAAAAA)-3' (SEQ ID NO: 140) | | | 33 | |
| 5'-d(TTTT**T**T**T**T**T**T**T**TTT)-3' | 5'-d(AAAAAAAAAAAAAA)-3' (SEQ ID NO: 142) | | | 36 | |
| (SEQ ID NO: 141) | 5'-(AAAAAAAAAAAAAA)-3' (SEQ ID NO: 143) | | | 36 | |
| 5'-d(**TTTTTTTTTTTTT**T)-3' | 5'-d(AAAAAAAAAAAAAA)-3' (SEQ ID NO: 145) | | | 58 | |
| (SEQ ID NO: 144) | 5'-(AAAAAAAAAAAAAA)-3' (SEQ ID NO: 146) | | | 58 | |
| 5'-d(G**T**GA**T**A**T**GC)-3' | 5'-d(GCATATCAC)-3' | | | 35 | |
| | 5'-(GCAUAUCAC)-3' | | | 35 | |

TABLE 5

| Monomer Z | | | | | | |
|---|---|---|---|---|---|---|
| | | | Melting temperature ($T_m$/° C.) | | | |
| Oligo | Target | $T_m$ No. | Y = A | Y = C | Y = T | Y = G |
| 5'-r(G**T**GA**T**A**T**GC)-3' | 5'-d(GCATYTCAC)-3' | 1 | 55 | 34 | 38 | 37 |
| 5'-r(GUGAUAUGC)-3' | 5'-d(GCATYTCAC)-3' | 2 | 27 | <10 | <10 | <10 |
| 5'-r(G**T**GA**T**A**T**GC)-3' | 5'-r(GCAUYUCAC)-3' | 3 | 63 | 45 | — | — |
| 5'-r(GUGAUAUGC)-3' | 5'-r(GCAUYUCAC)-3' | 4 | 38 | 22 | — | — |

TABLE 6

| Monomer Z | | | |
|---|---|---|---|
| Oligo | Target | $T_m$ No. | Melting temperature ($T_m$/° C.) |
| 5'-d(GTGATATGC)-3' | 5'-d(GCATATCAC)-3' | 1 | 28 |
| 5'-d(G**T**GA**T**A**T**GC)-3' | 5'-d(GCATATCAC)-3' | 2 | 44 |

TABLE 6-continued

| Monomer Z | | | |
|---|---|---|---|
| Oligo | Target | $T_m$ No. | Melting temperature ($T_m$/° C.) |
| 5'-d(GTGATATGC)-3' | 5'-d(GC**A**T**A**TC**A**C)-3' | 3 | 40 |
| 5'-d(G**T**GA**T**A**T**GC)-3' | 5'-d(GC**A**T**A**TC**A**C)-3' | 4 | 63 |
| 5'-r(G**T**GA**T**A**T**GC)-3' | 5'-d(GC**A**T**A**TC**A**C)-3' | 5 | 74 |
| 5'-(**GTGATATG**$^{Me}$**C**)-3' | 5'-d(GC**A**T**A**TC**A**C)-3' | 6 | 85 |

TABLE 7

| Monomer Z (all-phosphoromonothioate oligonucleotides) | | | |
|---|---|---|---|
| Oligo | Target | $T_m$ No. | Melting temperature ($T_m$/° C.) |
| 5'-d(G$^s$T$^s$G$^s$A$^s$T$^s$A$^s$T$^s$G$^s$C)-3' | 5'-d(GCATATCAC)-3' | 1 | 21 |
| 5'-d(G$^s$T$^s$G$^s$A$^s$T$^s$A$^s$T$^s$G$^s$C)-3' | 5'-r(GCAUAUCAC)-3' | 2 | 17 |
| 5'-d(G$^s$**T**$^s$G$^s$A$^s$**T**$^s$A$^s$**T**$^s$G$^s$C)-3' | 5'-d(GCATATCAC)-3' | 3 | 41 |
| 5'-d(G$^s$**T**$^s$G$^s$A$^s$**T**$^s$A$^s$**T**$^s$G$^s$C)-3' | 5'-r(GCAUAUCAC)-3' | 4 | 47 |

TABLE 8

| Monomer thio-Z (U$^s$) | | | |
|---|---|---|---|
| Oligo | Target | $T_m$ No. | Melting temperature ($T_m$/° C.) |
| 5'-d(GTGA**U**$^s$ATGC)-3' | 5'-d(GCATATCAC)-3' | 1 | 34 |
| 5'-d(GTGA**U**$^s$ATGC)-3' | 5'-(GCAUAUCAC)-3' | 2 | 36 |
| 5'-d(G**U**$^s$GA**U**$^s$A**U**$^s$GC)-3' | 5'-d(GCATATCAC)-3' | 3 | 42 |
| 5'-d(G**U**$^s$GA**U**$^s$A**U**$^s$GC)-3' | 5'-(GCAUAUCAC)-3' | 4 | 52 |
| 5'-d(GTGTTTTGC)-3' | 5'-(GCAAAACAC)-3' | 5 | 27 |
| 5'-d(G**U**$^s$G**U**$^s$**U**$^s$**U**$^s$**U**$^s$GC)-3' | 5'-d(GCAAAACAC)-3' | 6 | 51 |

TABLE 9

| Monomers amino-Z (T$^{NH}$) and methylamino-Z (T$^{NMe}$) | | | |
|---|---|---|---|
| Oligo | Target | $T_m$ No. | Melting temperature ($T_m$/° C.) |
| 5'-d(GTGA**T**$^{NH}$ATGC)-3' | 5'-d(GCATATCAC)-3' | 1 | 33 |
| 5'-d(GTGA**T**$^{NH}$ATGC)-3' | 5'-(GCAUAUCAC)-3' | 2 | 34 |
| 5'-d(G**T**$^{NH}$GA**T**$^{NH}$A**T**$^{NH}$GC)-3' | 5'-d(GCATATCAC)-3' | 3 | 39 |
| 5'-d(G**T**$^{NH}$GA**T**$^{NH}$A**T**$^{NH}$GC)-3' | 5'-(GCAUAUCAC)-3' | 4 | 47 |
| 5'-d(GTGA**T**$^{NMe}$ATGC)-3' | 5'-d(GCATATCAC)-3' | 5 | 33 |
| 5'-d(GTGA**T**$^{NMe}$ATGC)-3' | 5'-(GCAUAUCAC)-3' | 6 | 36 |

TABLE 9-continued

| Monomers amino-Z ($T^{NH}$) and methylamino-Z ($T^{NMe}$) | | | |
|---|---|---|---|
| Oligo | Target | $T_m$ No. | Melting temperature ($T_m$/° C.) |
| 5'-d(G$T^{NMe}$GA$T^{NMe}$A$T^{NMe}$GC)-3' | 5'-d(GCATATCAC)-3' | 7 | 39 |
| 5'-d(G$T^{NMe}$GA$T^{NMe}$A$T^{NMe}$GC)-3' | 5'-(GCAUAUCAC)-3' | 8 | 49 |
| 5'-d(G$T^{NMe}$G$T^{NH}$$T^{NMe}$$T^{NH}$$T^{NMe}$GC)-3' | 5'-d(GCAAAACAC)-3' | 9 | 47 |
| 5'-d(G$T^{NMe}$G$T^{NH}$$T^{NMe}$$T^{NH}$$T^{NMe}$GC)-3' | 5'-(GCAAAACAC)-3' | 10 | 63 |

TABLE 10

| Steps | T9 oligo $A_{260}$ units | T16 oligos $A_{260}$ units | LNA T9 oligo $A_{260}$ units | No oligo Control |
|---|---|---|---|---|
| poly (rA) added | 5.0/5.0 | 5.0/5.0 | 5.0/5.0 | 5.0/5.0 |
| poly (rA) breakthrough | 1.75/1.61 | 1.84/1.78 | 1.83/1.82 | 5.09/5.14 |
| ∴poly (rA) bound | 3.25/3.39 | 3.16/3.22 | 3.17/3.18 | 0.0/0.0 |
| % poly (rA) bound | 65.0%/67.8% | 63.2%/64.4% | 63.4%/63.6% | 0.0%/0.0% |
| Low Salt Wash/Elute | 0.24/0.24 | 0.11/0.12 | .053/.055 | 0.14/0.13 |
| TE Elute 15 min RT | 2.37/2.72 | 0.83/0.93 | 0.02/0.04 | 0.01/0.02 |
| TE Elute O.N. RT | 0.38/0.37 | 1.76/1.69 | 0.11/0.07 | .003/.004 |
| TE Elute 30 min 65° C. | .047/.040 | 0.38/0.46 | 1.62/1.70 | .005/.004 |
| 10 mM Tris pH 10 Elute | .002/.002 | 0.03/0.03 | 0.10/0.10 | 0.01/0.01 |
| 1 mM HCl pH 4.0 Elute | 0.07/0.06 | 0.06/0.04 | 0.26/0.23 | 0.01/0.01 |
| Ave. $A_{260}$ Recovered | 3.20 | 3.14 | 2.18 | — |
| Ave. % $A_{260}$ Recovered | 96.4% | 98.4% | 68.7% | — |

The invention claimed is:

1. An oligomer comprising at least one LNA nucleoside of the general formula I

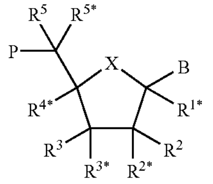

I wherein X is selected from —O—;

B is selected from hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$;

one of the substituents $R^2$, $R^{2*}$, $R^3$, and $R^{3*}$ is a group P* which designates an internucleoside linkage to a preceding monomer, or a 3'-terminal group;

$R^{2*}$ and $R^{4*}$ together designate a biradical selected from
—$(CR^*R^*)_r$—Y—$(CR^*R^*)_s$—,
—$(CR^*R^*)_r$—Y—$(CR^*R^*)_s$—Y—,
—Y—$(CR^*R^*)_{r+s}$—Y—,
—Y—$(CR^*R^*)_r$—Y—$(CR^*R^*)_s$— or
—$(CR^*R^*)_{r+s}$—, each R* is independently selected from hydrogen, halogen, hydroxy, mercapto, amino, optionally substituted $C_{1-6}$-alkoxy, optionally substituted $C_{1-6}$-alkyl, DNA intercalators, photochemically active groups, thermochemically active groups, chelating groups, reporter groups, and ligands, Y is —O—, —S—, 0 (zero) or —$N(R^N)$— where $R^N$ is selected from hydrogen and $C_{1-4}$-alkyl, and each of r and s is 0-4 with the proviso that the sum r+s is 1-4, and provided that when the biradical is —$(CR^*R^*)_r$—Y—$(CR^*R^*)_s$—, then Y is —S— or —$N(R^N)$—; and each of the substituents $R^{1*}$, $R^2$, $R^3$, $R^5$, and $R^{5*}$, which are present and not involved in P, P* or the biradical, is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxycarbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkylaminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted;

and basic salts and acid addition salts thereof.

2. The oligomer of claim 1 wherein the oligomer comprises 1 to 10,000 nucleosides of the formula I and 0-10,000 nucleosides selected from naturally occurring nucleosides and nucleoside analogues, with the proviso that the sum of the number of nucleosides and the number of LNA(s) is at least 2.

3. The oligomer of claim 2 wherein at least one LNA nucleoside comprises a nucleobase as the substituent B.

4. The oligomer of claim 1 wherein one of the substituents $R^3$ and $R^{3*}$ designates P*.

5. The oligomer of claim 1, wherein one or more nucleosides have the following formula 1a:

Ia

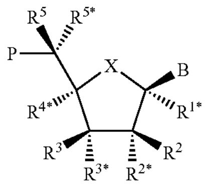

wherein P, P*, B, X, $R^{1*}$, $R^2$, $R^{2*}$, $R^1$, $R^{4*}$, $R^5$ and $R^{5*}$ are as defined in claim 1.

6. The oligomer of claim 5 wherein $R^{3*}$ designates P*.

7. The oligomer of claim 6 wherein the oligomer comprises one biradical constituted by two non-geminal substituents.

8. The oligomer of claim 1 wherein $R^{3*}$ designates P*.

9. The oligomer of claim 8 wherein $R^2$ is selected from hydrogen, hydroxy, and optionally substituted $C_{1-4}$-alkoxy, and $R^{3*}$, $R^3$, $R^5$, and $R^{5*}$ designate hydrogen.

10. The oligomer of claim 9 wherein B is selected from nucleobases.

11. The oligomer of claim 10 wherein the oligomer comprises at least one LNA nucleoside wherein B is selected from adenine, guanine, thymine, cytosine, uracil, purine, xanthine, diaminopurine, 8-oxo-$N^6$- methyladenine, 7-deazaxanthine, 7-deazaguanine, $N^4$, $N^6$-ethanocytosin, $N^6$, $N^6$-ethano-2,6-diaminopurine, 5-methylcytosine, 5-($C^3$-$C^6$)-alkynylcytosine, 2,6-diaminopyrimidino, 2,6-diaminopyrazine, 1-methyl-pyrazolo[4,3-d]pyrimidino-5,7(4H,6H)-dione, 1-methyl-pyrazolo[4, 3-d]pyrimidine-5,7(4H,6H)-dione, 5-fluorouracil, 5-bromouracil, pseudoisocytosine, 2-hydroxy-5-methyl-4-triazolopyridine, isocytosine, isoguanin, and inosine.

12. The oligomer according to claim 1 wherein any internucleoside linkage of the one or more LNA nucleosides is selected from linkages consisting of 2 to 4 groups/atoms selected from —$CH_2$—, —O—, —S—, —$NR^H$—, >C═O, >$N^R$H, >C═S, —$Si(R'')_2$—, —SO—, —$S(O)_2$—, —$P(O)_2$—, —P(O,S)—, —$P(S)_2$—, —PO(R'')—, —PO($OCH_2$)—, and —PO($NHR^H$)—, where $R_H$ is selected from hydrogen and $C_{1-4}$-alkyl, and R'' is selected from $C_{1-6}$-alkyl and phenyl.

13. The oligomer of claim 12 wherein any internucleoside linkage of the one or more LNA nucleosides is selected from —$CH_2$—$CH_2$—$CH_2$—, —$CH_2$—CO—$CH_2$, —$CH_2$—CHOH—$CH_2$—, —O—$CH_2$—O—, —O—$CH_2$—$CH_2$, —O—$CH_2$—CH═, —$CH_2$—$CH_2$—O—, —$NR^H$—$CH_2$—$CH_2$, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(═$NR^H$)—$NR^H$—, —$NR^H$—CO—$CH_2$—$NR^H$—, —O—CO—O—, —O—CO—$CH_2$—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH═N—O—, —$CH_2$—$NR^H$—O—, —$CH_2$—O—N═, —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH=, —S—$CH_2$—$CH_2$—, —$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —$S(O)_2$—O—, —O—$S(O)_2$—$CH_2$—, —O—$S(O)_2$—$NR^H$—, —$NR^H$—$S(O)_2$—$CH_2$—, —O—$S(O)_2$—$CH_2$—, —O—$P(O)_2$—O—, —O—P(O,S)—O—, —O—$P(S)_2$—O—, —S—$P(O)_2$—O—, —S—P(O,S)—O—, —S—$P(S)_2$—O—, —O—$P(O)_2$—S—, —O—P(O,S)—S—, —O—$P(S)_2$—S—, —S—$P(O)_2$—S—, —S—P(O,S)—S—, —S—$P(S)_2$—S—, —O—PO(R")—O—, —O—$PO(OCH_3)$—O—, —O—$PO(BH_3)$—O—, —O—$PO(NHR^H)$—O—, —O—P(O)2—$NR^H$—, —$NR^H$—$P(O)_2$—O—, —O—$P(O,NR^H)$—O—, and —O—$Si(R")_2$—O—.

14. The oligomer of claim 13 wherein any internucleoside linkage of the one or more LNA nucleosides is selected from —$CH_2$—CO—$NR^H$—, —$CH_2$—$NR^H$—O—, —S—$CH_2$—O—, —O—$P(O)_2$—O—, —O—P(O,S)—O—, —O—$P(S)_2$—O—, —$NR^H$—$P(O)_2$—O—, —O—$P(O,NR^H)$—O—, —O—PO(R")—O—, —O—$PO(OCH_3)$—O—, and —O—$PO(NHR^H)$—O—, where $R^H$ is selected form hydrogen and $C_{1-4}$-alkyl, and R" is selected from $C_{1-6}$-alkyl and phenyl.

15. The oligomer of claim 1 wherein each of the substituents $R^{1*}$, $R^2$, $R^3$, $R^{3*}$, $R^5$, and $R^{5*}$, of the one or more LNA nucleosides, which are present and not involved in P, P* is independently selected from hydrogen, optionally substituted $C_{1-6}$-alkyl, optionally substituted $C_{2-6}$-alkenyl, hydroxy, $C_{1-6}$-alkoxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl) amino, carbamoyl, mono- and di($C_{1-6}$-alkyl)-amino-carbonyl, $C_{1-6}$-alkyl-carbonylamino, carbamido, azido, $C_{1-6}$-alkanoyloxy, sulphono, sulphanyl, $C_{1-6}$-alkylthio, DNA intercalators, photochemically active groups, thermochemically active groups, chelating groups, reporter groups, and ligands, and halogen, where two geminal substituents together may designate oxo, and where $R^{N*}$, when present and not involved in a biradical, is selected from hydrogen and $C_{1-4}$-alkyl.

16. The oligomer of claim 1 wherein each of the substituents $R^{1*}$, $R^2$, $R^1$, $R^{3*}$, $R^5$, and $R^{5*}$, of the LNA(s), which are present and not involved in P, P* designate hydrogen.

17. The oligomer of claim 1 wherein P is a 5'- terminal group selected from hydrogen, hydroxy, optionally substituted $C_{1-6}$-alkyl, optionally substituted $C_{1-6}$-alkoxy, optionally substituted $C_{1-6}$-alkylcarbonyloxy, optionally substituted aryloxy, monophosphate, diphosphate, triphosphate, and —W-A', wherein W is selected from —O—, —S—, and —$N(R^H)$— where $R^H$ is selected from hydrogen and $C_{1-6}$-alkyl, and where A' is selected from DNA intercalators, photochemically active groups, thermochemically active groups, chelating groups, reporter groups, and ligands.

18. The oligomer of claim 1 wherein P* is a 3'-terminal group selected from hydrogen, hydroxy, optionally substituted $C_{1-6}$-alkoxy, optionally substituted $C_{1-6}$-alkylcarbonyloxy, optionally substituted aryloxy, and —W-A', wherein W is selected from —O—, —S—, and —$N(R^H)$— where $R^H$ is selected from hydrogen and $C_{1-6}$-alkyl, and where A' is selected from DNA intercalators, photochemically active groups, thermochemically active groups, chelating groups, reporter groups, and ligands.

19. The oligomer of claim 1 wherein the oligomer corresponds to the following formula V:

$$G\text{-}[Nu\text{-}L]_{n(0)}\text{-}\{[LNA\text{-}L]_{m(q)}\text{-}[Nu\text{-}L]_{n(q)}\}_q\text{-}G^* \quad \text{V}$$

wherein q is 1-50;

each of n(0), . . . , n(q) is independently 0-10000;

each of m(1), . . . , m(q) is independently 1-10000; with the proviso that the sum of n(0), . . . , n(q) and m(1), . . . , m(q) is 2-15000;

G designates a 5'-terminal group;

each Nu independently designates a nucleoside selected from naturally occurring nucleosides and nucleoside analogues;

each LNA independently designates a nucleoside analogue;

each L independently designates an internucleoside linkage between two groups selected from Nu and LNA, or L together with G* designates a 3'-terminal group; and each LNA-L independently designates a nucleoside analogue of the general formula I:

I

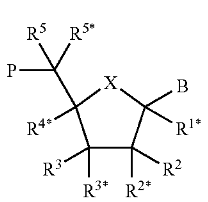

wherein the substituents B, P, P*, $R^{1*}$, $R^2$, $R^{2*}$, $R^3$, $R^{4*}$, $R^5$, and $R^{5*}$, and X are as defined in claim 1.

20. The oligomer of claim 1 further comprising a PNA mono- or oligomer segment of the formula

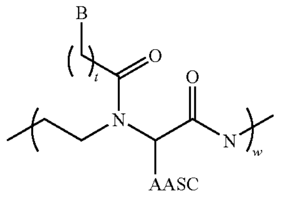

wherein B is a defined above for the formula I, AASC designates hydrogen or an amino acid side chain, t is 1-5, and w is 1-50.

21. The oligomer of claim 1 which has an increased specificity towards complementary ssRNA or ssDNA compared to a corresponding reference oligonucleotide which does not contain any LNA units.

22. The oligomer of claim 1 which has an increased affinity towards complementary ssRNA or ssDNA compared to a corresponding reference oligonucleotide which does not contain any LNA units.

23. The oligomer of claim 1 which is capable of binding to a target sequence in a dsDNA or dsRNA molecule by of strand displacement or by triple helix formation.

24. The oligomer of claim 1 which is more resistant to nucleases than a corresponding reference oligonucleotide which does not contain any LNA units.

25. The oligomer according to claim 1 which has nucleic acid catalytic activity.

26. A diagnostic or analysis kit comprising an oligonucleotide of claim 1.

27. The kit of claim 26 wherein the oligonucleotide is immobilized on a solid support.

28. A diagnostic or analysis kit comprising a reaction body and one or more oligonucleotides of claim 1.

29. The kit of claim 28 wherein the one or more oligonucleotides are immobilized on the reaction body.

* * * * *